(12) United States Patent
Dupont et al.

(10) Patent No.: US 9,359,444 B2
(45) Date of Patent: Jun. 7, 2016

(54) METHODS AND MONITORING OF TREATMENT WITH A WNT PATHWAY INHIBITOR

(71) Applicant: OncoMed Pharmaceuticals, Inc., Redwood City, CA (US)

(72) Inventors: Jakob Dupont, Hillsborough, CA (US); Robert J. Stagg, Moraga, CA (US)

(73) Assignee: OncoMed Pharmaceuticals Inc., Redwood City, CA (US)

(*) Notice: Subject to any disclaimer, the term of this patent is extended or adjusted under 35 U.S.C. 154(b) by 0 days.

(21) Appl. No.: 14/171,151

(22) Filed: Feb. 3, 2014

(65) Prior Publication Data

US 2014/0242078 A1    Aug. 28, 2014

Related U.S. Application Data

(60) Provisional application No. 61/760,523, filed on Feb. 4, 2013.

(51) Int. Cl.
| | |
|---|---|
| *A61K 39/395* | (2006.01) |
| *A61K 38/17* | (2006.01) |
| *C07K 16/28* | (2006.01) |
| *C07K 16/30* | (2006.01) |
| *A61K 31/675* | (2006.01) |
| *A61K 45/06* | (2006.01) |
| *G01N 33/574* | (2006.01) |
| *A61K 39/00* | (2006.01) |

(52) U.S. Cl.
CPC ............... *C07K 16/30* (2013.01); *A61K 31/675* (2013.01); *A61K 38/177* (2013.01); *A61K 39/39558* (2013.01); *A61K 45/06* (2013.01); *C07K 16/2863* (2013.01); *G01N 33/574* (2013.01); *A61K 2039/505* (2013.01); *A61K 2039/545* (2013.01); *C07K 2317/73* (2013.01); *G01N 2800/52* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,109,496 A | 8/1978 | Allemann et al. |
| 4,323,546 A | 4/1982 | Crockford et al. |
| 4,411,990 A | 10/1983 | Salmon et al. |
| 4,612,282 A | 9/1986 | Schlom et al. |
| 4,670,393 A | 6/1987 | Seeburg |
| 4,873,191 A | 10/1989 | Wagner et al. |
| 4,968,103 A | 11/1990 | McNab et al. |
| 4,981,785 A | 1/1991 | Nayak |
| 5,019,497 A | 5/1991 | Olsson |
| 5,034,506 A | 7/1991 | Summerton et al. |
| 5,061,620 A | 10/1991 | Tsukamoto et al. |
| 5,087,570 A | 2/1992 | Weissman et al. |
| 5,223,409 A | 6/1993 | Ladner et al. |
| 5,225,539 A | 7/1993 | Winter |
| 5,283,317 A | 2/1994 | Saifer et al. |
| 5,358,691 A | 10/1994 | Clark et al. |
| 5,489,677 A | 2/1996 | Sanghvi et al. |
| 5,534,617 A | 7/1996 | Cunningham et al. |
| 5,538,848 A | 7/1996 | Livak et al. |
| 5,539,082 A | 7/1996 | Nielsen et al. |
| 5,565,332 A | 10/1996 | Hoogenboom et al. |
| 5,585,089 A | 12/1996 | Queen et al. |
| 5,589,376 A | 12/1996 | Anderson et al. |
| 5,599,677 A | 2/1997 | Dowell et al. |
| 5,602,240 A | 2/1997 | De Mesmaeker et al. |
| 5,614,396 A | 3/1997 | Bradley et al. |
| 5,631,169 A | 5/1997 | Lakowicz et al. |
| 5,639,606 A | 6/1997 | Willey |
| 5,643,741 A | 7/1997 | Tsukamoto et al. |
| 5,643,765 A | 7/1997 | Willey |
| 5,648,464 A | 7/1997 | Artavanis-Tsakonas et al. |
| 5,650,317 A | 7/1997 | Chang et al. |
| 5,654,183 A | 8/1997 | Anderson et al. |
| 5,672,499 A | 9/1997 | Anderson et al. |
| 5,674,739 A | 10/1997 | Shyjan |
| 5,688,666 A | 11/1997 | Bass et al. |
| 5,693,482 A | 12/1997 | Anderson et al. |
| 5,705,188 A | 1/1998 | Junichi et al. |
| 5,714,331 A | 2/1998 | Buchardt et al. |
| 5,719,262 A | 2/1998 | Buchardt et al. |
| 5,739,277 A | 4/1998 | Presta et al. |
| 5,750,373 A | 5/1998 | Garrard et al. |
| 5,750,376 A | 5/1998 | Weiss et al. |
| 5,753,229 A | 5/1998 | Mordoh et al. |
| 5,753,506 A | 5/1998 | Johe |
| 5,780,300 A | 7/1998 | Artavanis-Tsakonas et al. |

(Continued)

FOREIGN PATENT DOCUMENTS

| | | |
|---|---|---|
| EP | 1 004 669 A1 | 5/1998 |
| EP | 0 861 894 A1 | 9/1998 |

(Continued)

OTHER PUBLICATIONS

Albers, J., et al., "Control of bone formation by the serpentine receptor Frizzled-9," The Journal of Cellular Biology 192(6)1057-1072, Rockefeller University Press, United States (2011).
Cao, Y., et al., "Nuclear-Cytoplasmic Shuttling of Menin Regulates Nuclear Translocation of {beta}-Catenin," Molecular and Cellular Biology 29(20):5477-5487, American Society for Microbiology, United States (2009).
GenBank, "Alkaline phosphatase [Pseudotermotoga lettingae TMO]," Accession No. ABV34137, Accessed at http://www.ncbi.nlm.nih.gov/protein/ABV34137, Accessed on May 13, 2015, 2 pages.
GenBank, "Hypothetical protein BarnMEX5DRAFT_6767 [Burkholderia ambifaria MEX-5]," Accession No. EDT37460, Accessed at http://www.ncbi.nlm.nih.gov/protein/EDT37460, Accessed on May 13, 2015, 1 page.

(Continued)

*Primary Examiner* — Daniel C Gamett
(74) *Attorney, Agent, or Firm* — Sterne, Kessler, Goldstein & Fox P.L.L.C.

(57) ABSTRACT

Methods for treating diseases such as cancer comprising administering a Wnt pathway inhibitor, either alone or in combination with other anti-cancer agents, and monitoring for skeletal-related side effects and/or toxicity.

29 Claims, 4 Drawing Sheets

(56) References Cited

U.S. PATENT DOCUMENTS

| | | |
|---|---|---|
| 5,786,158 A | 7/1998 | Artavanis-Tsakonas et al. |
| 5,789,195 A | 8/1998 | Artavanis-Tsakonas et al. |
| 5,814,511 A | 9/1998 | Chang et al. |
| 5,821,108 A | 10/1998 | Akashi et al. |
| 5,824,489 A | 10/1998 | Anderson et al. |
| 5,824,544 A | 10/1998 | Armentano et al. |
| 5,830,730 A | 11/1998 | German et al. |
| 5,834,598 A | 11/1998 | Lowman et al. |
| 5,849,535 A | 12/1998 | Cunningham et al. |
| 5,849,553 A | 12/1998 | Anderson et al. |
| 5,849,869 A | 12/1998 | Artavanis-Tsakonas et al. |
| 5,854,026 A | 12/1998 | Cunningham et al. |
| 5,856,441 A | 1/1999 | Artavanis-Tsakonas et al. |
| 5,859,535 A | 1/1999 | Liu |
| 5,861,832 A | 1/1999 | Nagaraj |
| 5,869,282 A | 2/1999 | Ish-Horowicz et al. |
| 5,872,154 A | 2/1999 | Wilson et al. |
| 5,876,978 A | 3/1999 | Willey et al. |
| 5,885,530 A | 3/1999 | Babson et al. |
| 5,885,808 A | 3/1999 | Spooner et al. |
| 5,914,108 A | 6/1999 | Tsukamoto et al. |
| 5,935,792 A | 8/1999 | Rubin et al. |
| 5,942,225 A | 8/1999 | Bruder et al. |
| 5,981,225 A | 11/1999 | Kochanek et al. |
| 5,986,170 A | 11/1999 | Subjeck |
| 5,994,106 A | 11/1999 | Kovesdi et al. |
| 5,994,128 A | 11/1999 | Fallaux et al. |
| 5,994,132 A | 11/1999 | Chamberlain et al. |
| 5,994,617 A | 11/1999 | Dick et al. |
| 6,001,557 A | 12/1999 | Wilson et al. |
| 6,004,528 A | 12/1999 | Bergstein |
| 6,004,924 A | 12/1999 | Ish-Horowicz et al. |
| 6,019,978 A | 2/2000 | Ertl et al. |
| 6,022,711 A | 2/2000 | Cunningham et al. |
| 6,033,908 A | 3/2000 | Bout et al. |
| 6,054,297 A | 4/2000 | Carter et al. |
| 6,080,912 A | 6/2000 | Bremel et al. |
| 6,083,904 A | 7/2000 | Artavanis-Tsakonas |
| 6,090,922 A | 7/2000 | Artavanis-Tsakonas et al. |
| 6,117,985 A | 9/2000 | Thomas et al. |
| 6,121,045 A | 9/2000 | McCarthy et al. |
| 6,127,526 A | 10/2000 | Blank |
| 6,135,653 A | 10/2000 | Aichi |
| 6,136,952 A | 10/2000 | Li et al. |
| 6,143,523 A | 11/2000 | Cunningham et al. |
| 6,149,902 A | 11/2000 | Artavanis-Tsakonas et al. |
| 6,156,305 A | 12/2000 | Brauker et al. |
| 6,159,750 A | 12/2000 | Edmonds |
| 6,180,370 B1 | 1/2001 | Queen et al. |
| 6,190,876 B1 | 2/2001 | Rubin et al. |
| 6,197,523 B1 | 3/2001 | Rimm et al. |
| 6,198,107 B1 | 3/2001 | Seville |
| 6,207,147 B1 | 3/2001 | Hiserodt et al. |
| 6,218,166 B1 | 4/2001 | Ravindranath et al. |
| 6,252,050 B1 | 6/2001 | Ashkenazi et al. |
| 6,262,025 B1 | 7/2001 | Ish-Horowicz et al. |
| 6,353,150 B1 | 3/2002 | Dick et al. |
| 6,379,925 B1 | 4/2002 | Kitajewski et al. |
| 6,380,362 B1 | 4/2002 | Watson et al. |
| 6,429,186 B1 | 8/2002 | Fuh et al. |
| 6,433,138 B1 | 8/2002 | Zimrin et al. |
| 6,433,155 B1 | 8/2002 | Umansky et al. |
| 6,448,229 B2 | 9/2002 | Teall et al. |
| 6,506,559 B1 | 1/2003 | Fire et al. |
| 6,537,775 B1 | 3/2003 | Tournier-Lasserve et al. |
| 6,551,795 B1 | 4/2003 | Rubenfield et al. |
| 6,583,115 B1 | 6/2003 | Kopchick et al. |
| 6,632,620 B1 | 10/2003 | Makarovskiy |
| 6,660,843 B1 | 12/2003 | Feige et al. |
| 6,664,098 B1 | 12/2003 | Sakano |
| 6,683,091 B2 | 1/2004 | Asberom et al. |
| 6,689,744 B2 | 2/2004 | Gao et al. |
| 6,703,221 B1 | 3/2004 | Chan et al. |
| 6,703,489 B1 | 3/2004 | Ish-Horowicz et al. |
| 6,713,206 B2 | 3/2004 | Markoski et al. |
| 6,716,974 B1 | 4/2004 | Maciag et al. |
| 6,756,511 B2 | 6/2004 | Castro Pineiro et al. |
| 6,894,522 B2 | 5/2005 | Averill et al. |
| 6,984,522 B2 | 1/2006 | Clarke et al. |
| 7,091,321 B2 | 8/2006 | Gillies et al. |
| 7,091,323 B2 | 8/2006 | Pan et al. |
| 7,115,360 B2 | 10/2006 | Clarke et al. |
| 7,115,653 B2 | 10/2006 | Baxter et al. |
| 7,118,853 B2 | 10/2006 | Botstein et al. |
| 7,138,370 B2 | 11/2006 | Oliner et al. |
| 7,211,404 B2 | 5/2007 | Lagasse et al. |
| 7,361,336 B1 | 4/2008 | Bergstein |
| 7,381,408 B2 | 6/2008 | Mezo et al. |
| 7,404,956 B2 | 7/2008 | Peters et al. |
| 7,413,873 B2 | 8/2008 | Waterman et al. |
| 7,442,778 B2 | 10/2008 | Gegg et al. |
| 7,507,406 B2 | 3/2009 | Gillies et al. |
| 7,608,453 B2 | 10/2009 | Cattaneo et al. |
| 7,635,530 B2 | 12/2009 | Kenis et al. |
| 7,659,116 B2 | 2/2010 | Buehring et al. |
| 7,662,931 B2 | 2/2010 | Gegg et al. |
| 7,682,607 B2 | 3/2010 | Rhee et al. |
| 7,713,526 B2 | 5/2010 | Rhee et al. |
| 7,723,477 B2 | 5/2010 | Gurney et al. |
| 7,803,370 B2 | 9/2010 | Nakamura et al. |
| 7,803,783 B2 | 9/2010 | Lee et al. |
| 7,803,913 B2 | 9/2010 | Dimitrov et al. |
| 7,867,705 B2 | 1/2011 | Wands et al. |
| 7,879,322 B2 | 2/2011 | Kneissel et al. |
| 7,947,277 B2 | 5/2011 | Ernst et al. |
| 7,982,013 B2 | 7/2011 | Gurney et al. |
| 8,017,559 B2 | 9/2011 | Etzerodt et al. |
| 8,158,761 B2 | 4/2012 | Wands et al. |
| 8,410,061 B2 | 4/2013 | Williams et al. |
| 8,431,532 B2 | 4/2013 | Brennan et al. |
| 8,507,442 B2 | 8/2013 | Gurney et al. |
| 8,551,789 B2 | 10/2013 | Gurney |
| 8,809,287 B2 | 8/2014 | Bafico et al. |
| 2002/0119565 A1 | 8/2002 | Clarke et al. |
| 2002/0137129 A1 | 9/2002 | Barnes et al. |
| 2002/0151487 A1 | 10/2002 | Nickoloff et al. |
| 2002/0169300 A1 | 11/2002 | Waterman et al. |
| 2002/0187502 A1 | 12/2002 | Waterman et al. |
| 2003/0032184 A1 | 2/2003 | Lagasse et al. |
| 2003/0044409 A1 | 3/2003 | Carson et al. |
| 2003/0064384 A1 | 4/2003 | Hung et al. |
| 2003/0086934 A1 | 5/2003 | Botstein et al. |
| 2003/0114387 A1 | 6/2003 | Castro Pineiro et al. |
| 2003/0119029 A1 | 6/2003 | Glick et al. |
| 2003/0135044 A1 | 7/2003 | Asberom et al. |
| 2003/0139457 A1 | 7/2003 | Baxter et al. |
| 2003/0162709 A1 | 8/2003 | Rossi et al. |
| 2003/0165500 A1 | 9/2003 | Rhee et al. |
| 2003/0166543 A1 | 9/2003 | Williams et al. |
| 2003/0175877 A1 | 9/2003 | Baker et al. |
| 2003/0180784 A1 | 9/2003 | McCarthy et al. |
| 2003/0185829 A1 | 10/2003 | Koller et al. |
| 2003/0229023 A1 | 12/2003 | Oliner et al. |
| 2004/0023244 A1 | 2/2004 | Griffin et al. |
| 2004/0037815 A1 | 2/2004 | Clarke et al. |
| 2004/0038876 A1 | 2/2004 | Pepinsky et al. |
| 2004/0048249 A1 | 3/2004 | Tang et al. |
| 2004/0058217 A1 | 3/2004 | Ohlsen et al. |
| 2004/0058443 A1 | 3/2004 | Artavanis-Tsakonas et al. |
| 2004/0105862 A1 | 6/2004 | Pan et al. |
| 2004/0127474 A1 | 7/2004 | Dudek et al. |
| 2004/0171559 A1 | 9/2004 | Weissman et al. |
| 2004/0203003 A1 | 10/2004 | Rhee et al. |
| 2004/0214186 A1 | 10/2004 | Engelberg et al. |
| 2004/0219579 A1 | 11/2004 | Aziz et al. |
| 2004/0247593 A1 | 12/2004 | He et al. |
| 2005/0123900 A1 | 6/2005 | Dimitrov et al. |
| 2005/0130199 A1 | 6/2005 | Carson et al. |
| 2005/0272063 A1 | 12/2005 | Nakamura et al. |
| 2005/0288864 A1 | 12/2005 | Cattaneo et al. |
| 2006/0019256 A1 | 1/2006 | Clarke et al. |
| 2006/0019320 A1 | 1/2006 | Civenni et al. |
| 2006/0040883 A1 | 2/2006 | You et al. |
| 2006/0210867 A1 | 9/2006 | Kenis et al. |

(56) References Cited

U.S. PATENT DOCUMENTS

| | | |
|---|---|---|
| 2007/0014776 A1 | 1/2007 | Gimeno et al. |
| 2007/0072238 A1 | 3/2007 | Bhat |
| 2007/0116701 A1 | 5/2007 | Gurney et al. |
| 2007/0117751 A1 | 5/2007 | Gurney et al. |
| 2007/0237770 A1 | 10/2007 | Lai et al. |
| 2007/0238658 A1 | 10/2007 | Levin et al. |
| 2008/0038272 A1 | 2/2008 | Buehring et al. |
| 2008/0044423 A1 | 2/2008 | Cochrane et al. |
| 2008/0075714 A1 | 3/2008 | Lee et al. |
| 2008/0118432 A1 | 5/2008 | Bergstein et al. |
| 2008/0171319 A1 * | 7/2008 | Urdea et al. ............... 435/6 |
| 2008/0194457 A1 | 8/2008 | Wands et al. |
| 2008/0299136 A1 | 12/2008 | Ernst et al. |
| 2009/0023905 A1 | 1/2009 | Askew et al. |
| 2009/0074777 A1 | 3/2009 | Wands et al. |
| 2009/0130113 A1 | 5/2009 | Kneissel et al. |
| 2009/0163407 A1 | 6/2009 | Bafico et al. |
| 2009/0186010 A1 | 7/2009 | Li et al. |
| 2009/0234104 A1 | 9/2009 | Gegg et al. |
| 2009/0263400 A1 | 10/2009 | Urdea et al. |
| 2009/0304695 A1 | 12/2009 | He et al. |
| 2010/0104574 A1 | 4/2010 | Gurney et al. |
| 2010/0169025 A1 | 7/2010 | Arthur et al. |
| 2011/0020368 A1 | 1/2011 | Hynes |
| 2011/0224243 A1 | 9/2011 | Rethore |
| 2011/0237514 A1 | 9/2011 | Kakitani et al. |
| 2011/0318341 A1 | 12/2011 | Gurney et al. |
| 2012/0003222 A1 | 1/2012 | Brennan et al. |
| 2012/0023600 A1 * | 1/2012 | Shulok et al. ............ 800/13 |
| 2012/0027778 A1 | 2/2012 | Gurney |
| 2012/0141481 A1 | 6/2012 | Ernst et al. |
| 2013/0209475 A1 | 8/2013 | Richards et al. |
| 2013/0252326 A1 | 9/2013 | Gurney et al. |
| 2013/0295105 A1 | 11/2013 | Gurney et al. |
| 2013/0295106 A1 | 11/2013 | Gurney et al. |
| 2014/0105917 A1 | 4/2014 | Gurney |
| 2014/0134159 A1 | 5/2014 | Stagg et al. |

FOREIGN PATENT DOCUMENTS

| | | |
|---|---|---|
| EP | 0 662 827 A1 | 4/2002 |
| EP | 0662827 B1 | 4/2002 |
| EP | 1 576 119 A | 9/2005 |
| EP | 1 805 221 A | 4/2006 |
| EP | 1 805 519 | 7/2007 |
| WO | WO 90/08832 A1 | 8/1990 |
| WO | WO 92/19734 A1 | 11/1992 |
| WO | WO 94/07474 A1 | 4/1994 |
| WO | WO 94/10300 A1 | 5/1994 |
| WO | WO 97/01571 A1 | 1/1997 |
| WO | WO 97/30731 A2 | 8/1997 |
| WO | WO 97/37004 A1 | 10/1997 |
| WO | WO 98/05775 A1 | 2/1998 |
| WO | WO 98/45434 A1 | 10/1998 |
| WO | WO 98/51799 A1 | 11/1998 |
| WO | WO 98/57621 A1 | 12/1998 |
| WO | WO 99/02685 A1 | 1/1999 |
| WO | WO 00/06726 A2 | 2/2000 |
| WO | WO 00/09675 A1 | 2/2000 |
| WO | WO 00/12738 A1 | 3/2000 |
| WO | WO 00/52143 A2 | 9/2000 |
| WO | WO-0102568 A2 | 1/2001 |
| WO | WO 01/26643 A1 | 4/2001 |
| WO | WO-0122920 A2 | 4/2001 |
| WO | WO 01/98354 A2 | 12/2001 |
| WO | WO 01/98537 A2 | 12/2001 |
| WO | WO 02/00576 A1 | 1/2002 |
| WO | WO 02/12447 A2 | 2/2002 |
| WO | WO 02/18544 A2 | 3/2002 |
| WO | WO 02/078703 A1 | 10/2002 |
| WO | WO 02/088081 A2 | 11/2002 |
| WO | WO 02/092635 A2 | 11/2002 |
| WO | WO 02/102978 A2 | 12/2002 |
| WO | WO 03/000893 A2 | 1/2003 |
| WO | WO 03/004045 A2 | 1/2003 |
| WO | WO 03/042246 A2 | 5/2003 |
| WO | WO 03/047316 A1 | 6/2003 |
| WO | WO 03/050502 A2 | 6/2003 |
| WO | WO 03/062273 A2 | 7/2003 |
| WO | WO-03053921 A2 | 7/2003 |
| WO | WO 03/088964 A1 | 10/2003 |
| WO | WO 03/080672 A1 | 10/2003 |
| WO | WO 04/001004 A2 | 12/2003 |
| WO | WO 2004/020668 A2 | 3/2004 |
| WO | WO 2004/032838 A2 | 4/2004 |
| WO | WO 2004/042028 A2 | 5/2004 |
| WO | WO 2004/053069 A2 | 6/2004 |
| WO | WO 2004/065545 A2 | 8/2004 |
| WO | WO 2004/073657 A2 | 9/2004 |
| WO | WO 2004/101739 A2 | 11/2004 |
| WO | WO 2005/001025 A2 | 1/2005 |
| WO | WO 2005/004912 A1 | 1/2005 |
| WO | WO 2005/005601 A2 | 1/2005 |
| WO | WO 2006/034328 A2 | 3/2006 |
| WO | WO 2006/036173 A2 | 4/2006 |
| WO | WO 2006/036175 A2 | 4/2006 |
| WO | WO 2006/040163 A1 | 4/2006 |
| WO | WO 2006/055635 A2 | 5/2006 |
| WO | WO 2006/056340 A2 | 6/2006 |
| WO | WO 2006/130076 A1 | 12/2006 |
| WO | WO 2007/053577 A2 | 5/2007 |
| WO | WO-2007070538 A2 | 6/2007 |
| WO | WO 2007/096149 A1 | 8/2007 |
| WO | WO 2007/133250 A2 | 11/2007 |
| WO | WO 2007/134876 A2 | 11/2007 |
| WO | WO 2007/142711 A2 | 12/2007 |
| WO | WO 2007/148417 A1 | 12/2007 |
| WO | WO 2008/031009 A2 | 3/2008 |
| WO | WO-2008039071 A2 | 4/2008 |
| WO | WO 2008/057459 A2 | 5/2008 |
| WO | WO 2008/061020 A2 | 5/2008 |
| WO | WO 2009/042971 A2 | 4/2009 |
| WO | WO 2009/118300 A1 | 10/2009 |
| WO | WO 2009124535 A1 | 10/2009 |
| WO | WO 2010/031979 A1 | 3/2010 |
| WO | WO 2010/037041 A2 | 4/2010 |
| WO | WO 2010/038756 A1 | 8/2010 |
| WO | WO-2011088123 A2 | 7/2011 |
| WO | WO-2011101409 A1 | 8/2011 |
| WO | WO-2011112678 A1 | 9/2011 |
| WO | WO 2011/123785 A3 | 10/2011 |
| WO | WO 2012/003189 A1 | 1/2012 |
| WO | WO 2012/006027 A1 | 1/2012 |
| WO | WO 2012/058393 A2 | 5/2012 |
| WO | WO 2014/121196 A1 | 8/2014 |

OTHER PUBLICATIONS

GenBank, "Hypothetical protein, conserved, partial [Trypanosoma cruzl]," Accession No. EAN81721, Accessed at http://www.ncbi.nlm/nih/gov/protein/EAN81721, Accessed on May 13, 2015, 2 pages.

He, X., et al., "LDL receptor-related proteins 5 and 6 in WNT/beta-catenin signaling: Arrows point the way," Development 131(8):1663-1677, Company of Biologists Limited, Englad (2004).

Hu, T. and Li, C., "Convergence between Wnt-beta-catenin and EGFR signaling in cancer," Molecular Cancer 9:236-242, BioMed Central Ltd., United States (2010).

Iverson, C., et al., "RDEA119/BAY 869766: A Potent, Selective, Allosteric Inhibitor of MEK1/2 for the Treatment of Cancer," Cancer Research 69:6839-6847, American Association for Cancer Research, United States (2009).

Kim, D., et al., "A Hidden Oncogenic Positive Feedback Loop Caused by Crosstalk between Wnt and ERK Pathways," Oncogene 26:4571-4579, Nature Publishing Group, England (2007).

Krishnan, V., et al., "Regulation of bone mass by Wnt signaling," The Journal of Clinical Investigation 116(5):1202-1209, American Society for Clinical Investigation, United States (2006).

O'Connell, M.P. and Weeraratna, A.T., "Hear the Wnt Ror: how melanoma cells adjust to changes in Wnt," Pigment Cell & Melanoma Research 22:724-739, Blackwell Munksgaard, England (2009).

(56) References Cited

OTHER PUBLICATIONS

OncoMed Pharmaceuticals Press Release, "OncoMed Presents Data on Clinical and Preclinical Anti-Cancer Stem Cell Programs at American Association for Cancer Research Annual Meeting," Apr. 21, 2015, 3 pages.
OncoMed Pharmaceuticals Press Release, "OncoMed to Present Data on Multiple Anti-Cancer Stem Cell Candidates at the American Association of Cancer Research Meeting," Mar. 19, 2015, 2 pages.
Schulte, G., "Frizzleds and WNT/beta-catenin Signaling—The Black Box of Ligand—receptor Selectivity, Complex Stoichiometry and Activation Kinetics," European Journal of Pharmacology, epub:1-5, Elsevier B.V., Netherlands (2015).
Semba, S., et al., "Nuclear Accumulation of B-Catenin in Human Endocrine Tumors: Association with Ki-67 (MIB-1) Proliferative Activity," Endocrine Pathology 11(3):243-250, Humana Press, United States (2000).
Tamura, M., et al., "Structural Correlates of an Anticarcinoma Antibody: Identification of Specificity-Determining Residues (SDRs) and Development of a Minimally Immunogenic Antibody Variant by Retention of SDRs Only," The Journal of Immunology 164(3):1432-1441, American Association of Immunologists, United States (2000).
UniProtKB Database, "Submitted name: Putative uncharacterized protein," Accession No. B7AJZ5, Accessed on May 13, 2015, 5 pages.
UniProtKB Database, "Submitted name: Helix-turn-helix protein," Accession No. A2W361, Accessed on May 13, 2015, 5 pages.
Written Opinion for the International Searching Authority for International Application No. PCT/US2014/014443, mailed on Apr. 15, 2014, International Searching Authority, United States, 17 pages.
US 5,962,233, 10/1999, Livak et al. (withdrawn).
Al-Hajj, M., et al., "Prospective Identification of Tumorigenic Breast Cancer Cells," Proceedings of the National Academy of Sciences 100(7):3983-3988, The National Academy of Sciences, United States (2003).
Caricasole, A., et al., "Functional Characterization of WNT7A Signaling in PC12 Cells," The Journal of Biological Chemistry 278(39):37024-37031, The American Society for Biochemistry and Molecular Biology, United States (2003).
Cong, F., et al., "Wnt Signals across the Plasma Membrane to Activate the Beta-catenin Pathway by Forming Oligomers Containing its Receptors, Frizzled and LRP," Development 131(20):5103-5115, Company of Biologists, England (2004).
"Frizzled Antibody (H-300): sc-9169" accessed at http://scbt.com/datasheet-9169-frizzled-h-300-antibody.html, accessed on Mar. 20, 2015, 6 pages.
Gore, L., et al., "Safety, pharmacokinetics, and pharmacodynamics results from a phase I trial of BAY 86-9766 (RDEA119), a MEK inhibitor, in patients with advanced cancer," J Clin Oncol 29:2 pages, presented at the 2011 ASCO Annual Meeting, American Society of Clinical Oncology, United States (2011) (Abstract 3007).
International Search Report for International Application No. PCT/US14/68097, United States Patent and Trademark Office, United States mailed on Apr. 30, 2015, 10 pages.
International Search Report for International Application No. PCT/US2012/068351, US Patent Office, Virginia, mailed on May 24, 2013, 7 pages.
Jimeno, A., et al., "A first-in-human phase 1 study of anticancer stem cell agent OMP-54F28 (FZD-Fc), decoy receptor for WNT ligands, in patient with advanced solid tumors," 2014 ASCO Annual Meeting, Abstract 2505, 2 pages (2014).
Kabacik, S., et al., "Gene Expression Following Ionising Radiation: Identification of Biomarkers for Dose Estimation and Prediction of Individual Response," International Journal of Radiation Biology 67(2):115-129, Informa Healthcare, England (2011).
Lin, S.Y. et al., "β-catenin, a novel prognostic marker for breast cancer: its roles in cyclin D1 expression and cancer progression," Proceedings of the National Academy of Sciences of the United States of America 97(8):4262-4266, National Academy of Sciences, United States (2000).
Lo, P.K., et al., "Epigenetic Suppression of Secreted Frizzled Related Protein 1 (SFRP1) Expression in Human Breast Cancer," Cancer Biology & Therapy 5(3):e1-e6, Landes Bioscience, Austin, United States (2006).
Miele, L. and Osborne, B., "Arbiter of Differentiation and Death: Notch Signaling Meets Apoptosis," Journal of Cellular Physiology 181(3):393-409, Wiley-Liss, Inc., United States (1999).
OncoMed Pharmaceuticals Press Release, "OncoMed Announces Abstracts Accepted at the 2014 ASCO Annual Meeting," Apr. 23, 2014, 2 pages.
OncoMed Pharmaceuticals Press Release, "OncoMed Pharmaceuticals Announces FDA Clearance to Commence Phase 1 Testing on Anti-Cancer Stem Cell Therapeutic OMP-18R5," Apr. 28, 2011, 2 pages.
OncoMed Pharmaceuticals Press Release, "OncoMed Pharmaceuticals Commences Third Phase 1b Clinical Trial for OMP-54F28 (Fzd8-Fc) With Carboplatin and Paclitaxel in Ovarian Cancer," Feb. 20, 2014, 3 pages.
OncoMed Pharmaceuticals Press Release, "OncoMed Pharmaceuticals Initiates First Phase 1b Clinical Trial of First-in-Class WNT-Pathway-Targeting Antibody Vantictumab (OMP-18R5) With Paclitaxel in Breast Cancer," Oct. 29, 2013, 3 pages.
OncoMed Pharmaceuticals Press Release, "OncoMed Pharmaceuticals Initiates First Phase 1b Clinical Trial of OMP-54F28 (Fzd8-Fc) With Nab-Paclitaxel (Abraxane(R)) and Gemcitabine in Pancreatic Cancer," Jan. 13, 2014, 3 pages.
OncoMed Pharmaceuticals Press Release, "OncoMed Pharmaceuticals Initiates Phase I Clinical Trial of Anti-Cancer Stem Cell Therapeutic OMP-54F28 (Fzd8-Fc)," Jul. 12, 2012, 2 pages.
OncoMed Pharmaceuticals Press Release, "OncoMed Pharmaceuticals Initiates Second Phase 1b Clinical Trial for OMP-54F28 (Fzd8-Fc) With Sorafenib (Nexavar(R)) in Hepatocellular Cancer," Feb. 18, 2013, 3 pages.
OncoMed Pharmaceuticals Press Release, "OncoMed Pharmaceuticals Initiates Second Phase 1b Clinical Trial of First-in-Class WNT Pathway-Targeting Antibody Vantictumab (OMP-18R5) With Docetaxel in Non-Small Cell Lung Cancer (NSCLC)," Nov. 15, 2013, 3 pages.
OncoMed Pharmaceuticals Press Release, "OncoMed Pharmaceuticals Initiates Third Phase 1b Clinical Trial of First-in-Class WNT Pathway-Targeting Antibody Vantictumab (OMP-18R5) With Nab-Paclitaxel (Abraxane®) and Gemcitabine in Stage IV Pancreatic Cancer," Dec. 4, 2013, 3 pages.
OncoMed Pharmaceuticals Press Release, "OncoMed Pharmaceuticals Presents Data From Clinical Trials of Four Novel Anti-Cancer Stem Cell (Anti-CSC) Therapeutics at the AACR-NCI-EORTC International Conference on Molecular Targets and Cancer Therapeutics in Boston, Oct. 19-23, 2013," Oct. 21, 2013, 4 pages.
OncoMed Pharmaceuticals Press Release, "OncoMed Pharmaceuticals Presents Phase 1 Data in Solid Tumor Patients for the First-in-Class Wnt Pathway Targeting Antibody Vantictumab (OMP-18R5) at ASCO," Jun. 3, 2013, 2 pages.
OncoMed Pharmaceuticals Press Release, "OncoMed Pharmaceuticals Presents Updated Phase 1a Data in Advanced Solid Tumor Patients for the First-in-Class WNT-Pathway-Targeting Antibody Vantictumab (OMP-18R5) at the European Cancer Congress 2013," Sep. 29, 2013, 3 pages.
OncoMed Pharmaceuticals Press Release, "OncoMed Pharmaceuticals Recaps New Data Presented at AACR," Apr. 3, 2012, 2 pages.
OncoMed Pharmaceuticals Press Release, "OncoMed Pharmaceuticals to Present Data From Clinical Trials of Four Novel Anti-Cancer Stem Cell (Anti-CSC) Therapeutics in Five Posters at the AACR-NCI-EORTC International Conference on Molecular Targets and Cancer Therapeutics in Boston, Oct. 19-23, 2013," Oct. 14, 2013, 4 pages.
OncoMed Pharmaceuticals Press Release, "OncoMed Pharmaceuticals to Present Phase 1a Data in Advanced Solid Tumor Patients for the First-in-Class WNT-Pathway-Targeting Antibody Vantictumab (OMP-18R5) at the European Cancer Congress 2013 (ECC 2013)," Sep. 23, 2013, 2 pages.
OncoMed Pharmaceuticals, Press Release, "OncoMed Presents Data on Multiple Anti-Cancer Stem Cell Programs at American Association for Cancer Research Annual Meeting," Apr. 8, 2014, 4 pages.

(56) References Cited

OTHER PUBLICATIONS

OncoMed Pharmaceuticals Press Release, "OncoMed Presents New Data in Six Anti-Cancer Stem Cell Programs at AACR," Apr. 9, 2013, 3 pages.
OncoMed Pharmaceuticals Press Release, "OncoMed Provides Update on FZD8-Fc (OMP-54F28) Phase I Clinical Trials," Jun. 18, 2014, 2 pages.
OncoMed Pharmaceuticals Press Release, "OncoMed to Present Data From Three Clinical Studies at the 2014 ASCO Annual Meeting," May 14, 2014, 4 pages.
OncoMed Pharmaceuticals Press Release, "OncoMed to Present New Data in Six Anti-Cancer Stem Cell Programs at AACR," Apr. 2, 2013, 2 pages.
OncoMed Pharmaceuticals Press Release, "PNAS Publishes OncoMed Data Demonstrating Potent Anti-Cancer Activity for Novel Wnt Pathway Antibody OMP-18R5," Jul. 3, 2012, 2 pages.
Smith, D.C., et al., "A first-in-human Phase 1 study of anti-cancer stem cell (CSC) agent OMP-54F28 (FZD8-Fc) targeting th WNT pathway in patients with advanced solid tumors," AACR-NCI-EORTC International Conference on Molecular Targets and Cancer Therapeutics, Oct. 19-23, 2013, Abstract B79, 1 page (2013).
Smith, D.C., et al., "Biomarker analysis in the first-in-human Phase 1a study for vantictumab (OMP-18R5; anti-Frizzled) demonstrates pharmacodynamics (PD) modulation of the Wnt pathway in patients with advanced solid tumors," AACR-NCI-EORTC International Conference on Molecular Targets and Cancer Therapeutics in Boston, Oct. 19-23, 2013, Poster 823, 1 page (2013).
Uren, A., et al., "Secreted Frizzled-related Protein-1 Binds Directly to Wingless and is a Biphasic Modulator of Wnt Signaling," The Journal of Biological Chemistry 275(6):4374-4382, American Society for Biochemistry and Molecular Biology, United States (2000).
Written Opinion for International Application No. PCT/US09/58635, ISA/US, Alexandria, VA, mailed on Nov. 19, 2010, 8 pages.
Written Opinion for International Application No. PCT/US14/68097, United States Patent and Trademark Office, United States, mailed on Apr. 30, 2015, 25 pages.
Written Opinion for the International Searching Authority for International Application No. PCT/US07/05443, mailed on Oct. 30, 2008, The International Bureau of WIPO, Switzerland, 4 pages.
Written Opinion for the International Searching Authority for International Application No. PCT/US11/20994, mailed on Aug. 15, 2011, International Searching Authority, United States, 7 pages.
Written Opinion for the International Searching Authority for International Application No. PCT/US13/66087 mailed on Jan. 16, 2014, The International Bureau of WIPO, Switzerland, 5 pages.
Yen, W-C., et al., "Enhanced anti-tumor effect of WNT pathway antagonists in combination with taxanes," AACR Annual Meeting 2014, Apr. 5-9, Abstract 4547, 1 page (2014).
Yeung, P. et al., "Wnt pathway antagonist OMP-54F28 (F2D8-Fc) inhibits tumor growth and reduces tumor-initiating cell frequency in patient-derived hepatocellular carcinoma and ovarian cancer xenograft models," AACR Annual Meeting 2014, Apr. 5-9, Abstract 1907, 1 page (2014).
Zhang, C., et al., "Predictive biomarker identification for response to vantictumab (OMP-18R5; anti-Frizzled) by mining gene expression data of human breast cancer xenografts," AACR Annual Meetinig, Apr. 5-9, Abstract 2830, 1 page (2014).
Austin, T.W., et al., "A role for the Wnt gene family in hematopoiesis: expansion of multilineage progenitor cells," Blood 89:3624-3635 (1997).
Ayyanan, A., et al., "Increased Wnt signaling triggers oncogenic conversion of human breast epithelial cells by a Notch-dependent mechanism," PNAS 103:3799-3804, the National Academy of Sciences, Washington, DC, U.S.A. (2006).
Bafico, A., et al., "An autocrine mechanism for constitutive Wnt pathway activation in human cancer cells," Cancer Cell 6:497-506 (2004).
Bafico, A., et al., "Interaction of Frizzled Related Protein (FRP) with Wnt Ligands and the Frizzled Receptor Suggests Alternative Mechanisms for FRP Inhibition of Wnt Signaling," J. Biol. Chem.
274:16180-16187, The American Society for Biochemistry and Molecular Biology, Inc., Bethesda, MD, U.S.A. (1999).
Barker, N. and Clevers, H., "Mining the Wnt pathway for cancer therapeutics," Nature Reviews/Drug Discovery 5:997-1014, Nature Publishing Group, New York, NY, U.S.A. (2006).
Battula, V.L., et al., "Prospective isolation and characterization of mesenchymal stem cells from human placenta using a frizzled-9-specific monoclonal antibody," Differentiation 76:326-336, International Society of Differentiation, Higgannum, CT, U.S.A. (2008).
Benhamouche, S., et al., "Apc Tumor Suppressor Gene Is the "Zonation-Keeper" of Mouse Liver," Developmental Cell 10:759-770, Elsevier Inc., Amsterdam, The Netherlands (2006).
Bhanot, P., et al., "A new member of the frizzled family from Drosophila functions as a Wingless receptor," Nature 382:225-230, Nature Publishing Group, New York, NY, U.S.A. (1996).
Bienz, M., "β-Catenin: A Pivot between Cell Adhesion and Wnt Signalling," Current Biology 15:R64-R67, Cell Press, St. Louis, MO, U.S.A. (2004).
Booy, E.P., et al., "Monoclonal and bispecific antibodies as novel therapeutics," Arch. Immunol. Ther. Exp. 54:85-101, Birkhäuser publications, Basel, Switzerland (2006).
Brabletz, T., et al., "Variable β-catenin expression in colorectal cancers indicates tumor progression driven by the tumor environment," PNAS 98(18):10356-10361 (2001).
Brennan, K.R. and Brown, A.M.C., "Wnt Proteins in Mammary Development and Cancer," J. Mammary Gland Biol. Neoplasia 9(2):119-131, Kluwer Academic/Plenum Publishers (2004).
Burgess, W.H., et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J. Cell Bio. 111:2129-2138, The Rockefeller University Press, New York, NY, U.S.A. (1990).
Cadigan, K.M. and Nusse, R., "Wnt signaling: a common theme in animal development," Genes & Development 11:3286-3305, Cold Spring Harbor Laboratory Press (1997).
Caldwell, G.M., et al., "The Wnt Antagonist sFRP1 in Colorectal Tumorigenesis," Cancer Res 64:883-888, American Association for Cancer Research, Philadelphia, PA, U.S.A. (2004).
Chan, E. F., et al., "A common human skin tumour is caused by activating mutations in β-catenin," Nature Genetics 21(4): 410-413 (1999)
Chen, Y., et al., "Selection and Analysis of an Optimized Anti-VEGF Antibody: Crystal Structure of an Affinity-matured Fab in Complex with Antigen," Journal of Molecular Biology 293(4): 865-881, Academic Press, England (1999).
Clevers, H., "Axin and hepatocellular carcinomas," Nature Genetics 24:206-208, Nature Publishing Group, New York, NY, U.S.A. (2000).
Daniel, C., et al., "Mapping of Linear Antigenic Sites on the S Glycoprotein of a Neurotropic Murine Coronavirus with Synthetic Peptides: A Combination of Nine Prediction Algorithms Fails to Identify Relevant Episodes and Peptide Immunogenicity is Drastically Influenced by the Nature of the Protein Carrier," Virology 202(2):540-549, Elsevier Inc., The Netherlands (1994).
Dann, C.E., et al., "Insights into Wnt binding and signalling from the structures of two Frizzled cysteine-rich domains," Nature 412:86-90, Nature Publishing Group, New York, NY, U.S.A. (2001).
Datta, D.V., "Viral Hepatitis," Jr. Asso. Phys. Ind. 25(5):325-330, Association of Physicians of India, Mumbai, India (1977).
Davidson, G., et al., "Casein kinase 1γ couples Wnt receptor activation to cytoplasmic signal transduction," Nature 438:867-872, Nature Publishing Group, U.S.A. (2005).
De Lau, W. and Clevers, H., "LEF1 turns over a new leaf," Nature Genetics 28:3-4, Nature Publishing Group, NY, U.S.A. (2001).
De Pascalis, R., et al., "Grafting of Abbreviated Complementarity-Determining Regions Containing Specificity-Determining Residues Essential for Ligand Contact to Engineer a Less Immunogenic Humanized Monoclonal Antibody," Journal of Immunology 169:3076-3084 (2002).

(56) References Cited

OTHER PUBLICATIONS

Dealmeida, V.I., et al., "The Soluble Wnt Receptor Frizzled8CRD-hFc Inhibits the Growth of Teratocarcinomas In vivo," *Cancer Res* 67(11):5371-5379, American Association for Cancer Research (Jun. 1, 2007).
Dorvillius, Mylene et al., "Targeting of Human Brest Cancer by a Bispecific Antibody Directed against Two Tumour-Associated Antigens: ErbB-2 and Carcinoembryonic Antigen," *Tumor Biology*, Nov. 2002, pp. 337-347, vol. 23, No. 6, S. Karger Medical and Scientific Publishers, Basel.
Fillmore et al., "Human breast cancer cell lines contain stem-like cells that self-renew, give rise to phenotypically diverse progeny and survive chemotherapy" Breast Cancer Res, 2008, voi10R25: 1-13.
Finch, P.W., et al., "Purification and molecular cloning of a secreted, Frizzled-related antagonist of Wnt action," *PNAS* 94:6770-6775, the National Academy of Sciences, Washington, DC, U.S.A. (1997).
Fogel, M. et al., "L1 expression as a predictor of progression and survival in patients with uterine and ovarian carcinomas," *The Lancet* 362:869-875, Elsevier Inc., Amsterdam, The Netherlands (2003).
Fukukawa, C., et al., "Radioimmunotherapy of human synovial sarcoma using a monoclonal antibody against FZD10," *Cancer Sci.* 99:432-440, Wiley-Blackwell, Hoboken, NJ, U.S.A. (2008).
Gavert, N. et al., "L1, a novel target of β-catenin signaling, transforms cells and is expressed at the invasive front of colon cancers," *Journal of Cell Biology* 168(4):633-642, The Rockefeller University Press (Feb. 14, 2005).
Gazit A. et al., "Human frizzles 1 interacts with transforming Wnts to transducer a TCF dependent transcriptional response," *Ocogene* 18:5959-5966, Stockton Press (1999).
Golan, T., et al., "The Human Frizzled 6 (HFz6) Acts as a Negative Regulator of the Canonical Wnt. β-Catenin Signaling Cascade," *J. Biol. Chem.* 279:14879-14888, American Society for Biochemistry and Molecular Biology (Apr. 2004).
Greenspan, N.S. and Di Cera, E., "Defining epitopes: It's not as easy as it seems," *Nature Biotechnology* 17:936-937, Nature Publishing Group, United States (1999).
Gregorieff, A., et al ., "Expression Pattern of Wnt Signaling Components in the Adult Intestine," *Gastroenterology* 129:626-638, American Gastroenterological Association (Aug. 2005).
Greiner, D.L., et al., "SCID Mouse Models of Human Stem Cell Engraftment," *Stem Cells* 16:166-177, AlphaMed Press (1998).
Guo, H.H., et al., "Protein tolerance to random amino acid change," *PNAS*, 101:9205-9210, the National Academy of Sciences, Washington, DC, U.S.A. (2004).
Harada, N., et al., "Intestinal polyposis in mice with a dominant stable mutation of the β-catenin gene," *EMBO J.* 18:5931-5942, Oxford University Press, New York, NY U.S.A. (1999).
He, X. and Axelrod, J.D., "A WNTer wonderland in Snowbird," *Development* 133:2597-2603, The Company of Biologists, Cambridge, UK, U.S.A. (2006).
Hering H et al., "Direct interaction of Frizzled-1, -2, -4 and -7 with PDZ domains of PSD-95" *FEBS Letters* 521:185-189, Elsevier, Netherlands (2002).
Hicks, et al., "Fringe differentially modulates Jagged1 and Delta1 signalling through Notch1 and Notch2" *Nat Cell Bioi.* (8):515-520 (2000).
Hill, R. P., "Identifying cancer stem cells in solid tumors: case not proven" *Cancer Research* 66:1891-1896, American Association for Cancer Research (2006).
Holcombe, R.F., et al., "Expression of Wnt ligands and Frizzled receptors in colonic mucosa and in colon carcinoma," *J. Clin. Pathol: Mol. Pathol.* 55:220-226, BMJ Publishing Group (2002).
Holmes, E.H., "PSMA specific antibodies and their diagnostic and therapeutic use," *Exp. Opin. Invest. Drugs* 10:511-519, Informa Pharmaceutical Science, London, UK (2001).
Hsieh, A.C. and Moasser, M.M., "Targeting HER proteins in cancer therapy and the role of the non-target HER3," *British J. Cancer* 97:453-457, Cancer Research UK, England (2007).
Hsieh, J-C., et al., "Biochemical characterization of Wnt-Frizzled interactions using a soluble, biologically active vertebrate Wnt protein," *Proc. Natl. Acad. Sci. U.S.A.* 96(7):3546-3551, National Academy of Sciences, United States (Mar. 1999).
Huang, H-C. and Klein, P.S., "The Frizzled family: receptors for multiple signal transduction pathways," *Genuine Biol.* 5:234.1-234.7, BioMed Central Ltd. (Jun. 2004).
Ilyas, M., Wnt signalling and the mechanistic basis of tumour development, *J Pathology* 205:130-144 (2005).
International Search Report for International Patent Application No. PCT/US11/30950, ISA/US, Alexandria, Virginia 22313-1450, mailed on Oct. 18, 2011.
Ishikawa, T., et al., "Mouse Wnt receptor gene Fzd5 is essential for yolk sac and placental angiogenesis," *Development* 128:25-33, Company of Biologists Limited (2001).
Ishitani, T., et al., "The TAK1-NLK Mitogen-Activated Protein Kinase Cascade Functions in the Wnt-5a/$Ca^{2+}$ Pathway to Antagonize Wnt/β-Catenin Signaling," *Mol. Cell. Biol.* 23:131-139, American Society for Microbiology (2003).
Jamieson, C.H.M., et al., "Granulocyte-Macrophage Progenitors as Candidate Leukemic Stem Cells in Blast-Crisis CML," *N. Engl. J. Med.* 351:657-667, Massachusetts Medical Society, Waltham, MA, U.S.A. (2004).
Janssens, N., et al., "Alteration of Frizzled Expression in Renal Cell Carcinoma," *Tumor Biol.* 25:161-171, Karger (Jul. 2004).
Jiang, B., et al., "A Novel Peptide Isolated from a Phage Display Peptide Library with Trastuzumab Can Mimic Antigen Epitope of HER-2," *J. Biol. Chem.* 280:4656-4662, The American Society for Biochemistry and Molecular Biology, Inc., Bethesda, MD, U.S.A. (2005).
Joesting, M.S., et al., "Identification of SFRP1 as a Candidate Mediator of Stromal-to-Epithelial Signaling in Prostate Cancer," *Cancer Res.* 65:10423-10430, the American Association for Cancer Research, Philadelphia, PA, U.S.A. (2005).
Johnson, M.L., et al., "LRP5 and Wnt Signaling: A Union Made for Bone," *J. Bone Mineral Res.* 19:1749-1757, American Society for Bone and Mineral Research, Washington DC, U.S.A. (2004).
Jones, D.T., "Critically assessing the state-of-the-art in protein structure prediction," *Pharmacogenomics Journal* 1:126-134, Nature Publishing Group, New York, NY, U.S.A. (2001).
Jonsson, M., et al., "Involvement of adenomatous polyposis coli (APC)/β-catenin signalling in human breast cancer," *Eur. J. Cancer* 36: 242-248 (2000).
Katoh, M. and Katoh, M., "WNT Signaling Pathway and Stem Cell Signaling Network," *Clin. Cancer Res.* 13:4042-4045, the American Association for Cancer Research, Philadelphia, PA, U.S.A. (2007).
Katoh, M. and Katoh, M., "STAT3-induced WNT5A signaling loop in embryonic stem cells, adult normal tissues, chronic persistent inflammation, rheumatoid arthritis and cancer (Review)," *Int. J. Mol. Med.* 19:273-278, D.A. Spandidos (Feb. 2007).
Katoh, M., "Molecular Cloning and Characterization of MFRP, a Novel Gene Encoding a Membrane-Type Frizzled-Related Protein," *Biochemical and Biophysical Research Communications* 282:116-123, Academic Press, United States (2001).
Kawakami, Y., et al., "Involvement of Frizzled-10 in Wnt-7a signaling during chick limb development," *Dev. Growth Differ.* 42:561-569, Blackwell Publishing (2000).
Kawano, Y. and Kypta, R., "Secreted antagonists of the Wnt signaling pathway," *Journal of Cell Science* 116:2627-2634, The Company of Biologists Ltd, London, UK (2003).
Kirikoshi et al., "Expression of WNT10A in human cancer," *Int J Oncology* 19:997-1001 (2001).
Kirikoshi, H., et al., "Expression profiles of 10 members of Frizzled gene family in human gastric cancer," *Int. J. Oncol.* 19:767-771, D.A. Spandidos (2001).
Kirikoshi, H., et al., "Molecular Cloning and Characterization of Human Frizzled-4 on Chromosome 11q14-q21," *Biochem. Biophys. Res, Commun.* 264:955-961, Academic Press (1999).
Kirikoshi, H., et al., "Up-regulation of Frizzled-7 (FZD7) in human gastric cancer," *Int. J. Oncol.* 19:111-115, D.A. Spandidos (2001).
Kirikoshi, H., et al., "Molecular Cloning and Genomic Structure of Human Frizzled-3 at Chromosome 8p21," *Biochemical and Biophysical Research Communications* 271:8-14, Academic Press, United States (2000).

(56) References Cited

OTHER PUBLICATIONS

Kirkin, A.F., et al., "Melanoma-associated antigens recognized by cytotoxic T lymphocytes," *APMIS* 106:665-679, AMPIS, Denmark (1998).

Klaus, A. and Birchmeier, W., "Wnt signaling and its impact on development and cancer," *Nature Reviews/Cancer* 8:387-398, Nature Publishing Group, New York, NY, U.S.A. (May 2008).

Kobielak, A. and Fuchs, E., "α-Catenin: at the junction of intercelullar adhesion and actin dynamics," *Nat Rev Mol Cell Bioi.* 5:614-25 (2004).

Koike, J., el al., "Molecular Cloning of Frizzled-10, a Novel Member of the Frizzled Gene Family," *Biochem. Biophys. Res. Commun.* 262:39-43, Academic Press (1999).

Korinek, V., et al., "Two Members of the Tcf Family Implicated in Wnt/β-catenin Signaling during Embryogenesis in the Mouse," *Mol Cell Bioi* 18: 1248-1256, American Society for Microbiology, United States (1998).

Kuhnert, F., et al., "Essential requirement for Wnt signaling in proliferation of adult small intestine and colon revealed by adenoviral expression of Dickkopf-1," *PNAS* 101:266-271, the National Academy of Sciences, Washington, DC, U.S.A. (2004).

Lazar, E., et al., "Transforming Growth Factor α: Mutation of Aspartic Acid 47 and Leucine 48 Results in Different Biological Activities," *Mol. Cell. Bio.* 8:1247-1252, American Society for Microbiology, Washington, DC, U.S.A. (1988).

Lee, H.X., et al., "Embryonic Dorsal-Ventral Signaling: Secreted Frizzled-related Proteins as Inhibitors of Tolloid Proteinases," *Cell* 124:147-159, Elsevier Inc., Amsterdam, The Netherlands (Jan. 13, 2006).

Li, Y., et al., "LRP6 expression promotes cancer cell proliferation and tumorigenesis by altering β-catenin subcellular distribution," *Oncogene* 23:9129-9135, Nature Publishing Group, New York, NY, U.S.A. (2004).

Li, Y., et al., "The Gene for Autosomal Dominant Familial Exudative Vitreoretinopathy (Criswick-Schepens) on the Long Arm of Chromosome 11," *Am. J. Opthamol.* 113:712-713, Elsevier Inc., Amsterdam, The Netherlands (1992).

Lin, S.Y., et al., "β-catenin, a novel prognostic marker for breast cancer: its roles in cyclin D1 expression and cancer progression," *Proc. Natl. Acad. Sci. USA* 97:4262-4266, (2000).

Liu, S., et al., "Interaction of hedgehog and notch pathways, and Bmi-1 in the regulation of human breast stem cell self-renewal" *Proc Amer Associ Cancer Res* 46: Apr. 2005.

Li, Y., et al., "Evidence that transgenes encoding components of the Wnt signaling pathway preferentially induce mammary cancers from progenitor cells." Proc. Nail. Acad. Sci. USA, 100:15853-8 (2003).

Lo, P.-K., et al., "Epigenetic Suppression of Secreted Frizzled Related Protein 1 (SFRP1) Expression in Human Breast Cancer," *Cancer Biology & Therapy* 5:e1-e6, Landes Bioscience, Austin, TX, U.S.A. (2006).

Lodygin, D., et al., "Functional Epigenomics Identifies Genes Frequently Silenced in Prostate Cancer," *Cancer Res.* 65:4218-4227, the American Association for Cancer Research, Philadelphia, PA, U.S.A. (2005).

Lu, D., et al., "Repression of β-catenin function in malignant cells by nonsteroidal antiinflammatory drugs," *PNAS* 102:18567-18571, the National Academy of Sciences, Washington, DC, U.S.A. (Dec. 20, 2005).

Lyons, J.P., et al., "Wnt-4 activates the canonical β-catenin-mediated Wnt pathway and binds Frizzled-6 CRD: functional implications of Wnt/β-catenin activity in kidney epithelial cells," *Exp. Cell Res.* 298:369-387, Elsevier Inc., United States (2004).

Mazieres, J., et al., "Wnt signaling in lung cancer," *Cancer Letters* 222:1-10, Elsevier Inc., Amsterdam, The Netherlands (2005).

Miller, J.R., et al., "Mechanism and function of signal transduction by the Wnt/β-catenin and Wnt/$Ca^{2+}$ pathways," *Oncogene* 18:7860-7872, Nature Publishing Group (1999).

Milovanovic, T., et al., "Expression of Wnt genes and frizzled 1 and 2 receptors in normal breast epithelium and infiltrating breast carcinoma," *Int. J. Oncol.* 25:1337-1342, D.A. Spandidos (Nov. 2004).

Moon, R.T., "Wnt/β-Catenin Pathway," *Sci. STKE* 271:1-3, American Association for the Advancement of Science, Washington, DC, 20005 (2005).

Morrell, N.T., et al., "Liposomal Packaging Generates Wnt protein with In Vivo Biological Activity," *PLoS ONE* 3:1-9, e2930, Public Library of Science (PLoS), San Francisco, CA, U.S.A. (Aug. 2008).

Murdoch, B., et al., "Wnt-5A augments repopulating capacity and primitive hemaropoietic development of human blood stem cells in vivo," *PNAS* 100:3422-3427, the National Academy of Sciences, Washington, DC, U.S.A. (2003).

Nagayama, S., et al., "Therapeutic potential of antibodies against FZD10, a cell-surface protein, for synovial sarcomas," *Oncogene* 24:6201-6212, Nature Publishing Group (Sep. 2005).

Nunnally, A.P. and Parr, B.A., "Analysis of Fz10 expression in mouse embryos," *Dev. Genes Evol.* 214:144-148, Springer-Verlag (Mar. 2004).

Nusse, R., et al., A new nomenclature for int-1 and related genes: the Wnt gene family. Cell 64, 231 (1991).

Nusse, R., "The Wnt gene family in tumorigenesis and in normal development," *Journal of Steroid Biochemistry & Molecular Biology* 43: 9-12 (1992).

Olson, D.J. and Gibo, D.M., "Antisense wnt-5a Mimics wnt-1-Mediated C57MG Mammary Epithelial Cell Transformation," *Exp. Cell Res.* 241:134-141, Elsevier Inc., Amsterdam, The Netherlands (1998).

Oshima, H., et al., Morphological and Molecular Processes of Polyp Formation in $Apc^{\Delta 716}$ Knockout Mice, *Cancer Res.* 57:1644-1649, The American Association for Cancer Research, Philadelphia, PA, U.S.A. (1997).

Patel, S., et al., "Glycogen synthase kinase-3 in insulin and Wnt signalling: a double-edged sword?" *Biochemical Society Transactions* 32:803-808, Portland Press Ltd., London, UK (2004).

Pinto, D. and Clevers, H., "Wnt control of stem cells and differentiation in the intestinal epithelium," *Experimental Cell Research* 306:357-363, Elsevier Inc., Amsterdam, The Netherlands (2005).

Polakis, P., "Wnt signaling and cancer," *Genes & Development* 14:1837-1851, Cold Spring Harbor Laboratory Press, Woodbury NY, U.S.A. (2000).

Radtke, F. and Clevers, H., "Self-Renewal and Cancer of the Gut: Two Sides of a Coin," *Science* 307:1904-1909, The Company of Biologists Ltd, London, UK (2005).

Reya, T., et al., "Wnt Signaling Regulates B Lymphocyte Proliferation through a LEF-1 Dependent Mechanism," *Immunity* 13:15-24 (2000).

Reya T., et al., "Stem cells, cancer, and cancer stem cells." *Nature* 414(6859):105-111, Nature Publishing Group, England (2001).

Reya, T. and Clevers, H., "Wnt signalling in stem cells and cancer," *Nature* 434:843-850, Nature Publishing Group, New York, NY, U.S.A. (2005).

Reya, T., et al., "A role for Wnt signalling in self-renewal of haematopoietic stem cells," *Nature* 423:409-414, Nature Publishing Group, New York, NY, U.S.A. (2003).

Rhee, C.S., et al., "Wnt and frizzled receptors as potential targets for immunotherapy in head and neck squamous cell carcinomas," *Oncogene* 21:6598-6605, Nature Publishing Group (2002).

Sagara, N., et al., "Molecular Cloning, Differential Expression, and Chromosomal Localization of Human Frizzled-1, Frizzled-2, and Frizzled-7," *Biochem. Biophys. Res. Commun.* 252:117-122, Academic Press (1998).

Saitoh, T., et al., "Frequent up-regulation of WNT5A mRNA in primary gastric cancer" *Inti J Mol Med* 9:515-519 (2002).

Saitoh, T., et al., "Molecular cloning and characterization of human Frizzled-8 gene on chromosome 10p11.2," *Int. J. Oncol.* 18:991-996, D.A. Spandidos (2001).

Saitoh, T., et al., "Up-regulation of Frizzled-10 (FZD10) by β-estradiol in MCF-7 cells and by retinoic acid in NT2 cells," *Int. J. Oncol.* 20:117-120, D.A. Spandidos (2002).

Sala, C.F., et al., "Identification, Gene Structure, and Expression of Human Frizzled-3 (FZD3)," *Biochem. Biophys. Res. Commun.* 273:27-34, Academic Press (2000).

(56) References Cited

OTHER PUBLICATIONS

Saldanha, J., et al., "Identification of a Frizzled-like cysteine rich domain in the extracellular region of developmental receptor tyrosine kinases," *Protein Science* 7:1632-1635, The Protein Society, United States (1998).

Saneyoshi, T., el al., "The Wnt/calcium pathway activates NF-AT and promotes ventral cell fate in Xenopus embryos," *Nature* 417:295-299, Nature Publishing Group, New York, NY, U.S.A. (2002).

Sagara, N., et al., "FZD4S, a Splicing Variant of Frizzled-4, Encodes a Soluble-Type Positive Regulator of the WNT Signaling Pathway," *Biochem. Biophys. Res. Commun.* 282:750-756, Academic Press, United States (2001).

Schweizer, L. and Varmus, H., "Wnt/Wingless signaling through β-catenin requires the function of both LRP/Arrow and frizzled classes of receptors," *BMC Cell Biology* 4, 11 pages, BioMed Central Ltd., London, UK (2003).

Semënov, M., et al., "SOST is a Ligand for LRP5/LRP6 and a Wnt Signaling Inhibitor," *The Journal of Biological Chemistry* 280:26770-26775, American Society for Biochemistry and Molecular Biology, Bethesda, MD, U.S.A. (2005).

Sen, M., et al., "Blockade of Wnt-5A/Frizzled 5 Signaling Inhibits Rheumatoid Synoviocyte Activation," *Arthritis Rheum.* 44:772-781, Wiley-Liss, Inc. (2001).

Shalaby, M.R., et al., "Bispecific HER X CD3 Antibodies Enhance T-Cell Cytotoxicity in Vitro and Localize to HER2-Overexpressing Xenografts in Nude Mice," *Clin. Imm. and Immunopath*, 74:185-192, Elsevier Inc., Amsterdam, The Netherlands 1995.

Skolnick, J. and Fetrow, J.S., "From genes to protein structure and function: novel applications of computational approaches in the genomic era," *Trends in Biotechnology* 18:34-39, Elsevier Inc., Amsterdam, The Netherlands (2000).

Sperger, J.M., et al., "Gene expression patterns in human embryonic stem cells and human pluripotent germ cell tumors," *PNAS* 23:13350-13355, The National Academy of Sciences of the USA, United States (2003).

Suresh M.R., et al., "Advantages of bispecific hybridomas in one-step immunocytochemistry and immunoassays," *Neurobiology, Proceedings of the National Academy of Sciences of the United States of America*, Oct. 1986, pp. 7989-7993, vol. 83, USA.

Suzuki, H., et al., "A genomic screen for genes unregulated by demethylation and histone deacetylase inhibition in human colorectal cancer," *Nature Genetics* 31:141-149, Nature Publishing Group, New York, NY, U.S.A. (Jun. 2002).

Suzuki, H., et al., "Epigenetic inactivation of SFRP genes allows constitutive WNT signaling in colorectal cancer," *Nature Genetics* 36:417-422, Nature Publishing Group, New York, NY, U.S.A. (Apr. 2004).

Suzuki, H., et al., "Frequent epigenetic inactivation of Wnt antagonist genes in breast cancer," *British Journal of Cancer* 98:1147-1156, Nature Publishing Group, New York, NY, U.S.A. (2008).

Tanaka, S., et al., "A novel frizzled gene identified in human esophageal carcinoma mediates APC/β-catenin signals," *Proc. Natl. Acad. Sci. U.S.A.* 95:10164-10169, National Academy of Sciences (1998).

Terasaki, H., et al., "Frizzled-10, up-regulated in primary colorectal cancer, is a positive regulator of the WNT-β-catenin-TCF signaling pathway," *Int. J. Mol. Med.* 9:107-112, D.A. Spandidos (2002).

Tokuhara, M., et al., "Molecular Cloning of Human Frizzled-6," *Biochem. Biophys. Res. Commun.* 243:622-627, Academic Press (1998).

Topol, L., et al., "Wnt-5a inhibits the canonical Wnt pathway by promoting GSK-3-independent β-catenin degradation," *J. Cell Biol.* 162:899-908, The Rockefeller University Press, New York, NY, U.S.A. (2003).

Tosatto, S.C.E. and Toppo, S., Large-Scale Prediction of Protein Structure and Function from Sequence, *Current Pharmaceutical Design* 12:2067-2086, Bentham Science Publishers, Oak Park, IL, U.S.A. (2006).

Townsend, A. and Trowsdale, J., "The transporters associates with antigen presentation" *Seminars in Cell Biology* 4:53-61, Academic Press Limited, United States (1993).

Toyofuku, T., et al., "Wnt/frizzled-2 Signaling Induces Aggregation and Adhesion among Cardiac Myocytes by Increased Cadherin-β-Catenin Complex," *J. Cell. Biol.* 150:225-241, Rockefeller University Press (2000).

Bourhis, E., et al., "Reconstitution of a Frizzled8.Wnt3a.LRP6 Signaling Complex Reveals Multiple Wnt andDkk1 Binding Sites on LRP6," *J. Biol. Chem.* 285(12):9172-9179, American Society for Biochemistry and Molecular Biology, United States (2010).

Umbhauer, M., et al., "The C-terminal cytoplasmic Lys-thr-X-X-X-Trp motif in frizzled receptors mediates Wnt/β-catenin signalling," *The EMBO Journal* 19:4944-4954, Oxford University Press, New York, NY, U.S.A. (2000).

Unkeless, J.C., "Characterization of a Monoclonal Antibody Directed Against Mouse Macrophage and Lymphocyte Fc Receptors," *J. Exp. Med.* 150:580-596, The Rockefeller University Press, New York, NY, U.S.A. (Sep. 1979).

Unknown Author, "Purified Rat Anti-Mouse CD16/CD32 (Mouse BD Fc BlockTM)," Technical Data Sheet 553142 Rev. 16, 2 pages, BD Biosciences (date unknown), URL:http://www.bdbiosciences.com/external_files/pm/doc/tds/mouse/live/web_enabled/01241D_553142.pdf.

Üren, A., et al., "Secreted Frizzled-related Protein-1 Binds Directly to Wingless and is a Biphasic Modulator of Wnt Signaling," *The Journal of Biological Chemistry* 275:4374-4382, American Society for Biochemistry and Molecular Biology, Bethesda, MD, U.S.A. (2000).

Uyttendaele, H., et al., "Notch4 and Wnt-1 Proteins Function to Regulate Branching Morphogeneses of Mammary Epithelial Cells in an Opposing Fashion" *Dev. Bioi.* 196:204-217, Elsevier Inc., The Netherlands (1998).

Van De Vijver, M., et al., "A gene-expression signature as a predictor of survival in breast cancer" *N Eng. J Med* 347:1999-2009 (2002).

Van De Wetering, M., et al., "The β-catenin/TCF-4 complex imposes a crypt progenitor phenotype on colorectal cancer cells," *Cell* 111:241-259, Cell Press, United States (2002).

Van Den Berg, D.J., et al., "Role of Members of the Wnt Gene Family in Human Hematopoiesis," *Blood* 92:3189-3202, The American Society of Hematology, Washington, DC, U.S.A. (1998).

Van Es, J.H. and Clevers, H., "Notch and Wnt inhibitors as potential new drugs for intestinal neoplastic disease," *Trends Mol. Med.* 11:496-502, Elsevier Inc., The Netherlands (2005).

Van't Veer, L.J., et al., "Gene expression profiling predicts clinical outcome of breast cancer" *Nature* 415:530-6 (2002).

Veeman, M.T., et al., "A Second Canon: Functions and Mechanisms of β-Catenin-Independent Wnt Signaling," *Dev. Cell* 5:367-377, Elsevier Inc., Amsterdam, The Netherlands (2003).

Vincan, E., et al., "Frizzled-7 receptor ectodomain expression in a colon cancer cell line induces morphological change and attenuates tumor growth," *Differentiation* 73:142-153, Blackwell (Apr. 2005).

Voronkov, A., et al., "Molecular Model of the Wnt Protein Binding Site on the Surface of Dimeric CRD Domain of the hFzd8 Receptor," *Doklady Biochemistry and Biophysics* 419:75-78, Pleiades Publishing Ltd., Russia (2008).

Wang, Y., et al., "A Large Family of Putative Transmembrane Receptors Homologous to the Product of the *Drosophila* Tissue Polarity Gene frizzled," *J. Biol. Chem.* 271:4468-4476, American Society for Biochemistry and Molecular Biology (1996).

Wang, Y-K., et al., "Characterization and Expression Pattern of the frizzled Gene Fzd9, the Mouse Homolog of FZD9 which Is Deleted in Williams-Beuren Syndrome," *Genomics* 57:235-248, Academic Press (1999).

Wang, Z., et al., "Wnt7b Activates Canonical Signaling in Epithelial and Vascular Smooth Muscle Cells through Interactions with Fzd1, Fzd10, and LRP5," *Mol. Cell. Biol.* 25:5022-5030, American Society for Microbiology (2005).

Webb, T., "Work on Breast Cancer Stem Cells Raises Questions About Treatment Strategies," *Journal of the National Cancer Institute.* 95(11): 774-775, Jun. 4, 2003, printed online, pp. 1-5.

(56) References Cited

OTHER PUBLICATIONS

Weeraratna, A.T., et al., "Wnt5a signaling directly affects cell motility and invasion of metastatic melanoma," *Cancer Cell* 1:279-288, Cell Press (2002).
Willert, K. and Jones, K.A., "Wnt signaling: is the party in the nucleus?" *Genes & Development* 20:1394-1404, Cold Spring Harbor Laboratory Press, Cold Spring Harbor, NY, U.S.A. (2006).
Willert, K., et al., "Wnt proteins are lipid-modified and can act as stem cell growth factors," *Nature* 423:448-452, Nature Publishing Group, New York, NY, U.S.A. (2003).
Wnt-3a COPE, (Online 2010), accessed on Oct. 1, 2010, accessed from http://www.copewithcytokines.de/cope.cgi?key=Wnt-3a.paras 2 and 5.
Wong, N.A.C.S. and Pignatelli, M., "β-catenin—A Linchpin in Colorectal Carcinogenesis?," *Am. J. Pathol.* 160:389-401, American Society for Investigative Pathology (2002).
Wong, S.C.C., et al., "Expression of frizzled-related protein and Wnt-signalling molecules in invasive human breast tumours," *J. Pathol.* 196:145-253 (2002).
Woodward, W.A., et al., "Wnt/β-catenin mediates radiation resistance of mouse mammary progenitor cells," *PNAS* 104:618-623, the National Academy of Sciences, Washington, DC, U.S.A. (2007).
Wu, C-H. and Nusse, R., "Ligand Receptor Interactions in the Wnt Signaling Pathway in *Drosophila*," *J. Biol. Chem.* 277:41762-41769, American Society for Biochemistry and Molecular Biology (2002).
Yamashita, J.K., et al., Prospective identification of cardiac progenitors by a novel single cell-based cardiomyocyte induction, *The FASEB Journal*, 29 pages (Published online Jul. 20, 2005).
Yang, P., et al., "Study design considerations in clinical outcome research of lung cancer using microarray analysis" 2004 Lung Cancer 46:215-226.
Yang-Snyder, J., et al., "A frizzled homolog functions in a vertebrate Wnt signaling pathway," *Curr. Biol.* 6:1302-1306, Cell Press (1996).
Zeng, X., et al., "A dual-kinase mechanism for Wnt co-receptor phosphorylation and activation," *Nature* 438:873-877 (Dec. 8, 2005).
Zhao, Z., et al.,"A Human Homologue of the *Drosophila* Polarity Gene frizzled Has Been Identified and Mapped to 17q21.1," *Genomics* 27:370-373, Academic Press (1995).
Zhu, A.J.Z., et al., "β-Catenin signaling modulates proliferative potential of human epidermal keratinocytes independently of intracellular adhesion," *Development* 126: 2285-2298, The Company of Biologists Limited, Great Britin (1999).
English language Abstract of German Patent Publication No. WO 02/00576 A1, European Patent Office, espacenet database (2002).
Lepourcelet, M., et al., "Small-molecule antagonists of the oncogenic Tcf/β-catenin protein complex," *Cancer Cell* 5:91-102, Cell Press, U.S.A. (2004).
International Search Report for International Application No. PCT/US09/58635, ISA/US, Alexandria, VA, mailed on Nov. 19, 2010.
Written Opinion for International Application No. PCT/US09/58635, ISA/US, Alexandria, VA, mailed on Nov. 19, 2010.
Lu, C., et al., "The Binding Sites for Competitive Antagonistic, Allosteric Antagonistic, and Agonistic Antibodies to the I Domain of Integrin LFA-1," *J. Immunol.* 173:3972-3978, American Society of Immunologists, Inc., United States (2004).
Wood, V., et al., "The genome sequence of *Schizosaccharomyces pombe*," *Nature* 415:871-880, Nature Publishing Group, United Kingdom (2002).
Decypher ClustalW Multiple Alignment, Stanford University (online, Sep. 2006), accessed on Sep. 30, 2010, accessed from http://web.archive.org/web/20060912071608/http://www2.stanford.edu/~rnusse/genealigns/mhfzalign.html>.
Polakis, P., "Evidence for Wnt Signaling in Cancers lacking Genetic Defects," PowerPoint NYAS Presentation and transcript, presented on Oct. 25, 2005, 71 pages.
International Search Report of the International Searching Authority for International Application No. PCT/US07/005443, mailed on Oct. 30, 2008, United States Patent and Trademark Office, United States, 4 pages.

Written Opinion for the International Searching Authority for International Application No. PC/US07/05443, mailed on Oct. 30, 2008, The International Bureau of WIPO, Switzerland, 4 pages.
Guyre, P.M., et al., "Increased potency of Fc-receptor-targeted antigens," *Cancer Immunol. Immunother.* 45:146-148, 1997.
Fredriksson, R., et al., "The G-Protein-Coupled Receptors in the Human Genome Form Five Main Families. Phylogenetic Analysis, Paralogon Groups, and Fingerprints" *Mol. Pharmacol.* 63:1256-1272, The American Society for Pharmacology and Experimental Therapeutics, United States (2003).
De Gruijl, T. and Curiel, D.T., "Cancer vaccine strategies get bigger and better," *Nat. Med.* 5(10):1124-1125, Nature Publishing Company, United States (1999).
Vajdos, F.F., et al., "Comprehensive functional maps of the antigen binding site of an anti-ErbB2 antibody obtained with shotgun scanning mutagenesis," *J. Mol. Biol.* 320:415-428, Elsevier, England (2002).
Lee, K-H., et al., "Increased vaccine specific T cell frequency after peptide based vaccination correlates with increased susceptibility to in vitro stimulation but does not lead to tumor regression," *J. Immunol.* 163(11):6292-300, Williams & Wilkins, United States (1999).
Bodey, B., et al., "Failure of cancer vaccines: the significant limitations of this approach to immunotherapy," *Anticancer Res.* 20(4):2665-2676, International Institute of Anticancer Research, Greece (2000).
MacCallum, R.M., et al., "Antibody antigen interactions: contact analysis and binding site topography," *J. Mol. Biol.* 262(5):732-745, Elsevier, England (1996).
Casset, F., et al., "A peptide mimetic of an anti-CD4 monoclonal antibody by rational design," *Biochem. Biophys. Res. Comm.* 37:198-205, Academic Press, United States (2003).
Holm, P., et al., "Functional mapping and single chain construction of the anti-cytokeratin 8 monoclonal antibody TS1," *Mol. Immunol.* 44:1075-1084, Pergamon Press, England (2007).
Donnelly, J., "Cancer vaccine targets leukemia," *Nat. Med.* 9(11):1354-6, Nature Publishing Company, United States (2003).
Wu, H., et al., "Humanization of a murine monoclonal antibody by simultaneous optimization of framework and CDR residues," *J. Mol. Biol.* 294:151-162, Elsevier, England (1999).
Ezzel, C., "Cancer 'Vaccines': An Idea Whose Time Has Come?" *Journal of NIH Research* 7:46-49, National Institutes of Health, United States (1995).
Forni, G., et al., "Immunoprevention of Cancer: Is the Time Ripe?" *Cancer Res* 60(10):2571-2575, American Association for Cancer Research, United States (2000).
Chatterjee, M.B., et al., "Idiotypic antibody immunotherapy of cancer," *Cancer Immunol. Immunother.* 38(2):75-82, Springer International, Germany (1994).
Rudikoff, S., et al., "Single amino acid substitution altering antigen binding specificity," *Proc. Natl. Acad. Sci.* 79(6):1979-83, National Academy of Sciences, United States (1982).
International Search Report of the International Searching Authority for International Application No. PCT/US11/20994, mailed on Aug. 15, 2011, United States Patent and Trademark Office, United States, 4 pages.
Written Opinion for the International Searching Authority for International Application No. PCT/US11/20994, mailed on Aug. 15, 2011, International Searching Authority, United States, 6 pages.
Unknown Author, "Biotinylated Anti-mouse Fzd-2 Antibody," 1 page, R&D Systems, dated Feb. 11, 2004, URL:http://www.rndsystems.com/pdf/baf1307.pdf, downloaded Sep. 27, 2012.
Schulte, G. and Bryja, V., "The Frizzled family of unconventional G-protein-coupled receptors," *Trends Pharmacol Sci.* 28(10):518-25, Elsevier in Association With The International Union of Pharmacology, England (2007).
Aruffo, A., et al., "CD44 is the principal cell surface receptor for hyaluronate," *Cell* 61(7):1303-13, Cell Press, United States (1990).
"Frizzled 8 precursor (Frizled 8) (Fz-8) (hFz8)." [online], Sep. 2005, Accession Q9H461, Retrieved on Feb. 1, 2013 from http://www.ncbi.nlm.nih.gov/protein/17433053?sat=34&satkey=5096022.

(56) References Cited

OTHER PUBLICATIONS

"Frizzled 4 precursor (Frizled-4) (Fz-4) (hFz4) (FzE4)." [online], Sep. 2005, Accession Q9ULV1, Retrieved on Feb. 1, 2013 from http://www.ncbi.nlm.nih.gov/protein/62298045?sat=34&satkey=861841.

MacLeod, R.J., et al., "Wnt5a secretion stimulated by extracellular calcium-sensing receptor inhibits defective Wnt signaling in colon cancer cells," *Am. J. Physiol. Gastrointest. Liver. Physiol.* 293(1):G403-G411, American Physiological Society, United States (2007).

Khan, N.I., et al., "Activation of Wnt/beta-catenin pathway mediates growth and survival in B-cell progenitor acute lymphoblastic leukaemia," *Br. J. Haematol.* 138(3):338-348, Wiley-Blackwell, England (2007).

You, L., et al., "Wnt-1 signal as a potential cancer therapeutic target," *Drug News Perspect.* 19(1):27-31, Thomson Reuters, United States (2006).

Katoh, Y. and Katoh, M., "Comparative genomics on Fzd8 orthologs," *Oncol. Rep.* 13(15):993-997, D.A. Spandidos, Greece (2005).

Merle, P., et al., "Functional consequences of frizzled-7 receptor overexpression in human hepatocellular carcinoma," *Gastroenterology* 127(4):1110-1122, W.B. Saunders, United States (2004).

Gurney, A., et al., "Wnt pathway inhibition via the targeting of Frizzled receptors results in decreased growth and tumorigenicity of human tumors," *Proc. Natl. Acad. Sci. USA* 109(29): 11717-22, National Academy of Sciences, United States (2012).

Luu, H.H., et al., "Wnt/β-Catenin Signaling Pathway as Novel Cancer Drug Targets," *Curr. Cancer Drug Targets* 4:653-671, Bentham Science Publishers, Netherlands (2004).

Ueno, K., et al., "Frizzled homolog proteins, microRNAs and Wnt Signaling in cancer," *Int. J. Cancer* 132:1731-1740, Wiley-Liss, United States (2013).

Accession No. UNITPROT: A6CA06, EBI database (Jul. 24, 2007).

Accession No. GSP: AVA85292, EBI database (Apr. 2, 2009).

Accession No. GSP: ARJ99386, EBI database (May 15, 2008).

International Search Report of the International Searching Authority for International Application No. PCT/US13/66087 mailed on Jan. 16, 2014, United States Patent and Trademark Office, United States, 4 pages.

Written Opinion for the International Searching Authority for International Application No. PCT/US13/66087 mailed on Jan. 16, 2014 The International Bureau of WIPO, Switzerland, 4 pages.

International Search Report for International Application No. PCT/US2014/014443, United States Patent and Trademark Office, United States, mailed on Apr. 15, 2014.

Gaudio, A., et al., "Increased Sclerostin Serum Levels Associated with Bone Formation and Resorption Markers in Patients with Immobilization-Induced Bone Loss," *J Clin Endcrinol Metab* 95(5):2248-2253, The Endocrine Society, United States (2010).

Wheater, G., et al., "The clinical utility of bone marker measurements in osteoporosis," *Journal of Translational Medicine* 11(201): 11 pages, BioMed Central Ltd. (2013).

\* cited by examiner

METHODS AND MONITORING OF TREATMENT WITH A WNT PATHWAY INHIBITOR

CROSS-REFERENCE TO RELATED APPLICATIONS

This application claims priority benefit of U.S. Provisional Application No. 61/760,523, filed Feb. 4, 2013, which is hereby incorporated by reference herein in its entirety.

FIELD OF INVENTION

The present invention relates to the field of treating diseases with a Wnt pathway inhibitor. More particularly, the invention provides methods for treating cancer comprising administering a Wnt pathway inhibitor, either alone or in combination with other anti-cancer agents, and monitoring for side effects and/or toxicity.

REFERENCE TO SEQUENCE LISTING SUBMITTED ELECTRONICALLY VIA EFS-WEB

The content of the electronically submitted sequence listing (Name: 2293_1060001.ascii.txt; Size: 101 kilobytes; and Date of Creation: Jan. 30, 2014) is herein incorporated by reference in its entirety.

BACKGROUND OF THE INVENTION

Cancer is one of the leading causes of death in the developed world, with over one million people diagnosed with cancer and 500,000 deaths per year in the United States alone. Overall it is estimated that more than 1 in 3 people will develop some form of cancer during their lifetime. There are more than 200 different types of cancer, four of which—breast, lung, colorectal, and prostate—account for almost half of all new cases (Siegel et al., 2011, *CA: A Cancer J. Clin.* 61:212-236).

Signaling pathways normally connect extracellular signals to the nucleus leading to expression of genes that directly or indirectly control cell growth, differentiation, survival, and death. In a wide variety of cancers, signaling pathways are dysregulated and may be linked to tumor initiation and/or progression. Signaling pathways implicated in human oncogenesis include, but are not limited to, the Wnt pathway, the Ras-Raf-MEK-ERK or MAPK pathway, the PI3K-AKT pathway, the CDKN2A/CDK4 pathway, the Bcl-2/TP53 pathway, and the Notch pathway.

The Wnt signaling pathway has been identified as a potential target for cancer therapy. The Wnt signaling pathway is one of several critical regulators of embryonic pattern formation, post-embryonic tissue maintenance, and stem cell biology. More specifically, Wnt signaling plays an important role in the generation of cell polarity and cell fate specification including self-renewal by stem cell populations. Unregulated activation of the Wnt pathway is associated with numerous human cancers where it is believed the activation can alter the developmental fate of cells. The activation of the Wnt pathway may maintain tumor cells in an undifferentiated state and/or lead to uncontrolled proliferation. Thus carcinogenesis can proceed by overtaking homeostatic mechanisms which control normal development and tissue repair (reviewed in Reya & Clevers, 2005, *Nature,* 434:843-50; Beachy et al., 2004, *Nature,* 432:324-31).

The Wnt signaling pathway was first elucidated in the *Drosophila* developmental mutant wingless (wg) and from the murine proto-oncogene int-1, now Wnt1 (Nusse & Varmus, 1982, *Cell,* 31:99-109; Van Ooyen & Nusse, 1984, *Cell,* 39:233-40; Cabrera et al., 1987, *Cell,* 50:659-63; Rijsewijk et al., 1987, *Cell,* 50:649-57). Wnt genes encode secreted lipid-modified glycoproteins of which 19 have been identified in mammals. These secreted ligands activate a receptor complex consisting of a Frizzled (FZD) receptor family member and low-density lipoprotein (LDL) receptor-related protein 5 or 6 (LRP5/6). The FZD receptors are seven transmembrane domain proteins of the G-protein coupled receptor (GPCR) superfamily and contain a large extracellular N-terminal ligand binding domain with 10 conserved cysteines, known as a cysteine-rich domain (CRD) or Fri domain. There are ten human FZD receptors, FZD1, FZD2, FZD3, FZD4, FZD5, FZD6, FZD7, FZD8, FZD9, and FZD10. Different FZD CRDs have different binding affinities for specific Wnt proteins (Wu & Nusse, 2002, *J. Biol. Chem.,* 277:41762-9), and FZD receptors have been grouped into those that activate the canonical β-catenin pathway and those that activate non-canonical pathways (Miller et al., 1999, *Oncogene,* 18:7860-72).

A role for Wnt signaling in cancer was first uncovered with the identification of Wnt1 (originally int1) as an oncogene in mammary tumors transformed by the nearby insertion of a murine virus (Nusse & Varmus, 1982, *Cell,* 31:99-109). Additional evidence for the role of Wnt signaling in breast cancer has since accumulated. For instance, transgenic over-expression of β-catenin in the mammary glands results in hyperplasias and adenocarcinomas (Imbert et al., 2001, *J. Cell Biol.,* 153:555-68; Michaelson & Leder, 2001, *Oncogene,* 20:5093-9) whereas loss of Wnt signaling disrupts normal mammary gland development (Tepera et al., 2003, *J. Cell Sci.,* 116: 1137-49; Hatsell et al., 2003, *J. Mammary Gland Biol. Neoplasia,* 8:145-58). In human breast cancer, β-catenin accumulation implicates activated Wnt signaling in over 50% of carcinomas, and though specific mutations have not been identified, up-regulation of Frizzled receptor expression has been observed (Brennan & Brown, 2004, *J. Mammary Gland Biol. Neoplasia,* 9:119-31; Malovanovic et al., 2004, *Int. J. Oncol.,* 25:1337-42).0

Activation of the Wnt pathway is also associated with colorectal cancer. Approximately 5-10% of all colorectal cancers are hereditary with one of the main forms being familial adenomatous polyposis (FAP), an autosomal dominant disease in which about 80% of affected individuals contain a germline mutation in the adenomatous polyposis coli (APC) gene. Mutations have also been identified in other Wnt pathway components including Axin and β-catenin. Individual adenomas are clonal outgrowths of epithelial cells containing a second inactivated allele, and the large number of FAP adenomas inevitably results in the development of adenocarcinomas through additional mutations in oncogenes and/or tumor suppressor genes. Furthermore, activation of the Wnt signaling pathway, including loss-of-function mutations in APC and stabilizing mutations in β-catenin, can induce hyperplastic development and tumor growth in mouse models (Oshima et al., 1997, *Cancer Res.,* 57:1644-9; Harada et al., 1999, *EMBO J.,* 18:5931-42).

Similar to breast cancer and colon cancer, melanoma often has constitutive activation of the Wnt pathway, as indicated by the nuclear accumulation of β-catenin. Activation of the Wnt/β-catenin pathway in some melanoma tumors and cell lines is due to modifications in pathway components, such as APC, ICAT, LEF1 and β-catenin (see e.g., Lame et al., 2006, *Frontiers Biosci.,* 11:733-742). However, there are conflicting reports in the literature as to the exact role of Wnt/β-catenin signaling in melanoma. For example, one study found that elevated levels of nuclear β-catenin correlated with improved survival from melanoma, and that activated Wnt/β-catenin signaling was associated with decreased cell proliferation (Chien et al., 2009, *PNAS*, 106:1193-1198).

Chemotherapy is a well-established therapeutic approach for numerous cancers, but its efficacy can be limited by side effects and/or toxicity. In addition, targeted therapies such as the anti-ErbB2 receptor (HER2) antibody trastuzumab (HERCEPTIN), tyrosine kinase inhibitors imatinib (GLEEVEC), dasatinib (SPRYCEL), nilotibib (TASIGNA), sunitinib (SUTENT), sorafenib (NEXAVAR), the anti-VEGF antibody bevacizumab (AVASTIN), and anti-angiogenesis drugs sunitinib (SUTENT) and sorafenib (NEXAVAR), are known to cause, or are likely to cause, side effects and/or toxicity in subjects who take them. Thus, new methods to identify drug-induced side effects, monitor those side effects, and/or mitigate those side effects so that effective cancer therapy can continue are still needed.

BRIEF SUMMARY OF THE INVENTION

The present invention provides improved methods for treating diseases comprising administering to a subject a therapeutically effective amount of a Wnt pathway inhibitor. For example, in one aspect the invention provides methods of screening for, detecting, identifying, monitoring, reducing, preventing, attenuating, and/or mitigating a skeletal-related side effect and/or toxicity related to treatment with a Wnt pathway inhibitor. In some embodiments, the methods comprise determining the level of a bone turnover marker in a sample from a patient who has received, is receiving, will receive, or is being considered for initial or further treatment with a Wnt pathway inhibitor, including but not limited to an anti-Frizzled (FZD) antibody or a soluble FZD receptor.

In another aspect, the invention provides methods of identifying a subject as eligible for treatment with a Wnt pathway inhibitor, comprising: obtaining a biological sample from the subject, determining the level of a biomarker in the sample, and identifying the subject as eligible for treatment with the Wnt pathway inhibitor if the level of the biomarker is below a predetermined level. In some embodiments, the biomarker is a bone turnover marker. In some embodiments, the biomarker is a bone resorption biomarker. In some embodiments, the method of identifying a subject as eligible for treatment with a Wnt pathway inhibitor, comprises: obtaining a biological sample from the subject, determining the level of a bone resorption biomarker in the sample, and identifying the subject as eligible for treatment with the Wnt pathway inhibitor if the level of the bone resorption biomarker is below a predetermined level. In some embodiments, the bone resorption biomarker is collagen type 1 cross-linked C-telopeptide (β-CTX).

In one aspect, the invention provides methods of monitoring a subject receiving treatment with a Wnt pathway inhibitor for the development of skeletal-related side effects and/or toxicity, comprising: obtaining a biological sample from the subject receiving treatment, determining the level of a biomarker in the sample, and comparing the level of the biomarker in the sample to a predetermined level of the biomarker, wherein an increase in the level of the biomarker indicates development of skeletal-related side effects and/or toxicity. In some embodiments, the biomarker is a bone turnover marker. In some embodiments, the biomarker is a bone resorption biomarker. In some embodiments, the method of monitoring a subject receiving treatment with a Wnt pathway inhibitor for the development of skeletal-related side effects and/or toxicity, comprises: obtaining a biological sample from the subject receiving treatment, determining the level of a bone resorption biomarker in the sample, and comparing the level of the bone resorption biomarker in the sample to a predetermined level of the bone resorption biomarker, wherein an increase in the level of the bone resorption biomarker indicates development of skeletal-related side effects and/or toxicity. In some embodiments, the bone resorption biomarker is β-CTX.

In another aspect, the invention provides methods of detecting the development of skeletal-related side effects and/or toxicity in a subject receiving treatment with a Wnt pathway inhibitor, comprising: obtaining a biological sample from the subject receiving treatment, determining the level of a biomarker in the sample, and comparing the level of the biomarker in the sample to a predetermined level of the biomarker, wherein an increase in the level of the biomarker indicates development of skeletal-related side effects and/or toxicity. In some embodiments, the biomarker is a bone turnover marker. In some embodiments, the biomarker is a bone resorption biomarker. In some embodiments, the method of detecting the development of a skeletal-related side effect and/or toxicity in a subject receiving treatment with a Wnt pathway inhibitor, comprises: obtaining a biological sample from the subject receiving treatment, determining the level of a bone resorption biomarker in the sample, and comparing the level of the bone resorption biomarker in the sample to a predetermined level of the bone resorption biomarker, wherein an increase in the level of the bone resorption biomarker indicates development of a skeletal-related side effect and/or toxicity. In some embodiments, the bone resorption biomarker is β-CTX.

In another aspect, the invention provides methods for identifying skeletal-related side effects and/or toxicity in a subject receiving treatment with a Wnt pathway inhibitor, comprising: obtaining a biological sample from the subject receiving treatment, determining the level of a biomarker in the sample, and comparing the level of the biomarker in the sample to a predetermined level of the biomarker, wherein if the level of the biomarker in the sample is higher than the predetermined level of the biomarker then a skeletal-related side effect and/or toxicity is indicated. In some embodiments, the biomarker is a bone turnover marker. In some embodiments, the biomarker is a bone resorption biomarker. In some embodiments, the method for identifying skeletal-related side effects and/or toxicity in a subject receiving treatment with a Wnt pathway inhibitor, comprises: obtaining a biological sample from the subject receiving treatment, determining the level of a bone resorption biomarker in the sample, and comparing the level of the bone resorption biomarker in the sample to a predetermined level of the bone resorption biomarker, wherein if the level of the bone resorption biomarker in the sample is higher than the predetermined level of the bone resorption biomarker then a skeletal-related side effect and/or toxicity is indicated. In some embodiments, the bone resorption biomarker is β-CTX.

In another aspect, the invention provides methods for monitoring skeletal-related side effects and/or toxicity in a subject receiving treatment with a Wnt pathway inhibitor, comprising: obtaining a biological sample from the subject receiving treatment, determining the level of a biomarker in the sample, and comparing the level of the biomarker in the sample to a predetermined level of the biomarker, wherein if the level of the biomarker in the sample is higher than the predetermined level of the biomarker then a skeletal-related side effect and/or toxicity is indicated. In some embodiments, the biomarker is a bone turnover marker. In some embodiments, the biomarker is a bone resorption biomarker. In some embodiments, the method for monitoring skeletal-related side effects and/or toxicity in a subject receiving treatment with a Wnt pathway inhibitor, comprises: obtaining a biological sample from the subject receiving treatment, determining the level of a bone resorption biomarker in the sample, and comparing the level of the bone resorption biomarker in the sample to a predetermined level of the bone resorption biomarker, wherein if the level of the bone resorption biomarker in the sample is higher than the predetermined level of the bone resorption biomarker then a skeletal-related side effect and/or toxicity is indicated. In some embodiments, the bone resorption biomarker is β-CTX.

In some aspects and/or embodiments of the methods described herein, wherein if the bone resorption biomarker level (e.g., β-CTX) in a sample increases 2-fold or greater as compared to a predetermined level, the subject is administered a therapeutically effective amount of an anti-resorptive medication. In some embodiments, the bone resorption biomarker is β-CTX and the predetermined level is less than about 1000 pg/ml. In some embodiments, the anti-resorptive medication is a bisphosphonate.

In another aspect, the invention provides methods of reducing skeletal-related side effects and/or toxicity in a subject receiving treatment with a Wnt pathway inhibitor, comprising: obtaining a biological sample from the subject receiving treatment, determining the level of a bone resorptive biomarker in the sample, comparing the level of the bone resorptive biomarker in the sample to a predetermined level of the bone resorptive biomarker, and administering to the subject a therapeutically effective amount of an anti-resorptive medication if the level of the bone resorptive biomarker in the sample is higher than the predetermined level of the bone resorptive biomarker. In some embodiments, the increase in the resorptive biomarker is about 1.5-fold or greater, about 2-fold or greater, about 2.5-fold or greater, or about 3-fold or greater than the predetermined level of the bone resorptive biomarker. In some embodiments, the bone resorption biomarker is β-CTX. In some embodiments, the anti-resorptive medication is a bisphosphonate.

In another aspect, the invention provides methods of preventing or attenuating the development of skeletal-related side effects and/or toxicity in a subject receiving treatment with a Wnt pathway inhibitor, comprising: obtaining a biological sample from the subject prior to treatment with the Wnt pathway inhibitor, determining the level of a bone resorptive biomarker in the sample, comparing the level of the bone resorptive biomarker in the sample to a predetermined level of the bone resorptive biomarker, administering to the subject a therapeutically effective amount of an anti-resorptive medication, and administering to the subject the Wnt pathway inhibitor. In some embodiments, the bone resorption biomarker is β-CTX. In some embodiments, the anti-resorptive medication is a bisphosphonate.

In another aspect, the invention provides methods of ameliorating skeletal-related side effects and/or toxicity in a subject administered a Wnt pathway inhibitor, comprising: determining the level of a bone resorptive biomarker in a sample, and administering to the subject a therapeutically effective amount of an anti-resorptive medication. In some embodiments, the bone resorption biomarker is β-CTX. In some embodiments, the anti-resorptive medication is a bisphosphonate.

In another aspect, the invention provides methods of screening a subject for the risk of skeletal-related side effects and/or toxicity from treatment with a Wnt pathway inhibitor, comprising: obtaining a biological sample from the subject prior to treatment with the Wnt pathway inhibitor, determining the level of a bone resorption biomarker in the sample, and comparing the level of the bone resorption biomarker in the sample to a predetermined level of the bone resorption biomarker, wherein if the level of the bone resorption biomarker in the sample is higher than the predetermined level then the subject is at risk for skeletal-related side effects and/or toxicity. In some embodiments, if the subject is at risk for skeletal-related side effects and/or toxicity, the subject is administered a therapeutically effective amount of a therapeutic agent directed to the skeletal-related side effect and/or toxicity prior to treatment with the Wnt pathway inhibitor. In some embodiments, the bone resorption biomarker is β-CTX. In some embodiments, the therapeutic agent directed to skeletal-related side effects is a bisphosphonate.

In another aspect, the invention provides methods of treating cancer in a subject, comprising: administering to the subject a therapeutically effective amount of a Wnt pathway inhibitor, and determining the level of a bone resorption biomarker in a sample from the subject. In some embodiments, the method of treating cancer further comprises comparing the level of the bone resorption biomarker in the sample to a predetermined level of the bone resorption biomarker. In some embodiments, the method of treating cancer further comprises comparing the level of the bone resorption biomarker in the sample to a predetermined level of the bone resorption biomarker, wherein if the level of the bone resorption biomarker is higher than the predetermined level of the bone resorption biomarker then the subject is at risk for a skeletal-related side effect and/or toxicity. In some embodiments, the method of treating cancer further comprises comparing the level of the bone resorption biomarker in the sample to a predetermined level of the bone resorption biomarker, wherein if the level of the bone resorption biomarker is higher than the predetermined level of the bone resorption biomarker then the subject is administered a therapeutically effective amount of an anti-resorptive medication. In some embodiments, the bone resorption biomarker is β-CTX. In some embodiments, the anti-resorptive medication is a bisphosphonate.

In another aspect, the invention provides methods of inhibiting tumor growth in a subject, comprising: administering to the subject a therapeutically effective amount of a Wnt pathway inhibitor, and determining the level of a bone resorption biomarker in a sample from the subject. In some embodiments, the method of inhibiting tumor growth further comprises comparing the level of the bone resorption biomarker in the sample to a predetermined level of the bone resorption biomarker. In some embodiments, the method of inhibiting tumor growth further comprises comparing the level of the bone resorption biomarker in the sample to a predetermined level of the bone resorption biomarker, wherein if the level of the bone resorption biomarker is higher than the predetermined level of the bone resorption biomarker then the subject is at risk for a skeletal-related side effect and/or toxicity. In some embodiments, the method of inhibiting tumor growth further comprises comparing the level of the bone resorption biomarker in the sample to a predetermined level of the bone resorption biomarker, wherein if the level of the bone resorption biomarker is higher than the predetermined level of the bone resorption biomarker then the subject is administered a therapeutically effective amount of an anti-resorptive medication. In some embodiments, the bone resorption biomarker is β-CTX. In some embodiments, the anti-resorptive medication is a bisphosphonate.

In some aspects and/or embodiments of the methods described herein, the biological sample is blood, serum, or plasma. In some embodiments, the biological sample is a "fasting sample". As used herein, a "fasting sample" refers to a sample taken from an individual who has not eaten food and drink anything for at least 9-12 hours. In some embodiments, the predetermined level is about 1500 pg/ml or less in a blood, serum, or plasma sample. In some embodiments, the predetermined level is about 1200 pg/ml or less in a blood, serum, or plasma sample. In some embodiments, the predetermined level is about 1000 pg/ml or less in a blood, serum, or plasma sample. In some embodiments, the predetermined level is about 800 pg/ml or less in a blood, serum, or plasma sample. In some embodiments, the predetermined level is about 600 pg/ml or less in a blood, serum, or plasma sample. In some embodiments, the predetermined level is about 400 pg/ml or less in a blood, serum, or plasma sample. In some embodiments, the predetermined level of a biomarker (e.g., a bone turnover marker) is the amount of the biomarker in a sample obtained at an earlier date. In some embodiments, the predetermined level of a biomarker (e.g., a bone turnover marker) is the amount of the biomarker in a sample obtained prior to treatment. In some embodiments, the predetermined level of a biomarker (e.g., a bone turnover marker) is the amount of the biomarker in a sample obtained at an initial screening. In some embodiments, the predetermined level of a biomarker (e.g., a bone turnover marker) is a normal reference level. In some embodiments, the predetermined level of a biomarker is a baseline level. In some embodiments, the baseline level is the amount of the biomarker determined at an initial screening. In some embodiments the bone resorption biomarker is β-CTX. In some embodiments, the predetermined level for β-CTX is about 1000 pg/ml or less in blood, serum, or plasma.

In some aspects and/or embodiments of the methods described herein, a biological sample is obtained approximately every week, every 2 weeks, every 3 weeks, every 4 weeks, every 5 weeks, or every 6 weeks.

In certain embodiments of each of the aforementioned aspects, as well as other aspects and embodiments described elsewhere herein, the Wnt pathway inhibitor is an antibody that specifically binds at least one human Wnt protein. Non-limiting examples of anti-Wnt antibodies have been described in, for example, U.S. Patent Publication No. 2012/0027778 and International Publication WO 2011/088127. In some embodiments, the Wnt pathway inhibitor is an antibody that specifically binds at least one human FZD protein. Non-limiting examples of anti-FZD antibodies have been described in, for example, U.S. Pat. No. 7,982,013. In some embodiments, the Wnt pathway inhibitor is a soluble FZD receptor. Non-limiting examples of soluble FZD receptors have been described in, for example, U.S. Pat. Nos. 7,723,477 and 8,324,361 and U.S. Patent Publication No. 2011/0305695.

In some embodiments, the Wnt pathway inhibitor is an antibody comprising: (a) a heavy chain CDR1 comprising GFTFSHYTLS (SEQ ID NO:1), a heavy chain CDR2 comprising VISGDGSYTYYADSVKG (SEQ ID NO:2), and a heavy chain CDR3 comprising NFIKYVFAN (SEQ ID NO:3), and/or (b) a light chain CDR1 comprising SGDNIGS-FYVH (SEQ ID NO:4), a light chain CDR2 comprising DKSNRPSG (SEQ ID NO:5), and a light chain CDR3 comprising QSYANTLSL (SEQ ID NO:6).

In certain embodiments of each of the aforementioned aspects, as well as other aspects and embodiments described elsewhere herein, the Wnt pathway inhibitor is an antibody comprising (a) a heavy chain variable region having at least about 90%, at least about 95%, or 100% sequence identity to SEQ ID NO:7; and/or (b) a light chain variable region having at least about 90%, at least about 95%, or 100% sequence identity to SEQ ID NO:8. In some embodiments, the Wnt pathway inhibitor is antibody OMP-18R5.

In certain embodiments of each of the aforementioned aspects, as well as other aspects and embodiments described elsewhere herein, the Wnt pathway inhibitor is a recombinant antibody. In some embodiments, the antibody is a monoclonal antibody, a chimeric antibody, a humanized antibody, or a human antibody. In some embodiments, the antibody is an antibody fragment comprising an antigen-binding site. In certain embodiments, the antibody or antibody fragment is monovalent, monospecific, or bivalent. In some embodiments, the antibody is a bispecific antibody or a multispecific antibody. In some embodiments, the antibody is an IgG1 antibody. In some embodiments, the antibody is an IgG2 antibody. In certain embodiments, the antibody is isolated. In other embodiments, the antibody is substantially pure.

In some embodiments, the Wnt pathway inhibitor is an antibody that binds at least one human FZD with a dissociation constant ($K_D$) of about 10 nM to about 0.1 nM.

In certain embodiments, the Wnt pathway inhibitor comprises the same heavy and light chain amino acid sequences as an antibody encoded by a plasmid deposited with ATCC having deposit no. PTA-9541. In certain embodiments, the Wnt pathway inhibitor is encoded by the plasmid having ATCC deposit no. PTA-9541 which was deposited with American Type Culture Collection (ATCC), at 10801 University Boulevard, Manassas, Va., 20110, under the conditions of the Budapest Treaty on Sep. 29, 2008. In certain embodiments, the Wnt pathway inhibitor competes for specific binding to a human FZD with an antibody encoded by the plasmid deposited with ATCC having deposit no. PTA-9541.

In any of the aspects and/or embodiments of the methods described herein, the subject has cancer. In some embodiments, the cancer is selected from the group consisting of: lung cancer, pancreatic cancer, breast cancer, colon cancer, colorectal cancer, melanoma, gastrointestinal cancer, gastric cancer, renal cancer, ovarian cancer, liver cancer, endometrial cancer, kidney cancer, prostate cancer, thyroid cancer, neuroblastoma, glioma, glioblastoma multiforme, cervical cancer, stomach cancer, bladder cancer, hepatoma, and head and neck cancer.

In any of the aspects and/or embodiments of the methods described herein, the subject is treated with the Wnt pathway inhibitor in combination with one or more additional anti-cancer agents.

Where aspects or embodiments of the invention are described in terms of a Markush group or other grouping of alternatives, the present invention encompasses not only the entire group listed as a whole, but also each member of the group individually and all possible subgroups of the main group, and also the main group absent one or more of the group members. The present invention also envisages the explicit exclusion of one or more of any of the group members in the claimed invention.

DETAILED DESCRIPTION OF THE INVENTION

Figure 1:
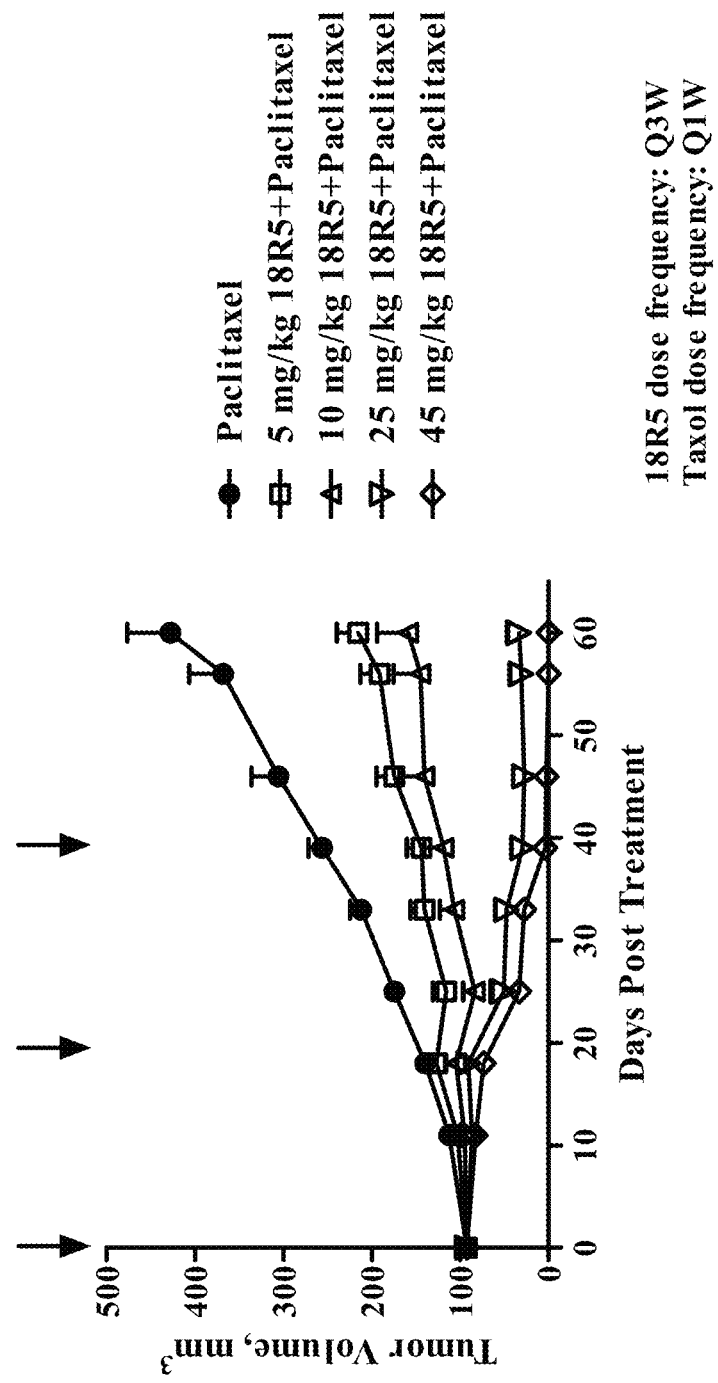
FIG. 1. Inhibition of breast tumor growth in vivo with intermittent dosing of a Wnt pathway inhibitor. Mice were treated with paclitaxel (-•-), 5 mg/kg OMP-18R5 in combination with paclitaxel (-■-), 10 mg/kg OMP-18R5 in combination with paclitaxel (-▲-), 25 mg/kg OMP-18R5 in combination with paclitaxel (-▼-), or 45 mg/kg OMP-18R5 in combination with paclitaxel (-♦-). Data is shown as tumor volume ($mm^3$) over days post-treatment. OMP-18R5 was administered intraperitoneally once every three weeks (indicated by arrows) and paclitaxel was administered at 10 mg/kg once a week.

The present invention relates to treating diseases with a Wnt pathway inhibitor. More particularly, the invention provides methods for treating cancer comprising administering a Wnt pathway inhibitor, either alone or in combination with other anti-cancer agents, and monitoring for skeletal-related side effects and/or toxicity, including those related to the Wnt pathway inhibitor.

The anti-FZD antibody OMP-18R5 was administered to subjects in a Phase 1 single agent dose escalation trial. The data from this early trial, as well as results from animal studies suggested that administration of a Wnt pathway inhibitor such as an anti-FZD antibody may result in skeletal-related side effects and/or toxicity in certain patients. Furthermore, the study showed that increased β-CTX levels may be an early indicator that a patient being treated with a Wnt pathway inhibitor is at risk of developing skeletal-related side effects and/or toxicities, allowing for intervention with appropriate medications.

These results made it desirable to develop risk mitigation and monitoring strategies for skeletal-related side effects and/or toxicities as described herein for subjects receiving treatment with a Wnt pathway inhibitor (e.g., an anti-FZD antibody or a soluble FZD receptor) as a single agent or in combination with additional anti-cancer agents.

I. DEFINITIONS

To facilitate an understanding of the present invention, a number of terms and phrases are defined below.

The terms "antagonist" and "antagonistic" as used herein refer to any molecule that partially or fully blocks, inhibits, reduces, or neutralizes a biological activity of a target and/or signaling pathway (e.g., the Wnt pathway). The term "antagonist" is used herein to include any molecule that partially or fully blocks, inhibits, reduces, or neutralizes the activity of a protein (e.g., a FZD protein or a Wnt protein). Suitable antagonist molecules specifically include, but are not limited to, antagonist antibodies, antibody fragments, soluble receptors, or small molecules.

The terms "modulation" and "modulate" as used herein refer to a change or an alteration in a biological activity. Modulation includes, but is not limited to, stimulating or inhibiting an activity. Modulation may be an increase or a decrease in activity (e.g., a decrease in Wnt pathway signaling), a change in binding characteristics, or any other change in the biological, functional, or immunological properties associated with the activity of a protein, pathway, or other biological point of interest.

The term "antibody" as used herein refers to an immunoglobulin molecule that recognizes and specifically binds a target, such as a protein, polypeptide, peptide, carbohydrate, polynucleotide, lipid, or combinations of the foregoing, through at least one antigen recognition site within the variable region of the immunoglobulin molecule. As used herein, the term encompasses intact polyclonal antibodies, intact monoclonal antibodies, single chain antibodies, antibody fragments (such as Fab, Fab', F(ab')2, and Fv fragments), single chain Fv (scFv) antibodies, multispecific antibodies such as bispecific antibodies, monospecific antibodies, monovalent antibodies, chimeric antibodies, humanized antibodies, human antibodies, fusion proteins comprising an antigen-binding site of an antibody, and any other modified immunoglobulin molecule comprising an antigen recognition site (e.g., antigen-binding site) as long as the antibodies exhibit the desired biological activity. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well-known subunit structures and three-dimensional configurations. Antibodies can be naked or conjugated to other molecules, including but not limited to, toxins and radioisotopes.

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, single chain antibodies, and multispecific antibodies formed from antibody fragments. "Antibody fragment" as used herein comprises an antigen-binding site or epitope-binding site.

The term "variable region" of an antibody refers to the variable region of an antibody light chain, or the variable region of an antibody heavy chain, either alone or in combination. The variable regions of the heavy and light chains each consist of four framework regions (FR) connected by three complementarity determining regions (CDRs), also known as "hypervariable regions". The CDRs in each chain are held together in close proximity by the framework regions and, with the CDRs from the other chain, contribute to the formation of the antigen-binding sites of the antibody. There are at least two techniques for determining CDRs: (1) an approach based on cross-species sequence variability (i.e., Kabat et al., 1991, *Sequences of Proteins of Immunological Interest, 5th Edition*, National Institutes of Health, Bethesda Md.), and (2) an approach based on crystallographic studies of antigen-antibody complexes (Al-Lazikani et al., 1997, *J. Mol. Biol.*, 273:927-948). In addition, combinations of these two approaches are sometimes used in the art to determine CDRs.

The term "monoclonal antibody" as used herein refers to a homogeneous antibody population involved in the highly specific recognition and binding of a single antigenic determinant or epitope. This is in contrast to polyclonal antibodies that typically include a mixture of different antibodies directed against a variety of different antigenic determinants. The term "monoclonal antibody" encompasses both intact and full-length monoclonal antibodies as well as antibody fragments (e.g., Fab, Fab', F(ab')2, Fv), single chain (scFv) antibodies, fusion proteins comprising an antibody portion, and any other modified immunoglobulin molecule comprising an antigen recognition site (antigen-binding site). Furthermore, "monoclonal antibody" refers to such antibodies made by any number of techniques, including but not limited to, hybridoma production, phage selection, recombinant expression, and transgenic animals.

The term "humanized antibody" as used herein refers to forms of non-human (e.g., murine) antibodies that are specific immunoglobulin chains, chimeric immunoglobulins, or fragments thereof that contain minimal non-human sequences. Typically, humanized antibodies are human immunoglobulins in which residues of the CDRs are replaced by residues from the CDRs of a non-human species (e.g., mouse, rat, rabbit, or hamster) that have the desired specificity, affinity, and/or binding capability (Jones et al., 1986, Nature, 321: 522-525; Riechmann et al., 1988, Nature, 332:323-327; Verhoeyen et al., 1988, Science, 239:1534-1536). In some instances, the Fv framework region residues of a human immunoglobulin are replaced with the corresponding residues in an antibody from a non-human species that has the desired specificity, affinity, and/or binding capability. The humanized antibody can be further modified by the substitution of additional residues either in the Fv framework region and/or within the replaced non-human residues to refine and optimize antibody specificity, affinity, and/or binding capability. In general, the humanized antibody will comprise substantially all of at least one, and typically two or three, variable domains containing all or substantially all of the CDRs that correspond to the non-human immunoglobulin whereas all or substantially all of the framework regions are those of a human immunoglobulin consensus sequence. The humanized antibody can also comprise at least a portion of an immunoglobulin constant region or domain (Fc), typically that of a human immunoglobulin.

The term "human antibody" as used herein refers to an antibody produced by a human or an antibody having an amino acid sequence corresponding to an antibody produced by a human. A human antibody may be made using any of the techniques known in the art. This definition of a human antibody specifically excludes a humanized antibody comprising non-human CDRs.

The term "chimeric antibody" as used herein refers to an antibody wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and/or binding capability, while the constant regions correspond to sequences in antibodies derived from another species (usually human).

The phrase "affinity-matured antibody" as used herein refers to an antibody with one or more alterations in one or more CDRs thereof that result in an improvement in the affinity of the antibody for antigen, compared to a parent antibody that does not possess those alterations(s). The definition also includes alterations in non-CDR residues made in conjunction with alterations to CDR residues. Preferred affinity-matured antibodies will have nanomolar or even picomolar affinities for the target antigen. Affinity-matured antibodies are produced by procedures known in the art. For example, Marks et al., 1992, Bio/Technology 10:779-783, describes affinity maturation by VH and VL domain shuffling. Random mutagenesis of CDR and/or framework residues is described by Barbas et al., 1994, PNAS, 91:3809-3813; Schier et al., 1995, Gene, 169:147-155; Yelton et al., 1995, J. Immunol. 155:1994-2004; Jackson et al., 1995, J. Immunol., 154:3310-9; and Hawkins et al., 1992, J. Mol. Biol., 226:889-896. Site-directed mutagenesis may also be used to obtain affinity-matured antibodies.

The terms "epitope" and "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids (also referred to as linear epitopes) are typically retained upon protein denaturing, whereas epitopes formed by tertiary folding (also referred to as conformational epitopes) are typically lost upon protein denaturing. An epitope typically includes at least 3, and more usually, at least 5 or 8-10 amino acids in a unique spatial conformation.

The terms "selectively binds" or "specifically binds" mean that a binding agent or an antibody reacts or associates more frequently, more rapidly, with greater duration, with greater affinity, or with some combination of the above to the epitope, protein, or target molecule than with alternative substances, including unrelated or related proteins. In certain embodiments "specifically binds" means, for instance, that an antibody binds a protein with a $K_D$ of about 0.1 mM or less, but more usually less than about 1 µM. In certain embodiments, "specifically binds" means that an antibody binds a target at times with a $K_D$ of at least about 0.1 µM or less, at other times at least about 0.01 µM or less, and at other times at least about 1 nM or less. Because of the sequence identity between homologous proteins in different species, specific binding can include an antibody that recognizes a protein in more than one species (e.g., human FZD and mouse FZD). Likewise, because of homology within certain regions of polypeptide sequences of different proteins, specific binding can include an antibody (or other polypeptide or binding agent) that recognizes more than one protein. It is understood that, in certain embodiments, an antibody or binding moiety that specifically binds a first target may or may not specifically bind a second target. As such, "specific binding" does not necessarily require (although it can include) exclusive binding, i.e. binding to a single target. Thus, an antibody may, in certain embodiments, specifically bind more than one target. In certain embodiments, multiple targets may be bound by the same antigen-binding site on the antibody. For example, an antibody may, in certain instances, comprise two identical antigen-binding sites, each of which specifically binds the same epitope on two or more proteins. In some embodiments, an antibody may be multispecific and comprise at least two antigen-binding sites with differing specificities. By way of non-limiting example, a bispecific antibody may comprise one antigen-binding site that recognizes an epitope on one protein and further comprise a second, different antigen-binding site that recognizes a different epitope on a second protein. Generally, but not necessarily, reference to binding means specific binding.

As used herein the term "soluble receptor" refers to an N-terminal extracellular fragment (or a portion thereof) of a receptor protein preceding the first transmembrane domain of the receptor that can be secreted from a cell in soluble form.

As used herein the term "FZD soluble receptor" or "soluble FZD receptor" refers to an N-terminal extracellular fragment of a FZD receptor protein preceding the first transmembrane domain of the receptor that can be secreted from a cell in soluble form. FZD soluble receptors comprising the entire N-terminal extracellular domain (ECD) as well as smaller fragments are encompassed by the term. Thus, FZD soluble receptors comprising the Fri domain are also included in this term.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids), as well as other modifications known in the art. It is understood that, because the polypeptides of this invention may be based upon antibodies, in certain embodiments, the polypeptides can occur as single chains or associated chains (e.g., dimers).

The terms "polynucleotide" and "nucleic acid" are used interchangeably herein and refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are well-known in the art. These include, but are not limited to, BLAST, ALIGN, Megalign, BestFit, GCG Wisconsin Package, and variations thereof. In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the sequences that is at least about 10, at least about 20, at least about 40-60 residues, at least about 60-80 residues in length or any integral value therebetween. In some embodiments, identity exists over a longer region than 60-80 residues, such as at least about 80-100 residues, and in some embodiments the sequences are substantially identical over the full length of the sequences being compared, such as the coding region of a nucleotide sequence.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Preferably, conservative substitutions in the sequences of the polypeptides and antibodies of the invention do not abrogate the binding of the polypeptide or antibody containing the amino acid sequence, to the antigen(s), i.e., the one or more RSPO protein(s) to which the polypeptide or antibody binds. Methods of identifying nucleotide and amino acid conservative substitutions which do not eliminate antigen binding are well-known in the art.

The term "vector" as used herein means a construct, which is capable of delivering, and usually expressing, one or more gene(s) or sequence(s) of interest in a host cell. Examples of vectors include, but are not limited to, viral vectors, naked DNA or RNA expression vectors, plasmid, cosmid, or phage vectors, DNA or RNA expression vectors associated with cationic condensing agents, and DNA or RNA expression vectors encapsulated in liposomes.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cells, or compositions include those which have been purified to a degree that they are no longer in a form in which they are found in nature. In some embodiments, a polypeptide, antibody, polynucleotide, vector, cell, or composition which is isolated is substantially pure.

The term "substantially pure" as used herein refers to material which is at least 50% pure (i.e., free from contaminants), at least 90% pure, at least 95% pure, at least 98% pure, or at least 99% pure.

The terms "cancer" and "cancerous" as used herein refer to or describe the physiological condition in mammals in which a population of cells are characterized by unregulated cell growth. Examples of cancer include, but are not limited to, carcinoma, blastoma, sarcoma, and hematologic cancers such as lymphoma and leukemia.

The terms "tumor" and "neoplasm" as used herein refer to any mass of tissue that results from excessive cell growth or proliferation, either benign (non-cancerous) or malignant (cancerous) including pre-cancerous lesions.

The term "metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates (e.g., via the bloodstream or lymph) from the primary site of disease to invade neighboring body structures.

The terms "cancer stem cell" and "CSC" and "tumor stem cell" and "tumor initiating cell" are used interchangeably herein and refer to cells from a cancer or tumor that: (1) have extensive proliferative capacity; 2) are capable of asymmetric cell division to generate one or more types of differentiated cell progeny wherein the differentiated cells have reduced proliferative or developmental potential; and (3) are capable of symmetric cell divisions for self-renewal or self-maintenance. These properties confer on the cancer stem cells the ability to form or establish a tumor or cancer upon serial transplantation into an immunocompromised host (e.g., a mouse) compared to the majority of tumor cells that fail to form tumors. Cancer stem cells undergo self-renewal versus differentiation in a chaotic manner to form tumors with abnormal cell types that can change over time as mutations occur.

The terms "cancer cell" and "tumor cell" refer to the total population of cells derived from a cancer or tumor or pre-cancerous lesion, including both non-tumorigenic cells, which comprise the bulk of the cancer cell population, and tumorigenic stem cells (cancer stem cells). As used herein, the terms "cancer cell" or "tumor cell" will be modified by the term "non-tumorigenic" when referring solely to those cells lacking the capacity to renew and differentiate to distinguish those tumor cells from cancer stem cells.

The term "tumorigenic" as used herein refers to the functional features of a cancer stem cell including the properties of self-renewal (giving rise to additional tumorigenic cancer stem cells) and proliferation to generate all other tumor cells (giving rise to differentiated and thus non-tumorigenic tumor cells).

The term "tumorigenicity" as used herein refers to the ability of a random sample of cells from the tumor to form palpable tumors upon serial transplantation into immunocompromised hosts (e.g., mice). This definition also includes enriched and/or isolated populations of cancer stem cells that form palpable tumors upon serial transplantation into immunocompromised hosts (e.g., mice).

The term "subject" refers to any animal (e.g., a mammal), including, but not limited to, humans, non-human primates, canines, felines, rodents, and the like, which is to be the recipient of a particular treatment. Typically, the terms "subject" and "patient" are used interchangeably herein in reference to a human subject.

The term "pharmaceutically acceptable" refers to a product or compound approved (or approvable) by a regulatory agency of the Federal government or a state government or listed in the U.S. Pharmacopeia or other generally recognized pharmacopeia for use in animals, including humans.

The terms "pharmaceutically acceptable excipient, carrier or adjuvant" or "acceptable pharmaceutical carrier" refer to an excipient, carrier or adjuvant that can be administered to a subject, together with at least one binding agent (e.g., an antibody) of the present disclosure, and which does not destroy the activity of the binding agent. The excipient, carrier, or adjuvant should be non-toxic when administered with a binding agent in doses sufficient to deliver a therapeutic effect.

The terms "effective amount" or "therapeutically effective amount" or "therapeutic effect" refer to an amount of a binding agent, an antibody, polypeptide, polynucleotide, small organic molecule, or other drug effective to "treat" a disease or disorder in a subject or mammal. In the case of cancer, the therapeutically effective amount of a drug (e.g., an antibody) has a therapeutic effect and as such can reduce the number of cancer cells; decrease tumorigenicity, tumorigenic frequency, or tumorigenic capacity; reduce the number or frequency of cancer stem cells; reduce the tumor size; reduce the cancer cell population; inhibit and/or stop cancer cell infiltration into peripheral organs including, for example, the spread of cancer into soft tissue and bone; inhibit and/or stop tumor or cancer cell metastasis; inhibit and/or stop tumor or cancer cell growth; relieve to some extent one or more of the symptoms associated with the cancer; reduce morbidity and mortality; improve quality of life; or a combination of such effects. To the extent the agent, for example an antibody, prevents growth and/or kills existing cancer cells, it can be referred to as cytostatic and/or cytotoxic.

The terms "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent or slow the development of a targeted pathologic condition or disorder. Thus those in need of treatment include those already with the disorder; those prone to have the disorder; and those in whom the disorder is to be prevented. In some embodiments, a subject is successfully "treated" according to the methods of the present invention if the patient shows one or more of the following: a reduction in the number of or complete absence of cancer cells; a reduction in the tumor size; inhibition of or an absence of cancer cell infiltration into peripheral organs including the spread of cancer cells into soft tissue and bone; inhibition of or an absence of tumor or cancer cell metastasis; inhibition or an absence of cancer growth; relief of one or more symptoms associated with the specific cancer; reduced morbidity and mortality; improvement in quality of life; reduction in tumorigenicity; reduction in the number or frequency of cancer stem cells; or some combination of effects.

As used in the present disclosure and claims, the singular forms "a", "an" and "the" include plural forms unless the context clearly dictates otherwise.

It is understood that wherever embodiments are described herein with the language "comprising" otherwise analogous embodiments described in terms of "consisting of" and/or "consisting essentially of" are also provided. It is also understood that wherever embodiments are described herein with the language "consisting essentially of" otherwise analogous embodiments described in terms of "consisting of" are also provided.

As used herein, reference to "about" or "approximately" a value or parameter includes (and describes) embodiments that are directed to that value or parameter. For example, description referring to "about X" includes description of "X".

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. WNT PATHWAY INHIBITORS

The present invention provides Wnt pathway inhibitors for use in methods of inhibiting tumor growth and/or for use in methods of treating cancer.

In certain embodiments, the Wnt pathway inhibitors are agents that bind one or more human Frizzled proteins (FZD). These agents are referred to herein as "FZD-binding agents". In some embodiments, the FZD-binding agents specifically bind one, two, three, four, five, six, seven, eight, nine, or ten FZD proteins. In some embodiments, the FZD-binding agent binds one or more FZD proteins selected from the group consisting of FZD1, FZD2, FZD3, FZD4, FZD5, FZD6, FZD7, FZD8, FZD9, and FZD10. In some embodiments, FZD-binding agent binds one or more FZD proteins comprising FZD1, FZD2, FZD5, FZD7, and/or FZD8. In certain embodiments, FZD-binding agent binds FZD7. In certain embodiments, FZD-binding agent binds FZD5 and/or FZD8. In certain embodiments, the FZD-binding agent specifically binds FZD1, FZD2, FZD5, FZD7, and FZD8. Non-limiting examples of FZD-binding agents can be found in U.S. Pat. No. 7,982,013.

In certain embodiments, the FZD-binding agent is a FZD antagonist. In certain embodiments, the FZD-binding agent is a Wnt pathway antagonist. In certain embodiments, the FZD-binding agent inhibits Wnt signaling. In some embodiments, the FZD-binding agent inhibits canonical Wnt signaling.

In some embodiments, the FZD-binding agents are antibodies. In some embodiments, the FZD-binding agents are polypeptides. In certain embodiments, the FZD-binding agent is an antibody or a polypeptide comprising an antigen-binding site. In certain embodiments, an antigen-binding site of a FZD-binding antibody or polypeptide described herein is capable of binding (or binds) one, two, three, four, five, or more human FZD proteins. In certain embodiments, an antigen-binding site of the FZD-binding antibody or polypeptide is capable of specifically binding one, two, three, four, or five human FZD proteins selected from the group consisting of FZD1, FZD2, FZD3, FZD4, FZD5, FZD6, FZD7, FZD8, FZD9 and FZD10. In some embodiments, when the FZD-binding agent is an antibody that binds more than one FZD protein, it may be referred to as a "pan-FZD antibody".

In certain embodiments, the FZD-binding agent (e.g., antibody) specifically binds the extracellular domain (ECD) within the one or more human FZD proteins to which it binds. In certain embodiments, the FZD-binding agent specifically binds within the Fri domain (also known as the cysteine-rich domain (CRD)) of the human FZD protein to which it binds. Sequences of the Fri domain of each of the human FZD proteins are known in the art and are provided as SEQ ID NO:13 (FZD1), SEQ ID NO:14 (FZD2), SEQ ID NO:15 (FZD3), SEQ ID NO:16 (FZD4), SEQ ID NO:17 (FZD5), SEQ ID NO:18 (FZD6), SEQ ID NO:19 (FZD7), SEQ ID NO:20 (FZD), SEQ ID NO:21 (FZD9), and SEQ ID NO:22 (FZD10).

In certain embodiments, the FZD-binding agent binds one, two, three, four, five, or more FZD proteins. In some embodiments, the FZD-binding agent specifically binds one, two, three, four, or five FZD proteins selected from the group consisting of FZD1, FZD2, FZD5, FZD7, and FZD8. In some embodiments, the FZD-binding agent specifically binds at least FZD5 and FZD8.

In some embodiments, the FZD-binding agent binds at least one human FZD protein with a dissociation constant ($K_D$) of about 1 µM or less, about 100 nM or less, about 40 nM or less, about 20 nM or less, about 10 nM or less, about 1 nM or less, or about 0.1 nM or less. In some embodiments, a FZD-binding agent binds at least one FZD protein with a $K_D$ of about 10 nM or less. In some embodiments, a FZD-binding agent binds at least one FZD protein with a $K_D$ of about 1 nM or less. In some embodiments, a FZD-binding agent binds at least one FZD protein with a $K_D$ of about 0.1 nM or less. In certain embodiments, a FZD-binding agent binds each of one or more (e.g., 1, 2, 3, 4, or 5) of FZD1, FZD2, FZD5, FZD7, and FZD8 with a $K_D$ of about 40 nM or less. In certain embodiments, the FZD-binding agent binds to each of one or more of FZD1, FZD2, FZD5, FZD7, and FZD8 with a $K_D$ of about 10 nM or less. In certain embodiments, the FZD-binding agent binds each of FZD1, FZD2, FZD5, FZD7, and FZD8 with a $K_D$ of about 10 nM. In some embodiments, the $K_D$ of the binding agent (e.g., an antibody) to a FZD protein is the $K_D$ determined using a FZD-Fc fusion protein comprising at least a portion of the FZD extracellular domain or FZD-Fri domain immobilized on a Biacore chip.

In certain embodiments, the FZD-binding agent binds one or more (for example, two or more, three or more, or four or more) human FZD proteins with an $EC_{50}$ of about 1 µM or less, about 100 nM or less, about 40 nM or less, about 20 nM or less, about 10 nM or less, or about 1 nM or less. In certain embodiments, a FZD-binding agent binds to more than one FZD protein with an $EC_{50}$ of about 40 nM or less, about 20 nM or less, or about 10 nM or less. In certain embodiments, the FZD-binding agent has an $EC_{50}$ of about 20 nM or less with respect to one or more (e.g., 1, 2, 3, 4, or 5) of the following FZD proteins: FZD1, FZD2, FZD5, FZD7, and FZD8. In certain embodiments, the FZD-binding agent has an $EC_{50}$ of about 10 nM or less with respect to one or more (e.g., 1, 2, 3, 4, or 5) of the following FZD proteins: FZD1, FZD2, FZD5, FZD7, and FZD8. In certain embodiments, the FZD-binding agent has an $EC_{50}$ of about 40 nM or less or 20 nM or less with respect to binding of FZD5 and/or FZD8.

In certain embodiments, the Wnt pathway inhibitor is a FZD-binding agent which is an antibody. In some embodiments, the antibody is a recombinant antibody. In some embodiments, the antibody is a monoclonal antibody. In some embodiments, the antibody is a chimeric antibody. In some embodiments, the antibody is a humanized antibody. In some embodiments, the antibody is a human antibody. In certain embodiments, the antibody is an IgG1 antibody. In certain embodiments, the antibody is an IgG2 antibody. In certain embodiments, the antibody is an antibody fragment comprising an antigen-binding site. In some embodiments, the antibody is monovalent, monospecific, or bivalent. In some embodiments, the antibody is a bispecific antibody or a multispecific antibody. In some embodiments, the antibody is conjugated to a cytotoxic moiety. In some embodiments, the antibody is isolated. In some embodiments, the antibody is substantially pure.

The FZD-binding agents (e.g., antibodies) of the present invention can be assayed for specific binding by any method known in the art. The immunoassays which can be used include, but are not limited to, competitive and non-competitive assay systems using techniques such as Biacore analysis, FACS analysis, immunofluorescence, immunocytochemistry, Western blot analysis, radioimmunoassays, ELISA, "sandwich" immunoassays, immunoprecipitation assays, precipitation reactions, gel diffusion precipitin reactions, immunodiffusion assays, agglutination assays, complement-fixation assays, immunoradiometric assays, fluorescent immunoassays, and protein A immunoassays. Such assays are routine and well-known in the art (see, e.g., Ausubel et al., Editors, 1994-present, *Current Protocols in Molecular Biology*, John Wiley & Sons, Inc., New York, N.Y.).

For example, the specific binding of an antibody to a human FZD protein may be determined using ELISA. An ELISA assay comprises preparing antigen, coating wells of a 96 well microtiter plate with antigen, adding to the well the FZD-binding agent (e.g., an antibody) conjugated to a detectable compound such as an enzymatic substrate (e.g. horseradish peroxidase or alkaline phosphatase), incubating for a period of time and detecting the presence of the FZD-binding agent bound to the antigen. In some embodiments, the FZD-binding antibody or agent is not conjugated to a detectable compound, but instead a second conjugated antibody that recognizes the FZD-binding antibody or agent (e.g., an anti-Fc antibody) is added to the well. In some embodiments, instead of coating the well with the antigen, the FZD-binding antibody or agent can be coated to the well and a second antibody conjugated to a detectable compound can be added following the addition of the antigen to the coated well. One of skill in the art would be knowledgeable as to the parameters that can be modified to increase and/or optimize the signal detected as well as other variations of ELISAs that may be used.

In another example, the specific binding of an antibody to a human FZD protein may be determined using FACS. A FACS screening assay may comprise generating a cDNA construct that expresses an antigen as a fusion protein, transfecting the construct into cells, expressing the antigen on the surface of the cells, mixing the FZD-binding antibody or other FZD-binding agent with the transfected cells, and incubating for a period of time. The cells bound by a FZD-binding antibody or other FZD-binding agent may be identified by using a secondary antibody conjugated to a detectable compound (e.g., PE-conjugated anti-Fc antibody) and a flow cytometer. One of skill in the art would be knowledgeable as to the parameters that can be modified to optimize the signal detected as well as other variations of FACS that may enhance screening (e.g., screening for blocking antibodies).

The binding affinity of an antibody or other binding-agent to an antigen (e.g., a FZD protein) and the off-rate of an antibody-antigen interaction can be determined by competitive binding assays. One example of a competitive binding assay is a radioimmunoassay comprising the incubation of labeled antigen (e.g., $^3$H or $^{125}$I), or fragment or variant thereof, with the antibody of interest in the presence of increasing amounts of unlabeled antigen followed by the detection of the antibody bound to the labeled antigen. The affinity of the antibody for an antigen (e.g., a FZD protein) and the binding off-rates can be determined from the data by Scatchard plot analysis. In some embodiments, Biacore kinetic analysis is used to determine the binding on and off rates of antibodies or agents that bind an antigen (e.g., a FZD protein). Biacore kinetic analysis comprises analyzing the binding and dissociation of antibodies from chips with immobilized antigen (e.g., a FZD protein) on their surface.

In certain embodiments, the invention provides a Wnt pathway inhibitor which is a FZD-binding agent (e.g., an antibody) that comprises a heavy chain CDR1 comprising GFTFSHYTLS (SEQ ID NO:1), a heavy chain CDR2 comprising VISGDGSYTYYADSVKG (SEQ ID NO:2), and a heavy chain CDR3 comprising NFIKYVFAN (SEQ ID NO:3). In some embodiments, the FZD-binding agent further comprises a light chain CDR1 comprising SGDNIGSFYVH (SEQ ID NO:4), a light chain CDR2 comprising DKSNRPSG (SEQ ID NO:5), and a light chain CDR3 comprising QSYANTLSL (SEQ ID NO:6). In some embodiments, the FZD-binding agent comprises a light chain CDR1 comprising SGDNIGSFYVH (SEQ ID NO:4), a light chain CDR2 comprising DKSNRPSG (SEQ ID NO:5), and a light chain CDR3 comprising QSYANTLSL (SEQ ID NO:6). In certain embodiments, the FZD-binding agent comprises: (a) a heavy chain CDR1 comprising GFTFSHYTLS (SEQ ID NO:1), a heavy chain CDR2 comprising VISGDGSYTYYADSVKG (SEQ ID NO:2), and a heavy chain CDR3 comprising NFIKYVFAN (SEQ ID NO:3), and (b) a light chain CDR1 comprising SGDNIGSFYVH (SEQ ID NO:4), a light chain CDR2 comprising DKSNRPSG (SEQ ID NO:5), and a light chain CDR3 comprising QSYANTLSL (SEQ ID NO:6).

In certain embodiments, the invention provides a FZD-binding agent (e.g., an antibody) that comprises: (a) a heavy chain CDR1 comprising GFTFSHYTLS (SEQ ID NO:1), or a variant thereof comprising 1, 2, 3, or 4 amino acid substitutions; (b) a heavy chain CDR2 comprising VISGDGSYTYYADSVKG (SEQ ID NO:2), or a variant thereof comprising 1, 2, 3, or 4 amino acid substitutions; (c) a heavy chain CDR3 comprising NFIKYVFAN (SEQ ID NO:3), or a variant thereof comprising 1, 2, 3, or 4 amino acid substitutions; (d) a light chain CDR1 comprising SGDNIGSFYVH (SEQ ID NO:4), or a variant thereof comprising 1, 2, 3, or 4 amino acid substitutions; (e) a light chain CDR2 comprising DKSNRPSG (SEQ ID NO:5), or a variant thereof comprising 1, 2, 3, or 4 amino acid substitutions; and (f) a light chain CDR3 comprising QSYANTLSL (SEQ ID NO:6), or a variant thereof comprising 1, 2, 3, or 4 amino acid substitutions. In certain embodiments, the amino acid substitutions are conservative substitutions.

In certain embodiments, the invention provides a FZD-binding agent (e.g., an antibody) that comprises a heavy chain variable region having at least about 80% sequence identity to SEQ ID NO:7, and/or a light chain variable region having at least 80% sequence identity to SEQ ID NO:8. In certain embodiments, the FZD-binding agent comprises a heavy chain variable region having at least about 85%, at least about 90%, at least about 95%, at least about 97%, or at least about 99% sequence identity to SEQ ID NO:7. In certain embodiments, the FZD-binding agent comprises a light chain variable region having at least about 85%, at least about 90%, at least about 95%, at least about 97%, or at least about 99% sequence identity to SEQ ID NO:8. In certain embodiments, the FZD-binding agent comprises a heavy chain variable region having at least about 95% sequence identity to SEQ ID NO:7, and/or a light chain variable region having at least about 95% sequence identity to SEQ ID NO:8. In certain embodiments, the FZD-binding agent comprises a heavy chain variable region comprising SEQ ID NO:7 and/or a light chain variable region comprising SEQ ID NO:8. In certain embodiments, the FZD-binding agent comprises a heavy chain variable region comprising SEQ ID NO:7 and a light chain variable region comprising SEQ ID NO:8. In certain embodiments, the FZD-binding agent comprises a heavy chain variable region consisting essentially of SEQ ID NO:7 and a light chain variable region consisting essentially of SEQ ID NO:8.

In certain embodiments, the invention provides a FZD-binding agent (e.g., an antibody) that comprises: (a) a heavy chain having at least 90% sequence identity to SEQ ID NO:9 (with or without the signal sequence) or SEQ ID NO:11; and/or (b) a light chain having at least 90% sequence identity to SEQ ID NO:10 (with or without the signal sequence) or SEQ ID NO:12. In some embodiments, the FZD-binding agent comprises: (a) a heavy chain having at least 95% sequence identity to SEQ ID NO:9 (with or without the signal sequence) or SEQ ID NO:11; and/or (b) a light chain having at least 95% sequence identity to SEQ ID NO:10 (with or without the signal sequence) or SEQ ID NO:12. In some embodiments, the FZD-binding agent comprises a heavy chain comprising SEQ ID NO:9 (with or without the signal sequence) or SEQ ID NO:11, and/or a light chain comprising SEQ ID NO:10 (with or without the signal sequence) or SEQ ID NO:12. In some embodiments, the FZD-binding agent comprises a heavy chain comprising SEQ ID NO:11 and a light chain comprising SEQ ID NO:12. In some embodiments, the FZD-binding agent comprises a heavy chain consisting essentially of amino acids 20-463 of SEQ ID NO:9 and a light chain consisting essentially of amino acids 20-232 of SEQ ID NO:10. In some embodiments, the FZD-binding agent comprises a heavy chain consisting essentially of SEQ ID NO:11 and a light chain consisting essentially of SEQ ID NO:12.

In certain embodiments, the invention provides a Wnt pathway inhibitor which is a FZD-binding agent (e.g., an antibody) that specifically binds at least one of FZD1, FZD2, FZD5, FZD7 and/or FZD8, wherein the FZD-binding agent (e.g., an antibody) comprises one, two, three, four, five, and/or six of the CDRs of antibody 18R5. Antibody 18R5 (also known as OMP-18R5 and vantictumab), as well as other FZD-binding agents, has been previously described in U.S. Pat. No. 7,982,013. DNA encoding the heavy chain and light chain of the 18R5 IgG2 antibody was deposited with the ATCC, under the conditions of the Budapest Treaty on Sep. 29, 2008, and assigned ATCC deposit designation number PTA-9541. In some embodiments, the FZD-binding agent comprises one or more of the CDRs of 18R5, two or more of the CDRs of 18R5, three or more of the CDRs of 18R5, four or more of the CDRs of 18R5, five or more of the CDRs of 18R5, or all six of the CDRs of 18R5.

The invention provides polypeptides which are Wnt pathway inhibitors. The polypeptides include, but are not limited to, antibodies that specifically bind human FZD proteins. In some embodiments, a polypeptide binds one or more FZD proteins selected from the group consisting of FZD1, FZD2, FZD3, FZD4, FZD5, FZD6, FZD7, FZD8, FZD9, and FZD10. In some embodiments, a polypeptide binds FZD1, FZD2, FZD5, FZD7, and/or FZD8. In some embodiments, a polypeptide binds FZD1, FZD2, FZD5, FZD7, and FZD8.

In certain embodiments, a polypeptide comprises one, two, three, four, five, and/or six of the CDRs of antibody 18R5. In some embodiments, a polypeptide comprises CDRs with up to four (i.e., 0, 1, 2, 3, or 4) amino acid substitutions per CDR. In certain embodiments, the heavy chain CDR(s) are contained within a heavy chain variable region. In certain embodiments, the light chain CDR(s) are contained within a light chain variable region.

In some embodiments, the invention provides a polypeptide that specifically binds one or more human FZD proteins, wherein the polypeptide comprises an amino acid sequence having at least about 80% sequence identity to SEQ ID NO:7, and/or an amino acid sequence having at least about 80% sequence identity to SEQ ID NO:8. In certain embodiments, the polypeptide comprises an amino acid sequence having at least about 85%, at least about 90%, at least about 95%, at least about 97%, or at least about 99% sequence identity to SEQ ID NO:7. In certain embodiments, the polypeptide comprises an amino acid sequence having at least about 85%, at least about 90%, at least about 95%, at least about 97%, or at least about 99% sequence identity to SEQ ID NO:8. In certain embodiments, the polypeptide comprises an amino acid sequence having at least about 95% sequence identity to SEQ ID NO:7, and/or an amino acid sequence having at least about 95% sequence identity to SEQ ID NO:8. In certain embodiments, the polypeptide comprises an amino acid sequence comprising SEQ ID NO:7, and/or an amino acid sequence comprising SEQ ID NO:8.

In some embodiments, a FZD-binding agent comprises a polypeptide comprising a sequence selected from the group consisting of: SEQ ID NO:7, SEQ ID NO:8, SEQ ID NO:9, SEQ ID NO:10, SEQ ID NO:11, and SEQ ID NO:12.

In certain embodiments, a FZD-binding agent comprises the heavy chain variable region and light chain variable region of the 18R5 antibody. In certain embodiments, a FZD-binding agent comprises the heavy chain and light chain of the 18R5 antibody (with or without the leader sequence).

In certain embodiments, a FZD-binding agent comprises, consists essentially of, or consists of, the antibody 18R5.

In certain embodiments, a FZD-binding agent (e.g., antibody) competes for specific binding to one or more human FZD proteins with an antibody that comprises a heavy chain variable region comprising SEQ ID NO:7 and a light chain variable region comprising SEQ ID NO:8. In certain embodiments, a FZD-binding agent (e.g., antibody) competes for specific binding to one or more human FZD proteins with an antibody that comprises a heavy chain comprising SEQ ID NO:9 (with or without the signal sequence) and a light chain comprising SEQ ID NO:10 (with or without the signal sequence). In certain embodiments, a FZD-binding agent (e.g., antibody) competes for specific binding to one or more human FZD proteins with an antibody that comprises a heavy chain comprising SEQ ID NO:11 and a light chain comprising SEQ ID NO:12. In certain embodiments, a FZD-binding agent competes with antibody 18R5 for specific binding to one or more human FZD proteins. In some embodiments, a FZD-binding agent or antibody competes for specific binding to one or more human FZD proteins in an in vitro competitive binding assay.

In certain embodiments, a FZD-binding agent (e.g., an antibody) binds the same epitope, or essentially the same epitope, on one or more human FZD proteins as an antibody of the invention. In another embodiment, a FZD-binding agent is an antibody that binds an epitope on one or more human FZD proteins that overlaps with the epitope on a FZD protein bound by an antibody of the invention. In certain embodiments, a FZD-binding agent (e.g., an antibody) binds the same epitope, or essentially the same epitope, on one or more FZD proteins as antibody 18R5. In another embodiment, the FZD-binding agent is an antibody that binds an epitope on one or more human FZD proteins that overlaps with the epitope on a FZD protein bound by antibody 18R5.

In certain embodiments, the Wnt pathway inhibitors are agents that bind one or more human Wnt proteins. These agents are referred to herein as "Wnt-binding agents". In certain embodiments, the agents specifically bind one, two, three, four, five, six, seven, eight, nine, ten, or more Wnt proteins. In some embodiments, the Wnt-binding agents bind one or more human Wnt proteins selected from the group consisting of Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16. In certain embodiments, a Wnt-binding agent binds one or more (or two or more, three or more, four or more, five or more, etc.) Wnt proteins selected from the group consisting of Wnt1, Wnt2, Wnt2b, Wnt3, Wnt3a, Wnt7a, Wnt7b, Wnt8a, Wnt8b, Wnt10a, and Wnt10b. In certain embodiments, the one or more (or two or more, three or more, four or more, five or more, etc.) Wnt proteins are selected from the group consisting of Wnt1, Wnt2, Wnt2b, Wnt3, Wnt3a, Wnt8a, Wnt8b, Wnt10a, and Wnt10b.

In certain embodiments, the Wnt-binding agent is a Wnt antagonist. In certain embodiments, the Wnt-binding agent is a Wnt pathway antagonist. In certain embodiments, the Wnt-binding agent inhibits Wnt signaling. In some embodiments, the Wnt-binding agent inhibits canonical Wnt signaling.

In some embodiments, the Wnt-binding agent is an antibody. In some embodiments, the Wnt-binding agent is a polypeptide. In certain embodiments, the Wnt-binding agent is an antibody or a polypeptide comprising an antigen-binding site. In certain embodiments, an antigen-binding site of a Wnt-binding antibody or polypeptide described herein is capable of binding (or binds) one, two, three, four, five, or more human Wnt proteins. In certain embodiments, an antigen-binding site of the Wnt-binding antibody or polypeptide is capable of specifically binding one, two, three, four, or five human Wnt proteins selected from the group consisting of Wnt1, Wnt2, Wnt2b, Wnt3, Wnt3a, Wnt7a, Wnt7b, Wnt8a, Wnt8b, Wnt10a, and Wnt10b. Non-limiting examples of Wnt-binding agents can be found in International Publication WO 2011/088127.

In certain embodiments, a Wnt-binding agent binds to the C-terminal cysteine rich domain of one or more human Wnt proteins. In certain embodiments, the Wnt-binding agent binds a domain within the one or more Wnt proteins to which the agent or antibody binds that is selected from the group consisting of: SEQ ID NO:46 (Wnt1), SEQ ID NO:47 (Wnt2), SEQ ID NO:48 (Wnt2b), SEQ ID NO:49 (Wnt3), SEQ ID NO:50 (Wnt3a), SEQ ID NO:51 (Wnt7a), SEQ ID NO:52 (Wnt7b), SEQ ID NO:53 (Wnt8a), SEQ ID NO:54 (Wnt8b), SEQ ID NO:55 (Wnt10a), and SEQ ID NO:56 (Wnt10b).

In certain embodiments, the Wnt-binding agent binds one or more (e.g., two or more, three or more, or four or more) Wnt proteins with a $K_D$ of about 1 µM or less, about 100 nM or less, about 40 nM or less, about 20 nM or less, or about 10 nM or less. For example, in certain embodiments, a Wnt-binding agent described herein that binds more than one Wnt protein, binds those Wnt proteins with a $K_D$ of about 100 nM or less, about 20 nM or less, or about 10 nM or less. In certain embodiments, the Wnt-binding agent binds each of one or more (e.g., 1, 2, 3, 4, or 5) Wnt proteins with a $K_D$ of about 40 nM or less, wherein the Wnt proteins are selected from the group consisting of: Wnt1, Wnt2, Wnt2b, Wnt3, Wnt3a, Wnt7a, Wnt7b, Wnt8a, Wnt8b, Wnt10a, and Wnt10b. In some embodiments, the $K_D$ of the binding agent (e.g., an antibody) to a Wnt protein is the $K_D$ determined using a Wnt fusion protein comprising at least a portion of the Wnt C-terminal cysteine rich domain immobilized on a Biacore chip.

In certain embodiments, the Wnt-binding agent binds one or more (for example, two or more, three or more, or four or more) human Wnt proteins with an $EC_{50}$ of about 1 µM or less, about 100 nM or less, about 40 nM or less, about 20 nM or less, about 10 nM or less, or about 1 nM or less. In certain embodiments, a Wnt-binding agent binds to more than one Wnt with an $EC_{50}$ of about 40 nM or less, about 20 nM or less, or about 10 nM or less. In certain embodiments, the Wnt-binding agent has an $EC_{50}$ of about 20 nM or less with respect to one or more (e.g., 1, 2, 3, 4, or 5) of Wnt proteins Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and/or Wnt16. In certain embodiments, the Wnt-binding agent has an $EC_{50}$ of about 10 nM or less with respect to one or more (e.g., 1, 2, 3, 4, or 5) of the following Wnt proteins Wnt1, Wnt2, Wnt2b, Wnt3, Wnt3a, Wnt8a, Wnt8b, Wnt10a, and/or Wnt10b.

In certain embodiments, the Wnt pathway inhibitor is a Wnt-binding agent which is an antibody. In some embodiments, the antibody is a recombinant antibody. In some embodiments, the antibody is a monoclonal antibody. In some embodiments, the antibody is a chimeric antibody. In some embodiments, the antibody is a humanized antibody. In some embodiments, the antibody is a human antibody. In certain embodiments, the antibody is an IgG1 antibody. In certain embodiments, the antibody is an IgG2 antibody. In certain embodiments, the antibody is an antibody fragment comprising an antigen-binding site. In some embodiments, the antibody is monovalent, monospecific, or bivalent. In some embodiments, the antibody is a bispecific antibody or a multispecific antibody. In some embodiments, the antibody is conjugated to a cytotoxic moiety. In some embodiments, the antibody is isolated. In some embodiments, the antibody is substantially pure.

The Wnt-binding agents (e.g., antibodies) of the present invention can be assayed for specific binding by any method known in the art as described herein for FZD-binding agents.

For example, the specific binding of an antibody to a human Wnt protein may be determined using ELISA. An ELISA assay comprises preparing antigen, coating wells of a 96 well microtiter plate with antigen, adding to the well the Wnt-binding agent (e.g., an antibody) conjugated to a detectable compound such as an enzymatic substrate (e.g. horseradish peroxidase or alkaline phosphatase), incubating for a period of time and detecting the presence of the Wnt-binding agent bound to the antigen. In some embodiments, the Wnt-binding antibody or agent is not conjugated to a detectable compound, but instead a second conjugated antibody that recognizes the Wnt-binding antibody or agent (e.g., an anti-Fc antibody) is added to the well. In some embodiments, instead of coating the well with the antigen, the Wnt-binding antibody or agent can be coated to the well and a second antibody conjugated to a detectable compound can be added following the addition of the antigen to the coated well. One of skill in the art would be knowledgeable as to the parameters that can be modified to increase and/or optimize the signal detected as well as other variations of ELISAs that may be used.

In another example, the specific binding of an antibody to a human Wnt protein may be determined using FACS. A FACS screening assay may comprise generating a cDNA construct that expresses an antigen as a fusion protein, transfecting the construct into cells, expressing the antigen on the surface of the cells, mixing the Wnt-binding antibody with the transfected cells, and incubating for a period of time. The cells bound by the Wnt-binding antibody may be identified by using a secondary antibody conjugated to a detectable compound (e.g., PE-conjugated anti-Fc antibody) and a flow cytometer. One of skill in the art would be knowledgeable as to the parameters that can be modified to optimize the signal detected as well as other variations of FACS that may enhance screening (e.g., screening for blocking antibodies).

The binding affinity of a Wnt-binding agent to an antigen (e.g., a Wnt protein) and the off-rate of an antibody-antigen interaction can be determined by competitive binding assays such as those described above for FZD-binding agents.

In certain embodiments, the Wnt-binding agent is a soluble receptor. In certain embodiments, the Wnt-binding agent comprises the extracellular domain of a FZD receptor protein. In some embodiments, the Wnt-binding agent comprises a Fri domain of a FZD protein. In some embodiments, a soluble receptor comprising a FZD Fri domain can demonstrate altered biological activity (e.g., increased protein half-life) compared to a soluble receptor comprising the entire FZD ECD. Protein half-life can be further increased by covalent modification with polyethylene glycol (PEG) or polyethylene oxide (PEO). In certain embodiments, the FZD protein is a human FZD protein. In certain embodiments, the human FZD protein is FZD1, FZD2, FZD3, FZD4, FZD5, FZD6, FZD7, FZD8, FZD9, or FZD10. Non-limiting examples of soluble FZD receptors can be found in U.S. Pat. Nos. 7,723,477 and 7,947,277; and U.S. Patent Publication No. 2011/0305695.

The predicted Fri domains for each of the human FZD1-10 proteins are provided as SEQ ID NOs:13-22. The predicted minimal Fri domains for each of the human FZD1-10 proteins are provided as SEQ ID NOs:23-32. Those of skill in the art may differ in their understanding of the exact amino acids corresponding to the various Fri domains. Thus, the N-terminus and/or C-terminus of the domains outlined above and herein may extend or be shortened by 1, 2, 3, 4, 5, 6, 7, 8, 9, or even 10 amino acids.

In certain embodiments, the Wnt-binding agent comprises a Fri domain of a human FZD protein, or a fragment or variant of the Fri domain that binds one or more human Wnt proteins. In certain embodiments, the human FZD protein is FZD1, FZD2, FZD3, FZD4, FZD5, FZD6, FZD7, FZD8, FZD9, or FZD10. In certain embodiments, the human FZD protein is FZD4. In certain embodiments, the human FZD protein is FZD5. In certain embodiments, the human FZD protein is FZD8. In certain embodiments, the human FZD protein is FZD10. In certain embodiments, the FZD protein is FZD4 and the Wnt-binding agent comprises SEQ ID NO:16. In certain embodiments, the FZD protein is FZD5 and the Wnt-binding agent comprises SEQ ID NO:17. In certain embodiments, the FZD protein is FZD7 and the Wnt-binding agent comprises SEQ ID NO:19. In certain embodiments, the FZD protein is FZD8 and the Wnt-binding agent comprises SEQ ID NO:20. In certain embodiments, the FZD protein is FZD10 and the Wnt-binding agent comprises SEQ ID NO:22. In certain embodiments, the FZD protein is FZD8 and the Wnt-binding agent comprises SEQ ID NO:33.

In some embodiments, the Wnt-binding agent comprises a Fri domain comprising the minimal Fri domain of FZD1 (SEQ ID NO:23), the minimal Fri domain of FZD2 (SEQ ID NO:24), the minimal Fri domain of FZD3 (SEQ ID NO:25), the minimal Fri domain of FZD4 (SEQ ID NO:26), the minimal Fri domain of FZD5 (SEQ ID NO:27), the minimal Fri domain of FZD6 (SEQ ID NO:28), the minimal Fri domain of FZD7 (SEQ ID NO:29), the minimal Fri domain of FZD8

(SEQ ID NO:30), the minimal Fri domain of FZD9 (SEQ ID NO:31), or the minimal Fri domain of FZD10 (SEQ ID NO:32). In some embodiments, the Wnt-binding agent comprises a Fri domain comprising the minimal Fri domain of FZD8 (SEQ ID NO:30).

In some embodiments, the Wnt-binding agent comprises a Fri domain consisting essentially of the Fri domain of FZD1, the Fri domain of FZD2, the Fri domain of FZD3, the Fri domain of FZD4, the Fri domain of FZD5, the Fri domain of FZD6, the Fri domain of FZD7, the Fri domain of FZD8, the Fri domain of FZD9, or the Fri domain of FZD10. In some embodiments, the Wnt-binding agent comprises a Fri domain consisting essentially of the Fri domain of FZD8.

In some embodiments, the Wnt-binding agent comprises a sequence selected from the group consisting of: SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, and SEQ ID NO:33. In some embodiments, the Wnt-binding agent comprises a Fri domain consisting essentially of SEQ ID NO:20. In some embodiments, the Wnt-binding agent comprises a Fri domain consisting essentially of SEQ ID NO:33.

In certain embodiments, the Wnt-binding agent comprises a variant of any one of the aforementioned FZD Fri domain sequences that comprises one or more (e.g., one, two, three, four, five, six, seven, eight, nine, ten, etc.) conservative substitutions and is capable of binding Wnt protein(s).

In certain embodiments, a Wnt-binding agent, such as an agent comprising a Fri domain of a human FZD receptor, further comprises a non-FZD polypeptide. In some embodiments, a FZD soluble receptor may include FZD ECD or Fri domains linked to other non-FZD functional and structural polypeptides including, but not limited to, a human Fc region, protein tags (e.g., myc, FLAG, GST), other endogenous proteins or protein fragments, or any other useful protein sequence including any linker region between a FZD ECD or Fri domain and a second polypeptide. In certain embodiments, the non-FZD polypeptide comprises a human Fc region. The Fc region can be obtained from any of the classes of immunoglobulin, IgG, IgA, IgM, IgD and IgE. In some embodiments, the Fc region is a human IgG1 Fc region. In some embodiments, the Fc region is a human IgG2 Fc region. In some embodiments, the Fc region is a wild-type Fc region. In some embodiments, the Fc region is a mutated Fc region. In some embodiments, the Fc region is truncated at the N-terminal end by 1, 2, 3, 4, 5, 6, 7, 8, 9, or 10 amino acids, (e.g., in the hinge domain). In some embodiments, an amino acid in the hinge domain is changed to hinder undesirable disulfide bond formation. In some embodiments, a cysteine is replaced with a serine to hinder or block undesirable disulfide bond formation. In some embodiments, the Fc region is truncated at the C-terminal end by 1, 2, 3, or more amino acids. In some embodiments, the Fc region is truncated at the C-terminal end by 1 amino acid. In certain embodiments, the non-FZD polypeptide comprises SEQ ID NO:34, SEQ ID NO:35, SEQ ID NO:36, SEQ ID NO:37, or SEQ ID NO:38. In certain embodiments, the non-FZD polypeptide consists essentially of SEQ ID NO:34, SEQ ID NO:35, SEQ ID NO:36, SEQ ID NO:37, or SEQ ID NO:38. In certain embodiments, the non-FZD polypeptide consists essentially of SEQ ID NO:36 or SEQ ID NO:37.

In certain embodiments, a Wnt-binding agent is a fusion protein comprising at least a minimal Fri domain of a FZD receptor and a Fc region. As used herein, a "fusion protein" is a hybrid protein expressed by a nucleic acid molecule comprising nucleotide sequences of at least two genes. In some embodiments, the C-terminus of the first polypeptide is linked to the N-terminus of the immunoglobulin Fc region. In some embodiments, the first polypeptide (e.g., a FZD Fri domain) is directly linked to the Fc region (i.e. without an intervening linker). In some embodiments, the first polypeptide is linked to the Fc region via a linker.

As used herein, the term "linker" refers to a linker inserted between a first polypeptide (e.g., a FZD component) and a second polypeptide (e.g., a Fc region). In some embodiments, the linker is a peptide linker. Linkers should not adversely affect the expression, secretion, or bioactivity of the polypeptide. Linkers should not be antigenic and should not elicit an immune response. Suitable linkers are known to those of skill in the art and often include mixtures of glycine and serine residues and often include amino acids that are sterically unhindered. Other amino acids that can be incorporated into useful linkers include threonine and alanine residues. Linkers can range in length, for example from 1-50 amino acids in length, 1-22 amino acids in length, 1-10 amino acids in length, 1-5 amino acids in length, or 1-3 amino acids in length. Linkers may include, but are not limited to, SerGly, GGSG, GSGS, GGGS, S(GGS)n where n is 1-7, GRA, poly (Gly), poly(Ala), ESGGGGVT (SEQ ID NO:57), LESGGGGVT (SEQ ID NO:58), GRAQVT (SEQ ID NO:59), WRAQVT (SEQ ID NO:60), and ARGRAQVT (SEQ ID NO:61). As used herein, a linker is an intervening peptide sequence that does not include amino acid residues from either the C-terminus of the first polypeptide (e.g., a FZD Fri domain) or the N-terminus of the second polypeptide (e.g., the Fc region).

In some embodiments, the Wnt-binding agent comprises a FZD Fri domain, a Fc region and a linker connecting the FZD Fri domain to the Fc region. In some embodiments, the FZD Fri domain comprises SEQ ID NO:20, SEQ ID NO:30, or SEQ ID NO:33. In some embodiments, the linker comprises ESGGGGVT (SEQ ID NO:57) or LESGGGGVT (SEQ ID NO:58).

In some embodiments, the Wnt-binding agent comprises a first polypeptide comprising SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, or SEQ ID NO:33; and a second polypeptide comprising SEQ ID NO:34, SEQ ID NO:35, SEQ ID NO:36, SEQ ID NO:37, or SEQ ID NO:38, wherein the first polypeptide is directly linked to the second polypeptide. In some embodiments, the Wnt-binding agent comprises a first polypeptide comprising SEQ ID NO:20 and a second polypeptide comprising SEQ ID NO:34, SEQ ID NO:35, SEQ ID NO:36, SEQ ID NO:37, or SEQ ID NO:38. In some embodiments, the Wnt-binding agent comprises a first polypeptide comprising SEQ ID NO:20 and a second polypeptide comprising SEQ ID NO:36 or SEQ ID NO:37. In some embodiments, the Wnt-binding agent comprises a first polypeptide consisting essentially of SEQ ID NO:20 and a second polypeptide consisting essentially of SEQ ID NO:36 or SEQ ID NO:37. In some embodiments, the Wnt-binding agent comprises a first polypeptide comprising SEQ ID NO:30 and a second polypeptide comprising SEQ ID NO:34, SEQ ID NO:35, SEQ ID NO:36, SEQ ID NO:37, or SEQ ID NO:38. In some embodiments, the Wnt-binding agent comprises a first polypeptide comprising SEQ ID NO:30 and a second polypeptide comprising SEQ ID NO:36 or SEQ ID NO:37. In some embodiments, the Wnt-binding agent comprises a first polypeptide comprising SEQ ID NO:33 and a second polypeptide comprising SEQ ID NO:34, SEQ ID NO:35, SEQ ID NO:36, SEQ ID NO:37, or SEQ ID NO:38. In some embodiments, the Wnt-binding agent comprises a first polypeptide comprising SEQ ID NO:33 and a second polypeptide comprising SEQ ID NO:36, SEQ ID NO:37, or SEQ ID NO:35. In some embodiments, the Wnt-binding agent comprises a first polypeptide consisting essentially of SEQ ID NO:33 and a second polypeptide consisting essentially of SEQ ID NO:36, SEQ ID NO:37, or SEQ ID NO:35.

In some embodiments, the Wnt-binding agent comprises a first polypeptide comprising SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, or SEQ ID NO:33; and a second polypeptide comprising SEQ ID NO:34, SEQ ID NO:35, SEQ ID NO:36, SEQ ID NO:37, or SEQ ID NO:38, wherein the first polypeptide is connected to the second polypeptide by a linker. In some embodiments, the Wnt-binding agent comprises a first polypeptide comprising SEQ ID NO:20 and a second polypeptide comprising SEQ ID NO:34, SEQ ID NO:35, SEQ ID NO:36, SEQ ID NO:37, or SEQ ID NO:38. In some embodiments, the Wnt-binding agent comprises a first polypeptide comprising SEQ ID NO:20 and a second polypeptide comprising SEQ ID NO:36 or SEQ ID NO:37. In some embodiments, the Wnt-binding agent comprises a first polypeptide consisting essentially of SEQ ID NO:20 and a second polypeptide consisting essentially of SEQ ID NO:36 or SEQ ID NO:37. In some embodiments, the Wnt-binding agent comprises a first polypeptide comprising SEQ ID NO:30 and a second polypeptide comprising SEQ ID NO:34, SEQ ID NO:35, SEQ ID NO:36, SEQ ID NO:37, or SEQ ID NO:38. In some embodiments, the Wnt-binding agent comprises a first polypeptide comprising SEQ ID NO:33 and a second polypeptide comprising SEQ ID NO:34, SEQ ID NO:35, SEQ ID NO:36, SEQ ID NO:37, or SEQ ID NO:38. In some embodiments, the Wnt-binding agent comprises a first polypeptide comprising SEQ ID NO:33 and a second polypeptide comprising SEQ ID NO:36, SEQ ID NO:37, or SEQ ID NO:35. In some embodiments, the Wnt-binding agent comprises a first polypeptide consisting essentially of SEQ ID NO:33 and a second polypeptide consisting essentially of SEQ ID NO:36, SEQ ID NO:37, or SEQ ID NO:35.

In some embodiments, the Wnt-binding agent comprises a first polypeptide that is at least 95% identical to SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, or SEQ ID NO:33; and a second polypeptide comprising SEQ ID NO:34, SEQ ID NO:35, SEQ ID NO:36, SEQ ID NO:37, or SEQ ID NO:38, wherein the first polypeptide is directly linked to the second polypeptide. In some embodiments, the Wnt-binding agent comprises a first polypeptide that is at least 95% identical to SEQ ID NO:20 and a second polypeptide comprising SEQ ID NO:34, SEQ ID NO:35, SEQ ID NO:36, SEQ ID NO:37, or SEQ ID NO:38. In some embodiments, the Wnt-binding agent comprises a first polypeptide that is at least 95% identical to SEQ ID NO:30 and a second polypeptide comprising SEQ ID NO:34, SEQ ID NO:35, SEQ ID NO:36, SEQ ID NO:37, or SEQ ID NO:38. In some embodiments, the Wnt-binding agent comprises a first polypeptide that is at least 95% identical to SEQ ID NO:33 and a second polypeptide comprising SEQ ID NO:34, SEQ ID NO:35, SEQ ID NO:36, SEQ ID NO:37, or SEQ ID NO:38.

In some embodiments, the Wnt-binding agent comprises a first polypeptide that is at least 95% identical to SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, or SEQ ID NO:33; and a second polypeptide comprising SEQ ID NO:34, SEQ ID NO:35, SEQ ID NO:36, SEQ ID NO:37, or SEQ ID NO:38, wherein the first polypeptide is connected to the second polypeptide by a linker. In some embodiments, the Wnt-binding agent comprises a first polypeptide that is at least 95% identical to SEQ ID NO:20 and a second polypeptide comprising SEQ ID NO:34, SEQ ID NO:35, SEQ ID NO:36, SEQ ID NO:37, or SEQ ID NO:38. In some embodiments, the Wnt-binding agent comprises a first polypeptide that is at least 95% identical to SEQ ID NO:30 and a second polypeptide comprising SEQ ID NO:34, SEQ ID NO:35, SEQ ID NO:36, SEQ ID NO:37, or SEQ ID NO:38. In some embodiments, the Wnt-binding agent comprises a first polypeptide that is at least 95% identical to SEQ ID NO:33 and a second polypeptide comprising SEQ ID NO:34, SEQ ID NO:35, SEQ ID NO:36, SEQ ID NO:37, or SEQ ID NO:38.

FZD proteins contain a signal sequence that directs the transport of the proteins. Signal sequences (also referred to as signal peptides or leader sequences) are located at the N-terminus of nascent polypeptides. They target the polypeptide to the endoplasmic reticulum and the proteins are sorted to their destinations, for example, to the inner space of an organelle, to an interior membrane, to the cell outer membrane, or to the cell exterior via secretion. Most signal sequences are cleaved from the protein by a signal peptidase after the proteins are transported to the endoplasmic reticulum. The cleavage of the signal sequence from the polypeptide usually occurs at a specific site in the amino acid sequence and is dependent upon amino acid residues within the signal sequence. Although there is usually one specific cleavage site, more than one cleavage site may be recognized and/or used by a signal peptidase resulting in a non-homogenous N-terminus of the polypeptide. For example, the use of different cleavage sites within a signal sequence can result in a polypeptide expressed with different N-terminal amino acids. Accordingly, in some embodiments, the polypeptides described herein may comprise a mixture of polypeptides with different N-termini. In some embodiments, the N-termini differ in length by 1, 2, 3, 4, 5, 6, 7, 8, 9, 10, or more amino acids. In some embodiments, the N-termini differ in length by 1, 2, 3, 4, or 5 amino acids. In some embodiments, the polypeptide is substantially homogeneous, i.e., the polypeptides have the same N-terminus. In some embodiments, the signal sequence of the polypeptide comprises one or more (e.g., one, two, three, four, five, six, seven, eight, nine, ten, etc.) amino acid substitutions and/or deletions. In some embodiments, the signal sequence of the polypeptide comprises amino acid substitutions and/or deletions that allow one cleavage site to be dominant, thereby resulting in a substantially homogeneous polypeptide with one N-terminus.

In some embodiments, the Wnt-binding agent comprises an amino acid sequence selected from the group consisting of: SEQ ID NO:39, SEQ ID NO:40, SEQ ID NO:41, SEQ ID NO:42, SEQ ID NO:43, SEQ ID NO:44, and SEQ ID NO:45.

In certain embodiments, the Wnt-binding agent comprises the sequence of SEQ ID NO:39. In certain embodiments, the agent comprises the sequence of SEQ ID NO:39, comprising one or more (e.g., one, two, three, four, five, six, seven, eight, nine, ten, etc.) conservative substitutions. In certain embodiments, the agent comprises a sequence having at least about 90%, about 95%, or about 98% sequence identity with SEQ ID NO:39. In certain embodiments, the variants of SEQ ID NO:39 maintain the ability to bind one or more human Wnt proteins.

In certain embodiments, the Wnt-binding agent comprises the sequence of SEQ ID NO:40. In some embodiments, the Wnt-binding agent is SEQ ID NO:40. In certain alternative embodiments, the agent comprises the sequence of SEQ ID NO:40, comprising one or more (e.g., one, two, three, four, five, six, seven, eight, nine, ten, etc.) conservative substitutions. In certain embodiments, the agent comprises a sequence having at least about 90%, about 95%, or about 98% sequence identity with SEQ ID NO:40. In certain embodiments, the variants of SEQ ID NO:40 maintain the ability to bind one or more human Wnt proteins.

In certain embodiments, the Wnt-binding agent comprises the sequence of SEQ ID NO:41. In some embodiments, the Wnt-binding agent is SEQ ID NO:41. In certain alternative embodiments, the agent comprises the sequence of SEQ ID NO:41, comprising one or more (e.g., one, two, three, four, five, six, seven, eight, nine, ten, etc.) conservative substitutions. In certain embodiments, the agent comprises a sequence having at least about 90%, about 95%, or about 98% sequence identity with SEQ ID NO:41. In certain embodiments, the variants of SEQ ID NO:41 maintain the ability to bind one or more human Wnt proteins.

In some embodiments, the Wnt-binding agent is OMP-54F28. In some embodiments, the Wnt-binding agent is not OMP-54F28.

In certain embodiments, a Wnt-binding agent is a polypeptide comprising an amino acid sequence selected from the group consisting of: SEQ ID NO:39, SEQ ID NO:40, SEQ ID NO:41, SEQ ID NO:42, SEQ ID NO:43, SEQ ID NO:44, and SEQ ID NO:45. In certain embodiments, the polypeptide comprises an amino acid sequence selected from the group consisting of SEQ ID NO:39, SEQ ID NO:40, and SEQ ID NO:41. In some embodiments, a polypeptide consists essentially of an amino acid sequence selected from the group consisting of: SEQ ID NO:39, SEQ ID NO:40, and SEQ ID NO:41. In certain embodiments, the polypeptide comprises the amino acid sequence of SEQ ID NO:39. In some embodiments, the polypeptide comprises the amino acid sequence of SEQ ID NO:40. In certain embodiments, the polypeptide comprises the amino acid sequence of SEQ ID NO:41. In certain embodiments, the polypeptide comprises the amino acid sequence of SEQ ID NO:42. In certain embodiments, the polypeptide comprises the amino acid sequence of SEQ ID NO:43. In certain embodiments, the polypeptide comprises the amino acid sequence of SEQ ID NO:44. In certain embodiments, the polypeptide comprises the amino acid sequence of SEQ ID NO:45.

In some embodiments, the polypeptide is a substantially purified polypeptide comprising an amino acid sequence selected from the group consisting of SEQ ID NO:39, SEQ ID NO:40, and SEQ ID NO:41. In some embodiments, the polypeptide is a substantially purified polypeptide comprising SEQ ID NO:41. In certain embodiments, the substantially purified polypeptide consists of at least 90% of a polypeptide that has an N-terminal sequence of ASA. In some embodiments, the nascent polypeptide comprises a signal sequence that results in a substantially homogeneous polypeptide product with one N-terminal sequence.

In certain embodiments, a Wnt-binding agent comprises a Fc region of an immunoglobulin. Those skilled in the art will appreciate that some of the binding agents of this invention will comprise fusion proteins in which at least a portion of the Fc region has been deleted or otherwise altered so as to provide desired biochemical characteristics, such as increased cancer cell localization, increased tumor penetration, reduced serum half-life, or increased serum half-life, when compared with a fusion protein of approximately the same immunogenicity comprising a native or unaltered constant region. Modifications to the Fc region may include additions, deletions, or substitutions of one or more amino acids in one or more domains. The modified fusion proteins disclosed herein may comprise alterations or modifications to one or more of the two heavy chain constant domains (CH2 or CH3) or to the hinge region. In other embodiments, the entire CH2 domain may be removed (ΔCH2 constructs). In some embodiments, the omitted constant region domain is replaced by a short amino acid spacer (e.g., 10 aa residues) that provides some of the molecular flexibility typically imparted by the absent constant region domain.

In some embodiments, the modified fusion proteins are engineered to link the CH3 domain directly to the hinge region. In other embodiments, a peptide spacer is inserted between the hinge region and the modified CH2 and/or CH3 domains. For example, constructs may be expressed wherein the CH2 domain has been deleted and the remaining CH3 domain (modified or unmodified) is joined to the hinge region with a 5-20 amino acid spacer. Such a spacer may be added to ensure that the regulatory elements of the constant domain remain free and accessible or that the hinge region remains flexible. However, it should be noted that amino acid spacers may, in some cases, prove to be immunogenic and elicit an unwanted immune response against the construct. Accordingly, in certain embodiments, any spacer added to the construct will be relatively non-immunogenic so as to maintain the desired biological qualities of the fusion protein.

In some embodiments, the modified fusion proteins may have only a partial deletion of a constant domain or substitution of a few or even a single amino acid. For example, the mutation of a single amino acid in selected areas of the CH2 domain may be enough to substantially reduce Fc binding and thereby increase cancer cell localization and/or tumor penetration. Similarly, it may be desirable to simply delete that part of one or more constant region domains that control a specific effector function (e.g., complement C1q binding). Such partial deletions of the constant regions may improve selected characteristics of the binding agent (e.g., serum half-life) while leaving other desirable functions associated with the subject constant region domain intact. Moreover, as alluded to above, the constant regions of the disclosed fusion proteins may be modified through the mutation or substitution of one or more amino acids that enhances the profile of the resulting construct. In this respect it may be possible to disrupt the activity provided by a conserved binding site (e.g., Fc binding) while substantially maintaining the configuration and immunogenic profile of the modified fusion protein. In certain embodiments, the modified fusion proteins comprise the addition of one or more amino acids to the constant region to enhance desirable characteristics such as decreasing or increasing effector function, or provide for more cytotoxin or carbohydrate attachment sites.

It is known in the art that the constant region mediates several effector functions. For example, binding of the C1 component of complement to the Fc region of IgG or IgM antibodies (bound to antigen) activates the complement system. Activation of complement is important in the opsonization and lysis of cell pathogens. The activation of complement also stimulates the inflammatory response and can also be involved in autoimmune hypersensitivity. In addition, the Fc region of an immunoglobulin can bind to a cell expressing a Fc receptor (FcR). There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells, release of inflammatory mediators, placental transfer, and control of immunoglobulin production.

In some embodiments, the modified fusion proteins provide for altered effector functions that, in turn, affect the biological profile of the administered agent. For example, in some embodiments, the deletion or inactivation (through point mutations or other means) of a constant region domain may reduce Fc receptor binding of the circulating modified agent, thereby increasing cancer cell localization and/or tumor penetration. In other embodiments, the constant region modifications increase or reduce the serum half-life of the agent. In some embodiments, the constant region is modified to eliminate disulfide linkages or oligosaccharide moieties.

In certain embodiments, a modified fusion protein does not have one or more effector functions normally associated with an Fc region. In some embodiments, the agent has no antibody-dependent cell-mediated cytotoxicity (ADCC) activity, and/or no complement-dependent cytotoxicity (CDC) activity. In certain embodiments, the agent does not bind to the Fc receptor and/or complement factors. In certain embodiments, the agent has no effector function.

In some embodiments, the Wnt-binding agent (e.g., a soluble receptor) described herein is modified to reduce immunogenicity. In general, immune responses against completely normal human proteins are rare when these proteins are used as therapeutics. However, although many fusion proteins comprise polypeptides sequences that are the same as the sequences found in nature, several therapeutic fusion proteins have been shown to be immunogenic in mammals. In some studies, a fusion protein comprising a linker has been found to be more immunogenic than a fusion protein that does not contain a linker. Accordingly, in some embodiments, the polypeptides of the invention are analyzed by computation methods to predict immunogenicity. In some embodiments, the polypeptides are analyzed for the presence of T-cell and/or B-cell epitopes. If any T-cell or B-cell epitopes are identified and/or predicted, modifications to these regions (e.g., amino acid substitutions) may be made to disrupt or destroy the epitopes. Various algorithms and software that can be used to predict T-cell and/or B-cell epitopes are known in the art. For example, the software programs SYFPEITHI, HLA Bind, PEPVAC, RANKPEP, DiscoTope, ElliPro, and Antibody Epitope Prediction are all publicly available.

In some embodiments, a cell producing any of the Wnt-binding agents (e.g., soluble receptors) or polypeptides described herein is provided. In some embodiments, a composition comprising any of the Wnt-binding agents (e.g., soluble receptors) or polypeptides described herein is provided. In some embodiments, the composition comprises a polypeptide wherein at least 80%, 90%, 95%, 97%, 98%, or 99% of the polypeptide has an N-terminal sequence of ASA. In some embodiments, the composition comprises a polypeptide wherein 100% of the polypeptide has an N-terminal sequence of ASA. In some embodiments, the composition comprises a polypeptide wherein at least 80% of the polypeptide has an N-terminal sequence of ASA. In some embodiments, the composition comprises a polypeptide wherein at least 90% of the polypeptide has an N-terminal sequence of ASA. In some embodiments, the composition comprises a polypeptide wherein at least 95% of the polypeptide has an N-terminal sequence of ASA.

The polypeptides described herein can be recombinant polypeptides, natural polypeptides, or synthetic polypeptides. It will be recognized in the art that some amino acid sequences of the invention can be varied without significant effect on the structure or function of the protein. If such differences in sequence are contemplated, it should be remembered that there will be critical areas on the protein which determine activity. Thus, the invention further includes variations of the polypeptides which show substantial activity or which include regions of FZD proteins, such as the protein portions discussed herein. Such mutants include deletions, insertions, inversions, repeats, and type substitutions.

Of course, the number of amino acid substitutions a skilled artisan would make depends on many factors, including those described above. In certain embodiments, the number of substitutions for any given soluble receptor polypeptide will not be more than 50, 40, 30, 25, 20, 15, 10, 5 or 3.

Fragments or portions of the polypeptides of the present invention can be employed for producing the corresponding full-length polypeptide by peptide synthesis; therefore, the fragments can be employed as intermediates for producing the full-length polypeptides. These fragments or portion of the polypeptides can also be referred to as "protein fragments" or "polypeptide fragments".

A "protein fragment" of this invention is a portion or all of a protein which is capable of binding to one or more human Wnt proteins or one or more human FZD proteins. In some embodiments, the fragment has a high affinity for one or more human Wnt proteins. In some embodiments, the fragment has a high affinity for one or more human FZD proteins. Some fragments of Wnt-binding agents described herein are protein fragments comprising at least part of the extracellular portion of a FZD protein linked to at least part of a constant region of an immunoglobulin (e.g., a Fc region). The binding affinity of the protein fragment can be in the range of about $10^{-11}$ to $10^{-12}$ M, although the affinity can vary considerably with fragments of different sizes, ranging from $10^{-7}$ to $10^{-13}$ M. In some embodiments, the fragment is about 100 to about 200 amino acids in length and comprises a binding domain linked to at least part of a constant region of an immunoglobulin.

In some embodiments, the Wnt pathway inhibitors are polyclonal antibodies. Polyclonal antibodies can be prepared by any known method. In some embodiments, polyclonal antibodies are raised by immunizing an animal (e.g., a rabbit, rat, mouse, goat, donkey) by multiple subcutaneous or intraperitoneal injections of an antigen of interest (e.g., a purified peptide fragment, full-length recombinant protein, or fusion protein). The antigen can be optionally conjugated to a carrier such as keyhole limpet hemocyanin (KLH) or serum albumin. The antigen (with or without a carrier protein) is diluted in sterile saline and usually combined with an adjuvant (e.g., Complete or Incomplete Freund's Adjuvant) to form a stable emulsion. After a sufficient period of time, polyclonal antibodies are recovered from blood and/or ascites of the immunized animal. The polyclonal antibodies can be purified from serum or ascites according to standard methods in the art including, but not limited to, affinity chromatography, ion-exchange chromatography, gel electrophoresis, and dialysis.

In some embodiments, the Wnt pathway inhibitors are monoclonal antibodies. Monoclonal antibodies can be prepared using hybridoma methods known to one of skill in the art (see e.g., Kohler and Milstein, 1975, *Nature*, 256:495-497). In some embodiments, using the hybridoma method, a mouse, hamster, or other appropriate host animal, is immunized as described above to elicit from lymphocytes the production of antibodies that will specifically bind the immunizing antigen. In some embodiments, lymphocytes can be immunized in vitro. In some embodiments, the immunizing antigen can be a human protein or a portion thereof. In some embodiments, the immunizing antigen can be a mouse protein or a portion thereof.

Following immunization, lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen may be identified by a variety of methods including, but not limited to, immunoprecipitation, immunoblotting, and in vitro binding assay (e.g., flow cytometry, FACS, ELISA, and radioimmunoassay). The hybridomas can be propagated either in in vitro culture using standard methods (J. W. Goding, 1996, *Monoclonal Antibodies: Principles and Practice*, 3rd Edition, Academic Press, San Diego, Calif.) or in vivo as ascites tumors in an animal. The monoclonal antibodies can be purified from the culture medium or ascites fluid according to standard methods in the art including, but not limited to, affinity chromatography, ion-exchange chromatography, gel electrophoresis, and dialysis.

In certain embodiments, monoclonal antibodies can be made using recombinant DNA techniques as known to one skilled in the art. The polynucleotides encoding a monoclonal antibody are isolated from mature B-cells or hybridoma cells, such as by RT-PCR using oligonucleotide primers that specifically amplify the genes encoding the heavy and light chains of the antibody, and their sequence is determined using conventional techniques. The isolated polynucleotides encoding the heavy and light chains are then cloned into suitable expression vectors which produce the monoclonal antibodies when transfected into host cells such as *E. coli*, simian COS cells, Chinese hamster ovary (CHO) cells, or myeloma cells that do not otherwise produce immunoglobulin proteins. In other embodiments, recombinant monoclonal antibodies, or fragments thereof, can be isolated from phage display libraries (see e.g., McCafferty et al., 1990, *Nature*, 348:552-554; Clackson et al., 1991, *Nature*, 352:624-628; and Marks et al., 1991, *J. Mol. Biol.*, 222:581-597).

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted for those regions of, for example, a human antibody to generate a chimeric antibody, or for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments, the Wnt pathway inhibitor is a humanized antibody. Typically, humanized antibodies are human immunoglobulins in which residues from the CDRs are replaced by residues from a CDR of a non-human species (e.g., mouse, rat, rabbit, hamster, etc.) that have the desired specificity, affinity, and/or binding capability using methods known to one skilled in the art. In some embodiments, the Fv framework region residues of a human immunoglobulin are replaced with the corresponding residues in an antibody from a non-human species that has the desired specificity, affinity, and/or binding capability. In some embodiments, the humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two, variable domain regions containing all, or substantially all, of the CDRs that correspond to the non-human immunoglobulin whereas all, or substantially all, of the framework regions are those of a human immunoglobulin consensus sequence. In some embodiments, the humanized antibody can also comprise at least a portion of an immunoglobulin constant region or domain (Fc), typically that of a human immunoglobulin. In certain embodiments, such humanized antibodies are used therapeutically because they may reduce antigenicity and HAMA (human anti-mouse antibody) responses when administered to a human subject.

In certain embodiments, the Wnt pathway inhibitor is a human antibody. Human antibodies can be directly prepared using various techniques known in the art. In some embodiments, immortalized human B lymphocytes immunized in vitro or isolated from an immunized individual that produces an antibody directed against a target antigen can be generated (see, e.g., Cole et al., 1985, *Monoclonal Antibodies and Cancer Therapy*, Alan R. Liss, p. 77; Boerner et al., 1991, *J. Immunol.*, 147:86-95; and U.S. Pat. Nos. 5,750,373; 5,567,610; and 5,229,275). In some embodiments, the human antibody can be selected from a phage library, where that phage library expresses human antibodies (Vaughan et al., 1996, *Nature Biotechnology*, 14:309-314; Sheets et al., 1998, *PNAS*, 95:6157-6162; Hoogenboom and Winter, 1991, *J. Mol. Biol.*, 227:381; Marks et al., 1991, *J. Mol. Biol.*, 222:581). Alternatively, phage display technology can be used to produce human antibodies and antibody fragments in vitro, from immunoglobulin variable domain gene repertoires from unimmunized donors. Techniques for the generation and use of antibody phage libraries are described in U.S. Pat. Nos. 5,969,108; 6,172,197; 5,885,793; 6,521,404; 6,544,731; 6,555,313; 6,582,915; 6,593,081; 6,300,064; 6,653,068; 6,706,484; and 7,264,963; and Rothe et al., 2008, *J. Mol. Bio.*, 376:1182-1200. Affinity maturation strategies including, but not limited to, chain shuffling (Marks et al., 1992, *Bio/Technology*, 10:779-783) and site-directed mutagenesis, are known in the art and may be employed to generate high affinity human antibodies.

In some embodiments, human antibodies can be made in transgenic mice that contain human immunoglobulin loci. These mice are capable, upon immunization, of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

This invention also encompasses bispecific antibodies that specifically recognize at least one human FZD protein or at least one Wnt protein. Bispecific antibodies are capable of specifically recognizing and binding at least two different epitopes. The different epitopes can either be within the same molecule (e.g., two different epitopes on human FZD5) or on different molecules (e.g., one epitope on FZD5 and a different epitope on a second protein). In some embodiments, the bispecific antibodies are monoclonal human or humanized antibodies. In some embodiments, the antibodies can specifically recognize and bind a first antigen target, (e.g., a FZD protein) as well as a second antigen target, such as an effector molecule on a leukocyte (e.g., CD2, CD3, CD28, CD80, or CD86) or a Fc receptor (e.g., CD64, CD32, or CD16) so as to focus cellular defense mechanisms to the cell expressing the first antigen target. In some embodiments, the antibodies can be used to direct cytotoxic agents to cells which express a particular target antigen. These antibodies possess an antigen-binding arm and an arm which binds a cytotoxic agent or a radionuclide chelator, such as EOTUBE, DPTA, DOTA, or TETA.

Techniques for making bispecific antibodies are known by those skilled in the art, see for example, Millstein et al., 1983, *Nature*, 305:537-539; Brennan et al., 1985, *Science*, 229:81; Suresh et al., 1986, *Methods in Enzymol.*, 121:120; Traunecker et al., 1991, *EMBO J.*, 10:3655-3659; Shalaby et al., 1992, *J. Exp. Med.*, 175:217-225; Kostelny et al., 1992, *J. Immunol.*, 148:1547-1553; Gruber et al., 1994, *J. Immunol.*, 152:5368; U.S. Pat. No. 5,731,168; and U.S. Patent Publication No. 2011/0123532. Bispecific antibodies can be intact antibodies or antibody fragments. Antibodies with more than two valencies are also contemplated. For example, trispecific antibodies can be prepared (Tutt et al., 1991, *J. Immunol.*, 147:60). Thus, in certain embodiments the antibodies are multispecific.

In certain embodiments, the antibodies (or other polypeptides) described herein may be monospecific. For example, in certain embodiments, each of the one or more antigen-binding sites that an antibody contains is capable of binding (or binds) a homologous epitope on different proteins. In certain embodiments, an antigen-binding site of a monospecific antibody described herein is capable of binding (or binds), for example, FZD5 and FZD7 (i.e., the same epitope is found on both FZD5 and FZD7 proteins).

In certain embodiments, the Wnt pathway inhibitor is an antibody fragment comprising an antigen-binding site. Antibody fragments may have different functions or capabilities than intact antibodies; for example, antibody fragments can have increased tumor penetration. Various techniques are known for the production of antibody fragments including, but not limited to, proteolytic digestion of intact antibodies. In some embodiments, antibody fragments include a F(ab')2 fragment produced by pepsin digestion of an antibody molecule. In some embodiments, antibody fragments include a Fab fragment generated by reducing the disulfide bridges of an F(ab')2 fragment. In other embodiments, antibody fragments include a Fab fragment generated by the treatment of the antibody molecule with papain and a reducing agent. In certain embodiments, antibody fragments are produced recombinantly. In some embodiments, antibody fragments include Fv or single chain Fv (scFv) fragments. Fab, Fv, and scFv antibody fragments can be expressed in and secreted from *E. coli* or other host cells, allowing for the production of large amounts of these fragments. In some embodiments, antibody fragments are isolated from antibody phage libraries as discussed herein. For example, methods can be used for the construction of Fab expression libraries (Huse et al., 1989, *Science*, 246:1275-1281) to allow rapid and effective identification of monoclonal Fab fragments with the desired specificity for a FZD or Wnt protein or derivatives, fragments, analogs or homologs thereof. In some embodiments, antibody fragments are linear antibody fragments. In certain embodiments, antibody fragments are monospecific or bispecific. In certain embodiments, the Wnt pathway inhibitor is a scFv. Various techniques can be used for the production of single-chain antibodies specific to one or more human FZD proteins or one or more human Wnt proteins.

It can further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis). In some embodiments, an antibody is modified to decrease its serum half-life.

Heteroconjugate antibodies are also within the scope of the present invention. Heteroconjugate antibodies are composed of two covalently joined antibodies. Such antibodies have, for example, been proposed to target immune cells to unwanted cells (U.S. Pat. No. 4,676,980). It is also contemplated that the heteroconjugate antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

For the purposes of the present invention, it should be appreciated that modified antibodies can comprise any type of variable region that provides for the association of the antibody with the target (i.e., a human FZD protein or a human Wnt protein). In this regard, the variable region may comprise or be derived from any type of mammal that can be induced to mount a humoral response and generate immunoglobulins against the desired tumor-associated antigen. As such, the variable region of the modified antibodies can be, for example, of human, murine, non-human primate (e.g. cynomolgus monkeys, macaques, etc.) or rabbit origin. In some embodiments, both the variable and constant regions of the modified immunoglobulins are human. In other embodiments, the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In certain embodiments, the variable domains in both the heavy and light chains are altered by at least partial replacement of one or more CDRs and, if necessary, by partial framework region replacement and sequence modification and/or alteration. Although the CDRs may be derived from an antibody of the same class or even subclass as the antibody from which the framework regions are derived, it is envisaged that the CDRs will be derived preferably from an antibody from a different species. It may not be necessary to replace all of the CDRs with all of the CDRs from the donor variable region to transfer the antigen binding capacity of one variable domain to another. Rather, it may only be necessary to transfer those residues that are necessary to maintain the activity of the antigen-binding site.

Alterations to the variable region notwithstanding, those skilled in the art will appreciate that the modified antibodies of this invention will comprise antibodies (e.g., full-length antibodies or immunoreactive fragments thereof) in which at least a fraction of one or more of the constant region domains has been deleted or otherwise altered so as to provide desired biochemical characteristics such as increased tumor localization and/or increased serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. The modified antibodies disclosed herein may comprise alterations or modifications to one or more of the three heavy chain constant domains (CH1, CH2 or CH3) and/or to the light chain constant domain (CL). In some embodiments, one or more domains are partially or entirely deleted from the constant regions of the modified antibodies. In some embodiments, the modified antibodies will comprise domain deleted constructs or variants wherein the entire CH2 domain has been removed (ΔCH2 constructs). In some embodiments, the omitted constant region domain is replaced by a short amino acid spacer (e.g., 10 amino acid residues) that provides some of the molecular flexibility typically imparted by the absent constant region.

In some embodiments, the modified antibodies are engineered to fuse the CH3 domain directly to the hinge region of the antibody. In other embodiments, a peptide spacer is inserted between the hinge region and the modified CH2 and/or CH3 domains. For example, constructs may be expressed wherein the CH2 domain has been deleted and the remaining CH3 domain (modified or unmodified) is joined to the hinge region with a 5-20 amino acid spacer. Such a spacer may be added to ensure that the regulatory elements of the constant domain remain free and accessible or that the hinge region remains flexible. However, it should be noted that amino acid spacers may, in some cases, prove to be immunogenic and elicit an unwanted immune response against the construct. Accordingly, in certain embodiments, any spacer added to the construct will be relatively non-immunogenic so as to maintain the desired biological qualities of the modified antibodies.

In some embodiments, the modified antibodies may have only a partial deletion of a constant domain or substitution of a few or even a single amino acid. For example, the mutation of a single amino acid in selected areas of the CH2 domain may be enough to substantially reduce Fc binding and thereby increase cancer cell localization and/or tumor penetration. Similarly, it may be desirable to simply delete the part of one or more constant region domains that control a specific effector function (e.g. complement C1q binding). Such partial deletions of the constant regions may improve selected characteristics of the antibody (serum half-life) while leaving other desirable functions associated with the subject constant region domain intact. Moreover, as alluded to above, the constant regions of the disclosed antibodies may be modified through the mutation or substitution of one or more amino acids that enhances the profile of the resulting construct. In this respect it may be possible to disrupt the activity provided by a conserved binding site (e.g., Fc binding) while substantially maintaining the configuration and immunogenic profile of the modified antibody. In certain embodiments, the modified antibodies comprise the addition of one or more amino acids to the constant region to enhance desirable characteristics such as decreasing or increasing effector function or provide for more cytotoxin or carbohydrate attachment sites.

It is known in the art that the constant region mediates several effector functions. For example, binding of the C1 component of complement to the Fc region of IgG or IgM antibodies (bound to antigen) activates the complement system. Activation of complement is important in the opsonization and lysis of cell pathogens. The activation of complement also stimulates the inflammatory response and can also be involved in autoimmune hypersensitivity. In addition, the Fc region of an antibody can bind a cell expressing a Fc receptor (FcR). There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells, release of inflammatory mediators, placental transfer, and control of immunoglobulin production.

In certain embodiments, the Wnt pathway inhibitors are antibodies that provide for altered effector functions. These altered effector functions may affect the biological profile of the administered antibody. For example, in some embodiments, the deletion or inactivation (through point mutations or other means) of a constant region domain may reduce Fc receptor binding of the circulating modified antibody (e.g., anti-FZD antibody) thereby increasing cancer cell localization and/or tumor penetration. In other embodiments, the constant region modifications increase or reduce the serum half-life of the antibody. In some embodiments, the constant region is modified to eliminate disulfide linkages or oligosaccharide moieties. Modifications to the constant region in accordance with this invention may easily be made using well known biochemical or molecular engineering techniques well within the purview of the skilled artisan.

In certain embodiments, a Wnt pathway inhibitor is an antibody does not have one or more effector functions. For instance, in some embodiments, the antibody has no ADCC activity, and/or no CDC activity. In certain embodiments, the antibody does not bind an Fc receptor, and/or complement factors. In certain embodiments, the antibody has no effector function.

The present invention further embraces variants and equivalents which are substantially homologous to the chimeric, humanized, and human antibodies, or antibody fragments thereof, set forth herein. These can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art and described herein.

Thus, the present invention provides methods for producing an antibody. In some embodiments, the method for producing an antibody comprises using hybridoma techniques. In some embodiments, a method for producing an antibody that binds a human FZD protein is provided. In some embodiments, a method for producing an antibody that binds a human Wnt protein is provided. In some embodiments, the method of generating an antibody comprises screening a human phage library. In some embodiments, the antibody is identified using a membrane-bound heterodimeric molecule comprising a single antigen-binding site. In some non-limiting embodiments, the antibody is identified using methods and polypeptides described in U.S. Patent Publication No. 2011/0287979.

The present invention further provides methods of identifying an antibody that binds at least one FZD protein. In some embodiments, the antibody is identified by screening by FACS for binding to a FZD protein or a portion thereof. In some embodiments, the antibody is identified by screening using ELISA for binding to a FZD protein. In some embodiments, the antibody is identified by screening by FACS for blocking of binding of a FZD protein to a human Wnt protein. In some embodiments, the antibody is identified by screening for inhibition or blocking of Wnt pathway signaling.

The present invention further provides methods of identifying an antibody that binds at least one Wnt protein. In some embodiments, the antibody is identified by screening by FACS for binding to a Wnt protein or a portion thereof. In some embodiments, the antibody is identified by screening using ELISA for binding to a Wnt protein. In some embodiments, the antibody is identified by screening by FACS for blocking of binding of a Wnt protein to a human FZD protein. In some embodiments, the antibody is identified by screening for inhibition or blocking of Wnt pathway signaling.

In some embodiments, a method of generating an antibody to at least one human FZD protein comprises screening an antibody-expressing library for antibodies that bind a human FZD protein. In some embodiments, the antibody-expressing library is a phage library. In some embodiments, the antibody-expressing library is a mammalian cell library. In some embodiments, the screening comprises panning. In some embodiments, antibodies identified in a first screening, are screened again using a different FZD protein thereby identifying an antibody that binds the first FZD protein and a second FZD protein. In some embodiments, the antibody identified in the screening binds the first FZD protein and at least one other FZD protein. In certain embodiments, the at least one other FZD protein is selected from the group consisting of FZD1, FZD2, FZD3, FZD4, FZD5, FZD6, FZD7, FZD8, FZD9, and FZD10. In certain embodiments, the antibody identified in the screening binds FZD1, FZD2, FZD5, FZD7, and FZD8. In some embodiments, the antibody identified in the screening is a FZD antagonist. In some embodiments, the antibody identified by the methods described herein inhibits the Wnt pathway. In some embodiments, the antibody identified in the screening inhibits β-catenin signaling.

In some embodiments, a method of generating an antibody to at least one human Wnt protein comprises screening an antibody-expressing library for antibodies that bind a human Wnt protein. In some embodiments, the antibody-expressing library is a phage library. In some embodiments, the antibody-expressing library is a mammalian cell library. In some embodiments, the screening comprises panning. In some embodiments, antibodies identified in a first screening, are screened again using a different Wnt protein thereby identifying an antibody that binds a first Wnt protein and a second Wnt protein. In some embodiments, the antibody identified in the screening binds a first Wnt protein and at least one other Wnt protein. In certain embodiments, the at least one other FZD protein is selected from the group consisting of Wnt1, Wnt2, Wnt2b, Wnt3, Wnt3a, Wnt7a, Wnt7b, Wnt8a, Wnt8b, Wnt10a, and Wnt10b. In some embodiments, the antibody identified in the screening is a Wnt antagonist. In some embodiments, the antibody identified by the methods described herein inhibits the Wnt pathway. In some embodiments, the antibody identified in the screening inhibits β-catenin signaling.

In certain embodiments, the antibodies described herein are isolated. In certain embodiments, the antibodies described herein are substantially pure.

In some embodiments of the present invention, the Wnt pathway inhibitors are polypeptides. The polypeptides can be recombinant polypeptides, natural polypeptides, or synthetic polypeptides comprising an antibody, or fragment thereof, that bind at least one human FZD protein or at least one Wnt protein. It will be recognized in the art that some amino acid sequences of the invention can be varied without significant effect on the structure or function of the protein. Thus, the invention further includes variations of the polypeptides which show substantial activity or which include regions of an antibody, or fragment thereof, against a human FZD protein or a Wnt protein. In some embodiments, amino acid sequence variations of FZD-binding polypeptides or Wnt-binding polypeptides include deletions, insertions, inversions, repeats, and/or other types of substitutions.

The polypeptides, analogs and variants thereof, can be further modified to contain additional chemical moieties not normally part of the polypeptide. The derivatized moieties can improve the solubility, the biological half-life, and/or absorption of the polypeptide. The moieties can also reduce or eliminate any undesirable side effects of the polypeptides and variants. An overview for chemical moieties can be found in *Remington: The Science and Practice of Pharmacy*, $22^{st}$ *Edition*, 2012, Pharmaceutical Press, London.

The isolated polypeptides described herein can be produced by any suitable method known in the art. Such methods range from direct protein synthesis methods to constructing a DNA sequence encoding polypeptide sequences and expressing those sequences in a suitable host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof.

In some embodiments, a DNA sequence encoding a polypeptide of interest may be constructed by chemical synthesis using an oligonucleotide synthesizer. Oligonucleotides can be designed based on the amino acid sequence of the desired polypeptide and selecting those codons that are favored in the host cell in which the recombinant polypeptide of interest will be produced. Standard methods can be applied to synthesize a polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis, or another method), the polynucleotide sequences encoding a particular polypeptide of interest can be inserted into an expression vector and operatively linked to an expression control sequence appropriate for expression of the protein in a desired host. Proper assembly can be confirmed by nucleotide sequencing, restriction enzyme mapping, and/or expression of a biologically active polypeptide in a suitable host. As is well-known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding binding agents (e.g., antibodies or soluble receptors), or fragments thereof, against a human FZD protein or a Wnt protein. For example, recombinant expression vectors can be replicable DNA constructs which have synthetic or cDNA-derived DNA fragments encoding a polypeptide chain of a FZD-binding agent, a Wnt-binding agent, an anti-FZD antibody or fragment thereof, an anti-Wnt antibody or fragment thereof, or a FZD-Fc soluble receptor operatively linked to suitable transcriptional and/or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences. Regulatory elements can include an operator sequence to control transcription. The ability to replicate in a host, usually conferred by an origin of replication, and a selection gene to facilitate recognition of transformants can additionally be incorporated. DNA regions are "operatively linked" when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. In some embodiments, structural elements intended for use in yeast expression systems include a leader sequence enabling extracellular secretion of translated protein by a host cell. In other embodiments, where recombinant protein is expressed without a leader or transport sequence, it can include an N-terminal methionine residue. This residue can optionally be subsequently cleaved from the expressed recombinant protein to provide a final product.

The choice of an expression control sequence and an expression vector depends upon the choice of host. A wide variety of expression host/vector combinations can be employed. Useful expression vectors for eukaryotic hosts include, for example, vectors comprising expression control sequences from SV40, bovine papilloma virus, adenovirus, and cytomegalovirus. Useful expression vectors for bacterial hosts include known bacterial plasmids, such as plasmids from *E. coli*, including pCR1, pBR322, pMB9 and their derivatives, and wider host range plasmids, such as M13 and other filamentous single-stranded DNA phages.

Suitable host cells for expression of a FZD-binding or Wnt-binding agent (or a protein to use as an antigen) include prokaryotes, yeast cells, insect cells, or higher eukaryotic cells under the control of appropriate promoters. Prokaryotes include gram-negative or gram-positive organisms, for example *E. coli* or *Bacillus*. Higher eukaryotic cells include established cell lines of mammalian origin as described below. Cell-free translation systems may also be employed. Appropriate cloning and expression vectors for use with bacterial, fungal, yeast, and mammalian cellular hosts are described by Pouwels et al. (1985, *Cloning Vectors: A Laboratory Manual*, Elsevier, New York, N.Y.). Additional information regarding methods of protein production, including antibody production, can be found, e.g., in U.S. Patent Publication No. 2008/0187954, U.S. Pat. Nos. 6,413,746 and 6,660,501, and International Patent Publication No. WO 2004/009823.

Various mammalian culture systems are used to express recombinant polypeptides. Expression of recombinant proteins in mammalian cells may be preferred because such proteins are generally correctly folded, appropriately modified, and biologically functional. Examples of suitable mammalian host cell lines include COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived), BHK (hamster kidney fibroblast-derived), HEK-293 (human embryonic kidney-derived) cell lines and variants thereof. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences.

Expression of recombinant proteins in insect cell culture systems (e.g., baculovirus) also offers a robust method for producing correctly folded and biologically functional proteins. Baculovirus systems for production of heterologous proteins in insect cells are well-known to those of skill in the art (see, e.g., Luckow and Summers, 1988, *Bio/Technology*, 6:47).

Thus, the present invention provides cells comprising the FZD-binding agents or the Wnt-binding agents described herein. In some embodiments, the cells produce the binding agents (e.g., antibodies or soluble receptors) described herein. In certain embodiments, the cells produce an antibody. In certain embodiments, the cells produce antibody 18R5. In some embodiments, the cells produce a soluble receptor. In some embodiments, the cells produce a FZD-Fc soluble receptor. In some embodiments, the cells produce a FZD8-Fc soluble receptor. In some embodiments, the cells produce FZD8-Fc soluble receptor 54F28.

The proteins produced by a transformed host can be purified according to any suitable method. Standard methods include chromatography (e.g., ion exchange, affinity, and sizing column chromatography), centrifugation, differential solubility, or by any other standard technique for protein purification. Affinity tags such as hexa-histidine, maltose binding domain, influenza coat sequence, and glutathione-S-transferase can be attached to the protein to allow easy purification by passage over an appropriate affinity column. Isolated proteins can also be physically characterized using such techniques as proteolysis, mass spectrometry (MS), nuclear magnetic resonance (NMR), high performance liquid chromatography (HPLC), and x-ray crystallography.

In some embodiments, supernatants from expression systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. In some embodiments, an anion exchange resin can be employed, for example, a matrix or substrate having pendant diethylaminoethyl (DEAE) groups. The matrices can be acrylamide, agarose, dextran, cellulose, or other types commonly employed in protein purification. In some embodiments, a cation exchange step can be employed. Suitable cation exchangers include various insoluble matrices comprising sulfopropyl or carboxymethyl groups. In some embodiments, a hydroxyapatite media can be employed, including but not limited to, ceramic hydroxyapatite (CHT). In certain embodiments, one or more reverse-phase HPLC steps employing hydrophobic RP-HPLC media, e.g., silica gel having pendant methyl or other aliphatic groups, can be employed to further purify a binding agent. Some or all of the foregoing purification steps, in various combinations, can also be employed to provide a homogeneous recombinant protein.

In some embodiments, recombinant protein produced in bacterial culture can be isolated, for example, by initial extraction from cell pellets, followed by one or more concentration, salting-out, aqueous ion exchange, or size exclusion chromatography steps. HPLC can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Publication Nos. 2008/0312425, 2008/0177048, and 2009/0187005.

In certain embodiments, the Wnt-binding agent or the FZD-binding agent is a polypeptide that is not an antibody. A variety of methods for identifying and producing non-antibody polypeptides that bind with high affinity to a protein target are known in the art. See, e.g., Skerra, 2007, *Curr. Opin. Biotechnol.*, 18:295-304; Hosse et al., 2006, *Protein Science*, 15:14-27; Gill et al., 2006, *Curr. Opin. Biotechnol.*, 17:653-658; Nygren, 2008, *FEBS J.*, 275:2668-76; and Skerra, 2008, *FEBS J.*, 275:2677-83. In certain embodiments, phage display technology may be used to produce and/or identify a FZD-binding or Wnt-binding polypeptide. In certain embodiments, the polypeptide comprises a protein scaffold of a type selected from the group consisting of protein A, protein G, a lipocalin, a fibronectin domain, an ankyrin consensus repeat domain, and thioredoxin.

In certain embodiments, the binding agents can be used in any one of a number of conjugated (i.e. an immunoconjugate or radioconjugate) or non-conjugated forms. In certain embodiments, antibodies can be used in a non-conjugated form to harness the subject's natural defense mechanisms including complement-dependent cytotoxicity and antibody dependent cellular toxicity to eliminate the malignant or cancer cells.

In some embodiments, the binding agent is conjugated to a cytotoxic agent. In some embodiments, the cytotoxic agent is a chemotherapeutic agent including, but not limited to, methotrexate, adriamicin, doxorubicin, melphalan, mitomycin C, chlorambucil, daunorubicin or other intercalating agents. In some embodiments, the cytotoxic agent is an enzymatically active toxin of bacterial, fungal, plant, or animal origin, or fragments thereof, including, but not limited to, diphtheria A chain, nonbinding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, Sapaonaria officinalis inhibitor, gelonin, mitogellin, restrictocin, phenomycin, enomycin, and the tricothecenes. In some embodiments, the cytotoxic agent is a radioisotope to produce a radioconjugate or a radioconjugated antibody. A variety of radionuclides are available for the production of radioconjugated antibodies including, but not limited to, $^{90}Y$, $^{125}I$, $^{131}I$, $^{123}I$, $^{111}In$, $^{131}In$, $^{105}Rh$, $^{153}Sm$, $^{67}Cu$, $^{67}Ga$, $^{166}Ho$, $^{177}Lu$, $^{186}Re$, $^{188}Re$ and $^{212}Bi$. In some embodiments, conjugates of an antibody and one or more small molecule toxins, such as a calicheamicin, maytansinoids, a trichothene, and CC1065, and the derivatives of these toxins that have toxin activity, can be produced. In certain embodiments, conjugates of an antibody and a cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

In certain embodiments, the Wnt pathway inhibitor (e.g., antibody or soluble receptor) is an antagonist of at least one Wnt protein (i.e., 1, 2, 3, 4, 5, 6, 7, 8, 9, or 10 Wnt proteins). In certain embodiments, the Wnt pathway inhibitor inhibits activity of the Wnt protein(s) to which it binds. In certain embodiments, the Wnt pathway inhibitor inhibits at least about 10%, at least about 20%, at least about 30%, at least about 50%, at least about 75%, at least about 90%, or about 100% of the activity of the human Wnt protein(s) to which it binds.

In certain embodiments, the Wnt pathway inhibitor (e.g., antibody or soluble receptor) inhibits binding of at least one human Wnt to an appropriate receptor. In certain embodiments, the Wnt pathway inhibitor inhibits binding of at least one human Wnt protein to one or more human FZD proteins. In some embodiments, the at least one Wnt protein is selected from the group consisting of: Wnt1, Wnt2, Wnt2b/13, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16. In some embodiments, the one or more human FZD proteins are selected from the group consisting of: FZD1, FZD2, FZD3, FZD4, FZD5, FZD6, FZD7, FZD8, FZD9, and FZD10. In certain embodiments, the Wnt pathway inhibitor inhibits binding of one or more Wnt proteins to FZD1, FZD2, FZD4, FZD5, FZD7, and/or FZD8. In certain embodiments, the Wnt pathway inhibitor inhibits binding of one or more Wnt proteins to FZD8. In certain embodiments, the inhibition of binding of a particular Wnt to a FZD protein by a Wnt pathway inhibitor is at least about 10%, at least about 25%, at least about 50%, at least about 75%, at least about 90%, or at least about 95%. In certain embodiments, an agent that inhibits binding of a Wnt to a FZD protein, also inhibits Wnt pathway signaling. In certain embodiments, a Wnt pathway inhibitor that inhibits human Wnt pathway signaling is an antibody. In certain embodiments, a Wnt pathway inhibitor that inhibits human Wnt pathway signaling is a FZD-Fc soluble receptor. In certain embodiments, a Wnt pathway inhibitor that inhibits human Wnt pathway signaling is a FZD8-Fc soluble receptor. In certain embodiments, a Wnt pathway inhibitor that inhibits human Wnt pathway signaling is soluble receptor 54F28.

In certain embodiments, the Wnt pathway inhibitors (e.g., antibody or soluble receptor) described herein are antagonists of at least one human Wnt protein and inhibit Wnt activity. In certain embodiments, the Wnt pathway inhibitor inhibits Wnt activity by at least about 10%, at least about 20%, at least about 30%, at least about 50%, at least about 75%, at least about 90%, or about 100%. In some embodiments, the Wnt pathway inhibitor inhibits activity of one, two, three, four, five or more Wnt proteins. In some embodiments, the Wnt pathway inhibitor inhibits activity of at least one human Wnt protein selected from the group consisting of: Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16. In some embodiments, the Wnt-binding agent binds at least one Wnt protein selected from the group consisting of Wnt1, Wnt2, Wnt2b, Wnt3, Wnt3a, Wnt7a, Wnt7b, Wnt8a, Wnt8b, Wnt10a, and Wnt10b. In certain embodiments, the at least one Wnt protein is selected from the group consisting of Wnt1, Wnt2, Wnt2b, Wnt3, Wnt3a, Wnt8a, Wnt8b, Wnt10a, and Wnt10b. In certain embodiments, a Wnt pathway inhibitor that inhibits human Wnt activity is an antibody. In certain embodiments, a Wnt pathway inhibitor that inhibits human Wnt activity is a FZD-Fc soluble receptor. In certain embodiments, a Wnt pathway inhibitor that inhibits human Wnt activity is a FZD8-Fc soluble receptor. In certain embodiments, a Wnt pathway inhibitor that inhibits human Wnt activity is soluble receptor 54F28.

In certain embodiments, the Wnt pathway inhibitor described herein is an antagonist of at least one human FZD protein and inhibits FZD activity. In certain embodiments, the Wnt pathway inhibitor inhibits FZD activity by at least about 10%, at least about 20%, at least about 30%, at least about 50%, at least about 75%, at least about 90%, or about 100%. In some embodiments, the Wnt pathway inhibitor inhibits activity of one, two, three, four, five or more FZD proteins. In some embodiments, the Wnt pathway inhibitor inhibits activity of at least one human FZD protein selected from the group consisting of: FZD1, FZD2, FZD3, FZD4, FZD5, FZD6, FZD7, FZD8, FZD9, and FZD10. In certain embodiments, the Wnt pathway inhibitor inhibits activity of FZD1, FZD2, FZD4, FZD5, FZD7, and/or FZD8. In certain embodiments, the Wnt pathway inhibitor inhibits activity of FZD8. In some embodiments, the Wnt pathway inhibitor is an anti-FZD antibody. In certain embodiments, the Wnt pathway inhibitor is anti-FZD antibody 18R5.

In certain embodiments, the Wnt pathway inhibitor described herein is an antagonist of at least one human Wnt protein and inhibits Wnt signaling. In certain embodiments, the Wnt pathway inhibitor inhibits Wnt signaling by at least about 10%, at least about 20%, at least about 30%, at least about 50%, at least about 75%, at least about 90%, or about 100%. In some embodiments, the Wnt pathway inhibitor inhibits signaling by one, two, three, four, five or more Wnt proteins. In some embodiments, the Wnt pathway inhibitor inhibits signaling of at least one Wnt protein selected from the group consisting of Wnt1, Wnt2, Wnt2b, Wnt3, Wnt3a, Wnt7a, Wnt7b, Wnt8a, Wnt8b, Wnt10a, and Wnt10b. In certain embodiments, a Wnt pathway inhibitor that inhibits Wnt signaling is an antibody. In certain embodiments, a Wnt pathway inhibitor that inhibits Wnt signaling is a soluble receptor. In certain embodiments, a Wnt pathway inhibitor that inhibits Wnt signaling is a FZD-Fc soluble receptor. In certain embodiments, a Wnt pathway inhibitor that inhibits Wnt signaling is a FZD8-Fc soluble receptor. In certain embodiments, a Wnt pathway inhibitor that inhibits Wnt signaling is soluble receptor 54F28.

In certain embodiments, a Wnt pathway inhibitor described herein is an antagonist of β-catenin signaling. In certain embodiments, the Wnt pathway inhibitor inhibits β-catenin signaling by at least about 10%, at least about 20%, at least about 30%, at least about 50%, at least about 75%, at least about 90%, or about 100%. In certain embodiments, a Wnt pathway inhibitor that inhibits β-catenin signaling is an antibody. In certain embodiments, a Wnt pathway inhibitor that inhibits β-catenin signaling is an anti-FZD antibody. In certain embodiments, a Wnt pathway inhibitor that inhibits β-catenin signaling is antibody 18R5. In certain embodiments, a Wnt pathway inhibitor that inhibits β-catenin signaling is a soluble receptor. In certain embodiments, a Wnt pathway inhibitor that inhibits β-catenin signaling is a FZD-Fc soluble receptor. In certain embodiments, a Wnt pathway inhibitor that inhibits β-catenin signaling is a FZD8-Fc soluble receptor.

In certain embodiments, the Wnt pathway inhibitor described herein inhibits binding of at least one Wnt protein to a receptor. In certain embodiments, the Wnt pathway inhibitor inhibits binding of at least one human Wnt protein to one or more of its receptors. In some embodiments, the Wnt pathway inhibitor inhibits binding of at least one Wnt protein to at least one FZD protein. In some embodiments, the Wnt-binding agent inhibits binding of at least one Wnt protein to FZD1, FZD2, FZD3, FZD4, FDZ5, FDZ6, FDZ7, FDZ8, FDZ9, and/or FZD10. In certain embodiments, the inhibition of binding of at least one Wnt to at least one FZD protein is at least about 10%, at least about 25%, at least about 50%, at least about 75%, at least about 90%, or at least about 95%. In certain embodiments, a Wnt pathway inhibitor that inhibits binding of at least one Wnt to at least one FZD protein further inhibits Wnt pathway signaling and/or β-catenin signaling. In certain embodiments, a Wnt pathway inhibitor that inhibits binding of at least one human Wnt to at least one FZD protein is an antibody. In certain embodiments, a Wnt pathway inhibitor that inhibits binding of at least one human Wnt to at least one FZD protein is an anti-FZD antibody. In certain embodiments, a Wnt pathway inhibitor that inhibits binding of at least one human Wnt to at least one FZD protein is antibody 18R5. In certain embodiments, a Wnt pathway inhibitor that inhibits binding of at least one human Wnt to at least one FZD protein is a soluble receptor. In certain embodiments, a Wnt pathway inhibitor that inhibits binding of at least one human Wnt to at least one FZD protein is a FZD-Fc soluble receptor. In certain embodiments, a Wnt pathway inhibitor that inhibits binding of at least one human Wnt to at least one FZD protein is a FZD8-Fc soluble receptor. In certain embodiments, a Wnt pathway inhibitor that inhibits binding of at least one human Wnt to at least one FZD protein is FZD8-Fc soluble receptor 54F28.

In certain embodiments, the Wnt pathway inhibitor described herein blocks binding of at least one Wnt to a receptor. In certain embodiments, the Wnt pathway inhibitor blocks binding of at least one human Wnt protein to one or more of its receptors. In some embodiments, the Wnt pathway inhibitor blocks binding of at least one Wnt to at least one FZD protein. In some embodiments, the Wnt pathway inhibitor blocks binding of at least one Wnt protein to FZD1, FZD2, FZD3, FZD4, FDZ5, FDZ6, FDZ7, FDZ8, FDZ9, and/or FZD10. In certain embodiments, the blocking of binding of at least one Wnt to at least one FZD protein is at least about 10%, at least about 25%, at least about 50%, at least about 75%, at least about 90%, or at least about 95%. In certain embodiments, a Wnt pathway inhibitor that blocks binding of at least one Wnt protein to at least one FZD protein further inhibits Wnt pathway signaling and/or β-catenin signaling. In certain embodiments, a Wnt pathway inhibitor that blocks binding of at least one human Wnt to at least one FZD protein is an antibody. In certain embodiments, a Wnt pathway inhibitor that blocks binding of at least one human Wnt to at least one FZD protein is an anti-FZD antibody. In certain embodiments, a Wnt pathway inhibitor that blocks binding of at least one human Wnt to at least one FZD protein is antibody 18R5. In certain embodiments, a Wnt pathway inhibitor that blocks binding of at least one human Wnt to at least one FZD protein is a soluble receptor. In certain embodiments, a Wnt pathway inhibitor that blocks binding of at least one human Wnt to at least one FZD protein is a FZD-Fc soluble receptor. In certain embodiments, a Wnt pathway inhibitor that blocks binding of at least one human Wnt to at least one FZD protein is a FZD8-Fc soluble receptor. In certain embodiments, a Wnt pathway inhibitor that blocks binding of at least one human Wnt to at least one FZD protein is soluble receptor 54F28.

In certain embodiments, the Wnt pathway inhibitor described herein inhibits Wnt pathway signaling. It is understood that a Wnt pathway inhibitor that inhibits Wnt pathway signaling may, in certain embodiments, inhibit signaling by one or more receptors in the Wnt signaling pathway but not necessarily inhibit signaling by all receptors. In certain alternative embodiments, Wnt pathway signaling by all human receptors may be inhibited. In certain embodiments, Wnt pathway signaling by one or more receptors selected from the group consisting of FZD1, FZD2, FZD3, FZD4, FDZ5, FDZ6, FDZ7, FDZ8, FDZ9, and FZD10 is inhibited. In certain embodiments, the inhibition of Wnt pathway signaling by a Wnt pathway inhibitor is a reduction in the level of Wnt pathway signaling of at least about 10%, at least about 25%, at least about 50%, at least about 75%, at least about 90%, or at least about 95%. In some embodiments, a Wnt pathway inhibitor that inhibits Wnt pathway signaling is an antibody. In some embodiments, a Wnt pathway inhibitor that inhibits Wnt pathway signaling is an anti-FZD antibody. In some embodiments, a Wnt pathway inhibitor that inhibits Wnt pathway signaling is antibody 18R5. In some embodiments, a Wnt pathway inhibitor that inhibits Wnt pathway signaling is a soluble receptor. In some embodiments, a Wnt pathway inhibitor that inhibits Wnt pathway signaling is a FZD-Fc soluble receptor. In some embodiments, a Wnt pathway inhibitor that inhibits Wnt pathway signaling is a FZD8-Fc soluble receptor. In some embodiments, a Wnt pathway inhibitor that inhibits Wnt pathway signaling is soluble receptor 54F28.

In certain embodiments, the Wnt pathway inhibitor described herein inhibits activation of β-catenin. It is understood that a Wnt pathway inhibitor that inhibits activation of β-catenin may, in certain embodiments, inhibit activation of β-catenin by one or more receptors, but not necessarily inhibit activation of β-catenin by all receptors. In certain alternative embodiments, activation of β-catenin by all human receptors may be inhibited. In certain embodiments, activation of β-catenin by one or more receptors selected from the group consisting of FZD1, FZD2, FZD3, FZD4, FDZ5, FDZ6, FDZ7, FDZ8, FDZ9, and FZD10 is inhibited. In certain embodiments, the inhibition of activation of β-catenin by a Wnt-binding agent is a reduction in the level of activation of β-catenin of at least about 10%, at least about 25%, at least about 50%, at least about 75%, at least about 90%, or at least about 95%. In some embodiments, a Wnt pathway inhibitor that inhibits activation of β-catenin is an antibody. In some embodiments, a Wnt pathway inhibitor that inhibits activation of β-catenin is an anti-FZD antibody. In some embodiments, a Wnt pathway inhibitor that inhibits activation of β-catenin is antibody 18R5. In some embodiments, a Wnt pathway inhibitor that inhibits activation of β-catenin is a soluble receptor. In some embodiments, a Wnt pathway inhibitor that inhibits activation of β-catenin is a FZD-Fc soluble receptor. In some embodiments, a Wnt pathway inhibitor that inhibits activation of β-catenin is a FZD8-Fc soluble receptor. In some embodiments, a Wnt pathway inhibitor that inhibits activation of β-catenin is soluble receptor 54F28.

In vivo and in vitro assays for determining whether a Wnt pathway inhibitor inhibits β-catenin signaling are known in the art. For example, cell-based, luciferase reporter assays utilizing a TCF/Luc reporter vector containing multiple copies of the TCF-binding domain upstream of a firefly luciferase reporter gene may be used to measure β-catenin signaling levels in vitro (Gazit et al., 1999, Oncogene, 18; 5959-66; TOPflash, Millipore, Billerica Mass.). The level of β-catenin signaling in the presence of one or more Wnt proteins (e.g., Wnt(s) expressed by transfected cells or provided by Wnt-conditioned media) in the presence of a binding agent is compared to the level of signaling without the binding agent present. In addition to the TCF/Luc reporter assay, the effect of a binding agent (or candidate agent) on β-catenin signaling may be measured in vitro or in vivo by measuring the effect of the agent on the level of expression of β-catenin-regulated genes, such as c-myc (He et al., 1998, Science, 281:1509-12), cyclin D1 (Tetsu et al., 1999, Nature, 398:422-6), and/or fibronectin (Gradl et al. 1999, Mol. Cell. Biol., 19:5576-87). In certain embodiments, the effect of a binding agent on β-catenin signaling may also be assessed by measuring the effect of the agent on the phosphorylation state of Dishevelled-1, Dishevelled-2, Dishevelled-3, LRP5, LRP6, and/or β-catenin.

In certain embodiments, a Wnt pathway inhibitor has one or more of the following effects: inhibit proliferation of tumor cells, inhibit tumor growth, reduce the frequency of cancer stem cells in a tumor, reduce the tumorigenicity of a tumor, reduce the tumorigenicity of a tumor by reducing the frequency of cancer stem cells in the tumor, trigger cell death of tumor cells, induce cells in a tumor to differentiate, differentiate tumorigenic cells to a non-tumorigenic state, induce expression of differentiation markers in the tumor cells, prevent metastasis of tumor cells, or decrease survival of tumor cells.

In certain embodiments, a Wnt pathway inhibitor is capable of inhibiting tumor growth. In certain embodiments, a Wnt pathway inhibitor is capable of inhibiting tumor growth in vivo (e.g., in a xenograft mouse model, and/or in a human having cancer). In some embodiments, the tumor is a tumor selected from the group consisting of colorectal tumor, colon tumor, pancreatic tumor, lung tumor, ovarian tumor, liver tumor, breast tumor, kidney tumor, prostate tumor, gastrointestinal tumor, melanoma, cervical tumor, bladder tumor, glioblastoma, and head and neck tumor. In certain embodiments, the tumor is melanoma. In certain embodiments, the tumor is a colorectal tumor. In certain embodiments, the tumor is a pancreatic tumor. In certain embodiments, the tumor is a breast tumor. In certain embodiments, the tumor is a Wnt-dependent tumor.

In certain embodiments, a Wnt pathway inhibitor is capable of reducing the tumorigenicity of a tumor. In certain embodiments, a Wnt pathway inhibitor is capable of reducing the tumorigenicity of a tumor comprising cancer stem cells in an animal model, such as a mouse xenograft model. In certain embodiments, the number or frequency of cancer stem cells in a tumor is reduced by at least about two-fold, about three-fold, about five-fold, about ten-fold, about 50-fold, about 100-fold, or about 1000-fold. In certain embodiments, the reduction in the number or frequency of cancer stem cells is determined by limiting dilution assay using an animal model. Additional examples and guidance regarding the use of limiting dilution assays to determine a reduction in the number or frequency of cancer stem cells in a tumor can be found, e.g., in International Publication No. WO 2008/042236, and U.S. Patent Publication Nos. 2008/0064049 and 2008/0178305.

In certain embodiments, the Wnt pathway inhibitors described herein are active in vivo for at least 1 hour, at least about 2 hours, at least about 5 hours, at least about 10 hours, at least about 24 hours, at least about 2 days, at least about 3 days, at least about 1 week, or at least about 2 weeks. In certain embodiments, the Wnt pathway inhibitor is an IgG (e.g., IgG1 or IgG2) antibody that is active in vivo for at least 1 hour, at least about 2 hours, at least about 5 hours, at least about 10 hours, at least about 24 hours, at least about 2 days, at least about 3 days, at least about 1 week, or at least about 2 weeks. In certain embodiments, the Wnt pathway inhibitor is a fusion protein that is active in vivo for at least 1 hour, at least about 2 hours, at least about 5 hours, at least about 10 hours, at least about 24 hours, at least about 2 days, at least about 3 days, at least about 1 week, or at least about 2 weeks.

In certain embodiments, the Wnt pathway inhibitors described herein have a circulating half-life in mice, cynomolgus monkeys, or humans of at least about 5 hours, at least about 10 hours, at least about 24 hours, at least about 2 days, at least about 3 days, at least about 1 week, or at least about 2 weeks. In certain embodiments, the Wnt pathway inhibitor is an IgG (e.g., IgG1 or IgG2) antibody that has a circulating half-life in mice, cynomolgus monkeys, or humans of at least about 5 hours, at least about 10 hours, at least about 24 hours, at least about 2 days, at least about 3 days, at least about 1 week, or at least about 2 weeks. In certain embodiments, the Wnt pathway inhibitor is a fusion protein that has a circulating half-life in mice, cynomolgus monkeys, or humans of at least about 5 hours, at least about 10 hours, at least about 24 hours, at least about 2 days, at least about 3 days, at least about 1 week, or at least about 2 weeks. Methods of increasing (or decreasing) the half-life of agents such as polypeptides and antibodies are known in the art. For example, known methods of increasing the circulating half-life of IgG antibodies include the introduction of mutations in the Fc region which increase the pH-dependent binding of the antibody to the neonatal Fc receptor (FcRn) at pH 6.0 (see, e.g., U.S. Patent Publication Nos. 2005/0276799, 2007/0148164, and 2007/0122403). Known methods of increasing the circulating half-life of antibody fragments lacking the Fc region include such techniques as PEGylation.

III. METHODS OF USE AND PHARMACEUTICAL COMPOSITIONS

The present invention provides methods of treating diseases such as cancer with a Wnt pathway inhibitor, while screening for, monitoring, reducing, preventing, attenuating, and/or mitigating side effects and/or toxicities, including, but not limited to skeletal-related side effects and/or toxicities associated with the Wnt pathway inhibitor. Side effects and/or toxicities associated with cancer treatment may include, but are not limited to, fatigue, vomiting, nausea, diarrhea, pain, hair loss, neutropenia, anemia, thrombocytopenia, cardiovascular-related complications, skeletal-related complications, and any combination thereof. As used herein, "skeletal-related complications" (e.g., skeletal-related side effects and/or toxicities) include but are not limited to, osteopenia, osteoporosis, bone fractures (including silent fractures), and combinations thereof. Thus, in some aspects and/or embodiments of the methods described herein, the screening for, monitoring, reducing, preventing, attenuating, and/or mitigating skeletal-related side effects and/or toxicities is screening for, monitoring, reducing, preventing, attenuating, and/or mitigating bone density loss and/or fracture risk. Often bone density loss is asymptomatic and/or early signs of skeletal-related side effects are not evident with, for example, bone density scanning.

Bone metabolism is a continuous dual process of bone formation and bone destruction. Bone destruction is referred to as bone resorption and is carried out by osteoclasts, while bone formation is carried out by osteoblasts. In adults, the dual processes of bone formation and bone destruction are in balance, maintaining a constant, homeostatically controlled amount of bone. Bone metabolism may be assessed and/or monitored by measurement of biomarkers (e.g., enzymes, proteins, and/or degradation products) released during bone formation and bone resorption. These biomarkers are often referred to as "bone turnover markers", and include bone formation markers and bone resorption markers. Bone formation biomarkers include serum total alkaline phosphatase, serum bone-specific alkaline phosphatase, serum osteocalcin, serum procollagen type 1 amino-terminal propeptide (P1NP) and serum procollagen type 1 carboxy-terminal propeptide (P1CP). Bone resorption biomarkers include, urinary hydroxyproline, urinary total pyridinoline (PYD), urinary free deoxypryidinoline (DPD), urinary collagen type 1 cross-linked N-telopeptide (NTX), urinary or serum collagen type 1 cross-linked C-telopeptide (CTX), bone sialoprotein (BSP), and tartrate-resistant acid phosphatase 5b.

Approximately 90% of the organic matrix of bone is type 1 collagen, a helical protein that is cross-linked at the N- and C-terminal ends of the molecule. During bone resorption, osteoclasts secrete a mixture of acid and neutral proteases that degrade the collagen fibrils into molecular fragments including C-telopeptide (CTX). As bone ages, the alpha form of aspartic acid present in CTX converts to the beta form (β-CTX). β-CTX is released into the bloodstream during bone resorption and serves as a specific marker for the degradation of mature type 1 collagen.

Bone turnover markers have been used to monitor anti-resorptive therapies (e.g., hormone replacement therapies and bisphosphonate therapies) in post-menopausal women, as well as in individuals diagnosed with osteopenia. In addition, bone turnover markers may be used to assess drug-induced osteoporosis resulting from therapy with hormonal and non-hormonal drugs. These drugs may include, but are not limited to, glucocorticoids, thyroid hormone, aromatase inhibitors, ovarian suppressing agents, androgen deprivation therapy, thiazolidinediones, selective serotonin reuptake inhibitors, anticonvulsants, heparins, oral anticoagulants, loop diuretics, calcineurin inhibitors, anti-retroviral therapy, and proton pump inhibitors. Bone turnover markers have not previously been used to assess the effect of Wnt pathway inhibitors. Accordingly, in some embodiments, the present invention provides methods for using bone turnover markers to monitor skeletal-related side effects and/or toxicities in subjects being treated with a Wnt pathway inhibitor. In some embodiments, the methods use a bone formation biomarker to monitor and/or detect decreased levels of bone formation. In some embodiments, the methods use a bone resorption biomarker to monitor and/or detect increased levels of bone resorption. In some embodiments, monitoring the level of a bone formation biomarker gives an early indication of decreased levels of bone formation and/or increased risk of bone fracture, osteopenia, and/or osteoporosis. In some embodiments, monitoring the level of a bone resorption biomarker gives an early indication of increased levels of bone resorption and/or increased risk of bone fracture, osteopenia, and/or osteoporosis. In some embodiments, the methods detect skeletal-related side effects and/or toxicities prior to any evidence of skeletal dysfunction as evaluated by bone density scans.

In certain embodiments, the skeletal-related side effects and/or toxicities that are detected, identified, monitored, reduced, prevented, attenuated, and/or screened for are skeletal-related side effects and/or toxicities caused by, associated with, and/or related to administration of a Wnt pathway inhibitor or treatment with a Wnt pathway inhibitor. In certain embodiments, the skeletal-related side effects and/or toxicities are related to the Wnt pathway inhibitor. In certain embodiments, the skeletal-related side effects and/or toxicities are related to the activity of the Wnt pathway inhibitor. In certain embodiments, the skeletal-related side effects and/or toxicities are related to a Wnt pathway inhibitor that is an anti-FZD antibody. In certain embodiments, the skeletal-related side effects and/or toxicities are related to a Wnt pathway inhibitor that is anti-FZD antibody OMP-18R5. In certain embodiments, the skeletal-related side effects and/or toxicities are related to the Wnt pathway inhibitor that is a FZD soluble receptor. In certain embodiments, the skeletal-related side effects and/or toxicities are related to the Wnt pathway inhibitor that is a FZD8-Fc soluble receptor. In certain embodiments, the skeletal-related side effects and/or toxicities are related to the Wnt pathway inhibitor that is FZD8-Fc soluble receptor 54F28.

The invention provides methods for selecting a subject for treatment with a Wnt pathway inhibitor, comprising: determining the level of a biomarker in a sample, and selecting the subject for treatment with the Wnt pathway inhibitor if the level of the biomarker is below a predetermined level. In some embodiments, the methods for selecting a subject for treatment with a Wnt pathway inhibitor comprise: obtaining a biological sample from the subject, determining the level of a biomarker in the sample, and selecting the subject for treatment with the Wnt pathway inhibitor if the level of the biomarker is below a predetermined level. In some embodiments, the biomarker is a bone turnover marker. In some embodiments, the bone turnover marker is a bone resorption biomarker. In some embodiments, the bone resorption biomarker is β-CTX.

In some embodiments, the method of selecting a subject for treatment with a Wnt pathway inhibitor comprises: obtaining a biological sample from the subject, determining the level of a bone turnover marker in the sample, and selecting the subject for treatment with the Wnt pathway inhibitor if the level of the bone turnover marker is below a predetermined level. In some embodiments, the biological sample is urine, blood, serum, or plasma. In some embodiments, the bone turnover marker is a bone resorptive biomarker. In some embodiments, the bone resorption biomarker is urinary hydroxyproline, urinary total pyridinoline (PYD), urinary free deoxypyridinoline (DPD), urinary collagen type 1 cross-linked N-telopeptide (NTX), urinary or serum collagen type 1 cross-linked C-telopeptide (CTX), bone sialoprotein (BSP), or tartrate-resistant acid phosphatase 5b. In some embodiments, the bone resorptive biomarker is CTX or β-CTX. Thus, in some embodiments, the methods of selecting a subject for treatment with a Wnt pathway inhibitor, comprising: obtaining a biological sample from the subject, determining the level of β-CTX in the sample, and selecting the subject for treatment with the Wnt pathway inhibitor if the level of β-CTX is below a predetermined level.

The invention provides methods of identifying a subject as eligible for treatment with a Wnt pathway inhibitor, comprising: determining the level of a biomarker in a sample, and identifying the subject as eligible for treatment with the Wnt pathway inhibitor if the level of the biomarker is below a predetermined level. In some embodiments, the methods of identifying a subject as eligible for treatment with a Wnt pathway inhibitor comprise: obtaining a biological sample from the subject, determining the level of a biomarker in the sample, and identifying the subject as eligible for treatment with the Wnt pathway inhibitor if the level of the biomarker is below a predetermined level. In some embodiments, the biomarker is a bone turnover marker. In some embodiments, the biomarker is a bone resorption biomarker. In some embodiments, the bone resorption biomarker is urinary hydroxyproline, urinary total pyridinoline (PYD), urinary free deoxypyridinoline (DPD), urinary collagen type 1 cross-linked N-telopeptide (NTX), urinary or serum collagen type 1 cross-linked C-telopeptide (CTX), bone sialoprotein (BSP), or tartrate-resistant acid phosphatase 5b. In some embodiments, the bone resorption biomarker is CTX. In some embodiments, the bone resorption biomarker is β-CTX. In some embodiments, the methods of identifying a subject as eligible for treatment with a Wnt pathway inhibitor comprise: obtaining a biological sample from the subject, determining the level of β-CTX in the sample, and identifying the subject as eligible for treatment with the Wnt pathway inhibitor if the level of β-CTX is below a predetermined level.

The invention also provides methods of monitoring a subject receiving treatment with a Wnt pathway inhibitor for the development of skeletal-related side effects and/or toxicity, comprising: determining the level of a biomarker in a sample, and comparing the level of the biomarker in the sample to a predetermined level of the biomarker, wherein an increase in the level of the biomarker indicates development of skeletal-related side effects and/or toxicity. In some embodiments, the methods of monitoring a subject receiving treatment with a Wnt pathway inhibitor for the development of skeletal-related side effects and/or toxicity comprise: obtaining a biological sample from the subject receiving treatment, determining the level of a biomarker in the sample, and comparing the level of the biomarker in the sample to a predetermined level of the biomarker, wherein an increase in the level of the biomarker indicates development of skeletal-related side effects and/or toxicity. In some embodiments, the skeletal-related side effect and/or toxicity is an increased risk of bone fracture. In some embodiments, the skeletal-related side effect and/or toxicity is osteopenia or osteoporosis. In some embodiments, the biomarker is a bone turnover marker. In some embodiments, the biomarker is a bone resorption biomarker. In some embodiments, the bone resorption biomarker is urinary hydroxyproline, urinary total pyridinoline (PYD), urinary free deoxypyridinoline (DPD), urinary collagen type 1 cross-linked N-telopeptide (NTX), urinary or serum collagen type 1 cross-linked C-telopeptide (CTX), bone sialoprotein (BSP), or tartrate-resistant acid phosphatase 5b. In some embodiments, the bone resorption biomarker is CTX. In some embodiments, the bone resorption biomarker is β-CTX. In some embodiments, a method of monitoring a subject receiving treatment with a Wnt pathway inhibitor for the development of skeletal-related side effects and/or toxicity, comprises: obtaining a biological sample from the subject receiving treatment, determining the level of β-CTX in the sample, and comparing the level of β-CTX in the sample to a predetermined level of β-CTX, wherein an increase in the level of β-CTX indicates development of skeletal-related side effects and/or toxicity.

The invention also provides methods of detecting the development of skeletal-related side effects and/or toxicity in a subject receiving treatment with a Wnt pathway inhibitor, comprising: determining the level of a biomarker in a sample, and comparing the level of a biomarker in the sample to a predetermined level of the biomarker, wherein an increase in the level of the biomarker indicates development of skeletal-related side effects and/or toxicity. In some embodiments, the methods of detecting the development of skeletal-related side effects and/or toxicity in a subject receiving treatment with a Wnt pathway inhibitor comprise: obtaining a biological sample from the subject receiving treatment, determining the level of a biomarker in the sample, and comparing the level of a biomarker in the sample to a predetermined level of the biomarker, wherein an increase in the level of the biomarker indicates development of skeletal-related side effects and/or toxicity. In some embodiments, the skeletal-related side effect and/or toxicity is an increased risk of bone fracture. In some embodiments, the skeletal-related side effect and/or toxicity is osteopenia or osteoporosis. In some embodiments, the biomarker is a bone turnover marker. In some embodiments, the biomarker is a bone resorption biomarker. In some embodiments, the bone resorption biomarker is urinary hydroxyproline, urinary total pyridinoline (PYD), urinary free deoxypyridinoline (DPD), urinary collagen type 1 cross-linked N-telopeptide (NTX), urinary or serum collagen type 1 cross-linked C-telopeptide (CTX), bone sialoprotein (BSP), or tartrate-resistant acid phosphatase 5b. In some embodiments, the bone resorption biomarker is CTX. In some embodiments, the bone resorption biomarker is β-CTX. In some embodiments, the methods of detecting the development of skeletal-related side effects and/or toxicity in a subject receiving treatment with a Wnt pathway inhibitor comprise: obtaining a biological sample from the subject receiving treatment, determining the level of β-CTX in the sample, and comparing the level of β-CTX in the sample to a predetermined level of β-CTX, wherein an increase in the level of β-CTX indicates development of skeletal-related side effects and/or toxicity.

The invention also provides methods for identifying skeletal-related side effects and/or toxicity in a subject receiving treatment with a Wnt pathway inhibitor, comprising: determining the level of a biomarker in a sample, and comparing the level of the biomarker in the sample to a predetermined level of the biomarker, wherein if the level of the biomarker in the sample is higher than the predetermined level of the biomarker then a skeletal-related side effect and/or toxicity is indicated. In some embodiments, the methods for identifying skeletal-related side effects and/or toxicity in a subject receiving treatment with a Wnt pathway inhibitor comprise: obtaining a biological sample from the subject receiving treatment, determining the level of a biomarker in the sample, and comparing the level of the biomarker in the sample to a predetermined level of the biomarker, wherein if the level of the biomarker in the sample is higher than the predetermined level of the biomarker then a skeletal-related side effect and/or toxicity is indicated. In some embodiments, the skeletal-related side effect and/or toxicity is an increased risk of bone fracture. In some embodiments, the skeletal-related side effect and/or toxicity is osteopenia or osteoporosis. In some embodiments, the biomarker is a bone turnover marker. In some embodiments, the biomarker is a bone resorption biomarker. In some embodiments, the bone resorption biomarker is urinary hydroxyproline, urinary total pyridinoline (PYD), urinary free deoxypyridinoline (DPD), urinary collagen type 1 cross-linked N-telopeptide (NTX), urinary or serum collagen type 1 cross-linked C-telopeptide (CTX), bone sialoprotein (BSP), or tartrate-resistant acid phosphatase 5b. In some embodiments, the bone resorption biomarker is CTX. In some embodiments, the bone resorption biomarker is β-CTX. In some embodiments, a method for identifying a skeletal-related side effect and/or toxicity in a subject receiving treatment with a Wnt pathway inhibitor comprises: obtaining a biological sample from the subject receiving treatment, determining the level of β-CTX in the sample, and comparing the level of β-CTX in the sample to a predetermined level of β-CTX, wherein if the level of β-CTX in the sample is higher than the predetermined level of β-CTX then a skeletal-related side effect and/or toxicity is indicated.

The invention also provides methods for monitoring skeletal-related side effects and/or toxicity in a subject receiving treatment with a Wnt pathway inhibitor, comprising: determining the level of a biomarker in a sample, and comparing the level of the biomarker in the sample to a predetermined level of the biomarker, wherein if the level of the biomarker in the sample is higher than the predetermined level of the biomarker then skeletal-related side effects and/or toxicity is indicated. In some embodiments, the methods for monitoring skeletal-related side effects and/or toxicity in a subject receiving treatment with a Wnt pathway inhibitor comprise: obtaining a biological sample from the subject receiving treatment, determining the level of a biomarker in the sample, and comparing the level of the biomarker in the sample to a predetermined level of the biomarker, wherein if the level of the biomarker in the sample is higher than the predetermined level of the biomarker then skeletal-related side effects and/or toxicity is indicated. In some embodiments, the skeletal-related side effect and/or toxicity is an increased risk of bone fracture. In some embodiments, the skeletal-related side effect and/or toxicity is osteopenia or osteoporosis. In some embodiments, the biomarker is a bone turnover marker. In some embodiments, the biomarker is a bone resorption biomarker. In some embodiments, the bone resorption biomarker is urinary hydroxyproline, urinary total pyridinoline (PYD), urinary free deoxypyridinoline (DPD), urinary collagen type 1 cross-linked N-telopeptide (NTX), urinary or serum collagen type 1 cross-linked C-telopeptide (CTX), bone sialoprotein (BSP), or tartrate-resistant acid phosphatase 5b. In some embodiments, the bone resorption biomarker is CTX. In some embodiments, the bone resorption biomarker is β-CTX. In some embodiments, a method for monitoring cardiotoxicity in a subject receiving treatment with a Wnt pathway inhibitor comprises: obtaining a biological sample from the subject receiving treatment, determining the level of β-CTX in the sample, and comparing the level of β-CTX in the sample to a predetermined level of β-CTX, wherein if the level of β-CTX in the sample is higher than the predetermined level of β-CTX then a skeletal-related side effect and/or toxicity is indicated.

The invention also provides methods of reducing skeletal-related side effects and/or toxicity in a subject receiving treatment with a Wnt pathway inhibitor, comprising: determining the level of a biomarker in a sample from the subject, comparing the level of the biomarker in the sample to a predetermined level of the biomarker, and administering to the subject a therapeutically effective amount of an anti-resorptive medication such as a bisphosphonate if the level of the biomarker in the sample is higher than the predetermined level of the biomarker. In some embodiments, the methods of reducing skeletal-related side effects and/or toxicity in a subject receiving treatment with a Wnt pathway inhibitor comprise: obtaining a biological sample from the subject receiving treatment, determining the level of a biomarker in the sample, comparing the level of the biomarker in the sample to a predetermined level of the biomarker, and administering to the subject a therapeutically effective amount of an anti-resorptive medication such as a bisphosphonate if the level of the biomarker in the sample is higher than the predetermined level of the biomarker. In some embodiments, the skeletal-related side effect and/or toxicity is an increased risk of bone fracture. In some embodiments, the skeletal-related side effect and/or toxicity is osteopenia or osteoporosis. In some embodiments, the biomarker is a bone turnover marker. In some embodiments, the biomarker is a bone resorption biomarker. In some embodiments, the bone resorption biomarker is urinary hydroxyproline, urinary total pyridinoline (PYD), urinary free deoxypyridinoline (DPD), urinary collagen type 1 cross-linked N-telopeptide (NTX), urinary or serum collagen type 1 cross-linked C-telopeptide (CTX), bone sialoprotein (BSP), or tartrate-resistant acid phosphatase 5b. In some embodiments, the bone resorption biomarker is CTX. In some embodiments, the bone resorption biomarker is β-CTX. In some embodiments, a method for reducing skeletal-related side effects and/or toxicity in a subject receiving treatment with a Wnt pathway inhibitor comprises: obtaining a biological sample from the subject receiving treatment, determining the level of β-CTX in the sample, and comparing the level of β-CTX in the sample to a predetermined level of β-CTX, and administering to the subject a therapeutically effective amount of an anti-resorptive medication if the level of β-CTX in the sample is higher than the predetermined level of β-CTX. In some embodiments, the anti-resorptive medication is a bisphosphonate.

The invention also provides methods of preventing or attenuating the development of skeletal-related side effects and/or toxicity in a subject receiving treatment with a Wnt pathway inhibitor, comprising: determining the level of a biomarker in a sample from the subject, comparing the level of the biomarker in the sample to a predetermined level of the biomarker; administering to the subject a therapeutically effective amount of an anti-resorptive medication, and administering to the subject the Wnt pathway inhibitor. In some embodiments, the methods of preventing or attenuating the development of skeletal-related side effects and/or toxicity in a subject receiving treatment with a Wnt pathway inhibitor comprise: obtaining a biological sample from the subject prior to treatment with the Wnt pathway inhibitor, determining the level of a biomarker in the sample, comparing the level of the biomarker in the sample to a predetermined level of the biomarker; administering to the subject a therapeutically effective amount of an anti-resorptive medication, and administering to the subject the Wnt pathway inhibitor. In some embodiments, the skeletal-related side effect and/or toxicity is an increased risk of bone fracture. In some embodiments, the skeletal-related side effect and/or toxicity is osteopenia or osteoporosis. In some embodiments, the biomarker is a bone turnover marker. In some embodiments, the biomarker is a bone resorption biomarker. In some embodiments, the bone resorption biomarker is urinary hydroxyproline, urinary total pyridinoline (PYD), urinary free deoxypyridinoline (DPD), urinary collagen type 1 cross-linked N-telopeptide (NTX), urinary or serum collagen type 1 cross-linked C-telopeptide (CTX), bone sialoprotein (BSP), or tartrate-resistant acid phosphatase 5b. In some embodiments, the bone resorption biomarker is CTX. In some embodiments, the bone resorption biomarker is β-CTX. In some embodiments, a method of preventing or attenuating the development of a skeletal-related side effect and/or toxicity in a subject receiving treatment with a Wnt pathway inhibitor comprises: obtaining a biological sample from the subject prior to treatment with the Wnt pathway inhibitor, determining the level of β-CTX in the sample, comparing the level of β-CTX in the sample to a predetermined level of β-CTX; administering to the subject a therapeutically effective amount of an anti-resorptive medication if the level of β-CTX in the sample is higher than the predetermined level of β-CTX; and administering to the subject the Wnt pathway inhibitor.

In some embodiments of the methods described herein, the predetermined level is about 1500 pg/ml or less in a blood, serum, or plasma sample. In some embodiments, the predetermined level is about 1200 pg/ml or less in a blood, serum, or plasma sample. In some embodiments, the predetermined level is about 1000 pg/ml or less in a blood, serum, or plasma sample. In some embodiments, the predetermined level is about 800 pg/ml or less in a blood, serum, or plasma sample. In some embodiments, the predetermined level is about 600 pg/ml or less in a blood, serum, or plasma sample. In some embodiments, the predetermined level is about 400 pg/ml or less in a blood, serum, or plasma sample. In the context of predetermined levels of β-CTX, the term "about" means the referenced amount plus or minus 10% of that referenced amount.

In some embodiments, the predetermined level of a biomarker (e.g., a bone resorption biomarker or β-CTX) is the amount of the biomarker in a sample obtained at an earlier date. In some embodiments, the predetermined level of a biomarker (e.g., a bone resorption biomarker or β-CTX) is the amount of the biomarker in a sample obtained at an initial screening. In some embodiments, the predetermined level of a biomarker (e.g., a bone resorption biomarker or β-CTX) is the amount of the biomarker in a sample obtained prior to treatment. In some embodiments, the predetermined level of a biomarker (e.g., a bone resorption biomarker or β-CTX) is the amount of the biomarker in a sample obtained at an initial screening. In some embodiments, the predetermined level of a biomarker (e.g., a bone resorption biomarker or β-CTX) is a normal reference level. In some embodiments, the predetermined level of a biomarker (e.g., a bone resorption biomarker or β-CTX) is a baseline level. In some embodiments, the baseline level is the amount of the biomarker determined at an initial screening. In some embodiments, the baseline level is the amount of the biomarker determined prior to treatment.

In some embodiments, if the β-CTX level in the sample is increased 2-fold or greater (i.e., a doubling or greater) as compared to a predetermined level, the subject is administered a therapeutically effective amount of an anti-resorptive medication. In some embodiments, if the β-CTX level in the sample is increased 2-fold or greater (i.e., a doubling or greater) as compared to a baseline level, the subject is administered a therapeutically effective amount of an anti-resorptive medication.

In any of the methods described herein, a biological sample is obtained approximately every week, every 2 weeks, every 3 weeks, every 4 weeks, every 5 weeks, or every 6 weeks.

In some embodiments of any of the methods described herein, the subjects are evaluated using a DEXA (dual energy X-ray absorptiometry) bone density scan. This technique is the most commonly used test for measuring bone mineral density (BMD). The DEXA output includes a T-score, which compares the subject's bone density to a 30-35 year old person, and a Z-score, which compares the subject's bone density to the average bone density of someone their age and gender. The T-score is used to determine if an individual has osteopenia or osteoporosis according to a standard scale. A T-score greater than −1 is considered normal bone density; a T-score between −1 and −2.5, is considered osteopenia; a T-score less than −2.5 is considered osteoporosis; and a T-score less than −2.5 and 1+ osteoporotic fractures is considered severe (established) osteoporosis. In some embodiments, a skeletal-related side effect and/or toxicity is indicated if the T-score declines to less than −2.5 in the total femur or vertebrae L1-L4. In some embodiments, a skeletal-related side effect and/or toxicity is indicated if the T-score declines to less than −2.0 in the total femur or vertebrae L1-L4. In some embodiments, a skeletal-related side effect and/or toxicity is indicated if the T-score declines to less than −1.5 in the total femur or vertebrae L1-L4. In some embodiments, a skeletal-related side effect and/or toxicity is indicated if the T-score declines to less than −1.0 in the total femur or vertebrae L1-L4.

The invention also provides methods of ameliorating skeletal-related side effects and/or toxicity in a subject administered a Wnt pathway inhibitor, comprising: administering to the subject a therapeutically effective amount of an anti-resorptive medication.

The invention also provides methods of screening a subject for the risk of skeletal-related side effects and/or toxicity from treatment with a Wnt pathway inhibitor, comprising: determining the level of a biomarker in a sample from the subject, and comparing the level of the biomarker in the sample to a predetermined level of the biomarker, wherein if the level of the biomarker in the sample is higher than the predetermined level of the biomarker then the subject is at risk for skeletal-related side effects and/or toxicity. In some embodiments, the methods of screening a subject for the risk of skeletal-related side effects and/or toxicity from treatment with a Wnt pathway inhibitor comprise: obtaining a biological sample from the subject prior to treatment with the Wnt pathway inhibitor, determining the level of a biomarker in the sample, and comparing the level of the biomarker in the sample to a predetermined level of the biomarker, wherein if the level of the biomarker in the sample is higher than the predetermined level of the biomarker then the subject is at risk for skeletal-related side effects and/or toxicity. In some embodiments, the skeletal-related side effect and/or toxicity is an increased risk of bone fracture. In some embodiments, the skeletal-related side effect and/or toxicity is osteopenia or osteoporosis. In some embodiments, the biomarker is a bone turnover marker. In some embodiments, the biomarker is a bone resorption biomarker. In some embodiments, the bone resorption biomarker is urinary hydroxyproline, urinary total pyridinoline (PYD), urinary free deoxypyridinoline (DPD), urinary collagen type 1 cross-linked N-telopeptide (NTX), urinary or serum collagen type 1 cross-linked C-telopeptide (CTX), bone sialoprotein (BSP), or tartrate-resistant acid phosphatase 5b. In some embodiments, the bone resorption biomarker is CTX. In some embodiments, the bone resorption biomarker is β-CTX. In some embodiments, a method of screening a subject for the risk of a skeletal-related side effect and/or toxicity from treatment with a Wnt pathway inhibitor comprises: obtaining a biological sample from the subject prior to treatment with the Wnt pathway inhibitor, determining the level of β-CTX in the sample, and comparing the level of β-CTX in the sample to a predetermined level of β-CTX, wherein if the level of β-CTX in the sample is higher than the predetermined level of β-CTX then the subject is at risk for a skeletal-related side effect and/or toxicity. In some embodiments, the predetermined level of β-CTX is a value determined at an initial screening. In some embodiments, the predetermined level of β-CTX is from about 400 to 1200 pg/ml. In some embodiments, if the subject is at risk for a skeletal-related side effect and/or toxicity, the subject is administered a therapeutically effective amount of an anti-resorptive medication prior to treatment with the Wnt pathway inhibitor.

In some embodiments of the methods described herein, the anti-resorptive medication is a bisphosphonate. It is believed that bisphosphonates prevent loss of bone mass by "inducing" osteoclasts to undergo apoptosis and thereby inhibiting the digestion of bone. In some embodiments, the bisphosphonate is selected from the group consisting of: etidronate, clodronate, tiludronate, pamidronate, neridronate, olpadronate, alendronate (FOSAMAX), ibandronate (BONIVA), risedronate (ACTONEL), and zoledronic acid (RECLAST). In some embodiments, the bisphosphonate is zoledronic acid. In some embodiments, the anti-resorptive medication is anti-RANKL antibody denosumab (PROLIA).

In any of the methods described herein, the Wnt pathway inhibitor is an anti-FZD antibody. In any of the methods described herein, the Wnt pathway inhibitor is an anti-Wnt antibody. In any of the methods described herein, the Wnt pathway inhibitor is a FZD soluble receptor.

In certain embodiments of any of the methods described herein, the Wnt pathway inhibitor is an antibody comprising: (a) a heavy chain CDR1 comprising GFTFSHYTLS (SEQ ID NO:1), a heavy chain CDR2 comprising VISGDGSYTYY-ADSVKG (SEQ ID NO:2), and a heavy chain CDR3 comprising NFIKYVFAN (SEQ ID NO:3), and (b) a light chain CDR1 comprising SGDNIGSFYVH (SEQ ID NO:4), a light chain CDR2 comprising DKSNRPSG (SEQ ID NO:5), and a light chain CDR3 comprising QSYANTLSL (SEQ ID NO:6).

In certain embodiments of any of the methods described herein, the Wnt pathway inhibitor is an antibody comprising a heavy chain variable region comprising SEQ ID NO:7 and a light chain variable region comprising SEQ ID NO:8.

In certain embodiments, the Wnt pathway inhibitor comprises the same heavy chain variable region and the same light chain variable region sequences as OMP-18R5. In some embodiments, the Wnt pathway inhibitor is antibody OMP-18R5. OMP-18R5 is an IgG2 human monoclonal antibody that binds human FZD1, FZD2, FZD5, FZD7, and FZD8 receptors and has been previously described in U.S. Pat. No. 7,982,013.

In certain embodiments, the Wnt pathway inhibitor comprises the same heavy and light chain amino acid sequences as an antibody encoded by a plasmid deposited with ATCC having deposit no. PTA-9541. In certain embodiments, the Wnt pathway inhibitor is encoded by the plasmid having ATCC deposit no. PTA-9541 which was deposited with American Type Culture Collection (ATCC), at 10801 University Boulevard, Manassas, Va., 20110, under the conditions of the Budapest Treaty on Sep. 29, 2008. In certain embodiments, the Wnt pathway inhibitor competes for specific binding to a human FZD with an antibody encoded by the plasmid deposited with ATCC having deposit no. PTA-9541.

In certain embodiments of any of the methods described herein, the Wnt pathway inhibitor is a FZD soluble receptor. In some embodiments, the Wnt pathway inhibitor is a FZD8 soluble receptor comprising SEQ ID NO:20, SEQ ID NO:30, or SEQ ID NO:33. In some embodiments, the Wnt pathway inhibitor is a FZD8 soluble receptor comprising SEQ ID NO:20. In some embodiments, the Wnt pathway inhibitor is a FZD8 soluble receptor comprising SEQ ID NO:30. In some embodiments, the Wnt pathway inhibitor is a FZD8 soluble receptor comprising SEQ ID NO:33.

In certain embodiments of any of the methods described herein, the Wnt pathway inhibitor is a FZD-Fc soluble receptor. In some embodiments, the Wnt pathway inhibitor is a FZD8-Fc soluble receptor. In some embodiments, the Wnt pathway inhibitor is a FZD8-Fc soluble receptor comprising SEQ ID NO:39, SEQ ID NO:40, or SEQ ID NO:41. In some embodiments, the Wnt pathway inhibitor is a FZD8-Fc soluble receptor comprising SEQ ID NO:39. In some embodiments, the Wnt pathway inhibitor is a FZD8-Fc soluble receptor comprising SEQ ID NO:40. In some embodiments, the Wnt pathway inhibitor is a FZD8-Fc soluble receptor comprising SEQ ID NO:41. In some embodiments, the Wnt pathway inhibitor is OMP-54F28. In some embodiments, the Wnt pathway inhibitor is not OMP-54F28.

In some embodiments, the subject has cancer. In some embodiments, the cancer is selected from the group consisting of: lung cancer, breast cancer, colon cancer, colorectal cancer, melanoma, pancreatic cancer, gastrointestinal cancer, renal cancer, ovarian cancer, liver cancer, endometrial cancer, kidney cancer, prostate cancer, thyroid cancer, neuroendocrine cancer, neuroblastoma, glioma, glioblastoma multiforme, cervical cancer, stomach cancer, bladder cancer, hepatoma, and head and neck cancer. As used herein, "lung cancer" refers to non-small cell lung cancer (NSCLC) and small cell lung cancer (SCLC). In certain embodiments, the cancer is a hematological cancer, such as a lymphoma or leukemia. In certain embodiments, the cancer is NSCLC. In certain embodiments, the cancer is ovarian cancer. In certain embodiments, the cancer is pancreatic cancer. In certain embodiments, the cancer is not a neuroendocrine cancer.

Thus, the invention also provides methods of treating cancer. In some embodiments, the methods comprise a method of treating cancer in a subject in need thereof, comprising: (a) administering to the subject a therapeutically effective amount of a Wnt pathway inhibitor; and (b) determining the level of a bone resorption biomarker in a sample from the subject. In some embodiments, a method of treating cancer comprises (a) administering to the subject a therapeutically effective amount of a Wnt pathway inhibitor; (b) determining the level of a bone resorption biomarker in a sample from the subject; and (c) comparing the level of the bone resorption biomarker in the sample to a predetermined level of the bone resorption biomarker. In some embodiments, a method of treating cancer comprises (a) administering to the subject a therapeutically effective amount of a Wnt pathway inhibitor; (b) determining the level of a bone resorption biomarker in a sample from the subject; and (c) comparing the level of the bone resorption biomarker in the sample to a predetermined level of the bone resorption biomarker; wherein if the level of the bone resorption biomarker in the sample is higher than the predetermined level of the bone resorption biomarker then the subject is at risk for a skeletal-related side effect and/or toxicity. In some embodiments, a method of treating cancer comprises (a) administering to the subject a therapeutically effective amount of a Wnt pathway inhibitor; (b) determining the level of a bone resorption biomarker in a sample from the subject; and (c) comparing the level of the bone resorption biomarker in the sample to a predetermined level of the bone resorption biomarker; wherein if the level of the bone resorption biomarker in the sample is higher than the predetermined level of the bone resorption biomarker then the subject is administered a therapeutically effective amount of an anti-resorptive medication.

The invention also provides methods of inhibiting tumor growth. In some embodiments, the methods comprise a method of inhibiting tumor growth in a subject in need thereof, comprising: (a) administering to the subject a therapeutically effective amount of a Wnt pathway inhibitor; and (b) determining the level of a bone resorption biomarker in a sample from the subject. In some embodiments, a method of inhibiting tumor growth comprises (a) administering to the subject a therapeutically effective amount of a Wnt pathway inhibitor; (b) determining the level of a bone resorption biomarker in a sample from the subject; and (c) comparing the level of the bone resorption biomarker in the sample to a predetermined level of the bone resorption biomarker. In some embodiments, a method of inhibiting tumor growth comprises (a) administering to the subject a therapeutically effective amount of a Wnt pathway inhibitor; (b) determining the level of a bone resorption biomarker in a sample from the subject; and (c) comparing the level of the bone resorption biomarker in the sample to a predetermined level of the bone resorption biomarker; wherein if the level of the bone resorption biomarker in the sample is higher than the predetermined level of the bone resorption biomarker then the subject is at risk for a skeletal-related side effect and/or toxicity. In some embodiments, a method of inhibiting tumor growth comprises (a) administering to the subject a therapeutically effective amount of a Wnt pathway inhibitor; (b) determining the level of a bone resorption biomarker in a sample from the subject; and (c) comparing the level of the bone resorption biomarker in the sample to a predetermined level of the bone resorption biomarker; wherein if the level of the bone resorption biomarker in the sample is higher than the predetermined level of the bone resorption biomarker then the subject is administered a therapeutically effective amount of an anti-resorptive medication.

In some embodiments, the biological sample is a body fluid. In some embodiments, the biological sample is blood, plasma, serum, or urine. In some embodiments, the biological sample is a venous whole blood specimen. In some embodiments, the biological sample is a venous whole blood specimen using EDTA or heparin as an anticoagulant. In some embodiments, the biological sample is a plasma specimen. In some embodiments, the biological sample is a plasma specimen using EDTA or heparin as an anticoagulant. Samples of body fluids may be obtained by any method known in the art. In some embodiments, the biological sample is a frozen tissue sample or is fresh tissue sample.

Assays for measuring or determining the level of a bone resorption biomarker (e.g., $\beta$-CTX) in a sample are known to those of skilled in the art. For example, in some embodiments an immunoassay that quantitatively measures $\beta$-CTX levels in whole blood or plasma specimens is used. In some embodiments, the sample contains EDTA as an anticoagulant. In some embodiments, the sample contains heparin as an anticoagulant. In some embodiments, the immunoassay comprises two highly specific monoclonal antibodies against the amino acid sequence of EKAHD-$\beta$-GGR of $\beta$-CTX, wherein the aspartic acid residue is $\beta$-isomerized. In order to obtain a specific signal in the immunoassay, two chains of EKAHD-$\beta$-GGR must be cross-linked. In some embodiments, a sample and appropriate controls are placed into streptavidin-coated microtiter wells, followed by a solution containing biotinylated monoclonal antibodies against the amino acid sequence of EKAHD-$\beta$-GGR of $\beta$-CTX. After incubation and washing, a chromogenic substrate solution is added to microtiter wells. After incubation, the reaction is stopped. Absorbance of the microtiter wells is read and the $\beta$-CTX concentration is determined.

In some embodiments, the Wnt pathway inhibitor is administered as an initial dose of about 0.5 mg/kg. For example, antibody OMP-18R5 is diluted with 5% dextrose in water (USP) to a total volume of 250 mL. The OMP-18R5 is delivered through a 0.22-micron filter over 30 minutes as an intravenous infusion. In some embodiments, subsequent doses are administered in a similar manner.

In another aspect of the invention, the methods described herein may further comprise administering one or more additional therapeutic agents. An additional therapeutic agent can be administered prior to, concurrently with, and/or subsequently to, administration of the Wnt pathway inhibitor. Pharmaceutical compositions comprising a Wnt pathway inhibitor and an additional therapeutic agent(s) are also provided. In some embodiments, the one or more additional therapeutic agents comprise 1, 2, 3, or more additional therapeutic agents.

Combination therapy with at least two therapeutic agents often uses agents that work by different mechanisms of action, although this is not required. Combination therapy using agents with different mechanisms of action may result in additive or synergetic effects. Combination therapy may allow for a lower dose of each agent than is used in monotherapy, thereby reducing side effects and/or toxicities. Combination therapy may increase the therapeutic index of one or both of the therapeutic agents. Combination therapy may decrease the likelihood that resistant cancer cells will develop. In some embodiments, combination therapy comprises a therapeutic agent that primarily affects (e.g., inhibits or kills) non-tumorigenic cells and a therapeutic agent that primarily affects (e.g., inhibits or kills) tumorigenic CSCs.

Therapeutic agents that may be administered in combination with the Wnt pathway inhibitor include chemotherapeutic agents. Thus, in some embodiments, the method or treatment involves the administration of a Wnt pathway inhibitor of the present invention in combination with a chemotherapeutic agent or cocktail of multiple different chemotherapeutic agents. Treatment with a Wnt pathway inhibitor (e.g., an antibody or soluble receptor) can occur prior to, concurrently with, or subsequent to administration of chemotherapies. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in *The Chemotherapy Source Book*, 4th Edition, 2008, M. C. Perry, Editor, Lippincott, Williams & Wilkins, Philadelphia, Pa.

Chemotherapeutic agents useful in the instant invention include, but are not limited to, alkylating agents such as thiotepa and cyclophosphamide (CYTOXAN); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytosine arabinoside, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishers such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); taxoids, e.g. paclitaxel (TAXOL) and docetaxel (TAXOTERE); chlorambucil; gemcitabine; 6-thioguanine; mercaptopurine; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; ibandronate; CPT11; topoisomerase inhibitor RFS 2000; difluoromethylornithine (DMFO); retinoic acid; esperamicins; capecitabine (XELODA); and pharmaceutically acceptable salts, acids or derivatives of any of the above. Chemotherapeutic agents also include anti-hormonal agents that act to regulate or inhibit hormone action on tumors such as anti-estrogens including, for example, tamoxifen, raloxifene, aromatase inhibiting 4(5)-imidazoles, 4-hydroxytamoxifen, trioxifene, keoxifene, LY117018, onapristone, and toremifene (FARESTON); and anti-androgens such as flutamide, nilutamide, bicalutamide, leuprolide, and goserelin; and pharmaceutically acceptable salts, acids or derivatives of any of the above. In certain embodiments, the additional therapeutic agent is cisplatin. In certain embodiments, the additional therapeutic agent is carboplatin. In certain embodiments, the additional therapeutic agent is paclitaxel. In certain embodiments, where the chemotherapeutic agent administered in combination with a Wnt pathway inhibitor is carboplatin, the cancer or tumor being treated is lung cancer or a lung tumor.

In certain embodiments, the chemotherapeutic agent is a topoisomerase inhibitor. Topoisomerase inhibitors are chemotherapeutic agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide (VM-26), and irinotecan, as well as pharmaceutically acceptable salts, acids, or derivatives of any of these. In certain embodiments, the additional therapeutic agent is irinotecan.

In certain embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, ralitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these. In certain embodiments, the additional therapeutic agent is gemcitabine. In some embodiments, the additional therapeutic agent is pemetrexed. In certain embodiments, where the chemotherapeutic agent administered in combination with a Wnt pathway inhibitor is gemcitabine, the cancer or tumor being treated is pancreatic cancer or a pancreatic tumor. In certain embodiments, where the chemotherapeutic agent administered in combination with a Wnt pathway inhibitor is pemetrexed, the cancer or tumor being treated is lung cancer or a lung tumor. In some embodiments, the Wnt pathway inhibitor is administered in combination with pemetrexed and carboplatin.

In certain embodiments, the chemotherapeutic agent is an antimitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain embodiments, the agent is paclitaxel (TAXOL), docetaxel (TAXOTERE), albumin-bound paclitaxel (ABRAXANE), DHA-paclitaxel, or PG-paclitaxel. In certain alternative embodiments, the antimitotic agent comprises a vinca alkaloid, such as vincristine, binblastine, vinorelbine, or vindesine, or pharmaceutically acceptable salts, acids, or derivatives thereof. In some embodiments, the antimitotic agent is an inhibitor of kinesin Eg5 or an inhibitor of a mitotic kinase such as Aurora A or Plk1. In certain embodiments, where the chemotherapeutic agent administered in combination with a Wnt pathway inhibitor is an anti-mitotic agent, the cancer or tumor being treated is breast cancer or a breast tumor.

In some embodiments, an additional therapeutic agent comprises an agent such as a small molecule. For example, treatment can involve the combined administration of a Wnt pathway inhibitor (e.g. an antibody) of the present invention with a small molecule that acts as an inhibitor against additional tumor-associated proteins including, but not limited to, EGFR, ErbB2, HER2, and/or VEGF. In certain embodiments, the additional therapeutic agent is a small molecule that inhibits a cancer stem cell pathway. In some embodiments, the additional therapeutic agent is a small molecule inhibitor of the Notch pathway. In some embodiments, the additional therapeutic agent is a small molecule inhibitor of the Wnt pathway. In some embodiments, the additional therapeutic agent is a small molecule inhibitor of the BMP pathway. In some embodiments, the additional therapeutic agent is a small molecule that inhibits β-catenin signaling.

In some embodiments, an additional therapeutic agent comprises a biological molecule, such as an antibody. For example, treatment can involve the combined administration of a Wnt pathway inhibitor (e.g. an antibody) of the present invention with other antibodies against additional tumor-associated proteins including, but not limited to, antibodies that bind EGFR, ErbB2, HER2, and/or VEGF. In certain embodiments, the additional therapeutic agent is an antibody that is an anti-cancer stem cell marker antibody. In some embodiments, the additional therapeutic agent is an antibody that binds a component of the Notch pathway. In some embodiments, the additional therapeutic agent is an antibody that binds a component of the Wnt pathway. In certain embodiments, the additional therapeutic agent is an antibody that inhibits a cancer stem cell pathway. In some embodiments, the additional therapeutic agent is an antibody inhibitor of the Notch pathway. In some embodiments, the additional therapeutic agent is an antibody inhibitor of the Wnt pathway. In some embodiments, the additional therapeutic agent is an antibody inhibitor of the BMP pathway. In some embodiments, the additional therapeutic agent is an antibody that inhibits β-catenin signaling. In certain embodiments, the additional therapeutic agent is an antibody that is an angiogenesis inhibitor or modulator (e.g., an anti-VEGF or VEGF receptor antibody). In certain embodiments, the additional therapeutic agent is bevacizumab (AVASTIN), trastuzumab (HERCEPTIN), panitumumab (VECTIBIX), or cetuximab (ERBITUX). Combined administration can include co-administration, either in a single pharmaceutical formulation or using separate formulations, or consecutive administration in either order but generally within a time period such that all active agents can exert their biological activities simultaneously.

Furthermore, treatment with a Wnt pathway inhibitor described herein can include combination treatment with other biologic molecules, such as one or more cytokines (e.g., lymphokines, interleukins, tumor necrosis factors, and/or growth factors) or can be accompanied by surgical removal of tumors, cancer cells, or any other therapy deemed necessary by a treating physician.

It will be appreciated that the combination of a Wnt pathway inhibitor and an additional therapeutic agent may be administered in any order or concurrently. In some embodiments, the Wnt pathway inhibitor is administered to subjects that have previously undergone treatment with a second therapeutic agent. In certain other embodiments, the Wnt pathway inhibitor and a second therapeutic agent is administered substantially simultaneously or concurrently. For example, a subject may be given a Wnt pathway inhibitor (e.g., an antibody) while undergoing a course of treatment with a second therapeutic agent (e.g., chemotherapy). In certain embodiments, a Wnt pathway inhibitor is administered within 1 year of the treatment with a second therapeutic agent. In certain alternative embodiments, a Wnt pathway inhibitor is administered within 10, 8, 6, 4, or 2 months of any treatment with a second therapeutic agent. In certain other embodiments, a Wnt pathway inhibitor is administered within 4, 3, 2, or 1 weeks of any treatment with a second therapeutic agent. In some embodiments, a Wnt pathway inhibitor is administered within 5, 4, 3, 2, or 1 days of any treatment with a second therapeutic agent. It will further be appreciated that the two (or more) agents or treatments may be administered to the subject within a matter of hours or minutes (i.e., substantially simultaneously).

As is known to those of skill in the art, administration of any therapeutic agent may lead to side effects and/or toxicities. In some cases, the side effects and/or toxicities are so severe as to preclude administration of the particular agent at a therapeutically effective dose. In some cases, drug therapy must be discontinued, and other agents may be tried. However, many agents in the same therapeutic class often display similar side effects and/or toxicities, meaning that the subject either has to stop therapy, or if possible, suffer from the unpleasant side effects associated with the therapeutic agent.

Side effects from therapeutic agents may include, but are not limited to, hives, skin rashes, itching, nausea, vomiting, decreased appetite, diarrhea, chills, fever, fatigue, muscle aches and pain, headaches, low blood pressure, high blood pressure, hypokalemia, low blood counts, bleeding, and cardiac problems.

Thus, in some embodiments, the methods described herein include using an intermittent dosing regimen, which may reduce side effects and/or toxicities associated with administration of a Wnt pathway inhibitor. As used herein, "intermittent dosing" refers to a dosing regimen using a dosing interval of more than once a week, e.g., dosing once every 2 weeks, once every 3 weeks, once every 4 weeks, etc. In some embodiments, a method for treating a subject comprises administering to the subject an effective dose of a Wnt pathway inhibitor (e.g., an anti-FZD antibody or a FZD soluble receptor) according to an intermittent dosing regimen. In some embodiments, the method comprises administering to the subject an effective dose of a Wnt pathway inhibitor (e.g., an anti-FZD antibody or a FZD soluble receptor) according to an intermittent dosing regimen, and increasing the therapeutic index of the Wnt pathway inhibitor. In some embodiments, the intermittent dosing regimen comprises administering an initial dose of a Wnt pathway inhibitor to the subject, and administering subsequent doses of the Wnt pathway inhibitor about once every 2 weeks. In some embodiments, the intermittent dosing regimen comprises administering an initial dose of a Wnt pathway inhibitor to the subject, and administering subsequent doses of the Wnt pathway inhibitor about once every 3 weeks. In some embodiments, the intermittent dosing regimen comprises administering an initial dose of a Wnt pathway inhibitor to the subject, and administering subsequent doses of the Wnt pathway inhibitor about once every 4 weeks.

In some embodiments, the subsequent doses in an intermittent dosing regimen are about the same amount or less than the initial dose. In other embodiments, the subsequent doses are a greater amount than the initial dose. As is known by those of skill in the art, doses used will vary depending on the clinical goals to be achieved. In some embodiments, the initial dose is about 0.25 mg/kg to about 20 mg/kg. In some embodiments, the initial dose is about 0.25, 0.5, 1, 2, 3, 4, 5, 6, 7, 8, 9, 10, 11, 12, 13, 14, 15, 16, 17, 18, 19, or 20 mg/kg. In certain embodiments, the initial dose is about 0.5 mg/kg. In certain embodiments, the initial dose is about 1 mg/kg. In certain embodiments, the initial dose is about 2.5 mg/kg. In certain embodiments, the initial dose is about 5 mg/kg. In certain embodiments, the initial dose is about 7.5 mg/kg. In certain embodiments, the initial dose is about 10 mg/kg. In certain embodiments, the initial dose is about 12.5 mg/kg. In certain embodiments, the initial dose is about 15 mg/kg. In certain embodiments, the initial dose is about 20 mg/kg. In some embodiments, the subsequent doses are about 0.25 mg/kg to about 15 mg/kg. In certain embodiments, the subsequent doses are about 0.5, 1, 2, 3, 4, 5, 6, 7, 8, 9, 10, 11, 12, 13, 14 or 15 mg/kg. In certain embodiments, the subsequent doses are about 0.5 mg/kg. In certain embodiments, the subsequent doses are about 1 mg/kg. In certain embodiments, the subsequent doses are about 2.5 mg/kg. In certain embodiments, the subsequent doses are about 5 mg/kg. In some embodiments, the subsequent doses are about 7.5 mg/kg. In some embodiments, the subsequent doses are about 10 mg/kg. In some embodiments, the subsequent doses are about 12.5 mg/kg.

In some embodiments, the intermittent dosing regimen comprises: (a) administering to the subject an initial dose of a Wnt pathway inhibitor of about 2.5 mg/kg and (b) administering subsequent doses of about 2.5 mg/kg once every 2 weeks. In some embodiments, the intermittent dosing regimen comprises: (a) administering to the subject an initial dose of a Wnt pathway inhibitor of about 5 mg/kg and (b) administering subsequent doses of about 5 mg/kg once every 2 weeks. In some embodiments, the intermittent dosing regimen comprises: (a) administering to the subject an initial dose of a Wnt pathway inhibitor of about 2.5 mg/kg and (b) administering subsequent doses of about 2.5 mg/kg once every 3 weeks. In some embodiments, the intermittent dosing regimen comprises: (a) administering to the subject an initial dose of a Wnt pathway inhibitor of about 5 mg/kg and (b) administering subsequent doses of about 5 mg/kg once every 3 weeks. In some embodiments, the intermittent dosing regimen comprises: (a) administering to the subject an initial dose of a Wnt pathway inhibitor of about 2.5 mg/kg and (b) administering subsequent doses of about 2.5 mg/kg once every 4 weeks. In some embodiments, the intermittent dosing regimen comprises: (a) administering to the subject an initial dose of a Wnt pathway inhibitor of about 5 mg/kg and (b) administering subsequent doses of about 5 mg/kg once every 4 weeks. In certain embodiments, the initial dose and the maintenance doses are different, for example, the initial dose is about 5 mg/kg and the subsequent doses are about 2.5 mg/kg. In certain embodiments, an intermittent dosing regimen may comprise a loading dose, for example, the initial dose is about 20 mg/kg and the subsequent doses are about 2.5 mg/kg or about 5 mg/kg administered once every 2 weeks, once every 3 weeks, or once every 4 weeks.

In some embodiments of the methods described herein, a method of treating cancer comprises administering a therapeutically effective amount of OMP-18R5 to a subject in need thereof at a dosage of (a) at least about 0.5 mg/kg about every one to two weeks or (b) at least about 1.0 mg/kg about every three weeks. In some embodiments, a method of treating cancer comprises administering a therapeutically effective amount of OMP-18R5 to a subject in need thereof at a dosage of about 0.5 mg/kg to about 1.0 mg/kg about every one to two weeks. In some embodiments, a method of treating cancer comprises administering a therapeutically effective amount of OMP-18R5 to a subject in need thereof at a dosage of about 1.0 mg/kg to about 10.0 mg/kg about every three weeks.

Another aspect of the present invention is directed to methods for reducing toxicity of a Wnt pathway inhibitor in a human subject comprises administering to the subject the Wnt pathway inhibitor using an intermittent dosing regimen. Another aspect of the present invention is directed to methods for reducing side effects of a Wnt pathway inhibitor in a human subject comprises administering to the subject the Wnt pathway inhibitor using an intermittent dosing regimen. Another aspect of the present invention is directed to methods for increasing the therapeutic index of a Wnt pathway inhibitor in a human subject comprises administering to the subject the Wnt pathway inhibitor using an intermittent dosing regimen.

The choice of delivery method for the initial and subsequent doses is made according to the ability of the subject to tolerate introduction of the Wnt pathway inhibitor into the body. Thus, in any of the aspects and/or embodiments described herein, the administration of the Wnt pathway inhibitor may be by intravenous injection or intravenously. In some embodiments, the administration is by intravenous infusion. In any of the aspects and/or embodiments described herein, the administration of the Wnt pathway inhibitor may be by a non-intravenous route.

In certain embodiments, the treatment involves the administration of a Wnt pathway inhibitor (e.g. an antibody) of the present invention in combination with radiation therapy. Treatment with a Wnt pathway inhibitor can occur prior to, concurrently with, or subsequent to administration of radiation therapy. Dosing schedules for such radiation therapy can be determined by the skilled medical practitioner.

Embodiments of the present disclosure can be further defined by reference to the following non-limiting examples, which describe the use of a Wnt pathway inhibitor for treatment of cancer. It will be apparent to those skilled in the art that many modifications, both to materials and methods, may be practiced without departing from the scope of the present disclosure.

EXAMPLES

Example 1

Intermittent Dosing with Anti-FZD Antibody OMP-18R5 in a Breast Xenograft Model and Effect on Tumor Growth UM-PE13 breast tumor cells (20,000 cells) were injected subcutaneously into 6-8 week old NOD/SCID mice. The animals were randomized into groups (n=10 per group) and treated with anti-FZD antibody OMP-18R5 in combination with paclitaxel (Taxol) and paclitaxel alone. Paclitaxel was administered at 10 mg/kg weekly and OMP-18R5 was administered at doses of 5, 10, 25, or 45 mg/kg once every 3 weeks. The agents were administered intraperitoneally. Tumor volumes were measured on the indicated days with electronic calipers.

As shown in FIG. 1, OMP-18R5 in combination with paclitaxel administered every 3 weeks was efficacious in reducing PE-13 tumor growth at doses as low as 5 mg/kg or 10 mg/kg. This tumor growth inhibition was greater than the growth inhibition seen with paclitaxel alone when administered weekly. Higher doses of OMP-18R5, 25 mg/kg and 45 mg/kg, in combination with paclitaxel inhibited tumor growth to an even greater extent and tumor regression was observed at later time points. These results demonstrate that the efficacy of anti-FZD antibody treatment in combination with a chemotherapeutic agent such as paclitaxel is maintained with intermittent dosing regimens.

Example 2

Effect of Intermittent Dosing with Anti-FZD Antibody OMP-18R5 on Bone Formation UM-PE13 breast tumor cells (20,000 cells) were injected subcutaneously into 6-8 week old NOD/SCID mice. The animals were randomized into groups (n=10 per group) and treated with anti-FZD antibody OMP-18R5 in combination with paclitaxel (Taxol) or paclitaxel alone. Paclitaxel was administered at 15 mg/kg once a week and OMP-18R5 was administered at 25 mg/kg once every 4 weeks, once every 2 weeks or once a week. The agents were administered intraperitoneally. Tumor volumes were measured on the indicated days with electronic calipers.

Figure 2:
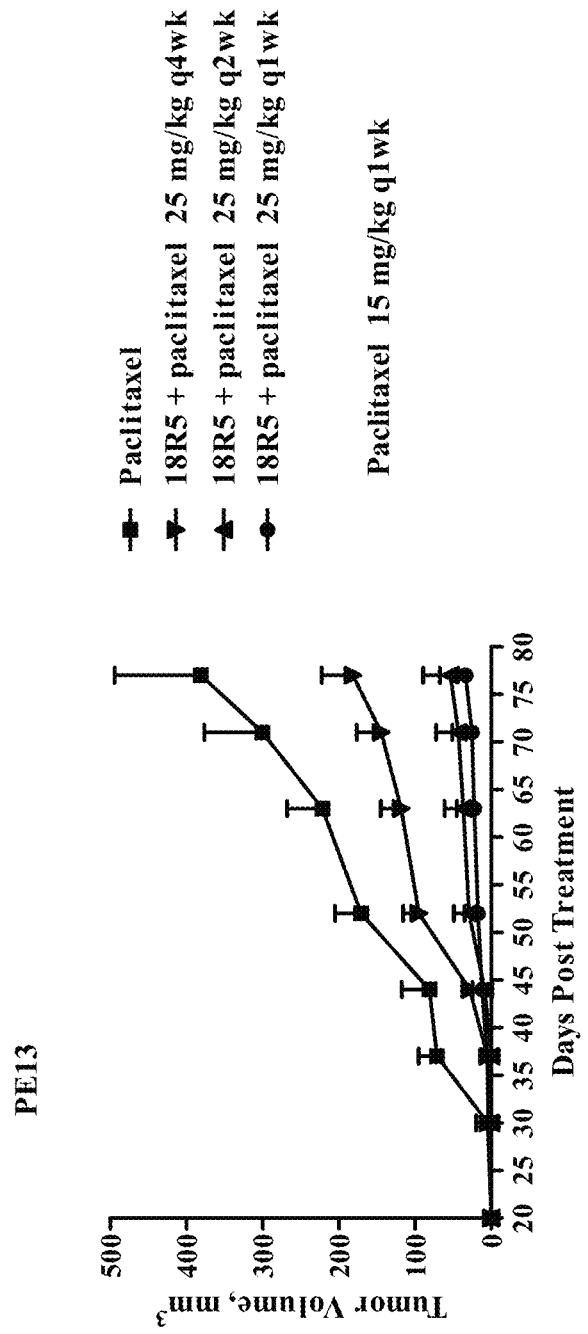
FIG. 2. Inhibition of breast tumor growth in vivo with intermittent dosing of a Wnt pathway inhibitor. Mice were treated with paclitaxel (-■-), 25 mg/kg OMP-18R5 in combination with paclitaxel once every 4 weeks (-▼-), 25 mg/kg OMP-18R5 in combination with paclitaxel once every 2 weeks (-▲-), or 25 mg/kg OMP-18R5 in combination with paclitaxel once a week (-•-). Data is shown as tumor volume (mm$^3$) over days post-treatment. OMP-18R5 was administered intraperitoneally and paclitaxel was administered at 15 mg/kg once a week.

As shown in FIG. 2, OMP-18R5 in combination with paclitaxel administered at 25 mg/kg was efficacious in reducing PE-13 tumor growth with dosing once a week, once every 2 weeks, and once every 4 weeks. Tumor growth inhibition with OMP-18R5 in combination with paclitaxel was greater than the growth inhibition seen with paclitaxel alone.

At the ending of dosing on day 77, trabecular bone formation was assessed in the OMP-18R5 treated mice as compared to mice treated with control (paclitaxel alone).

Tissue sections were prepared from the tibia of control and OMP-18R5-treated mice and stained with hemotoxylin and eosin (H&E). The light pink staining regions highlighted by the white arrows correspond to trabecular bone.

Figure 3:
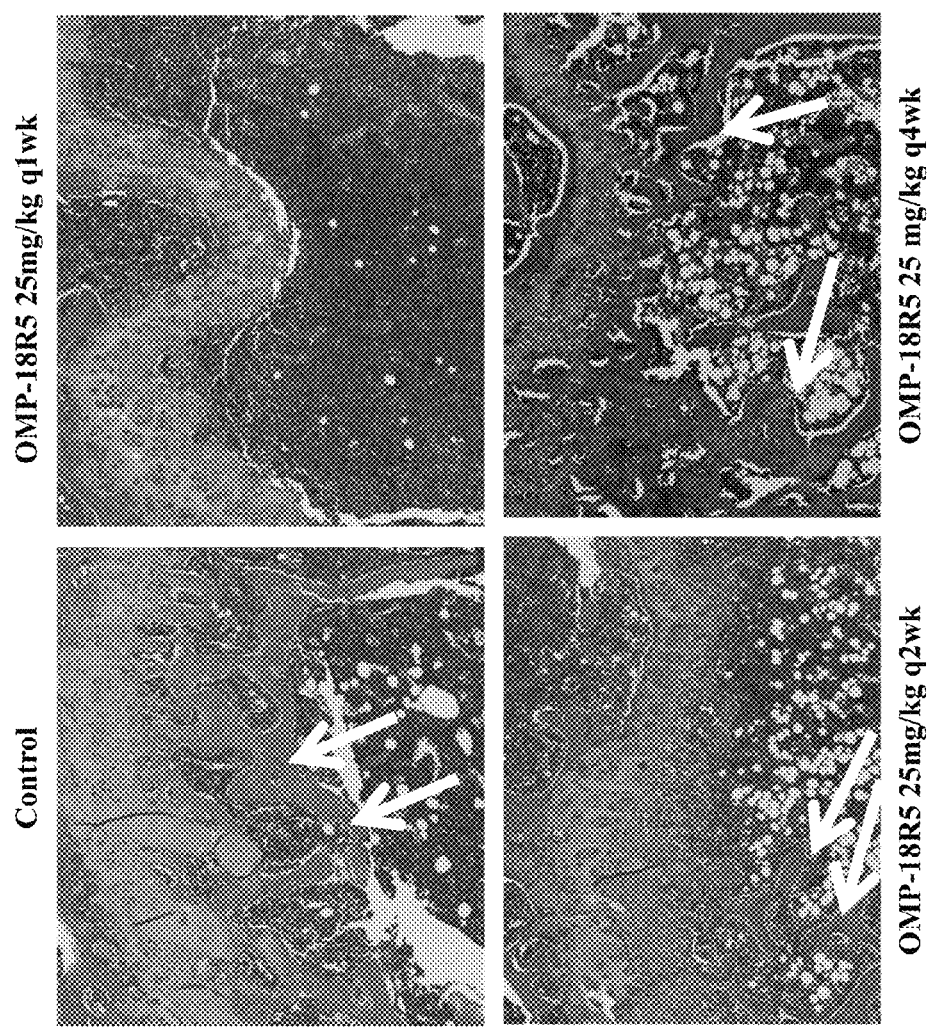
FIG. 3. Effect of OMP-18R5 on bone formation in mice.

As observed in FIG. 3, there was a reduction in bone loss with treatment of OMP-18R5 at 25 mg/kg once every 2 weeks as compared to treatment of 25 mg/kg once every week. Importantly, treatment of OMP-18R5 at 25 mg/kg every 4 weeks appeared to have no perceptible effect on bone formation.

Example 3

Effect of Zolendronic Acid in Reducing the Effect of OMP-18R5 on Bone Formation NOD/SCID mice were randomized into groups (n=5 per group) and treated with anti-FZD antibody OMP-18R5 or OMP-18R5 in combination with zolendronic acid. Mice were treated with 20 mg/kg OMP-18R5 on days 1 and 15 only, or 20 mg/kg OMP-18R5 on days 1 and 15 in combination with a single IV dose of 100 ug/kg zoledronic acid on day 1. At the end of dosing on day 29, femurs and tibias from mice treated with OMP-18R5 alone were compared to femurs and tibias from mice treated with the combination of OMP-18R5 and zoledronic acid and to mice treated with a control antibody.

Tissues sections of femur and tibia were prepared as described in Example 2.

Figure 4:
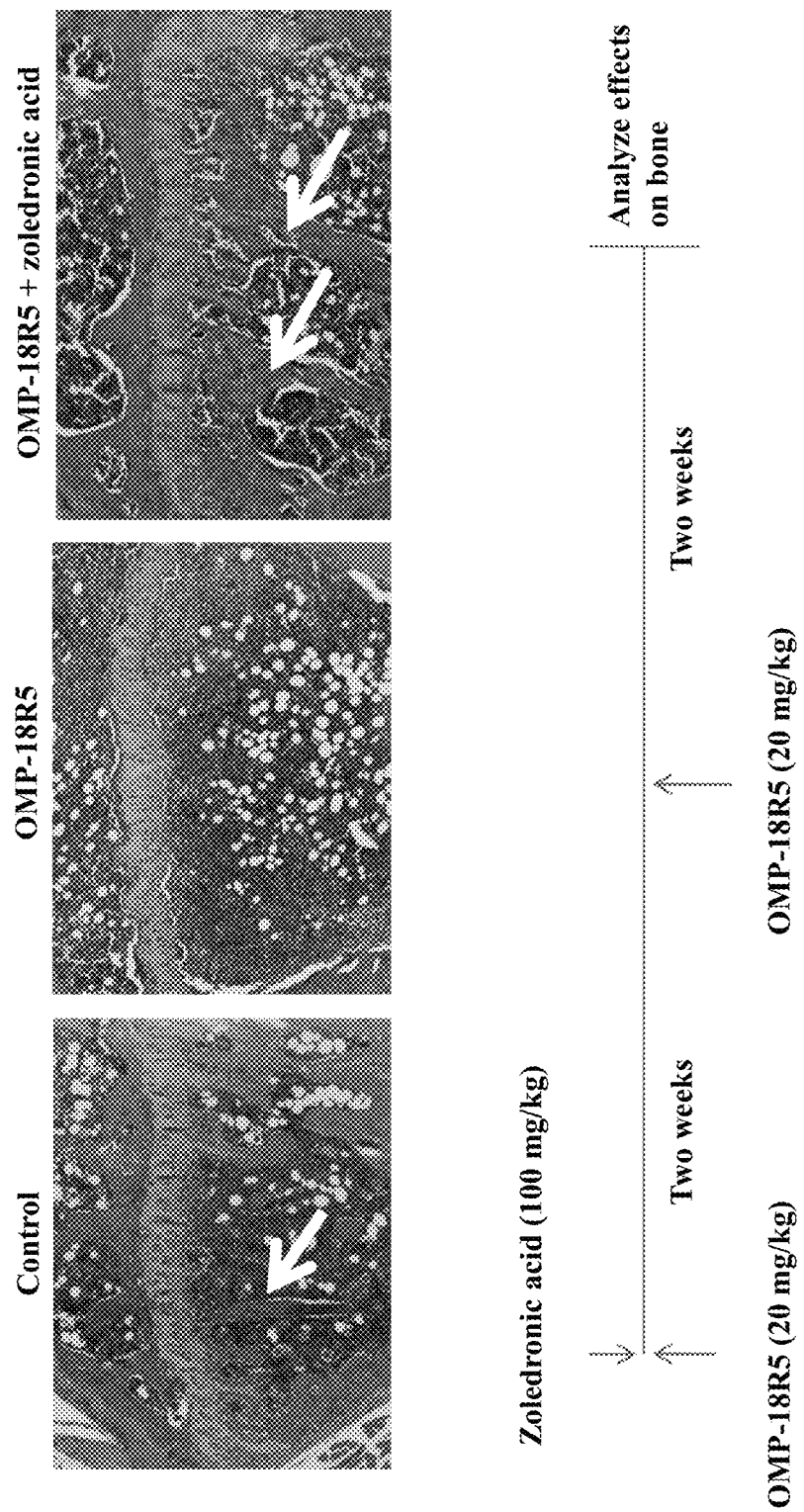
FIG. 4. Effect of zolendronic acid on bone formation in mice treated with OMP-18R5.

As shown in FIG. 4, a single IV administration of zoledronic acid to mice treated with OMP-18R5 resulted in subchondral bone formation comparable to mice treated with a control antibody. Additional studies have demonstrated that co-administration of zolendronic acid does not affect the anti-tumor efficacy of OMP-18R5. These data support the hypothesis that bisphosphonate administration may be protective against the catabolic effects of Wnt inhibition, providing a path to preserve bone integrity and allow the benefits of targeting the Wnt pathway.

Example 4

Phase 1 Study of OMP-18R5 in Patients with Solid Tumors

The study is an open-label Phase 1 dose-escalation study of OMP-18R5 in patients with a solid tumor for which there is no remaining standard curative therapy and no therapy with a demonstrated survival benefit. The primary objectives of the study are to determine the safety and the maximum tolerated dose of OMP-18R5. The secondary objectives are to determine the rate of immunogenicity, the preliminary efficacy, and the pharmacokinetics of OMP-18R5.

The patients in the initial portion of the trial were treated with a dosing regimen of OMP-18R5 of 0.5 mg/kg every week (n=3) and 1.0 mg/kg every week (n=5). One patient who received 0.5 mg/kg once a week developed fractures of their anterior ribs and lumbar spine after receiving study drug for approximately 100 days. As a result, in the current phase of the trial (study is ongoing and patients are still being enrolled) less frequent dosing is being utilized. Specifically, the dose levels are 0.5 mg/kg once every two weeks (n=3), and 1 mg/kg (n=4), 2.5 mg/kg (n=3), 5 mg/kg, and 10 mg/kg once every 3 weeks. Cohorts of 3 subjects are treated and evaluated for dose-limiting toxicities (DLTs) through Day 28. If 0 of 3 subjects have a DLT, escalation to the next dose cohort occurs. If 1 of 3 subjects experiences a DLT, 3 additional subjects are treated. If 2 or more subjects experience a DLT, no further subjects are dosed at that level and 3 additional subjects are added to the preceding dose cohort unless 6 subjects have already been treated at that dose level. Tumor assessments are performed on Day 56 and then every 56 days thereafter. Patients with stable disease or a response at Day 56 will be allowed to continue to receive OMP-18R5 until disease progression.

After a patient experienced a skeletal-related (bone fracture) event, samples from the first 8 patients were used to measure four bone turnover markers—bone specific alkaline phosphatase, procollagen type 1 N-terminal propeptide (P1NP), osteocalcin, and collagen type 1 cross-linked C-telopeptide (β-CTX). While no change during therapy was noted for bone specific alkaline phosphatase, P1NP, and osteocalcin, an increase in β-CTX was noted in all 7 subjects who had at least one follow-up value (Table 1, increased β-CTX values are underlined).

TABLE 1

| Patient | Tumor Type | Dose (mg/kg) | Day | β-CTX |
|---|---|---|---|---|
| 1 | Colorectal | 0.5 QW | Day 0 | 570 |
| 2 | Colorectal | 0.5 QW | Day 0 | 196 |
|   |   |   | Day 28 | 308 |
|   |   |   | Treatment Terminated | 217 |
| 3 | Neuroendocrine (carcinoid) | 0.5 QW | Day 0 | 219 |
|   |   |   | Day 28 | 825 |
|   |   |   | Day 56 | 896 |
|   |   |   | Treatment Terminated | 708 |
| 4 | Leiomyosarcoma | 1 QW | Day 0 | 298 |
|   |   |   | Treatment Terminated | 401 |
| 5 | Breast | 1 QW | Day 0 | 229 |
|   |   |   | Day 28 | 681 |
|   |   |   | Treatment Terminated | 370 |
| 6 | Colorectal | 1 QW | Day 0 | 162 |
|   |   |   | Day 28 | 598 |
| 7 | Colon | 1 QW | Day 0 | 144 |
|   |   |   | Day 28 | 301 |
| 8 | Pancreatic | 1 QW | Day 0 | 406 |
|   |   |   | Day 28 | 551 |

Thus, β-CTX appeared to be an early and sensitive biomarker of the effect of OMP-18R5 on bone.

Based on the initial Phase 1 study results, the study protocol was amended to include monitoring for skeletal-related side effects and/or toxicities with DEXA bone density scans, bone scans, and measurements of bone turnover biomarkers bone specific alkaline phosphatase, P1NP, osteocalcin, and β-CTX. The amended protocol also included a strategy for treatment of skeletal-related side effects and/or toxicities.

Any patient who had at least a doubling of their β-CTX level from their screening value or a T-score decline to less than −2.5 in the total femur or L1-L4 DEXA scan measurement would be administered an anti-resorptive medication, specifically the bisphosphonate zoledronic acid. The zoledronic acid will be administered intravenously at a dose of 5 mg at the time of the doubling of the β-CTX value or decline in T-score.

Table 2 shows the results (as of January 2013) from the 10 patients who were subsequently enrolled and treated with less frequent dosing (i.e., intermittent dosing) of OMP-18R5 (β-CTX values at least twice as high as baseline are underlined).

TABLE 2

| Patient | Tumor Type | Dose (mg/kg) | Day | β-CTX |
|---|---|---|---|---|
| 9 | Melanoma | 0.5 QOW | Day 0 | 203 |
|  |  |  | Day 28 | 195 |
|  |  |  | Day 56 | 287 |
| 10 | Neuroendocrine (pancreas) | 0.5 QOW | Day 0 | 306 |
|  |  |  | Day 28 | 286 |
|  |  |  | Day 56 | 304 |
|  |  |  | Day 84 | <u>664</u> |
|  |  |  | Day 112 | 270 |
|  |  |  | Day 140 | 288 |
|  |  |  | Day 168 | 413 |
|  |  |  | Day 196 | 372 |
|  |  |  | Day 224 | 377 |
|  |  |  | Day 252 | 363 |
| 11 | Colorectal | 0.5 QOW | Day 0 | 721 |
|  |  |  | Day 56 | 327 |
| 12 | Neuroendocrine (carcinoid) | 1 Q3W | Day 0 | 689 |
|  |  |  | Day 28 | 846 |
|  |  |  | Day 56 | 707 |
|  |  |  | Day 84 | 350 |
|  |  |  | Day 112 | 759 |
|  |  |  | Day 140 | 526 |
|  |  |  | Day 168 | 967 |
|  |  |  | Day 196 | 688 |
| 13 | Bladder | 1 Q3W | Day 0 | 618 |
| 14 | Colon | 1 Q3W | Day 0 | 471 |
|  |  |  | Day 28 | 760 |
| 15 | Colon | 1 Q3W | Day 0 | 340 |
|  |  |  | Day 28 | 469 |
|  |  |  | Day 56 | 586 |
|  |  |  | Day 84 | 156 |
| 16 | Breast | 2.5 Q3W | Day 0 | 386 |
|  |  |  | Day 28 | <u>805</u> |
|  |  |  | Day 56 | 345 |
| 17 | Thymic | 2.5 Q3W | Day 0 | 232 |
|  |  |  | Day 28 | 309 |
| 18 | Desmoid | 2.5 Q3W | Day 0 | 607 |
|  |  |  | Day 28 | 555 |

Only two of these ten patients had a doubling of their β-CTX (patient 10 from a value of 306 at baseline to a value of 664 at Day 84; and patient 16 from a value of 386 at baseline to a value of 805 at Day 28). These data suggest that less frequent dosing of OMP-18R5 at the dose levels studied results in fewer rises in β-CTX and less bone toxicity. According to the amended protocol, patient 10 was administered an intravenous dose of 5 mg of zoledronic acid. Following the administration of zoledronic acid, the β-CTX value returned to approximately baseline, a value of 270 at day 112, and remained at approximately that level in subsequent measurements. Patient 16 also received zolendronic acid for doubling of their β-CTX level, and their β-CTX levels also returned to baseline after treatment. These data suggest that zoledronic acid blocks the bone resorptive properties of OMP-18R5, and can be used to mitigate this skeletal-related side effect.

None of the patients enrolled in the study had a significant change in their bone mineral density (BMD) as assessed by DEXA scans (T-scores) while on treatment with OMP-18R5 (Table 3).

TABLE 3

| Patient | DEXA timepoint | Location | T-Score |
|---|---|---|---|
| 1 | Screening | AP spine L1-L4 | −1.6 |
|  | Termination | AP spine L1-L4 | −1.9 |
|  | Screening | AP spine L3 | −2.0 |
|  | Termination | AP spine L3-L4 | −2.1 |
|  | Screening | Dual femur neck left | −1.8 |
|  | Termination | Dual femur neck right | −1.7 |
|  | Screening | Dual femur total mean | −1.7 |
|  | Termination | Dual femur total mean | −2.2 |
| 3 | Screening | AP spine L1-L2 | −0.1 |
|  | Screening | AP spine L1-L4 | +0.2 |
|  | Termination | AP spine L1-L4 | +0.7 |
|  | Termination | AP spine L3-L4 | +0.5 |
|  | Screening | Dual femur neck left | −0.1 |
|  | Termination | Dual femur neck right | +0.2 |
|  | Screening | Dual femur total mean | +1.0 |
|  | Termination | Dual femur total mean | +0.7 |
| 5 | Screening | Femur | −1.2 |
|  | Termination | Femur | −1.0 |
|  | Screening | Lumbar spine | −0.6 |
|  | Termination | Lumbar spine | −0.5 |
| 7 | Screening | Femur | +1.2 |
|  | Termination | Femur | +0.7 |
|  | Screening | Lumbar spine | +0.9 |
|  | Termination | Lumbar spine | +0.9 |
| 9 | Screening | Lumbar spine | −0.7 |
|  | Termination | Lumbar spine | −0.9 |
|  | Screening | Hip | +0.2 |
|  | Termination | Hip | +0.2 |
| 10 | Screening | AP spine L1-L2 | −0.9 |
|  | Screening | AP spine L1-L4 | −0.4 |
|  | Screening | Dual femur neck left | −1.4 |
|  | Screening | Dual femur total mean | −0.9 |
|  | Day 56 | Lumbar spine | −0.3 |
|  | Day 56 | Hip | −0.8 |
| 11 | Screening | Femur | +1.0 |
|  | Termination | Hip | +0.9 |
|  | Screening | Lumbar spine | +0.9 |
|  | Termination | Lumbar spine | +1.1 |
| 13 | Screening | Lumbar spine | +0.1 |
|  | Termination | Lumbar spine | +0.3 |
|  | Screening | Hip | −0.9 |
|  | Termination | Hip | −1.2 |
| 14 | Screening | Lumbar spine | 3.6 |
|  | Termination | Lumbar spine | 3.9 |
|  | Screening | Hip | 2.4 |
|  | Termination | Hip | 2.2 |
| 16 | Screening | Lumbar spine | 0.7 |
|  | Termination | Lumbar spine | 0.8 |

These data suggest that osteopenic patients can be treated with OMP-18R5 without a significant risk of developing a further decline in their bone mineral density. Furthermore, it confirms that β-CTX appears to be an early and sensitive biomarker of skeletal-related side effects and/or toxicities resulting from treatment with a Wnt pathway inhibitor. Finally, the study has shown that the skeletal-related side effects tied to treatment with OMP-18R5 appear to be manageable and reversible.

Example 5

Phase 1 Study of OMP-54F28 in Patients with Solid Tumors

The study is an open-label Phase 1 dose-escalation study of OMP-54F28 in patients with a solid tumor for which there is no remaining standard curative therapy. The primary objectives of the study are to determine the safety and the maximum tolerated dose of OMP-54F28. The secondary objectives are to determine the rate of immunogenicity, the preliminary efficacy, and the pharmacokinetics of OMP-54F28.

The patients in the initial portion of the trial were treated with a dosing regimen of OMP-54F28 of 0.5 mg/kg every 3 weeks (n=3) and 1.0 mg/kg every 3 weeks (n=3). This study is ongoing and patients are still being enrolled. Cohorts of 3 subjects are treated and evaluated for dose-limiting toxicities (DLTs) through Day 28. If 0 of 3 subjects have a DLT, escalation to the next dose cohort occurs. If 1 of 3 subjects experiences a DLT, 3 additional subjects are treated. If 2 or more subjects experience a DLT, no further subjects are dosed at that level and 3 additional subjects are added to the preceding dose cohort unless 6 subjects have already been treated at that dose level. Tumor assessments are performed on Day 56 and then every 56 days thereafter. Patients with stable disease or a response at Day 56 will be allowed to continue to receive OMP-54F28 until disease progression.

Based on information gathered from the Phase 1 OMP-18R5 study, any patient who has at least a doubling of their β-CTX level from their screening value or a T-score decline to less than −2.5 in their total femur or L1-L4 DEXA scan measurement will be administered zoledronic acid. The zoledronic acid will be administered intravenously at a dose of 5 mg at the time of the doubling of the β-CTX value or decline in T-score.

Table 4 shows the results (as of January 2013) from the first 6 patients who were enrolled and treated with OMP-54F28 once every 3 weeks (β-CTX values at least twice as high as baseline are underlined).

TABLE 4

| Patient | Tumor Type | Dose (mg/kg) | Day | β-CTX |
|---|---|---|---|---|
| 1 | Ovarian | 0.5 Q3W | Day 0 | 215 |
|   |   |   | Day 28 | 144 |
|   |   |   | Day 56 | 119 |
|   |   |   | Treatment Terminated | 104 |
| 2 | Colorectal | 0.5 Q3W | Day 0 | 538 |
|   |   |   | Day 28 | 604 |
|   |   |   | Treatment Terminated | <u>1122</u> |
| 3 | Pancreatic | 0.5 Q3W | Day 0 | 497 |
|   |   |   | Day 28 | 360 |
|   |   |   | Day 56 | 414 |
|   |   |   | Day 84 | 614 |
| 4 | Adenocystic | 1 Q3W | Day 0 | 346 |
|   |   |   | Day 28 | 289 |
| 5 | Renal cell | 1 Q3W | Day 0 | 657 |
|   |   |   | Day 28 | 346 |
| 6 | Cervical | 1 Q3W | Day 0 | 262 |
|   |   |   | Day 28 | 238 |

Patient 2 had a doubling of their β-CTX from a value of 538 at baseline to a value of 1122 at Day 42. This patient's disease progressed and treatment with OMP-54F28 was stopped. Similar to results seen with OMP-18R5 treatment, these initial data suggest that treatment with OMP-54F28 at dose levels of 0.5 mg/kg and 1.0 mg/kg once every 3 weeks results in few rises in β-CTX and less bone toxicity. These early results from treatment with OMP-54F28 are further evidence that the skeletal-related side effects tied to treatment with Wnt pathway inhibitors appear to be manageable with reasonable mitigation strategies.

It is understood that the examples and embodiments described herein are for illustrative purposes only and that various modifications or changes in light thereof will be suggested to persons skilled in the art and are to be included within the spirit and purview of this application.

All publications, patents, and patent applications cited herein are hereby incorporated by reference in their entirety for all purposes to the same extent as if each individual publication, patent, or patent application were specifically and individually indicated to be so incorporated by reference.

Following are the sequences disclosed in the application:

```
18R5 Heavy chain CDR1
                                                           (SEQ ID NO: 1)
GFTFSHYTLS 18R5 Heavy chain CDR2
                                                           (SEQ ID NO: 2)
VISGDGSYTYYADSVKG 18R5 Heavy chain CDR3
                                                           (SEQ ID NO: 3)
NFIKYVFAN 18R5 Light chain CDR1
                                                           (SEQ ID NO: 4)
SGDNIGSFYVH 18R5 Light chain CDR2
                                                           (SEQ ID NO: 5)
DKSNRPSG 18R5 Light chain CDR3
                                                           (SEQ ID NO: 6)
QSYANTLSL 18R5 Heavy chain variable region amino acid sequence
                                                           (SEQ ID NO: 7)
EVQLVESGGGLVQPGGSLRLSCAASGFTFSHYTLSWVRQAPGKGLEWVSVISGDGSYTYYADSVKGRFTIS

SDNSKNTLYLQMNSLRAEDTAVYYCARNFIKYVFANWGQGTLVTVSS

18R5 Light chain variable region amino acid sequence
                                                           (SEQ ID NO: 8)
DIELTQPPSVSVAPGQTARISCSGDNIGSFYVHWYQQKPGQAPVLVIYDKSNRPSGIPERFSGSNSGNTAT

LTISGTQAEDEADYYCQSYANTLSLVFGGGTKLTVLG
```

18R5 Heavy chain amino acid sequence with predicted signal sequence underlined (SEQ ID NO: 9)

<u>MKHLWFFLLLVAAPRWVLS</u>EVQLVESGGGLVQPGGSLRLSCAASGFTFSHYTLSWVRQAPGKGLEWVSVIS

GDGSYTYYADSVKGRFTISSDNSKNTLYLQMNSLRAEDTAVYYCARNFIKYVFANWGQGTLVTVSSASTKG

PSVFPLAPCSRSTSESTAALGCLVKDYFPEPVTVSWNSGALTSGVHTFPAVLQSSGLYSLSSVVTVPSSNF

GTQTYTCNVDHKPSNTKVDKTVERKCCVECPPCPAPPVAGPSVFLFPPKPKDTLMISRTPEVTCVVVDVSH

EDPEVQFNWYVDGVEVHNAKTKPREEQFNSTFRVVSVLTVVHQDWLNGKEYKCKVSNKGLPAPIEKTISKT

KGQPREPQVYTLPPSREEMTKNQVSLTCLVKGFYPSDIAVEWESNGQPENNYKTTPPMLDSDGSFFLYSKL

TVDKSRWQQGNVFSCSVMHEALHNHYTQKSLSLSPGK

18R5 Light chain amino acid sequence with predicted signal sequence underlined (SEQ ID NO: 10)

<u>MAWALLLLTLLTQGTGSWA</u>DIELTQPPSVSVAPGQTARISCSGDNIGSFYVHWYQQKPGQAPVLVIYDKSN

RPSGIPERFSGSNSGNTATLTISGTQAEDEADYYCQSYANTLSLVFGGGTKLTVLGQPKAAPSVTLFPPSS

EELQANKATLVCLISDFYPGAVTVAWKADSSPVKAGVETTTPSKQSNNKYAASSYLSLTPEQWKSHRSYSC

QVTHEGSTVEKTVAPTECS

18R5 Heavy chain amino acid sequence without predicted signal sequence (SEQ ID NO: 11)

EVQLVESGGGLVQPGGSLRLSCAASGFTFSHYTLSWVRQAPGKGLEWVSVISGDGSYTYYADSVKGRFTIS

SDNSKNTLYLQMNSLRAEDTAVYYCARNFIKYVFANWGQGTLVTVSSASTKGPSVFPLAPCSRSTSESTAA

LGCLVKDYFPEPVTVSWNSGALTSGVHTFPAVLQSSGLYSLSSVVTVPSSNFGTQTYTCNVDHKPSNTKVD

KTVERKCCVECPPCPAPPVAGPSVFLFPPKPKDTLMISRTPEVTCVVVDVSHEDPEVQFNWYVDGVEVHNA

KTKPREEQFNSTFRVVSVLTVVHQDWLNGKEYKCKVSNKGLPAPIEKTISKTKGQPREPQVYTLPPSREEM

TKNQVSLTCLVKGFYPSDIAVEWESNGQPENNYKTTPPMLDSDGSFFLYSKLTVDKSRWQQGNVFSCSVMH

EALHNHYTQKSLSLSPGK

18R5 Light chain amino acid sequence without predicted signal sequence (SEQ ID NO: 12)

DIELTQPPSVSVAPGQTARISCSGDNIGSFYVHWYQQKPGQAPVLVIYDKSNRPSGIPERFSGSNSGNTAT

LTISGTQAEDEADYYCQSYANTLSLVFGGGTKLTVLGQPKAAPSVTLFPPSSEELQANKATLVCLISDFYP

GAVTVAWKADSSPVKAGVETTTPSKQSNNKYAASSYLSLTPEQWKSHRSYSCQVTHEGSTVEKTVAPTECS

Human FZD1 Fri domain amino acid sequence without predicted signal sequence (SEQ ID NO: 13)

QQPPPPPQQQQSGQQYNGERGISVPDHGYCQPISIPLCTDIAYNQTIMPNLLGHTNQEDAGLEVHQFYPLV

KVQCSAELKFFLCSMYAPVCTVLEQALPPCRSLCERARQGCEALMNKFGFQWPDTLKCEKFPVHGAGELCV

GQNTSDKGT

Human FZD2 Fri domain amino acid sequence without predicted signal sequence (SEQ ID NO: 14)

QFHGEKGISIPDHGFCQPISIPLCTDIAYNQTIMPNLLGHTNQEDAGLEVHQFYPLVKVQCSPELRFFLCS

MYAPVCTVLEQAIPPCRSICERARQGCEALMNKFGFQWPERLRCEHFPRHGAEQICVGQNHSEDG

Human FZD3 Fri domain amino acid sequence without predicted signal sequence (SEQ ID NO: 15)

HSLFSCEPITLRMCQDLPYNTTFMPNLLNHYDQQTAALAMEPFHPMVNLDCSRDFRPFLCALYAPICMEYG

RVTLPCRRLCQRAYSECSKLMEMFGVPWPEDMECSRFPDCDEPYPRLVDL

```
Human FZD4 Fri domain amino acid sequence without predicted signal
sequence
                                                     (SEQ ID NO: 16)
FGDEEERRCDPIRISMCQNLGYNVTKMPNLVGHELQTDAELQLTTFTPLIQYGCSSQLQFFLCSVYVPMCT

EKINIPIGPCGGMCLSVKRRCEPVLKEFGFAWPESLNCSKFPPQNDHNHMCMEGPGDEEV

Human FZD5 Fri domain amino acid sequence without predicted signal
sequence
                                                     (SEQ ID NO: 17)
ASKAPVCQEITVPMCRGIGYNLTHMPNQFNHDTQDEAGLEVHQFWPLVEIQCSPDLRFFLCSMYTPICLPD

YHKPLPPCRSVCERAKAGCSPLMRQYGFAWPERMSCDRLPVLGRDAEVLCMDYNRSEATT

Human FZD6 Fri domain amino acid sequence without predicted signal
sequence
                                                     (SEQ ID NO: 18)
HSLFTCEPITVPRCMKMAYNMTFFPNLMGHYDQSIAAVEMEHFLPLANLECSPNIETFLCKAFVPTCIEQI

HVVPPCRKLCEKVYSDCKKLIDTFGIRWPEELECDRLQYCDETVPVTFDPHTEFLG

Human FZD7 Fri domain amino acid sequence without predicted signal
sequence
                                                     (SEQ ID NO: 19)
QPYHGEKGISVPDHGFCQPISIPLCTDIAYNQTILPNLLGHTNQEDAGLEVHQFYPLVKVQCSPELRFFLC

SMYAPVCTVLDQAIPPCRSLCERARQGCEALMNKFGFQWPERLRCENFPVHGAGEICVGQNTSDGSG

Human FZD8 Fri domain amino acid sequence without predicted signal
sequence
                                                     (SEQ ID NO: 20)
ASAKELACQEITVPLCKGIGYNYTYMPNQFNHDTQDEAGLEVHQFWPLVEIQCSPDLKFFLCSMYTPICLE

DYKKPLPPCRSVCERAKAGCAPLMRQYGFAWPDRMRCDRLPEQGNPDTLCMDYNRTDLTT

Human FZD9 Fri domain amino acid sequence without predicted signal
sequence
                                                     (SEQ ID NO: 21)
LEIGRFDPERGRGAAPCQAVEIPMCRGIGYNLTRMPNLLGHTSQGEAAAELAEFAPLVQYGCHSHLRFFLC

SLYAPMCTDQVSTPIPACRPMCEQARLRCAPIMEQFNFGWPDSLDCARLPTRNDPHALCMEAPENA

Human FZD10 Fri domain amino acid sequence without predicted signal
sequence
                                                     (SEQ ID NO: 22)
ISSMDMERPGDGKCQPIEIPMCKDIGYNMTRMPNLMGHENQREAAIQLHEFAPLVEYGCHGHLRFFLCSLY

APMCTEQVSTPIPACRVMCEQARLKCSPIMEQFNFKWPDSLDCRKLPNKNDPNYLCMEAPNNG

Human FZD1 amino acids 116-227
                                                     (SEQ ID NO: 23)
CQPISIPLCTDIAYNQTIMPNLLGHTNQEDAGLEVHQFYPLVKVQCSAELKFFLCSMYAPVCTVLEQALPP

CRSLCERARQGCEALMNKFGFQWPDTLKCEKFPVHGAGELC

Human FZD2 amino acids 39-150
                                                     (SEQ ID NO: 24)
CQPISIPLCTDIAYNQTIMPNLLGHTNQEDAGLEVHQFYPLVKVQCSPELRFFLCSMYAPVCTVLEQAIPP

CRSICERARQGCEALMNKFGFQWPERLRCEHFPRHGAEQIC

Human FZD3 amino acids 28-133
                                                     (SEQ ID NO: 25)
CEPITLRMCQDLPYNTTFMPNLLNHYDQQTAALAMEPFHPMVNLDCSRDFRPFLCALYAPICMEYGRVTLP

CRRLCQRAYSECSKLMEMFGVPWPEDMECSRFPDC

Human FZD4 amino acids 48-161
                                                     (SEQ ID NO: 26)
CDPIRISMCQNLGYNVTKMPNLVGHELQTDAELQLTTFTPLIQYGCSSQLQFFLCSVYVPMCTEKINIPIG

PCGGMCLSVKRRCEPVLKEFGFAWPESLNCSKFPPQNDHNHMC

Human FZD5 amino acids 33-147
                                                     (SEQ ID NO: 27)
CQEITVPMCRGIGYNLTHMPNQFNHDTQDEAGLEVHQFWPLVEIQCSPDLRFFLCSMYTPICLPDYHKPLP

PCRSVCERAKAGCSPLMRQYGFAWPERMSCDRLPVLGRDAEVLC
```

Human FZD6 amino acids 24-129

(SEQ ID NO: 28)
CEPITVPRCMKMAYNMTFFPNLMGHYDQSIAAVEMEHFLPLANLECSPNIETFLCKAFVPTCIEQIHVVPP

CRKLCEKVYSDCKKLIDTFGIRWPEELECDRLQYC

Human FZD7 amino acids 49-160

(SEQ ID NO: 28)
CQPISIPLCTDIAYNQTILPNLLGHTNQEDAGLEVHQFYPLVKVQCSPELRFFLCSMYAPVCTVLDQAIPP

CRSLCERARQGCEALMNKFGFQWPERLRCENFPVHGAGEIC

Human FZD8 amino acids 35-148

(SEQ ID NO: 30)
CQEITVPLCKGIGYNYTYMPNQFNHDTQDEAGLEVHQFWPLVEIQCSPDLKFFLCSMYTPICLEDYKKPLP

PCRSVCERAKAGCAPLMRQYGFAWPDRMRCDRLPEQGNPDTLC

Human FZD9 amino acids 39-152

(SEQ ID NO: 31)
CQAVEIPMCRGIGYNLTRMPNLLGHTSQGEAAAELAEFAPLVQYGCHSHLRFFLCSLYAPMCTDQVSTPIP

ACRPMCEQARLRCAPIMEQFNFGWPDSLDCARLPTRNDPHALC

Human FZD10 amino acids 34-147

(SEQ ID NO: 32)
CQPIEIPMCKDIGYNMTRMPNLMGHENQREAAIQLHEFAPLVEYGCHGHLRFFLCSLYAPMCTEQVSTPIP

ACRVMCEQARLKCSPIMEQFNFKWPDSLDCRKLPNKNDPNYLC

Human FZD8 Fri domain amino acid sequence without predicted signal
sequence (variant)

(SEQ ID NO: 33)
ASAKELACQEITVPLCKGIGYNYTYMPNQFNHDTQDEAGLEVHQFWPLVEIQCSPDLKFFLCSMYTPICLE

DYKKPLPPCRSVCERAKAGCAPLMRQYGFAWPDRMRCDRLPEQGNPDTLCMDYNRTDL

Human IgG$_1$ Fc region (SEQ ID NO: 34)
DKTHTCPPCPAPELLGGPSVFLFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLTVDKSRWQQGNVFSCSVMHEALH

NHYTQKSLSLSPGK

Human IgG$_1$ Fc region (variant)

(SEQ ID NO: 35)
DKTHTCPPCPAPELLGGPSVFLFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKGQPREPQVYTLPPSREEMTKNQ

VSLTCLVKGFYPSDIAVEWESNGQPENNYKTTPPVLDSDGSFFLYSKLTVDKSRWQQGNVFSCSVMHEALH

NHYTQKSLSLSPGK

Human IgG$_1$ Fc region (SEQ ID NO: 36)
KSSDKTHTCPPCPAPELLGGPSVFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYSKLTVDKSRWQQGNVFSCSVMHE

ALHNHYTQKSLSLSPGK

Human IgG$_1$ Fc region (SEQ ID NO: 37)
EPKSSDKTHTCPPCPAPELLGGPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFFLYSKLTVDKSRWQQGNVFSCSVM

HEALHNHYTQKSLSLSPGK

-continued

Human IgG₂ Fc region
(SEQ ID NO: 38)
CVECPPCPAPPVAGPSVFLFPPKPKDTLMISRTPEVTCVVVDVSHEDPEVQFNWYVDGVEVHNAKTKPREE

QFNSTFRVVSVLTVVHQDWLNGKEYKCKVSNKGLPAPIEKTISKTKGQPREPQVYTLPPSREEMTKNQVSL

TCLVKGFYPSDIAVEWESNGQPENNYKTTPPMLDSDGSFFLYSKLTVDKSRWQQGNVFSCSVMHEALHNHY

TQKSLSLSPGK

FZD8-Fc variant 54F03 amino acid sequence (without predicted signal
sequence)
(SEQ ID NO: 39)
ASAKELACQEITVPLCKGIGYNYTYMPNQFNHDTQDEAGLEVHQFWPLVEIQCSPDLKFFLCSMYTPICLE

DYKKPLPPCRSVCERAKAGCAPLMRQYGFAWPDRMRCDRLPEQGNPDTLCMDYNRTDLTTGRADKTHTCPP

CPAPELLGGPSVFLFPPKPKDTLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQGNVFSCSVMHEALHNHYTQKSL

SLSPGK

FZD8-Fc variant 54F16, 54F17, 54F18, 54F23, 54F25, 54F27, 54F29, 54F31,
and 54F34 amino acid sequence (without predicted signal sequence)
(SEQ ID NO: 40)
ASAKELACQEITVPLCKGIGYNYTYMPNQFNHDTQDEAGLEVHQFWPLVEIQCSPDLKFFLCSMYTPICLE

DYKKPLPPCRSVCERAKAGCAPLMRQYGFAWPDRMRCDRLPEQGNPDTLCMDYNRTDLTTKSSDKTHTCPP

CPAPELLGGPSVFLFPPKPKDTLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQGNVFSCSVMHEALHNHYTQKSL

SLSPGK

FZD8-Fc variant 54F19, 54F20, 54F24, 54F26, 54F28, 54F30, 54F32,
54F34 and 54F35 amino acid sequence (without predicted signal sequence)
(SEQ ID NO: 41)
ASAKELACQEITVPLCKGIGYNYTYMPNQFNHDTQDEAGLEVHQFWPLVEIQCSPDLKFFLCSMYTPICLE

DYKKPLPPCRSVCERAKAGCAPLMRQYGFAWPDRMRCDRLPEQGNPDTLCMDYNRTDLTTEPKSSDKTHTC

PPCPAPELLGGPSVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQGNVFSCSVMHEALHNHYTQK

SLSLSPGK

FZD8-Fc variant 54F03 amino acid sequence with signal sequence
(SEQ ID NO: 42)
MEWGYLLEVTSLLAALALLQRSSGAAAASAKELACQEITVPLCKGIGYNYTYMPNQFNHDTQDEAGLEVHQ

FWPLVEIQCSPDLKFFLCSMYTPICLEDYKKPLPPCRSVCERAKAGCAPLMRQYGFAWPDRMRCDRLPEQG

NPDTLCMDYNRTDLTTGRADKTHTCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYKCKVSNKALPAPIEKTISKAKGQP

REPQVYTLPPSRDELTKNQVSLTCLVKGFYPSDIAVEWESNGQPENNYKTTPPVLDSDGSFFLYSKLTVDK

SRWQQGNVFSCSVMHEALHNHYTQKSLSLSPGK

FZD8-Fc variant 54F16 amino acid sequence with signal sequence
(SEQ ID NO: 43)
MEWGYLLEVTSLLAALALLQRSSGAAAASAKELACQEITVPLCKGIGYNYTYMPNQFNHDTQDEAGLEVHQ

FWPLVEIQCSPDLKFFLCSMYTPICLEDYKKPLPPCRSVCERAKAGCAPLMRQYGFAWPDRMRCDRLPEQG

NPDTLCMDYNRTDLTTKSSDKTHTCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYKCKVSNKALPAPIEKTISKAKGQP

-continued

REPQVYTLPPSRDELTKNQVSLTCLVKGFYPSDIAVEWESNGQPENNYKTTPPVLDSDGSFFLYSKLTVDK

SRWQQGNVFSCSVMHEALHNHYTQKSLSLSPGK

FZD8-Fc variant 54F26 with signal sequence
(SEQ ID NO: 44)

MEWGYLLEVTSLLAALFLLQRSPIVHAASAKELACQEITVPLCKGIGYNYTYMPNQFNHDTQDEAGLEVHQ

FWPLVEIQCSPDLKFFLCSMYTPICLEDYKKPLPPCRSVCERAKAGCAPLMRQYGFAWPDRMRCDRLPEQG

NPDTLCMDYNRTDLTTEPKSSDKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENNYKTTPPVLDSDGSFFLYSKLTV

DKSRWQQGNVFSCSVMHEALHNHYTQKSLSLSPGK

FZD8-Fc variant 54F28 with signal sequence
(SEQ ID NO: 45)

MEWGYLLEVTSLLAALLLLQRSPFVHAASAKELACQEITVPLCKGIGYNYTYMPNQFNHDTQDEAGLEVHQ

FWPLVEIQCSPDLKFFLCSMYTPICLEDYKKPLPPCRSVCERAKAGCAPLMRQYGFAWPDRMRCDRLPEQG

NPDTLCMDYNRTDLTTEPKSSDKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENNYKTTPPVLDSDGSFFLYSKLTV

DKSRWQQGNVFSCSVMHEALHNHYTQKSLSLSPGK

Human Wnt1 C-terminal cysteine rich domain (aa 288-370)
(SEQ ID NO: 46)

DLVYFEKSPNFCTYSGRLGTAGTAGRACNSSSPALDGCELLCCGRGHRTRTQRVTERCNCTFHWCCHVSCR

NCTHTRVLHECL

Human Wnt2 C-terminal cysteine rich domain (aa 267-360)
(SEQ ID NO: 47)

DLVYFENSPDYCIRDREAGSLGTAGRVCNLTSRGMDSCEVMCCGRGYDTSHVTRMTKCGCKFHWCCAVRCQ

DCLEALDVHTCKAPKNADWTTAT

Human Wnt2b C-terminal cysteine rich domain (aa 298-391)
(SEQ ID NO: 48)

DLVYFDNSPDYCVLDKAAGSLGTAGRVCSKTSKGTDGCEIMCCGRGYDTTRVTRVTQCECKFHWCCAVRCK

ECRNTVDVHTCKAPKKAEWLDQT

Human Wnt3 C-terminal cysteine rich domain (aa 273-355)
(SEQ ID NO: 49)

DLVYYENSPNFCEPNPETGSFGTRDRTCNVTSHGIDGCDLLCCGRGHNTRTEKRKEKCHCIFHWCCYVSCQ

ECIRIYDVHTCK

Human Wnt3a C-terminal cysteine rich domain (aa 270-352)
(SEQ ID NO: 50)

DLVYYEASPNFCEPNPETGSFGTRDRTCNVSSHGIDGCDLLCCGRGHNARAERRREKCRCVFHWCCYVSCQ

ECTRVYDVHTCK

Human Wnt7a C-terminal cysteine rich domain (aa 267-359)
(SEQ ID NO: 51)

DLVYIEKSPNYCEEDPVTGSVGTQGRACNKTAPQASGCDLMCCGRGYNTHQYARVWQCNCKFHWCCYVKCN

TCSERTEMYTCK

Human Wnt7b C-terminal cysteine rich domain (aa 267-349)
(SEQ ID NO: 52)

DLVYIEKSPNYCEEDAATGSVGTQGRLCNRTSPGADGCDTMCCGRGYNTHQYTKVWQCNCKFHWCCFVKCN

TCSERTEVFTCK

Human Wnt8a C-terminal cysteine rich domain (aa 248-355)
(SEQ ID NO: 53)

ELIFLEESPDYCTCNSSLGIYGTEGRECLQNSHNTSRWERRSCGRLCTECGLQVEERKTEVISSCNCKFQW

CCTVKCDQCRHVVSKYYCARSPGSAQSLGRVWFGVYI

-continued

Human Wnt8b C-terminal cysteine rich domain (aa 245-351)
(SEQ ID NO: 54)
ELVHLEDSPDYCLENKTLGLLGTEGRECLRRGRALGRWELRSCRRLCGDCGLAVEERRAETVSSCNCKFHW

CCAVRCEQCRRRVTKYFCSRAERPRGGAAHKPGRKP

Human Wnt10a C-terminal cysteine rich domain (aa 335-417)
(SEQ ID NO: 55)
DLVYFEKSPDFCEREPRLDSAGTVGRLCNKSSAGSDGCGSMCCGRGHNILRQTRSERCHCRFHWCCFVVCE

ECRITEWVSVCK

Human Wnt10b C-terminal cysteine rich domain (aa 307-389)
(SEQ ID NO: 56)
ELVYFEKSPDFCERDPTMGSPGTRGRACNKTSRLLDGCGSLCCGRGHNVLRQTRVERCHCRFHWCCYVLCD

ECKVTEWVNVCK

Linker
(SEQ ID NO: 57)
ESGGGGVT

Linker
(SEQ ID NO: 58)
LESGGGGVT

Linker
(SEQ ID NO: 59)
GRAQVT

Linker
(SEQ ID NO: 60)
WRAQVT

Linker
(SEQ ID NO: 61)
ARGRAQVT

---

What is claimed is:

1. A method for reducing a skeletal-related side effect and/or toxicity in a human subject having cancer and receiving treatment with a Wnt pathway inhibitor for the cancer, comprising:

(a) administering a therapeutically effective amount of a Wnt pathway inhibitor to the subject;

(b) determining the level of collagen type 1 cross-linked C-telopeptide (β-CTX) in a sample from the subject after the administration of the Wnt pathway inhibitor; and (c) administering to the subject a therapeutically effective amount of a bisphosphonate if the level of β-CTX in the sample is higher than a predetermined level of the β-CTX; and wherein the Wnt pathway inhibitor is:

(i) an antibody that specifically binds human FZD1, FZD2, FZD5, FZD7, and FZD8 and comprises a heavy chain CDR1 comprising GFTFSHYTLS (SEQ ID NO:1), a heavy chain CDR2 comprising VISGDGSYTYYADS-VKG (SEQ ID NO:2), and a heavy chain CDR3 comprising NFIKYVFAN (SEQ ID NO:3), and a light chain CDR1 comprising SGDNIGSFYVH (SEQ ID NO:4), a light chain CDR2 comprising DKSNRPSG (SEQ ID NO:5), and a light chain CDR3 comprising QSYANTLSL (SEQ ID NO:6); or (ii) a soluble receptor comprising a Fri domain of human FZD8 and a human Fc region.

2. The method of claim 1, wherein the Wnt pathway inhibitor is an antibody that specifically binds human FZD1, FZD2, FZD5, FZD7, and FZD8 and comprises a heavy chain CDR1 comprising GFTFSHYTLS (SEQ ID NO:1), a heavy chain CDR2 comprising VISGDGSYTYYADSVKG (SEQ ID NO:2), and a heavy chain CDR3 comprising NFIKYVFAN (SEQ ID NO:3), and a light chain CDR1 comprising SGD-NIGSFYVH (SEQ ID NO:4), a light chain CDR2 comprising DKSNRPSG (SEQ ID NO:5), and a light chain CDR3 comprising QSYANTLSL (SEQ ID NO:6).

3. The method of claim 2, wherein the antibody is a monoclonal antibody, a recombinant antibody, a chimeric antibody, a bispecific antibody, a human antibody, or an antibody fragment comprising an antigen-binding site.

4. The method of claim 2, wherein the antibody is OMP-18R5.

5. The method of claim 1, wherein the antibody comprises a heavy chain variable region comprising SEQ ID NO:7 and a light chain variable region comprising SEQ ID NO:8.

6. The method of claim 1, wherein the Wnt pathway inhibitor is a soluble receptor comprising a Fri domain of human FZD8 and a human Fc region.

7. The method of claim 6, wherein the soluble receptor comprises SEQ ID NO:41.

8. The method of claim 6, wherein the soluble receptor is OMP-54F28.

9. The method of claim 1, wherein the sample is blood, serum, or plasma.

10. The method of claim 1, wherein the predetermined level of β-CTX is determined at an earlier timepoint, at an initial screening, and/or prior to treatment.

11. The method of claim 1, wherein the level of β-CTX in the sample is at least two-fold higher than the predetermined level of the β-CTX.

12. The method of claim 1, wherein the skeletal-related side effect and/or toxicity is an increased risk of bone fracture, osteopenia, or osteoporosis.

13. The method of claim 1, wherein the bisphosphonate is zoledronic acid.

14. The method of claim 1, wherein the subject is treated with the Writ pathway inhibitor in combination with one or more additional therapeutic agents.

15. A method of selecting a human subject having cancer for treatment with a Wnt pathway inhibitor for the cancer, comprising:

(a) determining the level of β-CTX in a sample from the subject;

(b) selecting the subject for treatment with the Wnt pathway inhibitor if the level of β-CTX is below a predetermined level; and (c) administering a therapeutically effective dose of the Wnt pathway inhibitor to the subject;

wherein the Wnt pathway inhibitor is:

(i) an antibody that specifically binds human FZD1, FZD2, FZD5, FZD7, and FZD8 and comprises a heavy chain CDR1 comprising GFTFSHYTLS (SEQ ID NO:1), a heavy chain CDR2 comprising VISGDGSYTYYADS-VKG (SEQ ID NO:2), and a heavy chain CDR3 comprising NFIKYVFAN (SEQ ID NO:3), and a light chain CDR1 comprising SGDNIGSFYVH (SEQ ID NO:4), a light chain CDR2 comprising DKSNRPSG (SEQ ID NO:5), and a light chain CDR3 comprising QSYANTLSL (SEQ ID NO:6); or (ii) a soluble receptor comprising a Fri domain of human FZD8 and a human Fc region.

16. The method of claim 15, wherein the sample is blood, serum, or plasma.

17. The method of claim 15, wherein the pre-determined level of β-CTX sample is a level of β-CTX determined at an initial screening.

18. The method of claim 15, wherein the predetermined level of β-CTX is 1000 pg/ml.

19. The method of claim 15, wherein the antibody is OMP-18R5.

20. The method of claim 15, wherein the soluble receptor is OMP-54F28.

21. A method of preventing or attenuating the development of a skeletal-related side effect and/or toxicity in a human subject having cancer, comprising:

(a) determining the level of β-CTX in a sample from the subject prior to treatment for cancer;

(b) administering to the subject a therapeutically effective amount of a bisphosphonate if the level of β-CTX in the sample is higher than a predetermined level of β-CTX; and (c) administering to the subject a Wnt pathway inhibitor;

wherein steps (b) and (c) are performed in any order after step (a); and wherein the Wnt pathway inhibitor is:

(i) an antibody that specifically binds human FZD1, FZD2, FZD5, FZD7 and FZD8 and comprises a heavy chain CDR1 comprising GFTFSHYTLS (SEQ ID NO:1), a heavy chain CDR2 comprising VISGDGSYTYYADS-VKG (SEQ ID NO:2), and a heavy chain CDR3 comprising NFIKYVFAN (SEQ ID NO:3), and a light chain CDR1 comprising SGDNIGSFYVH (SEQ ID NO:4), a light chain CDR2 comprising DKSNRPSG (SEQ ID NO:5), and a light chain CDR3 comprising QSYANTLSL (SEQ ID NO:6); or (ii) a soluble receptor comprising a Fri domain of human FZD8 and a human Fc region.

22. The method of claim 21, wherein the antibody is OMP-18R5.

23. The method of claim 21, wherein the soluble receptor is OMP-54F28.

24. A method of preventing or attenuating the development of a skeletal-related side effect and/or toxicity in a human subject having cancel and receiving treatment with a Wnt pathway inhibitor, comprising administering to the subject a therapeutically effective amount of a bisphosphonate;

wherein the Wnt pathway inhibitor is:

(i) an antibody that specifically binds human FZD1, FZD2, FZD5, FZD7, and FZD8 and comprises a heavy chain CDR1 comprising GFTFSHYTLS (SEQ ID NO:1), a heavy chain CDR2 comprising VISGDGSYTYYADS- VKG (SEQ ID NO:2), and a heavy chain CDR3 comprising NFIKYVFAN (SEQ ID NO:3), and a light chain CDR1 comprising SGDNIGSFYVH (SEQ ID NO:4), a light chain CDR2 comprising DKSNRPSG (SEQ ID NO:5), and a light chain CDR3 comprising QSYANTLSL (SEQ ID NO:6); or
  (ii) a soluble receptor comprising a Fri domain of human FZD8 and a human Fc region.

25. The method of claim 24, wherein the antibody is OMP-18R5.

26. The method of claim 24, wherein the soluble receptor is OMP-54F28.

27. A method of treating cancer in a human subject having cancer, comprising:
  (a) administering to the subject a therapeutically effective amount of a Wnt pathway inhibitor; and
  (b) determining the level of β-CTX in a sample from the subject;

wherein the Wnt pathway inhibitor is:
  (i) an antibody that specifically binds human FZD1, FZD2, FZD5, FZD7, and FZD8 and comprises a heavy chain CDR1 comprising GFTFSHYTLS (SEQ ID NO:1), a heavy chain CDR2 comprising VISGDGSYTYYADSVKG (SEQ ID NO:2), and a heavy chain CDR3 comprising NFIKYVFAN (SEQ ID NO:3), and a light chain CDR1 comprising SGDNIGSFYVH (SEQ ID NO:4), a light chain CDR2 comprising DKSNRPSG (SEQ ID NO:5), and a light chain CDR3 comprising QSYANTLSL (SEQ ID NO:6); or
  (ii) a soluble receptor comprising a Fri domain of human FZD8 and a human Fc region.

28. The method of claim 27, wherein the antibody is OMP-18R5.

29. The method of claim 27, wherein the soluble receptor is OMP-54F28.

* * * * *

SEQUENCE LISTING

<160> NUMBER OF SEQ ID NOS: 61

<210> SEQ ID NO 1
<211> LENGTH: 10
<212> TYPE: PRT
<213> ORGANISM: Artificial Sequence
<220> FEATURE:
<223> OTHER INFORMATION: 18R5 Heavy chain CDR1

<400> SEQUENCE: 1

Gly Phe Thr Phe Ser His Tyr Thr Leu Ser
1               5                   10

<210> SEQ ID NO 2
<211> LENGTH: 17
<212> TYPE: PRT
<213> ORGANISM: Artificial Sequence
<220> FEATURE:
<223> OTHER INFORMATION: 18R5 Heavy chain CDR2

<400> SEQUENCE: 2

Val Ile Ser Gly Asp Gly Ser Tyr Thr Tyr Tyr Ala Asp Ser Val Lys
1               5                   10                  15

Gly

<210> SEQ ID NO 3
<211> LENGTH: 9
<212> TYPE: PRT
<213> ORGANISM: Artificial Sequence
<220> FEATURE:
<223> OTHER INFORMATION: 18R5 Heavy chain CDR3

```
<400> SEQUENCE: 3

Asn Phe Ile Lys Tyr Val Phe Ala Asn
1               5

<210> SEQ ID NO 4
<211> LENGTH: 11
<212> TYPE: PRT
<213> ORGANISM: Artificial Sequence
<220> FEATURE:
<223> OTHER INFORMATION: 18R5 Light chain CDR1

<400> SEQUENCE: 4

Ser Gly Asp Asn Ile Gly Ser Phe Tyr Val His
1               5                   10

<210> SEQ ID NO 5
<211> LENGTH: 8
<212> TYPE: PRT
<213> ORGANISM: Artificial Sequence
<220> FEATURE:
<223> OTHER INFORMATION: 18R5 Light chain CDR2

<400> SEQUENCE: 5

Asp Lys Ser Asn Arg Pro Ser Gly
1               5

<210> SEQ ID NO 6
<211> LENGTH: 9
<212> TYPE: PRT
<213> ORGANISM: Artificial Sequence
<220> FEATURE:
<223> OTHER INFORMATION: 18R5 Light chain CDR3

<400> SEQUENCE: 6

Gln Ser Tyr Ala Asn Thr Leu Ser Leu
1               5

<210> SEQ ID NO 7
<211> LENGTH: 118
<212> TYPE: PRT
<213> ORGANISM: Artificial Sequence
<220> FEATURE:
<223> OTHER INFORMATION: 18R5 Heavy chain variable region amino acid
      sequence

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Thr Leu Ser Trp Val Arg Gln Ala Pro Gly Lys Gly Leu Glu Trp Val
        35                  40                  45

Ser Val Ile Ser Gly Asp Gly Ser Tyr Thr Tyr Tyr Ala Asp Ser Val
    50                  55                  60

Lys Gly Arg Phe Thr Ile Ser Ser Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Phe Ile Lys Tyr Val Phe Ala Asn Trp Gly Gln Gly Thr
            100                 105                 110

Leu Val Thr Val Ser Ser
        115
```

```
<210> SEQ ID NO 8
<211> LENGTH: 108
<212> TYPE: PRT
<213> ORGANISM: Artificial Sequence
<220> FEATURE:
<223> OTHER INFORMATION: 18R5 Light chain variable region amino acid
      sequence

<400> SEQUENCE: 8

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Ser Phe Tyr Val
            20                  25                  30

His Trp Tyr Gln Gln Lys Pro Gly Gln Ala Pro Val Leu Val Ile Tyr
        35                  40                  45

Asp Lys Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Ala Asn Thr Leu Ser Leu
                85                  90                  95

Val Phe Gly Gly Gly Thr Lys Leu Thr Val Leu Gly
            100                 105

<210> SEQ ID NO 9
<211> LENGTH: 463
<212> TYPE: PRT
<213> ORGANISM: Artificial Sequence
<220> FEATURE:
<223> OTHER INFORMATION: 18R5 Heavy chain amino acid sequence

<400> SEQUENCE: 9

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser His Tyr Thr Leu Ser Trp Val Arg Gln Ala Pro Gly Lys Gly Leu
    50                  55                  60

Glu Trp Val Ser Val Ile Ser Gly Asp Gly Ser Tyr Thr Tyr Tyr Ala
65                  70                  75                  80

Asp Ser Val Lys Gly Arg Phe Thr Ile Ser Ser Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asn Phe Ile Lys Tyr Val Phe Ala Asn Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
```

```
                195                 200                 205
Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Val Ala Gly Pro Ser Val
                245                 250                 255

Phe Leu Phe Pro Pro Lys Pro Lys Asp Thr Leu Met Ile Ser Arg Thr
                260                 265                 270

Pro Glu Val Thr Cys Val Val Val Asp Val Ser His Glu Asp Pro Glu
                275                 280                 285

Val Gln Phe Asn Trp Tyr Val Asp Gly Val Glu Val His Asn Ala Lys
                290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
                340                 345                 350

Ser Lys Thr Lys Gly Gln Pro Arg Glu Pro Gln Val Tyr Thr Leu Pro
                355                 360                 365

Pro Ser Arg Glu Glu Met Thr Lys Asn Gln Val Ser Leu Thr Cys Leu
                370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
                420                 425                 430

Trp Gln Gln Gly Asn Val Phe Ser Cys Ser Val Met His Glu Ala Leu
                435                 440                 445

His Asn His Tyr Thr Gln Lys Ser Leu Ser Leu Ser Pro Gly Lys
    450                 455                 460

<210> SEQ ID NO 10
<211> LENGTH: 232
<212> TYPE: PRT
<213> ORGANISM: Artificial Sequence
<220> FEATURE:
<223> OTHER INFORMATION: 18R5 Light chain amino acid sequence

<400> SEQUENCE: 10

Met Ala Trp Ala Leu Leu Leu Thr Leu Leu Thr Gln Gly Thr Gly
1               5                   10                  15

Ser Trp Ala Asp Ile Glu Leu Thr Gln Pro Pro Ser Val Ser Val Ala
                20                  25                  30

Pro Gly Gln Thr Ala Arg Ile Ser Cys Ser Gly Asp Asn Ile Gly Ser
                35                  40                  45

Phe Tyr Val His Trp Tyr Gln Gln Lys Pro Gly Gln Ala Pro Val Leu
    50                  55                  60

Val Ile Tyr Asp Lys Ser Asn Arg Pro Ser Gly Ile Pro Glu Arg Phe
65                  70                  75                  80

Ser Gly Ser Asn Ser Gly Asn Thr Ala Thr Leu Thr Ile Ser Gly Thr
                85                  90                  95

Gln Ala Glu Asp Glu Ala Asp Tyr Tyr Cys Gln Ser Tyr Ala Asn Thr
```

```
                100             105             110
Leu Ser Leu Val Phe Gly Gly Gly Thr Lys Leu Thr Val Leu Gly Gln
        115                 120             125

Pro Lys Ala Ala Pro Ser Val Thr Leu Phe Pro Pro Ser Ser Glu Glu
    130                 135             140

Leu Gln Ala Asn Lys Ala Thr Leu Val Cys Leu Ile Ser Asp Phe Tyr
145                 150             155                 160

Pro Gly Ala Val Thr Val Ala Trp Lys Ala Asp Ser Ser Pro Val Lys
                165             170             175

Ala Gly Val Glu Thr Thr Thr Pro Ser Lys Gln Ser Asn Asn Lys Tyr
            180             185             190

Ala Ala Ser Ser Tyr Leu Ser Leu Thr Pro Glu Gln Trp Lys Ser His
        195             200             205

Arg Ser Tyr Ser Cys Gln Val Thr His Glu Gly Ser Thr Val Glu Lys
            210             215             220

Thr Val Ala Pro Thr Glu Cys Ser
225                 230

<210> SEQ ID NO 11
<211> LENGTH: 444
<212> TYPE: PRT
<213> ORGANISM: Artificial Sequence
<220> FEATURE:
<223> OTHER INFORMATION: 18R5 Heavy chain amino acid sequence

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Thr Leu Ser Trp Val Arg Gln Ala Pro Gly Lys Gly Leu Glu Trp Val
        35                  40                  45

Ser Val Ile Ser Gly Asp Gly Ser Tyr Thr Tyr Tyr Ala Asp Ser Val
    50                  55                  60

Lys Gly Arg Phe Thr Ile Ser Ser Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Phe Ile Lys Tyr Val Phe Ala Asn Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
```

```
                225                 230                 235                 240
Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
                260                 265                 270

Asn Trp Tyr Val Asp Gly Val Glu Val His Asn Ala Lys Thr Lys Pro
                275                 280                 285

Arg Glu Glu Gln Phe Asn Ser Thr Phe Arg Val Val Ser Val Leu Thr
                290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
                370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
                435                 440

<210> SEQ ID NO 12
<211> LENGTH: 213
<212> TYPE: PRT
<213> ORGANISM: Artificial Sequence
<220> FEATURE:
<223> OTHER INFORMATION: 18R5 Light chain amino acid sequence

<400> SEQUENCE: 12

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Ser Phe Tyr Val
                20                  25                  30

His Trp Tyr Gln Gln Lys Pro Gly Gln Ala Pro Val Leu Val Ile Tyr
                35                  40                  45

Asp Lys Ser Asn Arg Pro Ser Gly Ile Pro Glu Arg Phe Ser Gly Ser
                50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Ala Asn Thr Leu Ser Leu
                85                  90                  95

Val Phe Gly Gly Gly Thr Lys Leu Thr Val Leu Gly Gln Pro Lys Ala
                100                 105                 110

Ala Pro Ser Val Thr Leu Phe Pro Pro Ser Ser Glu Glu Leu Gln Ala
                115                 120                 125

Asn Lys Ala Thr Leu Val Cys Leu Ile Ser Asp Phe Tyr Pro Gly Ala
                130                 135                 140

Val Thr Val Ala Trp Lys Ala Asp Ser Ser Pro Val Lys Ala Gly Val
```

```
145                 150                 155                 160
Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
                195                 200                 205

Pro Thr Glu Cys Ser
    210

<210> SEQ ID NO 13
<211> LENGTH: 151
<212> TYPE: PRT
<213> ORGANISM: Homo sapiens

<400> SEQUENCE: 13

Gln Gln Pro Pro Pro Pro Gln Gln Gln Ser Gly Gln Tyr
1               5                   10              15

Asn Gly Glu Arg Gly Ile Ser Val Pro Asp His Gly Tyr Cys Gln Pro
                20                  25                  30

Ile Ser Ile Pro Leu Cys Thr Asp Ile Ala Tyr Asn Gln Thr Ile Met
            35                  40                  45

Pro Asn Leu Leu Gly His Thr Asn Gln Glu Asp Ala Gly Leu Glu Val
    50                  55                  60

His Gln Phe Tyr Pro Leu Val Lys Val Gln Cys Ser Ala Glu Leu Lys
65                  70                  75                  80

Phe Phe Leu Cys Ser Met Tyr Ala Pro Val Cys Thr Val Leu Glu Gln
                85                  90                  95

Ala Leu Pro Pro Cys Arg Ser Leu Cys Glu Arg Ala Arg Gln Gly Cys
            100                 105                 110

Glu Ala Leu Met Asn Lys Phe Gly Phe Gln Trp Pro Asp Thr Leu Lys
        115                 120                 125

Cys Glu Lys Phe Pro Val His Gly Ala Gly Glu Leu Cys Val Gly Gln
    130                 135                 140

Asn Thr Ser Asp Lys Gly Thr
145                 150

<210> SEQ ID NO 14
<211> LENGTH: 136
<212> TYPE: PRT
<213> ORGANISM: Homo sapiens

<400> SEQUENCE: 14

Gln Phe His Gly Glu Lys Gly Ile Ser Ile Pro Asp His Gly Phe Cys
1               5                   10                  15

Gln Pro Ile Ser Ile Pro Leu Cys Thr Asp Ile Ala Tyr Asn Gln Thr
                20                  25                  30

Ile Met Pro Asn Leu Leu Gly His Thr Asn Gln Glu Asp Ala Gly Leu
            35                  40                  45

Glu Val His Gln Phe Tyr Pro Leu Val Lys Val Gln Cys Ser Pro Glu
    50                  55                  60

Leu Arg Phe Phe Leu Cys Ser Met Tyr Ala Pro Val Cys Thr Val Leu
65                  70                  75                  80

Glu Gln Ala Ile Pro Pro Cys Arg Ser Ile Cys Glu Arg Ala Arg Gln
                85                  90                  95

Gly Cys Glu Ala Leu Met Asn Lys Phe Gly Phe Gln Trp Pro Glu Arg
```

```
               100                 105                 110
Leu Arg Cys Glu His Phe Pro Arg His Gly Ala Glu Gln Ile Cys Val
        115                 120                 125

Gly Gln Asn His Ser Glu Asp Gly
        130                 135

<210> SEQ ID NO 15
<211> LENGTH: 121
<212> TYPE: PRT
<213> ORGANISM: Homo sapiens

<400> SEQUENCE: 15

His Ser Leu Phe Ser Cys Glu Pro Ile Thr Leu Arg Met Cys Gln Asp
1               5                   10                  15

Leu Pro Tyr Asn Thr Thr Phe Met Pro Asn Leu Leu Asn His Tyr Asp
            20                  25                  30

Gln Gln Thr Ala Ala Leu Ala Met Glu Pro Phe His Pro Met Val Asn
        35                  40                  45

Leu Asp Cys Ser Arg Asp Phe Arg Pro Phe Leu Cys Ala Leu Tyr Ala
    50                  55                  60

Pro Ile Cys Met Glu Tyr Gly Arg Val Thr Leu Pro Cys Arg Arg Leu
65                  70                  75                  80

Cys Gln Arg Ala Tyr Ser Glu Cys Ser Lys Leu Met Glu Met Phe Gly
                85                  90                  95

Val Pro Trp Pro Glu Asp Met Glu Cys Ser Arg Phe Pro Asp Cys Asp
            100                 105                 110

Glu Pro Tyr Pro Arg Leu Val Asp Leu
        115                 120

<210> SEQ ID NO 16
<211> LENGTH: 131
<212> TYPE: PRT
<213> ORGANISM: Homo sapiens

<400> SEQUENCE: 16

Phe Gly Asp Glu Glu Arg Arg Cys Asp Pro Ile Arg Ile Ser Met
1               5                   10                  15

Cys Gln Asn Leu Gly Tyr Asn Val Thr Lys Met Pro Asn Leu Val Gly
            20                  25                  30

His Glu Leu Gln Thr Asp Ala Glu Leu Gln Leu Thr Thr Phe Thr Pro
        35                  40                  45

Leu Ile Gln Tyr Gly Cys Ser Ser Gln Leu Gln Phe Phe Leu Cys Ser
    50                  55                  60

Val Tyr Val Pro Met Cys Thr Glu Lys Ile Asn Ile Pro Ile Gly Pro
65                  70                  75                  80

Cys Gly Gly Met Cys Leu Ser Val Lys Arg Arg Cys Glu Pro Val Leu
                85                  90                  95

Lys Glu Phe Gly Phe Ala Trp Pro Glu Ser Leu Asn Cys Ser Lys Phe
            100                 105                 110

Pro Pro Gln Asn Asp His Asn His Met Cys Met Glu Gly Pro Gly Asp
        115                 120                 125

Glu Glu Val
    130

<210> SEQ ID NO 17
<211> LENGTH: 131
<212> TYPE: PRT
```

<213> ORGANISM: Homo sapiens

<400> SEQUENCE: 17

Ala Ser Lys Ala Pro Val Cys Gln Glu Ile Thr Val Pro Met Cys Arg
1               5                   10                  15

Gly Ile Gly Tyr Asn Leu Thr His Met Pro Asn Gln Phe Asn His Asp
            20                  25                  30

Thr Gln Asp Glu Ala Gly Leu Glu Val His Gln Phe Trp Pro Leu Val
        35                  40                  45

Glu Ile Gln Cys Ser Pro Asp Leu Arg Phe Phe Leu Cys Ser Met Tyr
50                  55                  60

Thr Pro Ile Cys Leu Pro Asp Tyr His Lys Pro Leu Pro Pro Cys Arg
65                  70                  75                  80

Ser Val Cys Glu Arg Ala Lys Ala Gly Cys Ser Pro Leu Met Arg Gln
                85                  90                  95

Tyr Gly Phe Ala Trp Pro Glu Arg Met Ser Cys Asp Arg Leu Pro Val
            100                 105                 110

Leu Gly Arg Asp Ala Glu Val Leu Cys Met Asp Tyr Asn Arg Ser Glu
        115                 120                 125

Ala Thr Thr
        130

<210> SEQ ID NO 18
<211> LENGTH: 127
<212> TYPE: PRT
<213> ORGANISM: Homo sapiens

<400> SEQUENCE: 18

His Ser Leu Phe Thr Cys Glu Pro Ile Thr Val Pro Arg Cys Met Lys
1               5                   10                  15

Met Ala Tyr Asn Met Thr Phe Phe Pro Asn Leu Met Gly His Tyr Asp
            20                  25                  30

Gln Ser Ile Ala Ala Val Glu Met Glu His Phe Leu Pro Leu Ala Asn
        35                  40                  45

Leu Glu Cys Ser Pro Asn Ile Glu Thr Phe Leu Cys Lys Ala Phe Val
50                  55                  60

Pro Thr Cys Ile Glu Gln Ile His Val Val Pro Pro Cys Arg Lys Leu
65                  70                  75                  80

Cys Glu Lys Val Tyr Ser Asp Cys Lys Lys Leu Ile Asp Thr Phe Gly
                85                  90                  95

Ile Arg Trp Pro Glu Glu Leu Cys Asp Arg Leu Gln Tyr Cys Asp
            100                 105                 110

Glu Thr Val Pro Val Thr Phe Asp Pro His Thr Glu Phe Leu Gly
        115                 120                 125

<210> SEQ ID NO 19
<211> LENGTH: 138
<212> TYPE: PRT
<213> ORGANISM: Homo sapiens

<400> SEQUENCE: 19

Gln Pro Tyr His Gly Glu Lys Gly Ile Ser Val Pro Asp His Gly Phe
1               5                   10                  15

Cys Gln Pro Ile Ser Ile Pro Leu Cys Thr Asp Ile Ala Tyr Asn Gln
            20                  25                  30

Thr Ile Leu Pro Asn Leu Leu Gly His Thr Asn Gln Glu Asp Ala Gly
        35                  40                  45

Leu Glu Val His Gln Phe Tyr Pro Leu Val Lys Val Gln Cys Ser Pro
    50                  55                  60

Glu Leu Arg Phe Phe Leu Cys Ser Met Tyr Ala Pro Val Cys Thr Val
65                  70                  75                  80

Leu Asp Gln Ala Ile Pro Pro Cys Arg Ser Leu Cys Glu Arg Ala Arg
                85                  90                  95

Gln Gly Cys Glu Ala Leu Met Asn Lys Phe Gly Phe Gln Trp Pro Glu
            100                 105                 110

Arg Leu Arg Cys Glu Asn Phe Pro Val His Gly Ala Gly Glu Ile Cys
            115                 120                 125

Val Gly Gln Asn Thr Ser Asp Gly Ser Gly
            130                 135

<210> SEQ ID NO 20
<211> LENGTH: 131
<212> TYPE: PRT
<213> ORGANISM: Homo sapiens

<400> SEQUENCE: 20

Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
            20                  25                  30

Asp Thr Gln Asp Glu Ala Gly Leu Glu Val His Gln Phe Trp Pro Leu
        35                  40                  45

Val Glu Ile Gln Cys Ser Pro Asp Leu Lys Phe Phe Leu Cys Ser Met
    50                  55                  60

Tyr Thr Pro Ile Cys Leu Glu Asp Tyr Lys Lys Pro Leu Pro Pro Cys
65                  70                  75                  80

Arg Ser Val Cys Glu Arg Ala Lys Ala Gly Cys Ala Pro Leu Met Arg
                85                  90                  95

Gln Tyr Gly Phe Ala Trp Pro Asp Arg Met Arg Cys Asp Arg Leu Pro
            100                 105                 110

Glu Gln Gly Asn Pro Asp Thr Leu Cys Met Asp Tyr Asn Arg Thr Asp
            115                 120                 125

Leu Thr Thr
    130

<210> SEQ ID NO 21
<211> LENGTH: 137
<212> TYPE: PRT
<213> ORGANISM: Homo sapiens

<400> SEQUENCE: 21

Leu Glu Ile Gly Arg Phe Asp Pro Glu Arg Gly Arg Gly Ala Ala Pro
1               5                   10                  15

Cys Gln Ala Val Glu Ile Pro Met Cys Arg Gly Ile Gly Tyr Asn Leu
            20                  25                  30

Thr Arg Met Pro Asn Leu Leu Gly His Thr Ser Gln Gly Glu Ala Ala
        35                  40                  45

Ala Glu Leu Ala Glu Phe Ala Pro Leu Val Gln Tyr Gly Cys His Ser
    50                  55                  60

His Leu Arg Phe Phe Leu Cys Ser Leu Tyr Ala Pro Met Cys Thr Asp
65                  70                  75                  80

Gln Val Ser Thr Pro Ile Pro Ala Cys Arg Pro Met Cys Glu Gln Ala
                85                  90                  95

```
Arg Leu Arg Cys Ala Pro Ile Met Glu Gln Phe Asn Phe Gly Trp Pro
            100                 105                 110
Asp Ser Leu Asp Cys Ala Arg Leu Pro Thr Arg Asn Asp Pro His Ala
        115                 120                 125
Leu Cys Met Glu Ala Pro Glu Asn Ala
    130                 135

<210> SEQ ID NO 22
<211> LENGTH: 134
<212> TYPE: PRT
<213> ORGANISM: Homo sapiens

<400> SEQUENCE: 22

Ile Ser Ser Met Asp Met Glu Arg Pro Gly Asp Gly Lys Cys Gln Pro
1               5                   10                  15
Ile Glu Ile Pro Met Cys Lys Asp Ile Gly Tyr Asn Met Thr Arg Met
            20                  25                  30
Pro Asn Leu Met Gly His Glu Asn Gln Arg Glu Ala Ala Ile Gln Leu
        35                  40                  45
His Glu Phe Ala Pro Leu Val Glu Tyr Gly Cys His Gly His Leu Arg
    50                  55                  60
Phe Phe Leu Cys Ser Leu Tyr Ala Pro Met Cys Thr Glu Gln Val Ser
65                  70                  75                  80
Thr Pro Ile Pro Ala Cys Arg Val Met Cys Glu Gln Ala Arg Leu Lys
                85                  90                  95
Cys Ser Pro Ile Met Glu Gln Phe Asn Phe Lys Trp Pro Asp Ser Leu
            100                 105                 110
Asp Cys Arg Lys Leu Pro Asn Lys Asn Asp Pro Asn Tyr Leu Cys Met
        115                 120                 125
Glu Ala Pro Asn Asn Gly
    130

<210> SEQ ID NO 23
<211> LENGTH: 112
<212> TYPE: PRT
<213> ORGANISM: Homo sapiens

<400> SEQUENCE: 23

Cys Gln Pro Ile Ser Ile Pro Leu Cys Thr Asp Ile Ala Tyr Asn Gln
1               5                   10                  15
Thr Ile Met Pro Asn Leu Leu Gly His Thr Asn Gln Glu Asp Ala Gly
            20                  25                  30
Leu Glu Val His Gln Phe Tyr Pro Leu Val Lys Val Gln Cys Ser Ala
        35                  40                  45
Glu Leu Lys Phe Phe Leu Cys Ser Met Tyr Ala Pro Val Cys Thr Val
    50                  55                  60
Leu Glu Gln Ala Leu Pro Pro Cys Arg Ser Leu Cys Glu Arg Ala Arg
65                  70                  75                  80
Gln Gly Cys Glu Ala Leu Met Asn Lys Phe Gly Phe Gln Trp Pro Asp
                85                  90                  95
Thr Leu Lys Cys Glu Lys Phe Pro Val His Gly Ala Gly Glu Leu Cys
            100                 105                 110

<210> SEQ ID NO 24
<211> LENGTH: 112
<212> TYPE: PRT
<213> ORGANISM: Homo sapiens
```

<400> SEQUENCE: 24

```
Cys Gln Pro Ile Ser Ile Pro Leu Cys Thr Asp Ile Ala Tyr Asn Gln
1               5                   10                  15

Thr Ile Met Pro Asn Leu Leu Gly His Thr Asn Gln Glu Asp Ala Gly
            20                  25                  30

Leu Glu Val His Gln Phe Tyr Pro Leu Val Lys Val Gln Cys Ser Pro
        35                  40                  45

Glu Leu Arg Phe Phe Leu Cys Ser Met Tyr Ala Pro Val Cys Thr Val
50                  55                  60

Leu Glu Gln Ala Ile Pro Pro Cys Arg Ser Ile Cys Glu Arg Ala Arg
65                  70                  75                  80

Gln Gly Cys Glu Ala Leu Met Asn Lys Phe Gly Phe Gln Trp Pro Glu
                85                  90                  95

Arg Leu Arg Cys Glu His Phe Pro Arg His Gly Ala Glu Gln Ile Cys
            100                 105                 110
```

<210> SEQ ID NO 25
<211> LENGTH: 106
<212> TYPE: PRT
<213> ORGANISM: Homo sapiens

<400> SEQUENCE: 25

```
Cys Glu Pro Ile Thr Leu Arg Met Cys Gln Asp Leu Pro Tyr Asn Thr
1               5                   10                  15

Thr Phe Met Pro Asn Leu Leu Asn His Tyr Asp Gln Gln Thr Ala Ala
            20                  25                  30

Leu Ala Met Glu Pro Phe His Pro Met Val Asn Leu Asp Cys Ser Arg
        35                  40                  45

Asp Phe Arg Pro Phe Leu Cys Ala Leu Tyr Ala Pro Ile Cys Met Glu
50                  55                  60

Tyr Gly Arg Val Thr Leu Pro Cys Arg Arg Leu Cys Gln Arg Ala Tyr
65                  70                  75                  80

Ser Glu Cys Ser Lys Leu Met Glu Met Phe Gly Val Pro Trp Pro Glu
                85                  90                  95

Asp Met Glu Cys Ser Arg Phe Pro Asp Cys
            100                 105
```

<210> SEQ ID NO 26
<211> LENGTH: 114
<212> TYPE: PRT
<213> ORGANISM: Homo sapiens

<400> SEQUENCE: 26

```
Cys Asp Pro Ile Arg Ile Ser Met Cys Gln Asn Leu Gly Tyr Asn Val
1               5                   10                  15

Thr Lys Met Pro Asn Leu Val Gly His Glu Leu Gln Thr Asp Ala Glu
            20                  25                  30

Leu Gln Leu Thr Thr Phe Thr Pro Leu Ile Gln Tyr Gly Cys Ser Ser
        35                  40                  45

Gln Leu Gln Phe Phe Leu Cys Ser Val Tyr Val Pro Met Cys Thr Glu
50                  55                  60

Lys Ile Asn Ile Pro Ile Gly Pro Cys Gly Gly Met Cys Leu Ser Val
65                  70                  75                  80

Lys Arg Arg Cys Glu Pro Val Leu Lys Glu Phe Gly Phe Ala Trp Pro
                85                  90                  95
```

```
Glu Ser Leu Asn Cys Ser Lys Phe Pro Pro Gln Asn Asp His Asn His
                100                 105                 110
Met Cys

<210> SEQ ID NO 27
<211> LENGTH: 115
<212> TYPE: PRT
<213> ORGANISM: Homo sapiens

<400> SEQUENCE: 27

Cys Gln Glu Ile Thr Val Pro Met Cys Arg Gly Ile Gly Tyr Asn Leu
1               5                   10                  15

Thr His Met Pro Asn Gln Phe Asn His Asp Thr Gln Asp Glu Ala Gly
            20                  25                  30

Leu Glu Val His Gln Phe Trp Pro Leu Val Glu Ile Gln Cys Ser Pro
        35                  40                  45

Asp Leu Arg Phe Phe Leu Cys Ser Met Tyr Thr Pro Ile Cys Leu Pro
    50                  55                  60

Asp Tyr His Lys Pro Leu Pro Pro Cys Arg Ser Val Cys Glu Arg Ala
65                  70                  75                  80

Lys Ala Gly Cys Ser Pro Leu Met Arg Gln Tyr Gly Phe Ala Trp Pro
                85                  90                  95

Glu Arg Met Ser Cys Asp Arg Leu Pro Val Leu Gly Arg Asp Ala Glu
            100                 105                 110

Val Leu Cys
        115

<210> SEQ ID NO 28
<211> LENGTH: 106
<212> TYPE: PRT
<213> ORGANISM: Homo sapiens

<400> SEQUENCE: 28

Cys Glu Pro Ile Thr Val Pro Arg Cys Met Lys Met Ala Tyr Asn Met
1               5                   10                  15

Thr Phe Phe Pro Asn Leu Met Gly His Tyr Asp Gln Ser Ile Ala Ala
            20                  25                  30

Val Glu Met Glu His Phe Leu Pro Leu Ala Asn Leu Glu Cys Ser Pro
        35                  40                  45

Asn Ile Glu Thr Phe Leu Cys Lys Ala Phe Val Pro Thr Cys Ile Glu
    50                  55                  60

Gln Ile His Val Val Pro Pro Cys Arg Lys Leu Cys Glu Lys Val Tyr
65                  70                  75                  80

Ser Asp Cys Lys Lys Leu Ile Asp Thr Phe Gly Ile Arg Trp Pro Glu
                85                  90                  95

Glu Leu Glu Cys Asp Arg Leu Gln Tyr Cys
            100                 105

<210> SEQ ID NO 29
<211> LENGTH: 112
<212> TYPE: PRT
<213> ORGANISM: Homo sapiens

<400> SEQUENCE: 29

Cys Gln Pro Ile Ser Ile Pro Leu Cys Thr Asp Ile Ala Tyr Asn Gln
1               5                   10                  15

Thr Ile Leu Pro Asn Leu Leu Gly His Thr Asn Gln Glu Asp Ala Gly
            20                  25                  30
```

```
Leu Glu Val His Gln Phe Tyr Pro Leu Val Lys Val Gln Cys Ser Pro
             35                  40                  45

Glu Leu Arg Phe Phe Leu Cys Ser Met Tyr Ala Pro Val Cys Thr Val
         50                  55                  60

Leu Asp Gln Ala Ile Pro Pro Cys Arg Ser Leu Cys Glu Arg Ala Arg
 65                  70                  75                  80

Gln Gly Cys Glu Ala Leu Met Asn Lys Phe Gly Phe Gln Trp Pro Glu
                 85                  90                  95

Arg Leu Arg Cys Glu Asn Phe Pro Val His Gly Ala Gly Glu Ile Cys
                100                 105                 110
```

<210> SEQ ID NO 30
<211> LENGTH: 114
<212> TYPE: PRT
<213> ORGANISM: Homo sapiens

<400> SEQUENCE: 30

```
Cys Gln Glu Ile Thr Val Pro Leu Cys Lys Gly Ile Gly Tyr Asn Tyr
 1               5                  10                  15

Thr Tyr Met Pro Asn Gln Phe Asn His Asp Thr Gln Asp Glu Ala Gly
             20                  25                  30

Leu Glu Val His Gln Phe Trp Pro Leu Val Glu Ile Gln Cys Ser Pro
             35                  40                  45

Asp Leu Lys Phe Phe Leu Cys Ser Met Tyr Thr Pro Ile Cys Leu Glu
         50                  55                  60

Asp Tyr Lys Lys Pro Leu Pro Pro Cys Arg Ser Val Cys Glu Arg Ala
 65                  70                  75                  80

Lys Ala Gly Cys Ala Pro Leu Met Arg Gln Tyr Gly Phe Ala Trp Pro
                 85                  90                  95

Asp Arg Met Arg Cys Asp Arg Leu Pro Glu Gln Gly Asn Pro Asp Thr
                100                 105                 110

Leu Cys
```

<210> SEQ ID NO 31
<211> LENGTH: 114
<212> TYPE: PRT
<213> ORGANISM: Homo sapiens

<400> SEQUENCE: 31

```
Cys Gln Ala Val Glu Ile Pro Met Cys Arg Gly Ile Gly Tyr Asn Leu
 1               5                  10                  15

Thr Arg Met Pro Asn Leu Leu Gly His Thr Ser Gln Gly Glu Ala Ala
             20                  25                  30

Ala Glu Leu Ala Glu Phe Ala Pro Leu Val Gln Tyr Gly Cys His Ser
             35                  40                  45

His Leu Arg Phe Phe Leu Cys Ser Leu Tyr Ala Pro Met Cys Thr Asp
         50                  55                  60

Gln Val Ser Thr Pro Ile Pro Ala Cys Arg Pro Met Cys Glu Gln Ala
 65                  70                  75                  80

Arg Leu Arg Cys Ala Pro Ile Met Glu Gln Phe Asn Phe Gly Trp Pro
                 85                  90                  95

Asp Ser Leu Asp Cys Ala Arg Leu Pro Thr Arg Asn Asp Pro His Ala
                100                 105                 110

Leu Cys
```

```
<210> SEQ ID NO 32
<211> LENGTH: 114
<212> TYPE: PRT
<213> ORGANISM: Homo sapiens

<400> SEQUENCE: 32

Cys Gln Pro Ile Glu Ile Pro Met Cys Lys Asp Ile Gly Tyr Asn Met
1               5                   10                  15

Thr Arg Met Pro Asn Leu Met Gly His Glu Asn Gln Arg Glu Ala Ala
            20                  25                  30

Ile Gln Leu His Glu Phe Ala Pro Leu Val Glu Tyr Gly Cys His Gly
        35                  40                  45

His Leu Arg Phe Phe Leu Cys Ser Leu Tyr Ala Pro Met Cys Thr Glu
    50                  55                  60

Gln Val Ser Thr Pro Ile Pro Ala Cys Arg Val Met Cys Glu Gln Ala
65                  70                  75                  80

Arg Leu Lys Cys Ser Pro Ile Met Glu Gln Phe Asn Phe Lys Trp Pro
                85                  90                  95

Asp Ser Leu Asp Cys Arg Lys Leu Pro Asn Lys Asn Asp Pro Asn Tyr
            100                 105                 110

Leu Cys

<210> SEQ ID NO 33
<211> LENGTH: 129
<212> TYPE: PRT
<213> ORGANISM: Homo sapiens

<400> SEQUENCE: 33

Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
            20                  25                  30

Asp Thr Gln Asp Glu Ala Gly Leu Glu Val His Gln Phe Trp Pro Leu
        35                  40                  45

Val Glu Ile Gln Cys Ser Pro Asp Leu Lys Phe Phe Leu Cys Ser Met
    50                  55                  60

Tyr Thr Pro Ile Cys Leu Glu Asp Tyr Lys Lys Pro Leu Pro Pro Cys
65                  70                  75                  80

Arg Ser Val Cys Glu Arg Ala Lys Ala Gly Cys Ala Pro Leu Met Arg
                85                  90                  95

Gln Tyr Gly Phe Ala Trp Pro Asp Arg Met Arg Cys Asp Arg Leu Pro
            100                 105                 110

Glu Gln Gly Asn Pro Asp Thr Leu Cys Met Asp Tyr Asn Arg Thr Asp
        115                 120                 125

Leu

<210> SEQ ID NO 34
<211> LENGTH: 227
<212> TYPE: PRT
<213> ORGANISM: Homo sapiens

<400> SEQUENCE: 34

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
```

```
            35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
210                 215                 220
Pro Gly Lys
225

<210> SEQ ID NO 35
<211> LENGTH: 227
<212> TYPE: PRT
<213> ORGANISM: Homo sapiens

<400> SEQUENCE: 35

Asp Lys Thr His Thr Cys Pro Pro Cys Pro Ala Pro Glu Leu Leu Gly
  1               5                  10                  15
Gly Pro Ser Val Phe Leu Phe Pro Pro Lys Pro Lys Asp Thr Leu Met
             20                  25                  30
Ile Ser Arg Thr Pro Glu Val Thr Cys Val Val Val Asp Val Ser His
         35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Glu Glu Met Thr Lys Asn Gln Val Ser
130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
```

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225

<210> SEQ ID NO 36
<211> LENGTH: 230
<212> TYPE: PRT
<213> ORGANISM: Homo sapiens

<400> SEQUENCE: 36

Lys Ser Ser Asp Lys Thr His Thr Cys Pro Pro Cys Pro Ala Pro Glu
1               5                   10                  15

Leu Leu Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser His Glu Asp Pro Glu Val Lys Phe Asn Trp Tyr Val Asp Gly
    50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
        115                 120                 125

Pro Gln Val Tyr Thr Leu Pro Pro Ser Arg Asp Glu Leu Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
        195                 200                 205

Ser Val Met His Glu Ala Leu His Asn His Tyr Thr Gln Lys Ser Leu
    210                 215                 220

Ser Leu Ser Pro Gly Lys
225                 230

<210> SEQ ID NO 37
<211> LENGTH: 232
<212> TYPE: PRT
<213> ORGANISM: Homo sapiens

<400> SEQUENCE: 37

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

```
Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 38
<211> LENGTH: 224
<212> TYPE: PRT
<213> ORGANISM: Homo sapiens

<400> SEQUENCE: 38

Cys Val Glu Cys Pro Pro Cys Pro Ala Pro Pro Val Ala Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Gln Phe Asn Trp Tyr Val Asp Gly Val Glu Val His Asn Ala
 50                  55                  60

Lys Thr Lys Pro Arg Glu Glu Gln Phe Asn Ser Thr Phe Arg Val Val
 65                  70                  75                  80

Ser Val Leu Thr Val Val His Gln Asp Trp Leu Asn Gly Lys Glu Tyr
                85                  90                  95

Lys Cys Lys Val Ser Asn Lys Gly Leu Pro Ala Pro Ile Glu Lys Thr
            100                 105                 110

Ile Ser Lys Thr Lys Gly Gln Pro Arg Glu Pro Gln Val Tyr Thr Leu
        115                 120                 125

Pro Pro Ser Arg Glu Glu Met Thr Lys Asn Gln Val Ser Leu Thr Cys
130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Met Leu Asp
                165                 170                 175
```

```
Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Lys
    210                 215                 220

<210> SEQ ID NO 39
<211> LENGTH: 361
<212> TYPE: PRT
<213> ORGANISM: Artificial Sequence
<220> FEATURE:
<223> OTHER INFORMATION: FZD8-Fc variant 54F03 amino acid sequence

<400> SEQUENCE: 39

Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
            20                  25                  30

Asp Thr Gln Asp Glu Ala Gly Leu Glu Val His Gln Phe Trp Pro Leu
        35                  40                  45

Val Glu Ile Gln Cys Ser Pro Asp Leu Lys Phe Phe Leu Cys Ser Met
    50                  55                  60

Tyr Thr Pro Ile Cys Leu Glu Asp Tyr Lys Lys Pro Leu Pro Pro Cys
65                  70                  75                  80

Arg Ser Val Cys Glu Arg Ala Lys Ala Gly Cys Ala Pro Leu Met Arg
                85                  90                  95

Gln Tyr Gly Phe Ala Trp Pro Asp Arg Met Arg Cys Asp Arg Leu Pro
            100                 105                 110

Glu Gln Gly Asn Pro Asp Thr Leu Cys Met Asp Tyr Asn Arg Thr Asp
        115                 120                 125

Leu Thr Thr Gly Arg Ala Asp Lys Thr His Thr Cys Pro Pro Cys Pro
    130                 135                 140

Ala Pro Glu Leu Leu Gly Gly Pro Ser Val Phe Leu Phe Pro Pro Lys
145                 150                 155                 160

Pro Lys Asp Thr Leu Met Ile Ser Arg Thr Pro Glu Val Thr Cys Val
                165                 170                 175

Val Val Asp Val Ser His Glu Asp Pro Glu Val Lys Phe Asn Trp Tyr
            180                 185                 190

Val Asp Gly Val Glu Val His Asn Ala Lys Thr Lys Pro Arg Glu Glu
        195                 200                 205

Gln Tyr Asn Ser Thr Tyr Arg Val Val Ser Val Leu Thr Val Leu His
    210                 215                 220

Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Ala Lys Gly Gln
                245                 250                 255

Pro Arg Glu Pro Gln Val Tyr Thr Leu Pro Pro Ser Arg Asp Glu Leu
            260                 265                 270

Thr Lys Asn Gln Val Ser Leu Thr Cys Leu Val Lys Gly Phe Tyr Pro
        275                 280                 285

Ser Asp Ile Ala Val Glu Trp Glu Ser Asn Gly Gln Pro Glu Asn Asn
    290                 295                 300

Tyr Lys Thr Thr Pro Pro Val Leu Asp Ser Asp Gly Ser Phe Phe Leu
305                 310                 315                 320
```

```
Tyr Ser Lys Leu Thr Val Asp Lys Ser Arg Trp Gln Gln Gly Asn Val
            325                 330                 335

Phe Ser Cys Ser Val Met His Glu Ala Leu His Asn His Tyr Thr Gln
            340                 345                 350

Lys Ser Leu Ser Leu Ser Pro Gly Lys
            355                 360

<210> SEQ ID NO 40
<211> LENGTH: 361
<212> TYPE: PRT
<213> ORGANISM: Artificial Sequence
<220> FEATURE:
<223> OTHER INFORMATION: FZD8-Fc variant 54F16, 54F17, 54F18, 54F23,
      54F25, 54F27, 54F29, 54F31, and 54F34 amino acid sequence

<400> SEQUENCE: 40

Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
            20                  25                  30

Asp Thr Gln Asp Glu Ala Gly Leu Glu Val His Gln Phe Trp Pro Leu
        35                  40                  45

Val Glu Ile Gln Cys Ser Pro Asp Leu Lys Phe Phe Leu Cys Ser Met
    50                  55                  60

Tyr Thr Pro Ile Cys Leu Glu Asp Tyr Lys Lys Pro Leu Pro Pro Cys
65                  70                  75                  80

Arg Ser Val Cys Glu Arg Ala Lys Ala Gly Cys Ala Pro Leu Met Arg
                85                  90                  95

Gln Tyr Gly Phe Ala Trp Pro Asp Arg Met Arg Cys Asp Arg Leu Pro
            100                 105                 110

Glu Gln Gly Asn Pro Asp Thr Leu Cys Met Asp Tyr Asn Arg Thr Asp
        115                 120                 125

Leu Thr Thr Lys Ser Ser Asp Lys Thr His Thr Cys Pro Pro Cys Pro
    130                 135                 140

Ala Pro Glu Leu Leu Gly Gly Pro Ser Val Phe Leu Phe Pro Pro Lys
145                 150                 155                 160

Pro Lys Asp Thr Leu Met Ile Ser Arg Thr Pro Glu Val Thr Cys Val
                165                 170                 175

Val Val Asp Val Ser His Glu Asp Pro Glu Val Lys Phe Asn Trp Tyr
            180                 185                 190

Val Asp Gly Val Glu Val His Asn Ala Lys Thr Lys Pro Arg Glu Glu
        195                 200                 205

Gln Tyr Asn Ser Thr Tyr Arg Val Val Ser Val Leu Thr Val Leu His
    210                 215                 220

Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Ala Lys Gly Gln
                245                 250                 255

Pro Arg Glu Pro Gln Val Tyr Thr Leu Pro Pro Ser Arg Asp Glu Leu
            260                 265                 270

Thr Lys Asn Gln Val Ser Leu Thr Cys Leu Val Lys Gly Phe Tyr Pro
        275                 280                 285

Ser Asp Ile Ala Val Glu Trp Glu Ser Asn Gly Gln Pro Glu Asn Asn
    290                 295                 300

Tyr Lys Thr Thr Pro Pro Val Leu Asp Ser Asp Gly Ser Phe Phe Leu
```

```
                    305                 310                 315                 320
Tyr Ser Lys Leu Thr Val Asp Lys Ser Arg Trp Gln Gln Gly Asn Val
                325                 330                 335

Phe Ser Cys Ser Val Met His Glu Ala Leu His Asn His Tyr Thr Gln
                340                 345                 350

Lys Ser Leu Ser Leu Ser Pro Gly Lys
                355                 360

<210> SEQ ID NO 41
<211> LENGTH: 363
<212> TYPE: PRT
<213> ORGANISM: Artificial Sequence
<220> FEATURE:
<223> OTHER INFORMATION: FZD8-Fc variant 54F19, 54F20, 54F24, 54F26,
      54F28, 54F30, 54F32, 54F34 and 54F35 amino acid sequence

<400> SEQUENCE: 41

Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
                20                  25                  30

Asp Thr Gln Asp Glu Ala Gly Leu Glu Val His Gln Phe Trp Pro Leu
            35                  40                  45

Val Glu Ile Gln Cys Ser Pro Asp Leu Lys Phe Phe Leu Cys Ser Met
        50                  55                  60

Tyr Thr Pro Ile Cys Leu Glu Asp Tyr Lys Lys Pro Leu Pro Pro Cys
65                  70                  75                  80

Arg Ser Val Cys Glu Arg Ala Lys Ala Gly Cys Ala Pro Leu Met Arg
                85                  90                  95

Gln Tyr Gly Phe Ala Trp Pro Asp Arg Met Arg Cys Asp Arg Leu Pro
                100                 105                 110

Glu Gln Gly Asn Pro Asp Thr Leu Cys Met Asp Tyr Asn Arg Thr Asp
            115                 120                 125

Leu Thr Thr Glu Pro Lys Ser Ser Asp Lys Thr His Thr Cys Pro Pro
130                 135                 140

Cys Pro Ala Pro Glu Leu Leu Gly Gly Pro Ser Val Phe Leu Phe Pro
145                 150                 155                 160

Pro Lys Pro Lys Asp Thr Leu Met Ile Ser Arg Thr Pro Glu Val Thr
                165                 170                 175

Cys Val Val Val Asp Val Ser His Glu Asp Pro Glu Val Lys Phe Asn
                180                 185                 190

Trp Tyr Val Asp Gly Val Glu Val His Asn Ala Lys Thr Lys Pro Arg
            195                 200                 205

Glu Glu Gln Tyr Asn Ser Thr Tyr Arg Val Val Ser Val Leu Thr Val
        210                 215                 220

Leu His Gln Asp Trp Leu Asn Gly Lys Glu Tyr Lys Cys Lys Val Ser
225                 230                 235                 240

Asn Lys Ala Leu Pro Ala Pro Ile Glu Lys Thr Ile Ser Lys Ala Lys
                245                 250                 255

Gly Gln Pro Arg Glu Pro Gln Val Tyr Thr Leu Pro Pro Ser Arg Asp
                260                 265                 270

Glu Leu Thr Lys Asn Gln Val Ser Leu Thr Cys Leu Val Lys Gly Phe
            275                 280                 285

Tyr Pro Ser Asp Ile Ala Val Glu Trp Glu Ser Asn Gly Gln Pro Glu
        290                 295                 300
```

```
Asn Asn Tyr Lys Thr Thr Pro Pro Val Leu Asp Ser Asp Gly Ser Phe
305                 310                 315                 320

Phe Leu Tyr Ser Lys Leu Thr Val Asp Lys Ser Arg Trp Gln Gln Gly
                325                 330                 335

Asn Val Phe Ser Cys Ser Val Met His Glu Ala Leu His Asn His Tyr
                340                 345                 350

Thr Gln Lys Ser Leu Ser Leu Ser Pro Gly Lys
                355                 360

<210> SEQ ID NO 42
<211> LENGTH: 388
<212> TYPE: PRT
<213> ORGANISM: Artificial Sequence
<220> FEATURE:
<223> OTHER INFORMATION: FZD8-Fc variant 54F03 amino acid sequence with
      signal sequence

<400> SEQUENCE: 42

Met Glu Trp Gly Tyr Leu Leu Glu Val Thr Ser Leu Leu Ala Ala Leu
1               5                   10                  15

Ala Leu Leu Gln Arg Ser Ser Gly Ala Ala Ala Ser Ala Lys Glu
                20                  25                  30

Leu Ala Cys Gln Glu Ile Thr Val Pro Leu Cys Lys Gly Ile Gly Tyr
                35                  40                  45

Asn Tyr Thr Tyr Met Pro Asn Gln Phe Asn His Asp Thr Gln Asp Glu
50                  55                  60

Ala Gly Leu Glu Val His Gln Phe Trp Pro Leu Val Glu Ile Gln Cys
65                  70                  75                  80

Ser Pro Asp Leu Lys Phe Phe Leu Cys Ser Met Tyr Thr Pro Ile Cys
                85                  90                  95

Leu Glu Asp Tyr Lys Lys Pro Leu Pro Pro Cys Arg Ser Val Cys Glu
                100                 105                 110

Arg Ala Lys Ala Gly Cys Ala Pro Leu Met Arg Gln Tyr Gly Phe Ala
                115                 120                 125

Trp Pro Asp Arg Met Arg Cys Asp Arg Leu Pro Glu Gln Gly Asn Pro
                130                 135                 140

Asp Thr Leu Cys Met Asp Tyr Asn Arg Thr Asp Leu Thr Thr Gly Arg
145                 150                 155                 160

Ala Asp Lys Thr His Thr Cys Pro Pro Cys Pro Ala Pro Glu Leu Leu
                165                 170                 175

Gly Gly Pro Ser Val Phe Leu Phe Pro Pro Lys Pro Lys Asp Thr Leu
                180                 185                 190

Met Ile Ser Arg Thr Pro Glu Val Thr Cys Val Val Val Asp Val Ser
                195                 200                 205

His Glu Asp Pro Glu Val Lys Phe Asn Trp Tyr Val Asp Gly Val Glu
                210                 215                 220

Val His Asn Ala Lys Thr Lys Pro Arg Glu Glu Gln Tyr Asn Ser Thr
225                 230                 235                 240

Tyr Arg Val Val Ser Val Leu Thr Val Leu His Gln Asp Trp Leu Asn
                245                 250                 255

Gly Lys Glu Tyr Lys Cys Lys Val Ser Asn Lys Ala Leu Pro Ala Pro
                260                 265                 270

Ile Glu Lys Thr Ile Ser Lys Ala Lys Gly Gln Pro Arg Glu Pro Gln
                275                 280                 285

Val Tyr Thr Leu Pro Pro Ser Arg Asp Glu Leu Thr Lys Asn Gln Val
                290                 295                 300
```

```
Ser Leu Thr Cys Leu Val Lys Gly Phe Tyr Pro Ser Asp Ile Ala Val
305                 310                 315                 320

Glu Trp Glu Ser Asn Gly Gln Pro Glu Asn Asn Tyr Lys Thr Thr Pro
            325                 330                 335

Pro Val Leu Asp Ser Asp Gly Ser Phe Phe Leu Tyr Ser Lys Leu Thr
            340                 345                 350

Val Asp Lys Ser Arg Trp Gln Gln Gly Asn Val Phe Ser Cys Ser Val
        355                 360                 365

Met His Glu Ala Leu His Asn His Tyr Thr Gln Lys Ser Leu Ser Leu
    370                 375                 380

Ser Pro Gly Lys
385

<210> SEQ ID NO 43
<211> LENGTH: 388
<212> TYPE: PRT
<213> ORGANISM: Artificial Sequence
<220> FEATURE:
<223> OTHER INFORMATION: FZD8-Fc variant 54F16 amino acid sequence with
      signal sequence

<400> SEQUENCE: 43

Met Glu Trp Gly Tyr Leu Leu Glu Val Thr Ser Leu Leu Ala Ala Leu
1               5                   10                  15

Ala Leu Leu Gln Arg Ser Ser Gly Ala Ala Ala Ser Ala Lys Glu
            20                  25                  30

Leu Ala Cys Gln Glu Ile Thr Val Pro Leu Cys Lys Gly Ile Gly Tyr
        35                  40                  45

Asn Tyr Thr Tyr Met Pro Asn Gln Phe Asn His Asp Thr Gln Asp Glu
    50                  55                  60

Ala Gly Leu Glu Val His Gln Phe Trp Pro Leu Val Glu Ile Gln Cys
65                  70                  75                  80

Ser Pro Asp Leu Lys Phe Phe Leu Cys Ser Met Tyr Thr Pro Ile Cys
                85                  90                  95

Leu Glu Asp Tyr Lys Lys Pro Leu Pro Pro Cys Arg Ser Val Cys Glu
            100                 105                 110

Arg Ala Lys Ala Gly Cys Ala Pro Leu Met Arg Gln Tyr Gly Phe Ala
        115                 120                 125

Trp Pro Asp Arg Met Arg Cys Asp Arg Leu Pro Glu Gln Gly Asn Pro
    130                 135                 140

Asp Thr Leu Cys Met Asp Tyr Asn Arg Thr Asp Leu Thr Thr Lys Ser
145                 150                 155                 160

Ser Asp Lys Thr His Thr Cys Pro Pro Cys Pro Ala Pro Glu Leu Leu
                165                 170                 175

Gly Gly Pro Ser Val Phe Leu Phe Pro Pro Lys Pro Lys Asp Thr Leu
            180                 185                 190

Met Ile Ser Arg Thr Pro Glu Val Thr Cys Val Val Val Asp Val Ser
        195                 200                 205

His Glu Asp Pro Glu Val Lys Phe Asn Trp Tyr Val Asp Gly Val Glu
    210                 215                 220

Val His Asn Ala Lys Thr Lys Pro Arg Glu Glu Gln Tyr Asn Ser Thr
225                 230                 235                 240

Tyr Arg Val Val Ser Val Leu Thr Val Leu His Gln Asp Trp Leu Asn
                245                 250                 255

Gly Lys Glu Tyr Lys Cys Lys Val Ser Asn Lys Ala Leu Pro Ala Pro
```

```
                260                 265                 270
Ile Glu Lys Thr Ile Ser Lys Ala Lys Gly Gln Pro Arg Glu Pro Gln
            275                 280                 285

Val Tyr Thr Leu Pro Pro Ser Arg Asp Glu Leu Thr Lys Asn Gln Val
        290                 295                 300

Ser Leu Thr Cys Leu Val Lys Gly Phe Tyr Pro Ser Asp Ile Ala Val
305                 310                 315                 320

Glu Trp Glu Ser Asn Gly Gln Pro Glu Asn Asn Tyr Lys Thr Thr Pro
                325                 330                 335

Pro Val Leu Asp Ser Asp Gly Ser Phe Phe Leu Tyr Ser Lys Leu Thr
            340                 345                 350

Val Asp Lys Ser Arg Trp Gln Gln Gly Asn Val Phe Ser Cys Ser Val
        355                 360                 365

Met His Glu Ala Leu His Asn His Tyr Thr Gln Lys Ser Leu Ser Leu
    370                 375                 380

Ser Pro Gly Lys
385

<210> SEQ ID NO 44
<211> LENGTH: 390
<212> TYPE: PRT
<213> ORGANISM: Artificial Sequence
<220> FEATURE:
<223> OTHER INFORMATION: FZD8-Fc variant 54F26 with signal sequence

<400> SEQUENCE: 44

Met Glu Trp Gly Tyr Leu Leu Glu Val Thr Ser Leu Leu Ala Ala Leu
1               5                   10                  15

Phe Leu Leu Gln Arg Ser Pro Ile Val His Ala Ala Ser Ala Lys Glu
            20                  25                  30

Leu Ala Cys Gln Glu Ile Thr Val Pro Leu Cys Lys Gly Ile Gly Tyr
        35                  40                  45

Asn Tyr Thr Tyr Met Pro Asn Gln Phe Asn His Asp Thr Gln Asp Glu
50                  55                  60

Ala Gly Leu Glu Val His Gln Phe Trp Pro Leu Val Glu Ile Gln Cys
65                  70                  75                  80

Ser Pro Asp Leu Lys Phe Phe Leu Cys Ser Met Tyr Thr Pro Ile Cys
                85                  90                  95

Leu Glu Asp Tyr Lys Lys Pro Leu Pro Pro Cys Arg Ser Val Cys Glu
            100                 105                 110

Arg Ala Lys Ala Gly Cys Ala Pro Leu Met Arg Gln Tyr Gly Phe Ala
        115                 120                 125

Trp Pro Asp Arg Met Arg Cys Asp Arg Leu Pro Glu Gln Gly Asn Pro
    130                 135                 140

Asp Thr Leu Cys Met Asp Tyr Asn Arg Thr Asp Leu Thr Thr Glu Pro
145                 150                 155                 160

Lys Ser Ser Asp Lys Thr His Thr Cys Pro Pro Cys Pro Ala Pro Glu
                165                 170                 175

Leu Leu Gly Gly Pro Ser Val Phe Leu Phe Pro Pro Lys Pro Lys Asp
            180                 185                 190

Thr Leu Met Ile Ser Arg Thr Pro Glu Val Thr Cys Val Val Val Asp
        195                 200                 205

Val Ser His Glu Asp Pro Glu Val Lys Phe Asn Trp Tyr Val Asp Gly
    210                 215                 220

Val Glu Val His Asn Ala Lys Thr Lys Pro Arg Glu Glu Gln Tyr Asn
```

```
            225                 230                 235                 240
Ser Thr Tyr Arg Val Val Ser Val Leu Thr Val Leu His Gln Asp Trp
                    245                 250                 255
Leu Asn Gly Lys Glu Tyr Lys Cys Lys Val Ser Asn Lys Ala Leu Pro
                260                 265                 270
Ala Pro Ile Glu Lys Thr Ile Ser Lys Ala Lys Gly Gln Pro Arg Glu
            275                 280                 285
Pro Gln Val Tyr Thr Leu Pro Pro Ser Arg Asp Glu Leu Thr Lys Asn
        290                 295                 300
Gln Val Ser Leu Thr Cys Leu Val Lys Gly Phe Tyr Pro Ser Asp Ile
305                 310                 315                 320
Ala Val Glu Trp Glu Ser Asn Gly Gln Pro Glu Asn Asn Tyr Lys Thr
                325                 330                 335
Thr Pro Pro Val Leu Asp Ser Asp Gly Ser Phe Phe Leu Tyr Ser Lys
                340                 345                 350
Leu Thr Val Asp Lys Ser Arg Trp Gln Gln Gly Asn Val Phe Ser Cys
                355                 360                 365
Ser Val Met His Glu Ala Leu His Asn His Tyr Thr Gln Lys Ser Leu
            370                 375                 380
Ser Leu Ser Pro Gly Lys
385                 390

<210> SEQ ID NO 45
<211> LENGTH: 390
<212> TYPE: PRT
<213> ORGANISM: Artificial Sequence
<220> FEATURE:
<223> OTHER INFORMATION: FZD8-Fc variant 54F28 with signal sequence

<400> SEQUENCE: 45

Met Glu Trp Gly Tyr Leu Leu Glu Val Thr Ser Leu Leu Ala Ala Leu
1               5                   10                  15
Leu Leu Leu Gln Arg Ser Pro Phe Val His Ala Ala Ser Ala Lys Glu
                20                  25                  30
Leu Ala Cys Gln Glu Ile Thr Val Pro Leu Cys Lys Gly Ile Gly Tyr
            35                  40                  45
Asn Tyr Thr Tyr Met Pro Asn Gln Phe Asn His Asp Thr Gln Asp Glu
        50                  55                  60
Ala Gly Leu Glu Val His Gln Phe Trp Pro Leu Val Glu Ile Gln Cys
65                  70                  75                  80
Ser Pro Asp Leu Lys Phe Phe Leu Cys Ser Met Tyr Thr Pro Ile Cys
                85                  90                  95
Leu Glu Asp Tyr Lys Lys Pro Leu Pro Pro Cys Arg Ser Val Cys Glu
                100                 105                 110
Arg Ala Lys Ala Gly Cys Ala Pro Leu Met Arg Gln Tyr Gly Phe Ala
            115                 120                 125
Trp Pro Asp Arg Met Arg Cys Asp Arg Leu Pro Glu Gln Gly Asn Pro
        130                 135                 140
Asp Thr Leu Cys Met Asp Tyr Asn Arg Thr Asp Leu Thr Thr Glu Pro
145                 150                 155                 160
Lys Ser Ser Asp Lys Thr His Thr Cys Pro Pro Cys Pro Ala Pro Glu
                165                 170                 175
Leu Leu Gly Gly Pro Ser Val Phe Leu Phe Pro Pro Lys Pro Lys Asp
            180                 185                 190
Thr Leu Met Ile Ser Arg Thr Pro Glu Val Thr Cys Val Val Val Asp
```

```
                195                 200                 205
Val Ser His Glu Asp Pro Glu Val Lys Phe Asn Trp Tyr Val Asp Gly
210                 215                 220

Val Glu Val His Asn Ala Lys Thr Lys Pro Arg Glu Glu Gln Tyr Asn
225                 230                 235                 240

Ser Thr Tyr Arg Val Val Ser Val Leu Thr Val Leu His Gln Asp Trp
                245                 250                 255

Leu Asn Gly Lys Glu Tyr Lys Cys Lys Val Ser Asn Lys Ala Leu Pro
            260                 265                 270

Ala Pro Ile Glu Lys Thr Ile Ser Lys Ala Lys Gly Gln Pro Arg Glu
        275                 280                 285

Pro Gln Val Tyr Thr Leu Pro Pro Ser Arg Asp Glu Leu Thr Lys Asn
    290                 295                 300

Gln Val Ser Leu Thr Cys Leu Val Lys Gly Phe Tyr Pro Ser Asp Ile
305                 310                 315                 320

Ala Val Glu Trp Glu Ser Asn Gly Gln Pro Glu Asn Asn Tyr Lys Thr
                325                 330                 335

Thr Pro Pro Val Leu Asp Ser Asp Gly Ser Phe Phe Leu Tyr Ser Lys
            340                 345                 350

Leu Thr Val Asp Lys Ser Arg Trp Gln Gln Gly Asn Val Phe Ser Cys
        355                 360                 365

Ser Val Met His Glu Ala Leu His Asn His Tyr Thr Gln Lys Ser Leu
    370                 375                 380

Ser Leu Ser Pro Gly Lys
385                 390

<210> SEQ ID NO 46
<211> LENGTH: 83
<212> TYPE: PRT
<213> ORGANISM: Homo sapiens

<400> SEQUENCE: 46

Asp Leu Val Tyr Phe Glu Lys Ser Pro Asn Phe Cys Thr Tyr Ser Gly
1               5                   10                  15

Arg Leu Gly Thr Ala Gly Thr Ala Gly Arg Ala Cys Asn Ser Ser Ser
            20                  25                  30

Pro Ala Leu Asp Gly Cys Glu Leu Leu Cys Cys Gly Arg Gly His Arg
        35                  40                  45

Thr Arg Thr Gln Arg Val Thr Glu Arg Cys Asn Cys Thr Phe His Trp
    50                  55                  60

Cys Cys His Val Ser Cys Arg Asn Cys Thr His Thr Arg Val Leu His
65                  70                  75                  80

Glu Cys Leu

<210> SEQ ID NO 47
<211> LENGTH: 94
<212> TYPE: PRT
<213> ORGANISM: Homo sapiens

<400> SEQUENCE: 47

Asp Leu Val Tyr Phe Glu Asn Ser Pro Asp Tyr Cys Ile Arg Asp Arg
1               5                   10                  15

Glu Ala Gly Ser Leu Gly Thr Ala Gly Arg Val Cys Asn Leu Thr Ser
            20                  25                  30

Arg Gly Met Asp Ser Cys Glu Val Met Cys Cys Gly Arg Gly Tyr Asp
        35                  40                  45
```

```
Thr Ser His Val Thr Arg Met Thr Lys Cys Gly Cys Lys Phe His Trp
        50                  55                  60

Cys Cys Ala Val Arg Cys Gln Asp Cys Leu Glu Ala Leu Asp Val His
65                  70                  75                  80

Thr Cys Lys Ala Pro Lys Asn Ala Asp Trp Thr Thr Ala Thr
                85                  90
```

<210> SEQ ID NO 48
<211> LENGTH: 94
<212> TYPE: PRT
<213> ORGANISM: Homo sapiens

<400> SEQUENCE: 48

```
Asp Leu Val Tyr Phe Asp Asn Ser Pro Asp Tyr Cys Val Leu Asp Lys
1               5                   10                  15

Ala Ala Gly Ser Leu Gly Thr Ala Gly Arg Val Cys Ser Lys Thr Ser
                20                  25                  30

Lys Gly Thr Asp Gly Cys Glu Ile Met Cys Cys Gly Arg Gly Tyr Asp
            35                  40                  45

Thr Thr Arg Val Thr Arg Val Thr Gln Cys Glu Cys Lys Phe His Trp
        50                  55                  60

Cys Cys Ala Val Arg Cys Lys Glu Cys Arg Asn Thr Val Asp Val His
65                  70                  75                  80

Thr Cys Lys Ala Pro Lys Lys Ala Glu Trp Leu Asp Gln Thr
                85                  90
```

<210> SEQ ID NO 49
<211> LENGTH: 83
<212> TYPE: PRT
<213> ORGANISM: Homo sapiens

<400> SEQUENCE: 49

```
Asp Leu Val Tyr Tyr Glu Asn Ser Pro Asn Phe Cys Glu Pro Asn Pro
1               5                   10                  15

Glu Thr Gly Ser Phe Gly Thr Arg Asp Arg Thr Cys Asn Val Thr Ser
                20                  25                  30

His Gly Ile Asp Gly Cys Asp Leu Leu Cys Cys Gly Arg Gly His Asn
            35                  40                  45

Thr Arg Thr Glu Lys Arg Lys Glu Lys Cys His Cys Ile Phe His Trp
        50                  55                  60

Cys Cys Tyr Val Ser Cys Gln Glu Cys Ile Arg Ile Tyr Asp Val His
65                  70                  75                  80

Thr Cys Lys
```

<210> SEQ ID NO 50
<211> LENGTH: 83
<212> TYPE: PRT
<213> ORGANISM: Homo sapiens

<400> SEQUENCE: 50

```
Asp Leu Val Tyr Tyr Glu Ala Ser Pro Asn Phe Cys Glu Pro Asn Pro
1               5                   10                  15

Glu Thr Gly Ser Phe Gly Thr Arg Asp Arg Thr Cys Asn Val Ser Ser
                20                  25                  30

His Gly Ile Asp Gly Cys Asp Leu Leu Cys Cys Gly Arg Gly His Asn
            35                  40                  45

Ala Arg Ala Glu Arg Arg Arg Glu Lys Cys Arg Cys Val Phe His Trp
```

```
            50                  55                  60
Cys Cys Tyr Val Ser Cys Gln Glu Cys Thr Arg Val Tyr Asp Val His
 65                  70                  75                  80

Thr Cys Lys

<210> SEQ ID NO 51
<211> LENGTH: 83
<212> TYPE: PRT
<213> ORGANISM: Homo sapiens

<400> SEQUENCE: 51

Asp Leu Val Tyr Ile Glu Lys Ser Pro Asn Tyr Cys Glu Glu Asp Pro
  1               5                  10                  15

Val Thr Gly Ser Val Gly Thr Gln Gly Arg Ala Cys Asn Lys Thr Ala
                 20                  25                  30

Pro Gln Ala Ser Gly Cys Asp Leu Met Cys Cys Gly Arg Gly Tyr Asn
             35                  40                  45

Thr His Gln Tyr Ala Arg Val Trp Gln Cys Asn Cys Lys Phe His Trp
         50                  55                  60

Cys Cys Tyr Val Lys Cys Asn Thr Cys Ser Glu Arg Thr Glu Met Tyr
 65                  70                  75                  80

Thr Cys Lys

<210> SEQ ID NO 52
<211> LENGTH: 83
<212> TYPE: PRT
<213> ORGANISM: Homo sapiens

<400> SEQUENCE: 52

Asp Leu Val Tyr Ile Glu Lys Ser Pro Asn Tyr Cys Glu Glu Asp Ala
  1               5                  10                  15

Ala Thr Gly Ser Val Gly Thr Gln Gly Arg Leu Cys Asn Arg Thr Ser
                 20                  25                  30

Pro Gly Ala Asp Gly Cys Asp Thr Met Cys Cys Gly Arg Gly Tyr Asn
             35                  40                  45

Thr His Gln Tyr Thr Lys Val Trp Gln Cys Asn Cys Lys Phe His Trp
         50                  55                  60

Cys Cys Phe Val Lys Cys Asn Thr Cys Ser Glu Arg Thr Glu Val Phe
 65                  70                  75                  80

Thr Cys Lys

<210> SEQ ID NO 53
<211> LENGTH: 108
<212> TYPE: PRT
<213> ORGANISM: Homo sapiens

<400> SEQUENCE: 53

Glu Leu Ile Phe Leu Glu Glu Ser Pro Asp Tyr Cys Thr Cys Asn Ser
  1               5                  10                  15

Ser Leu Gly Ile Tyr Gly Thr Glu Gly Arg Glu Cys Leu Gln Asn Ser
                 20                  25                  30

His Asn Thr Ser Arg Trp Glu Arg Arg Ser Cys Gly Arg Leu Cys Thr
             35                  40                  45

Glu Cys Gly Leu Gln Val Glu Glu Arg Lys Thr Glu Val Ile Ser Ser
         50                  55                  60

Cys Asn Cys Lys Phe Gln Trp Cys Cys Thr Val Lys Cys Asp Gln Cys
 65                  70                  75                  80
```

Arg His Val Val Ser Lys Tyr Tyr Cys Ala Arg Ser Pro Gly Ser Ala
            85                  90                  95

Gln Ser Leu Gly Arg Val Trp Phe Gly Val Tyr Ile
            100                 105

<210> SEQ ID NO 54
<211> LENGTH: 107
<212> TYPE: PRT
<213> ORGANISM: Homo sapiens

<400> SEQUENCE: 54

Glu Leu Val His Leu Glu Asp Ser Pro Asp Tyr Cys Leu Glu Asn Lys
1               5                   10                  15

Thr Leu Gly Leu Leu Gly Thr Glu Gly Arg Glu Cys Leu Arg Arg Gly
            20                  25                  30

Arg Ala Leu Gly Arg Trp Glu Leu Arg Ser Cys Arg Arg Leu Cys Gly
            35                  40                  45

Asp Cys Gly Leu Ala Val Glu Glu Arg Arg Ala Glu Thr Val Ser Ser
        50                  55                  60

Cys Asn Cys Lys Phe His Trp Cys Cys Ala Val Arg Cys Glu Gln Cys
65                  70                  75                  80

Arg Arg Arg Val Thr Lys Tyr Phe Cys Ser Arg Ala Glu Arg Pro Arg
                85                  90                  95

Gly Gly Ala Ala His Lys Pro Gly Arg Lys Pro
            100                 105

<210> SEQ ID NO 55
<211> LENGTH: 83
<212> TYPE: PRT
<213> ORGANISM: Homo sapiens

<400> SEQUENCE: 55

Asp Leu Val Tyr Phe Glu Lys Ser Pro Asp Phe Cys Glu Arg Glu Pro
1               5                   10                  15

Arg Leu Asp Ser Ala Gly Thr Val Gly Arg Leu Cys Asn Lys Ser Ser
            20                  25                  30

Ala Gly Ser Asp Gly Cys Gly Ser Met Cys Cys Gly Arg Gly His Asn
        35                  40                  45

Ile Leu Arg Gln Thr Arg Ser Glu Arg Cys His Cys Arg Phe His Trp
    50                  55                  60

Cys Cys Phe Val Val Cys Glu Glu Cys Arg Ile Thr Glu Trp Val Ser
65                  70                  75                  80

Val Cys Lys

<210> SEQ ID NO 56
<211> LENGTH: 83
<212> TYPE: PRT
<213> ORGANISM: Homo sapiens

<400> SEQUENCE: 56

Glu Leu Val Tyr Phe Glu Lys Ser Pro Asp Phe Cys Glu Arg Asp Pro
1               5                   10                  15

Thr Met Gly Ser Pro Gly Thr Arg Gly Arg Ala Cys Asn Lys Thr Ser
            20                  25                  30

Arg Leu Leu Asp Gly Cys Gly Ser Leu Cys Cys Gly Arg Gly His Asn
        35                  40                  45

Val Leu Arg Gln Thr Arg Val Glu Arg Cys His Cys Arg Phe His Trp

```
                50                  55                  60
Cys Cys Tyr Val Leu Cys Asp Glu Cys Lys Val Thr Glu Trp Val Asn
 65                  70                  75                  80

Val Cys Lys

<210> SEQ ID NO 57
<211> LENGTH: 8
<212> TYPE: PRT
<213> ORGANISM: Artificial Sequence
<220> FEATURE:
<223> OTHER INFORMATION: Linker

<400> SEQUENCE: 57

Glu Ser Gly Gly Gly Gly Val Thr
 1               5

<210> SEQ ID NO 58
<211> LENGTH: 9
<212> TYPE: PRT
<213> ORGANISM: Artificial Sequence
<220> FEATURE:
<223> OTHER INFORMATION: Linker

<400> SEQUENCE: 58

Leu Glu Ser Gly Gly Gly Gly Val Thr
 1               5

<210> SEQ ID NO 59
<211> LENGTH: 6
<212> TYPE: PRT
<213> ORGANISM: Artificial Sequence
<220> FEATURE:
<223> OTHER INFORMATION: Linker

<400> SEQUENCE: 59

Gly Arg Ala Gln Val Thr
 1               5

<210> SEQ ID NO 60
<211> LENGTH: 6
<212> TYPE: PRT
<213> ORGANISM: Artificial Sequence
<220> FEATURE:
<223> OTHER INFORMATION: Linker

<400> SEQUENCE: 60

Trp Arg Ala Gln Val Thr
 1               5

<210> SEQ ID NO 61
<211> LENGTH: 8
<212> TYPE: PRT
<213> ORGANISM: Artificial Sequence
<220> FEATURE:
<223> OTHER INFORMATION: Linker

<400> SEQUENCE: 61

Ala Arg Gly Arg Ala Gln Val Thr
 1               5
```